(12) United States Patent
Koehn et al.

(10) Patent No.: US 10,111,435 B2
(45) Date of Patent: Oct. 30, 2018

(54) HERBICIDAL COMPOSITIONS CONTAINING N-(1,3,4-OXADIAZOL-2-YL)-ARYL CARBOXYLIC ACID AMIDES

(71) Applicant: BAYER CROPSCIENCE AKTIENGESELLSCHAFT, Monheim an Rhein (DE)

(72) Inventors: Arnim Koehn, Klein-Winternheim (DE); Christian Waldraff, Bad Vilbel (DE); Elmar Gatzweiler, Bad Nauheim (DE); Klaus Trabold, Heidelberg (DE); Hubert Menne, Mainz-Kastel (DE); Hartmut Ahrens, Egelsbach (DE); Simon Doerner-Rieping, Neu-Anspach (DE); Ralf Braun, Ramberg (DE); Ines Heinemann, Hofheim (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 14 days.

(21) Appl. No.: 15/026,143

(22) PCT Filed: Oct. 22, 2014

(86) PCT No.: PCT/EP2014/072645
§ 371 (c)(1),
(2) Date: Mar. 30, 2016

(87) PCT Pub. No.: WO2015/059187
PCT Pub. Date: Apr. 30, 2015

(65) Prior Publication Data
US 2016/0242419 A1    Aug. 25, 2016

(30) Foreign Application Priority Data

Oct. 25, 2013  (EP) ..................... 13190182

(51) Int. Cl.

| | | |
|---|---|---|
| *A01N 43/82* | (2006.01) |
| *A01N 43/80* | (2006.01) |
| *A01N 43/84* | (2006.01) |
| *A01N 43/90* | (2006.01) |
| *A01N 43/76* | (2006.01) |
| *A01N 43/08* | (2006.01) |
| *A01N 43/40* | (2006.01) |
| *A01N 43/54* | (2006.01) |
| *A01N 43/56* | (2006.01) |
| *A01N 43/66* | (2006.01) |
| *A01N 43/68* | (2006.01) |
| *A01N 43/707* | (2006.01) |
| *A01N 43/653* | (2006.01) |
| *A01N 37/20* | (2006.01) |
| *A01N 37/10* | (2006.01) |
| *A01N 41/04* | (2006.01) |
| *A01N 41/08* | (2006.01) |
| *A01N 43/42* | (2006.01) |
| *A01N 47/32* | (2006.01) |
| *A01N 47/36* | (2006.01) |
| *A01N 47/38* | (2006.01) |
| *A01N 57/20* | (2006.01) |
| *A01N 37/34* | (2006.01) |
| *A01N 51/00* | (2006.01) |

(52) U.S. Cl.
CPC ............. *A01N 43/82* (2013.01); *A01N 37/10* (2013.01); *A01N 37/20* (2013.01); *A01N 37/34* (2013.01); *A01N 41/04* (2013.01); *A01N 41/08* (2013.01); *A01N 43/08* (2013.01); *A01N 43/40* (2013.01); *A01N 43/42* (2013.01); *A01N 43/54* (2013.01); *A01N 43/56* (2013.01); *A01N 43/653* (2013.01); *A01N 43/68* (2013.01); *A01N 43/707* (2013.01); *A01N 43/76* (2013.01); *A01N 43/80* (2013.01); *A01N 43/84* (2013.01); *A01N 43/90* (2013.01); *A01N 47/32* (2013.01); *A01N 47/36* (2013.01); *A01N 47/38* (2013.01); *A01N 51/00* (2013.01); *A01N 57/20* (2013.01)

(58) Field of Classification Search
None
See application file for complete search history.

(56) References Cited

U.S. PATENT DOCUMENTS

| | | |
|---|---|---|
| 4,902,340 A | 2/1990 | Hubele |
| 6,251,827 B1 | 6/2001 | Ziemer et al. |
| 6,914,035 B2 | 7/2005 | Ziemer et al. |
| 8,404,618 B2 | 3/2013 | Plant et al. |

(Continued)

FOREIGN PATENT DOCUMENTS

| | | |
|---|---|---|
| CH | 2004/000767 | 4/2004 |
| EP | 00049071 A1 | 4/1982 |

(Continued)

OTHER PUBLICATIONS

International Search Report of PCT/EP2014/072645 dated Jan. 13, 2015.

(Continued)

*Primary Examiner* — John Pak
*Assistant Examiner* — Daniel L Branson
(74) *Attorney, Agent, or Firm* — McBee Moore Woodward & Vanik IP, LLC

(57) ABSTRACT

What are described are herbicidal compositions comprising active ingredients from the group of the N-(1,3,4-oxadiazol-2-yl)arylcarboxamides and further herbicides and optionally safeners. These herbicidal compositions are particularly suitable for use against harmful plants in crops of useful plants.

6 Claims, No Drawings

(56) References Cited

U.S. PATENT DOCUMENTS

| | | |
|---|---|---|
| 8,551,918 B2 | 10/2013 | Polge |
| 2014/0080705 A1 | 3/2014 | Koehn et al. |

FOREIGN PATENT DOCUMENTS

| | | |
|---|---|---|
| WO | 98/47356 A2 | 10/1998 |
| WO | 02/060255 A2 | 8/2002 |
| WO | 03/022050 A1 | 3/2003 |
| WO | 2004/014138 A1 | 2/2004 |
| WO | 2005/055716 A2 | 6/2005 |
| WO | 2005/104848 A1 | 11/2005 |
| WO | 2012/126932 A1 | 9/2012 |

OTHER PUBLICATIONS

Owen "Herbicidal Compositions", Declaration of Dr. Michael D.K. Owen, (Mar. 26, 2013), pp. 1-71.
Owen "Professor and Weed Science Extension Specialist", Resume, pp. 1-118.
Polge "Herbicidal Compositions", U.S. Appl. No. 60/527,061, (Dec. 4, 2003), pp. 1-22.
Owen et al. "Evaluation of preemergence applications of KIH-485, s-metolachlor & CGA-154281, and s-metolachlor & atrazine & CGA-154281 for crop phytotoxicity and weed control in corn, Nashua, IA, 2003," (2003), NCWSS Research Report, vol. 60, pp. 51-52 (2003).
Joanna Davies "Herbicide Safeners—Commercial Products and Tools for Agrochemical Research", Pesticide Outlook, The Royal Society of Chemistry, (Feb. 2001) pp. 10-15.
Fedtke et al. "Synergistic Activity of the Herbicide Safener Dichlormid with Herbicides Affecting Photosynthesis", Zeitschrift Für Naturforschung, Section C, Biosciences 1990 vol. 45 No. 5 pp. 565-56.
Sprague et al. "Enhancing the Margin of Selectivity of RPA 201772 in Zea mays with Antidotes", Weed Science, vol. 47, No. 5, pp. 492-497 (Sep.-Oct. 1999).
Leuschen et al. "Effects of a Seed-Applied Safener on Corn Injury From Clomazone, Imazaquin and Imazethapyr", University of Minnesota Southern Experiment Station Research Report, pp. 72-73 (1989).
Pyroxasulfone (KIH-485) chemical structure, Wildlife International, Ltd., pp. 1-7.
"Corn Injury from Balance Herbicide", University of Illinois Extension Publication (May 28, 1999), pp. 1-5.
"Herbicide Manual for Agricultural Professionals", Iowa State University Manual for Agricultural Professionals (2004).
Friesen et al. "The Influence of Temperature and Soil Moisture on the Phytotoxicity of Dicamba, Picloram, Bromoxynil, and 2,4-D Ester", Can. J. Plant Sci. (1966); vol. 46: pp. 653-660.
"Herbicide Injury Symptoms on Corn and Soybean", Purdue Extension Publication, printed (Apr. 13, 2017), pp. 1-17.
David W. Cudney "Why Herbicides are Selective", California Exotic Pest Plant Council (1996) Symposium Proceedings, pp. 1-3.
J.D. Burton et al. "Sulfonylurea Selectivity and Safener Activity in Landmark and 'Merit' Sweet Corn", Pesticide Biochem. and Physiol. (1994); vol. 48(3): pp. 163-172.
Maxwell et al. "Crop response from corn herbicides on two sweet corn varieties". Urbana, Illinois, (2004). NCWSS Research Report, vol. 61, pp. 8-10.
Gunsolus et al. "Herbicide Mode of Action and Injury Symptoms", North Central Regional Publication 377: (2002) pp. 1-19.
O'Sullivan et al. "Sweet corn (Zea mays) cultivar tolerance to primisulfuron", Can. J. Plant Sci. (2001); pp. 261-264.
Hwang et al. "Mode of Safening Action of Naphthalic Anhydride Against Injury of Sulfonylurea and Imidazolinone Herbicides in Maize", Council of the Australasian Weed Soc. Inc., 10th Australian Weeds Conference/14th Asian-Pacific Weed Science Society Conference 1993.
Rowe et al. I., Efficacy and Mode of Action of CGA-154281, A Protectant for Corn (Zea mays) from Metolachlor Injury. Weed Science. 1991; 39:78-82.
Zidua Herbicide Label from BASF.
Ritter et al., First Year Experiences with KIH-485. NEWSS 58:18 (2004) http://www.newss.org/proceedings/proceedings_2004_vol58.pdf., pp. 1-5.
Zollinger et al. "Crop Response to KIH-485 carryover". NCWSS Research Report, vol. 61, pp. 34-35 (2004).
Mallory-Smith et al. "Revised Classification of Herbicides by Site of Action for Weed Resistance Management Strategies", Weed Technology. (2003); vol. 17: pp. 605-619.
Wicks et al. "Isoxaflutole (Balance) Herbicide Injury to Corn in Nebraska", pp. 1-8.
Dewell et al. "Preemergence weed control in corn with s-metolachlor &atrazine&mesotrione and s-metolachlor&mesotrion premixes. Wanatah, IN, 2003", (2003), NCWSS Research Report, vol. 60, pp. 70-71.
Nelson et al. "Safening of Isoxaflutole in Corn", NCWSS Research Report, vol. 56, p. 76 (2001).
Steckel et al. "Soil Factor Effects on Isoxaflutole Plus Flufenacet Phytotoxicity in Two Corn Hybrids". NCWSS Research Report, vol. 56, p. 145 (2001).
Kelley et al. "Soybean Response to Plant Growth Regulatory Herbicides", NCWSS Research Report, vol. 56, p. 100 (2001).
Ditmarsen et al. "Crop Tolerance and Efficacy of Flumetsulam + Clopyralid Tank Mixed With Reduced Rates of Dicamba + Diflufenzopyr in Field Corn", NCWSS Research Report, vol. 56, p. 218 (2001).
Wyk et al. "Maize Cultivars Differ in Tolerance to Imazethapyr", South African Journal of Plant and Soil (2000); 17:2, p. 86-89.
Curran et al. "Herbicide Injury-Photosynthetic Inhibitors and Contact Herbicides", University of Illinois Extension.
Phatak et al. "Chapter 13: Growth Regulators, Fungicides and other Agrochemicals as Herbicide Safeners", Crop Safeners for Herbicides (1989) pp. 299-315.
Owen et al. "Evaluation of Crop Phytotoxicity and Weed Control in Corn With Postemergence Applied Nicosulfuron & Rimsulfuron, Atrazine, Mesotrione and others, Ames, IA, 2002," (2002), NCWSS Research Report, vol. 59, p. 108-109.
Trower "Sweet Corn Tolerance to Postemergence Applications of Formasulfuron" (2003) NCWSS Research Report, vol. 60, pp. 16-17.
Johnson et al. "Nicosulfuron, Primisulfuron, Imazethapyr and DPX-PE350 Injury to Succeeding Crops" (1993), Weed Tech.; vol. 7(3): 641-644.
Striegel et al. "Formasulfuron + Isoxadifen—Success and Lessons Learned from a Launch Year", North Central Weed Science Proceedings, vol. 57: 225 (2002).
DuPont Web Printout explaining "Q" herbicides, "Safened Sulfonylurea Herbicides Reduce Risk of Corn Injury", Pioneer, printed (Apr. 14, 2007), pp. 1-6.
Schultz et al. "A Comparison of Safeners for Metolachlor on Corn", North Central Weed Science Proceedings, vol. 59:11 (2004), pp. 1-2.
Rowe et al. "Factors Affecting Chloroacetanilide Injury to Corn" (Zea mays). Weed Technology. 1990; 4(4): 904-906.
"Postemergence Control of Grass Weeds in field Corn" Purdue Weed Science, Publication (May 21, 2003), pp. 1-3.
David Hest "Mixing It Up", Farm Industry News (Jan. 1, 2003), pp. 1-10.
Hartzler et al. "2005 Iowa State University Manual for Agricultural Professionals" (1996-2006) pp. 1-115.
"Isoxaflutole" chemical structure, Phenomenex Applications; printed (Apr. 26, 2017). pp. 1-2.

HERBICIDAL COMPOSITIONS CONTAINING N-(1,3,4-OXADIAZOL-2-YL)-ARYL CARBOXYLIC ACID AMIDES

CROSS REFERENCE TO RELATED APPLICATIONS

This application is a § 371 National Stage Application of PCT/EP2014/072645, filed Oct. 22, 2014, which claims priority to European 13190182.9 filed Oct. 25, 2013.

BACKGROUND

Field of the Invention

The present invention relates to agrochemically active herbicidal compositions, to processes for production thereof and to the use thereof for control of harmful plants.

Description of Related Art

WO 2012/126932 A1 discloses particular N-(1,3,4-oxadiazol-2-yl)arylcarboxamides having herbicidal properties. However, these active ingredients do not always exhibit sufficient efficacy against harmful plants and/or some of them are not fully compatible with some important crop plants such as cereal species, corn or rice.

SUMMARY

It is therefore an object of the present invention to provide herbicidal compositions in which efficacy against harmful plants and/or selectivity of the abovementioned herbicides with respect to important crop plants is increased. This object is achieved by the inventive herbicidal compositions described hereinafter, comprising particular N-(1,3,4-oxadiazol-2-yl)arylcarboxamides, further herbicides and optionally safeners.

The present invention provides herbicidal compositions comprising (A) one or more compounds of the formula (I) (component A) or salts thereof

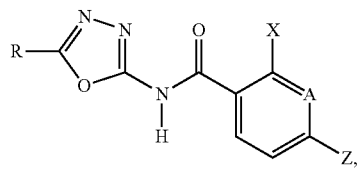

in which the substituents are defined as follows:

A is N or CY,

R is hydrogen, $(C_1-C_6)$-alkyl, $R^1O$—$(C_1-C_6)$-alkyl, $CH_2R^6$, $(C_3-C_7)$-cycloalkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $OR^1$, $NHR^1$, methoxycarbonyl, ethoxycarbonyl, methoxycarbonylmethyl, ethoxycarbonylmethyl, methylcarbonyl, trifluoromethylcarbonyl, dimethylamino, acetylamino, methylsulfenyl, methylsulfinyl, methylsulfonyl, or heteroaryl, heterocyclyl, benzyl or phenyl each substituted by s radicals from the group of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl, X is nitro, halogen, cyano, formyl, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $C(O)NR^1OR^1$, $OR^1$, $OCOR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $NR_1R_2$, $P(O)(OR^5)_2$, $CH_2P(O)(OR^5)_2$, $(C_1-C_6)$-alkylheteroaryl, $(C_1-C_6)$-alkylheterocyclyl, where the two latter radicals are each by s halogen, $(C_1-C_6)$-alkyl, halo-$(C_1-C_6)$-alkyl, $S(O)_n$—$(C_1-C_6)$-alkyl, $(C_1-C_6)$-alkoxy, halo-$(C_1-C_6)$-alkoxy radicals, and where heterocyclyl bears n oxo groups, Y is hydrogen, nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, $(C_3-C_6)$-cycloalkenyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $CO(NOR^1)R^1$, $NR^1SO_2R^2$, $NR^1COR^1$, $OR^1$, $OSO_2R^2$, $S(O)_nR^2$, $SO_2OR^1$, $SO_2N(R^1)_2$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$CN$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $N(R^1)_2$, $P(O)(OR^5)_2$, $CH_2P(O)(OR^5)_2$, $(C_1-C_6)$-alkylphenyl, $(C_1-C_6)$-alkylheteroaryl, $(C_1-C_6)$-alkylheterocyclyl, phenyl, heteroaryl or heterocyclyl, where the 6 latter radicals are each substituted by s radicals from the group of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and where heterocyclyl bears n oxo groups, Z is hydrogen, halogen, cyano, thiocyanato, $(C_1-C_6)$-alkyl, $(C_1-C_6)$-alkoxy, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $C(O)NR^1OR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $N(R^1)_2$, $P(O)(OR^5)_2$, heteroaryl, heterocyclyl or phenyl, where the last three radicals are each substituted by s radicals from the group of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy and halo-$(C_1-C_6)$-alkoxy, and where heterocyclyl bears n oxo groups, $R^1$ is hydrogen, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkylheteroaryl, heterocyclo, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl, $(C_1-C_6)$-alkyl-$NR^3$-heterocyclyl, where the 21 latter radicals are substituted by s radicals from the group consisting of cyano, halogen, nitro, thiocyanato, $OR^3$, $S(O)_nR^4$, $N(R^3)_2$, $NR^3OR^3$, $COR^3$, $OCOR^3$, $SCOR^4$, $NR^3COR^3$, $NR^3SO_2R^4$, CO$_2$R$^3$, COSR$^4$, CON(R$^3$)$_2$ and (C$_1$-C$_4$)-alkoxy-(C$_2$-C$_6$)-alkoxycarbonyl, and where heterocyclyl bears n oxo groups, R$^2$ is (C$_1$-C$_6$)-alkyl, (C$_1$-C$_6$)-haloalkyl, (C$_2$-C$_6$)-alkenyl, (C$_2$-C$_6$)-haloalkenyl, (C$_2$-C$_6$)-alkynyl, (C$_2$-C$_6$)-haloalkynyl, (C$_3$-C$_6$)-cycloalkyl, (C$_3$-C$_6$)-cycloalkenyl, (C$_3$-C$_6$)-halocycloalkyl, (C$_1$-C$_6$)-alkyl-O—(C$_1$-C$_6$)-alkyl, (C$_3$-C$_6$)-cycloalkyl-(C$_1$-C$_6$)-alkyl, phenyl, phenyl-(C$_1$-C$_6$)-alkyl, heteroaryl, (C$_1$-C$_6$)-alkylheteroaryl, heterocyclyl, (C$_1$-C$_6$)-alkylheterocyclyl, (C$_1$-C$_6$)-alkyl-O-heteroaryl, (C$_1$-C$_6$)-alkyl-O-heterocyclyl, (C$_1$-C$_6$)-alkyl-NR$^3$-heteroaryl, (C$_1$-C$_6$)-alkyl-NR$^3$-heterocyclyl, where the 21 latter radicals are substituted by s radicals from the group consisting of cyano, halogen, nitro, thiocyanato, OR$^3$, S(O)$_n$R$^4$, N(R$^3$)$_2$, NR$^3$OR$^3$, COR$^3$, OCOR$^3$, SCOR$^4$, NR$^3$COR$^3$, NR$^3$SO$_2$R$^4$, CO$_2$R$^3$, COSR$^4$, CON(R$^3$)$_2$ and (C$_1$-C$_4$)-alkoxy-(C$_2$-C$_6$)-alkoxycarbonyl, and where heterocyclyl bears n oxo groups, R$^3$ is hydrogen, (C$_1$-C$_6$)-alkyl, (C$_2$-C$_6$)-alkenyl, (C$_2$-C$_6$)-alkynyl, (C$_3$-C$_6$)-cycloalkyl or (C$_3$-C$_6$)-cycloalkyl-(C$_1$-C$_6$)-alkyl, R$^4$ is (C$_1$-C$_6$)-alkyl, (C$_2$-C$_6$)-alkenyl or (C$_2$-C$_6$)-alkynyl, R$^5$ is methyl or ethyl, R$^6$ is acetoxy, acetamido, N-methylacetamido, benzoyloxy, benzamido, N-methylbenzamido, methoxycarbonyl, ethoxycarbonyl, benzoyl, methylcarbonyl, piperidinylcarbonyl, morpholinylcarbonyl, trifluoromethylcarbonyl, aminocarbonyl, methylaminocarbonyl, dimethylaminocarbonyl, (C$_1$-C$_6$)-alkoxy, (C$_3$-C$_6$)-cycloalkyl, or heteroaryl, heterocyclyl or phenyl each substituted by s radicals from the group of methyl, ethyl, methoxy, trifluoromethyl and halogen, n is 0, 1 or 2, s is 0, 1, 2 or 3, and (B) one or more herbicides (component B) selected from groups (B1) to (B11):

B1 1,3-diketo compounds comprising prohexadione, prohexadione-calcium, trinexapac-ethyl, alloxydim, alloxydim-sodium, butroxydim, clethodim, cycloxydim, ketospiradox, profoxydim, sethoxydim, tepraloxydim, tralkoxydim, mesotrione, sulcotrione, tefuryltrione, tembotrione, bicyclopyrone, pinoxaden, B2 (sulfon)amides comprising beflubutamide, bromobutide, dimethenamide, dimethenamide-P, diphenamide, napropamide, pethoxamid, N-[3-chloro-4-(1-methylethyl)-phenyl]-2-methylpentanamide, propyzamide, diflufenican, etobenzanid, flufenacet, mefenacet, mefluidide, picolinafen, propanil, N-phenylphthalamic acid, acetochlor, alachlor, amidochlor, butachlor, butenachlor, dimethachlor, metazachlor, metolachlor, S-metolachlor, pretilachlor, propachlor, propisochlor, (2-chloro-6'-ethyl-N-isopropoxymethylaceto-o-toluidide), thenylchlor, asulam, carbaryl, carbetamide, chlorpropham, desmedipham, phenmedipham, propham, butylate, cycloate, dimepiperate, EPTC, esprocarb, methasulfocarb, molinate, orbencarb, pebulate, prosulfocarb, pyributicarb, thiobencarb, tri-allate, vernolate, amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron-methyl-sodium, foramsulfuron, halosulfuron-methyl, imazosulfuron, iodosulfuron, iodosulfuron-methyl-sodium, mesosulfuron, mesosulfuron-methyl, metazasulfuron, methiopyrsulfuron, metsulfuron, metsulfuron-methyl, monosulfuron, monosulfuron-ester, nicosulfuron, orthosulfamuron, oxasulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, trifloxysulfuron (sodium), triflusulfuron, triflusulfuron-methyl, tritosulfuron, (benzoic acid, 2-[[[[[4-methoxy-6-(methylthio)-2-pyrimidinyl]amino]carbonyl]amino]sulfonyl]methyl ester), flucarbazone, flucarbazone-sodium, ipfencarbazone, propoxycarbazone, propoxycarbazone-sodium, thiencarbazone, thiencarbazone-methyl, cloransulam, cloransulam-methyl, diclosulam, florasulam, flumetsulam, metosulam, penoxsulam, pyroxsulam, 3-chloro-N-[(4,6-dimethoxypyrimidin-2-yl)carbamoyl]-1-methyl-4-(5-methyl-5,6-dihydro-1,4,2-dioxazin-3-yl)-1H-pyrazole-5-sulfonamide, B3 arylnitriles comprising bromoxynil, bromoxynil-butyrate, bromoxynil-potassium, bromoxynil-heptanoate, bromoxynil-octanoate, detosyl-pyrazolate (DTP), dichlobenil, ioxynil, ioxynil-octanoate, ioxynil-potassium, ioxynil-sodium, pyraclonil, B4 azoles comprising benzofenap, pyrazolynate (pyrazolate), pyrazoxyfen, pyroxasulfone, topramezone, pyrasulfotole, 3-(3-chloro-5-{[1-methyl-3-(trifluoromethyl)-1H-pyrazol-5-yl]oxy}phenoxy)-1-methyl-5-(trifluoromethyl)-1H-pyrazole, 3-(3-iodo-5-{[1-methyl-3-(trifluoromethyl)-1H-pyrazol-5-yl]oxy}phenoxy)-1-methyl-5-(trifluoromethyl)-1H-pyrazole, 1-ethyl-3-(3-fluoro-5-{[1-methyl-3-(trifluoromethyl)-1H-pyrazol-5-yl]oxy}phenoxy)-5-(trifluoromethyl)-1H-pyrazole, pyraflufen, pyraflufen-ethyl, fenoxasulfone, isouron, isoxaben, isoxaflutole, imazamethabenz, imazamethabenz-methyl, imazamox, imazamox-ammonium, imazapic, imazapic-ammonium, imazapyr, imazapyr-isopropyl-ammonium, imazaquin, imazaquin-ammonium, imazethapyr, imazethapyr-immonium, azafenidin, oxadiargyl, oxadiazon, amicarbazone, carfentrazone, carfentrazone-ethyl, sulfentrazone, amitrole, paclobutrazol, uniconazole, uniconazole-P, cafenstrole, fentrazamide, B5 other herbicides comprising allidochlor, aminocyclopyrachlor, aminocyclopyrachlor-potassium, aminocyclopyrachlor-methyl, N-acetylthiazolidine-4-carboxylic acid, aminopyralid, ammonium pelargonate, ammonium sulfamate, aviglycine, benazolin, benazolin-ethyl, benfluralin, benfuresate, bentazone, benzobicyclon, 6-benzylaminopurine, brassinolide, bromofenoxim, butralin, chlorfenac, chlorfenac-sodium, chlorfenprop, chlorflurenol, chlorflurenol-methyl, chloridazon, chlormequat chloride, chlorphthalim, chlorthal-dimethyl, cinidon, cinidon-ethyl, cinmethylin, clofencet, clomazone, cloxyfonac, cyanamide, cyclanilide, cyclopyrimorate, 6-isopentylaminopurine, kinetin, zeatin, dalapon, daminozide, dazomet, n-decanol, difenzoquat metilsulfate, 2,6-diisopropylnaphthalene, dikegulac, dikegulac-sodium, dimethipin, dinitramine, dinoterb, diquat, diquat dibromide, dithiopyr, DNOC, endothal, endothal-dipotassium, endothal-disodium, endothal-mono(N,N-dimethylalkylammonium), ethafluralin, ethofumesate, ethylchlozate, flamprop, flamprop-M-isopropyl, flamprop-M-methyl, fluchloralin, flufenpyr, flufenpyr-ethyl, flumetralin, flumichlorac, flumiclorac-pentyl, flumioxazin, flupropanate, flurenol, flurenol-butyl, flurenol-dimethylammonium-methyl, fluridone, flurochloridone, flurtamone, fluthiacet, fluthiacet-methyl, gibberillic acid, halauxifen, indanofan, isoprothiolane, maleic hydrazide, mepiquat chloride, metam, methiozolin, methylarsonic acid, 1-methylcyclopropene, methyl isothiocyanate, nitrophenolate mixture, nonanoic acid, norflurazon, oleic acid, oryzalin, oxaziclomefone, paraquat, paraquat dichloride, pendimethalin, pentachlorophenol, pentoxazone, petroleum oils, prodiamine, n-propyl dihydrojasmonate, pyridafol, pyridate, quinoclamine, sintofen, TCA, TCA sodium, tecnazene, thiazopyr, triacontanol, triafamone, trifluralin, urea sulfate, B6 (het)arylcarboxylic acids comprising chloramben, dicamba, 2,3,6-TBA, clopyralid, fluroxypyr, fluroxypyr-meptyl, inabenfide, picloram, triclopyr, quinclorac, quinmerac, indol-3-ylacetic acid, 4-indol-3-yl-butyric acid, 2-(1-naphthyl)acetamide, 1-naphthylacetic acid, 2-naphthyloxyacetic acid, B7 organic phosphorus compounds comprising anilofos, bensulide, bilanafos, bilanafos-sodium, butamifos, clacyfos, fosamine, glufosinate, glufosinate salts, glufosinate-ammonium, glufosinate-sodium, glufosinate-P, L-glufosinate-ammonium, L-glufosinate-sodium, glyphosate, glyphosate salts, glyphosate-isopropyl-ammonium, glyphosate-ammonium, glyphosate-dimethylammonium, glyphosate-trimesium (=sulfosate), glyphosate-diammonium, glyphosate-potassium, glyphosate-sodium, piperophos, ethephon, tribufos, B8 phenyl ethers comprising acifluorfen-sodium, aclonifen, fluoroglycofen, fluoroglycofen-ethyl, fomesafen, fomesafen-sodium, halosafen, lactofen, oxyfluorfen, acifluorfen, bifenox, ethoxyfen-ethyl, clomeprop, cloprop, dichlorprop, dichlorprop-P, mecoprop, mecoprop-sodium, mecoprop-butotyl, mecoprop-P, mecoprop-P-butotyl, mecoprop-P-dimethylammonium, mecoprop-P-2-ethylhexyl, mecoprop-P-patassium, 4-CPA, 2,4-D, 2,4-D-butotyl, 2,4-D-butyl, 2,4-D-dimethylammonium, 2,4-D-diolamine, 2,4-D-ethyl, 2,4-D-2-ethylhexyl, 2,4-D-isobutyl, 2,4-D-isooctyl, 2,4-D-isopropylammonium, 2,4-D-potassium, 2,4-D-triisopropanolammonium, 2,4-D-trolamine, MCPA, MCPA-butotyl, MCPA-dimethylammonium, MCPA-2-ethylhexyl, MCPA-isopropylammonium, MCPA-potassium, MCPA-sodium, 2,4-DB, MCPB, MCPB-methyl, MCPB-ethyl-sodium, clodinafop-ethyl, clodinafop-propargyl, cyhalofop, cyhalofop-butyl, diclofop, diclofop-P, diclofop-methyl, diclofop-P-methyl, fenoxaprop, fenoxaprop-P, fenoxaprop-P-ethyl, fluazifop, fluazifop-P, fluazifop-butyl, fluazifop-P-butyl, haloxyfop, haloxyfop-P, metamifop, propaquizafop quizalofop, quizalofop-ethyl, quizalofop-P, quizalofop-P-ethyl, quizalofop-P-tefuryl, B9 pyrimidines, comprising ancymidol, flurprimidol, pyrimisulfan, bispyribac, bispyribac-sodium, pyribenzoxim, pyriminobac, pyriminobac-methyl, pyribambenz, pyribambenz-isopropyl, pyribambenz-propyl, pyriftalid, pyrithiobac, pyrithiobac-sodium, bromacil, butafenacil, lenacil, saflufenacil, terbacil, tifenacil, 2-chloro-4-fluoro-5-[3-methyl-2,6-dioxo-4-(trifluoromethyl)-3,6-dihydropyrimidin-1 (2H)-yl]-N-[methyl(1-methylethyl)sulfamoyl]benzamide, ethyl [(3-{2-chloro-5-[2,6-dioxo-4-(trifluoromethyl)-3,6-dihydropyrimidin-1 (2H)-yl]-4-fluorophenoxy}pyridin-2-yl)oxy]acetate, B10 (thio)ureas comprising cumyluron, chlorbromuron, chlorotoluron, daimuron, diflufenzopyr, diflufenzopyr-sodium, dimefuron, diuron, fluometuron, forchlorfenuron, isoproturon, karbutilate, linuron, metobromuron, metoxuron, monolinuron, neburon, siduron, terbucarb, thidiazuron, tebuthiuron, methabenzthiazuron, B11 triazines comprising triaziflam, indaziflam, atrazine, cyanazine, cyprazine, propazine, simazine, terbumeton, terbuthylazine, trietazine, prometon, ametryn, dimethametryn, prometryn, simetryn, terbutryn, ethiozin, hexazinon, metamitron, metribuzin.

DETAIL DESCRIPTION OF A PREFERRED EMBODIMENT

In a further embodiment, these herbicidal compositions comprise (C) one or more safeners (component C) from the group consisting of benoxacor (C1), cloquintocet-mexyl (C2), cyprosulfamide (C3), dichlormid (C4), fenclorim (C5), fenchlorazole (C6), furilazole (C7), isoxadifen-ethyl (C8), mefenpyr-diethyl (C9), 4-(dichloroacetyl)-1-oxa-4-azaspiro[4.5]decane (CAS 71526-07-3) (C10), 2,2,5-trimethyl-3-(dichloroacetyl)-1,3-oxazolidine (CAS 52836-31-4) (C11), 2-methoxy-N-({4-[(methylcarbamoyl)amino]phenyl}sulfonyl)benzamide (CAS 129531-12-0) (C12).

Components B) and C) are known, for example, from "The Pesticide Manual", 16th edition, 2012, The British Crop Protection Council and the Royal Soc. of Chemistry.

The inventive herbicidal compositions may comprise or be used together with additional further components, for example other kinds of active crop protection ingredients and/or additives and/or formulation auxiliaries customary in crop protection.

The herbicides (A), (B) and optionally the safeners (C) can be applied in a known manner, for example together (for example as a co-formulation or as a tank-mix) or else at different times in short succession (splitting), for example to the plants, plant parts, plant seeds or the area on which the plants grow. It is possible, for example, to apply the individual active ingredients or the herbicide-safener combination in several portions (sequential application), for example by pre-emergence applications followed by post-emergence applications, or by early post-emergence applications followed by post-emergence applications at an intermediate or late stage. Preference is given to the joint or immediately successive application of the active ingredients in the respective combination. It is also possible to use the individual active ingredients or the herbicide-safener combination for seed treatment.

Preference is given to those inventive compositions which comprise, as herbicide (A), compounds of the general formula (I) and salts thereof in which A is N or CY, R is hydrogen, $(C_1-C_6)$-alkyl, $(C_3-C_7)$-cycloalkyl, halo-$(C_1-C_6)$-alkyl, $(C_3-C_7)$-cycloalkylmethyl, methoxycarbonylmethyl, ethoxycarbonylmethyl, acetylmethyl, methoxymethyl, methoxyethyl, benzyl, pyrazin-2-yl, furan-2-yl, tetrahydrofuran-2-yl, morpholine, dimethylamino, or phenyl substituted by s radicals from the group of methyl, methoxy, trifluoromethyl and halogen;

X is nitro, halogen, cyano, $(C_1-C_6)$-alkyl, halo-$(C_1-C_6)$-alkyl, $(C_3-C_6)$-cycloalkyl, $OR^1$, $S(O)_nR^2$, $(C_1-C_6)$-alkyl-S$(O)_nR^2$, $(C_1-C_6)$-alkyl-$OR^1$, $(C_1-C_6)$-alkyl-CON$(R^1)_2$, $(C_1-C_6)$-alkyl-SO$_2$N$(R^1)_2$, $(C_1-C_6)$-alkyl-NR$^1$COR$^1$, $(C_1-C_6)$-alkyl-NR$^1$SO$_2$R$^2$, $(C_1-C_6)$-alkylheteroaryl, $(C_1-C_6)$-alkylheterocyclyl, where the two latter radicals are each substituted by s halogen, $(C_1-C_6)$-alkyl, halo-$(C_1-C_6)$-alkyl, S(O)$_n$—$(C_1-C_6)$-alkyl, $(C_1-C_6)$-alkoxy, halo-$(C_1-C_6)$-alkoxy radicals, and where heterocyclyl bears n oxo groups, Y hydrogen, nitro, halogen, cyano, $(C_1-C_6)$-alkyl, $(C_1-C_6)$-haloalkyl, $OR^1$, $S(O)_nR^2$, $SO_2N(R^1)_2$, $N(R^1)_2$, $NR^1SO_2R^2$, $NR^1COR^1$, $(C_1-C_6)$-alkyl-S(O)$_n$R$^2$, $(C_1-C_6)$-alkyl-OR$^1$, $(C_1-C_6)$-alkyl-CON(R$^1$)$_2$, $(C_1-C_6)$-alkyl-SO$_2$N(R$^1$)$_2$, $(C_1-C_6)$-alkyl-NR$^1$COR$^1$, $(C_1-C_6)$-alkyl-NR$^1$SO$_2$R$^2$, $(C_1-C_6)$-alkylphenyl, $(C_1-C_6)$-alkylheteroaryl, $(C_1-C_6)$-alkylheterocyclyl, phenyl, heteroaryl or heterocyclyl, where the 6 latter radicals are each substituted by s radicals from the group consisting of halogen, nitro, cyano, $(C_1-C_6)$-alkyl, halo-$(C_1-C_6)$-alkyl, $(C_3-C_6)$-cycloalkyl, S(O)$_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and where heterocyclyl bears n oxo groups, Z is halogen, cyano, nitro, methyl, halo-$(C_1-C_6)$-alkyl, $(C_3-C_6)$-cycloalkyl, $S(O)_nR^2$, 1,2,4-triazol-1-yl, pyrazol-1-yl, or Z may also be hydrogen if Y is the $S(O)_nR^2$ radical, $R^1$ is hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl or $(C_1-C_6)$-alkyl-$NR^3$-heterocyclyl, where the 16 latter radicals are substituted by s radicals from the group consisting of cyano, halogen, nitro, $OR^3$, $S(O)_nR^4$, $N(R^3)_2$, $NR^3OR^3$, $COR^3$, $OCOR^3$, $NR^3COR^3$, $NR^3SO_2R^4$, $COO_2R^3$, $CON(R^3)_2$ and $(C_1-C_4)$-alkoxy-$(C_2-C_6)$-alkoxycarbonyl, and where heterocyclyl bears n oxo groups, $R^2$ is $(C_1-C_6)$-alkyl, $(C_3-C_6)$-cycloalkyl or $(C_3-C_6)$-cycloalkyl-$(C_1-C_6)$-alkyl, where these three aforementioned radicals are each substituted by s radicals from the group consisting of halogen and $OR^3$, $R^3$ is hydrogen or $(C_1-C_6)$-alkyl, $R^4$ is $(C_1-C_6)$-alkyl, n is 0, 1 or 2, s is 0, 1, 2 or 3.

Particular preference is given to inventive compositions which comprise, as herbicide (A), compounds of the general formula (I) and salts thereof in which A is N or CY, R is hydrogen, $(C_1-C_4)$-alkyl, cyclopropyl, halo-$(C_1-C_4)$-alkyl, $(C_3-C_6)$-cycloalkylmethyl, methoxymethyl, methoxyethyl, benzyl, X is nitro, halogen, cyano, $(C_1-C_6)$-alkyl, halo-$(C_1-C_6)$-alkyl, cyclopropyl, $OR^1$, $S(O)_nR^2$, $(C_1-C_6)$-alkyl-$S(O)_nR^2$, $(C_1-C_5)$-alkyl-$OR^1$, $(C_1-C_2)$-alkylheteroaryl, $(C_1-C_2)$-alkyl-heterocyclyl, where the two latter radicals are each substituted by s halogen, $(C_1-C_6)$-alkyl, halo-$(C_1-C_6)$-alkyl, $S(O)_n$—$(C_1-C_6)$-alkyl, $(C_1-C_6)$-alkoxy, halo-$(C_1-C_6)$-alkoxy radicals, and where heterocyclyl bears n oxo groups, Y hydrogen, nitro, halogen, cyano, $(C_1-C_6)$-alkyl, $(C_1-C_6)$-haloalkyl, $OR^1$, $S(O)_nR^2$, $SO_2N(R^1)_2$, $N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $(C_1-C_6)$-alkylphenyl, $(C_1-C_6)$-alkylheteroaryl, $(C_1-C_6)$-alkylheterocyclyl, phenyl, heteroaryl or heterocyclyl, where the 6 latter radicals are each substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and where heterocyclyl bears n oxo groups, Z is halogen, cyano, nitro, methyl, halo-$(C_1-C_6)$-alkyl, $(C_3-C_6)$-cycloalkyl, $S(O)_nR^2$, 1,2,4-triazol-1-yl, pyrazol-1-yl, or $R^1$ is hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl or $(C_1-C_6)$-alkyl-$NR^3$-heterocyclyl, where the 16 latter radicals are substituted by s radicals from the group consisting of cyano, halogen, nitro, $OR^3$, $S(O)_nR^4$, $N(R^3)_2$, $NR^3OR^3$, $COR^3$, $OCOR^3$, $NR^3COR^3$, $NR^3SO_2R^4$, $CO_2R^3$, $CON(R^3)_2$ and $(C_1-C_4)$-alkoxy-$(C_2-C_6)$-alkoxycarbonyl, and where heterocyclyl bears n oxo groups, $R^2$ is $(C_1-C_6)$-alkyl, $(C_3-C_6)$-cycloalkyl or $(C_3-C_6)$-cycloalkyl-$(C_1-C_6)$-alkyl, where these three aforementioned radicals are each substituted by s radicals from the group consisting of halogen and $OR^3$, $R^3$ is hydrogen or $(C_1-C_6)$-alkyl, $R^4$ is $(C_1-C_6)$-alkyl, n is 0, 1 or 2, s is 0, 1, 2 or 3.

In the formula (I) and all the formulae which follow, alkyl radicals having more than two carbon atoms may be straight-chain or branched. Alkyl radicals are, for example, methyl, ethyl, n- or i-propyl, n-, i-, t- or 2-butyl, pentyls, hexyls such as n-hexyl, i-hexyl and 1,3-dimethylbutyl. Analogously, alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl. Alkynyl is, for example, propargyl, but-2-yn-1-yl, but-3-ynl-1-yl, 1-methylbut-3-yn-1-yl. The multiple bond may be in any position in each unsaturated radical. Cycloalkyl is a carbocyclic saturated ring system having three to six carbon atoms, for example cyclopropyl, cyclobutyl, cyclopentyl or cyclohexyl. Analogously, cycloalkenyl is a monocyclic alkenyl group having three to six carbon ring members, for example cyclopropenyl, cyclobutenyl, cyclopentenyl and cyclohexenyl, where the double bond may be in any position.

Halogen is fluorine, chlorine, bromine or iodine.

Heterocyclyl is a saturated, partly saturated or fully unsaturated cyclic radical which contains 3 to 6 ring atoms, of which 1 to 4 are from the group of oxygen, nitrogen and sulfur, and which may additionally be fused by a benzo ring. For example, heterocyclyl is piperidinyl, pyrrolidinyl, tetrahydrofuranyl, dihydrofuranyl and oxetanyl.

Heteroaryl is an aromatic cyclic radical which contains 3 to 6 ring atoms, of which 1 to 4 are from the group of oxygen, nitrogen and sulfur, and which may additionally be fused by a benzo ring. Heteroaryl represents, for example, benzimidazol-2-yl, furanyl, imidazolyl, isoxazolyl, isothiazolyl, oxazolyl, pyrazinyl, pyrimidinyl, pyridazinyl, pyridinyl, benzisoxazolyl, thiazolyl, pyrrolyl, pyrazolyl, thiophenyl, 1,2,3-oxadiazolyl, 1,2,4-oxadiazolyl, 1,2,5-oxadiazolyl, 1,3,4-oxadiazolyl, 1,2,4-triazolyl, 1,2,3-triazolyl, 1,2,5-triazolyl, 1,3,4-triazolyl, 1,2,4-triazolyl, 1,2,4-thiadiazolyl, 1,3,4-thiadiazolyl, 1,2,3-thiadiazolyl, 1,2,5-thiadiazolyl, 2H-1,2,3,4-tetrazolyl, 1H-1,2,3,4-tetrazolyl, 1,2,3,4-oxatriazolyl, 1,2,3,5-oxatriazolyl, 1,2,3,4-thiatriazolyl and 1,2,3,5-thiatriazolyl.

When a group is polysubstituted by radicals, this means that this group is substituted by one or more identical or different radicals from those mentioned. The same applies to the formation of ring systems by different atoms and elements. At the same time, the scope of the claims shall exclude those compounds known by the person skilled in the art to be chemically unstable under standard conditions.

The present invention also provides herbicidal compositions comprising stereoisomers and mixtures thereof which are encompassed by formula (I) or by the formulae of component B. Such compounds of the formula (I) or of the formulae of component B contain, for example, one or more asymmetrically substituted carbon atoms or sulfoxides. The possible stereoisomers defined by the specific three-dimensional shape thereof, such as enantiomers and diastereomers, are all encompassed by the formula (I) or by components (B) and (C); especially also the racemic mixtures and—where enantiomers are possible—both enantiomers and especially the respective biologically active enantiomer. The individual stereoisomers can be obtained by customary methods from mixtures of the stereoisomers or else be prepared by stereoselective reactions in combination with the use of stereochemically pure starting materials or auxiliaries.

Examples of compounds very particularly preferred as herbicide (A) are listed in the tables which follow.

In these tables, the abbreviations used mean:

| | | | |
|---|---|---|---|
| Et = ethyl | Me = methyl | n-Pr = n-propyl | i-Pr = isopropyl |
| c-Pr = cyclopropyl | Ph = phenyl | Ac = acetyl | i-Bu = isobutyl |

TABLE 1

Compounds of the general formula (I) in which A is CY

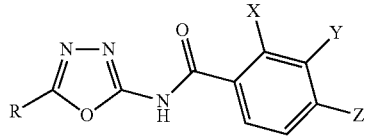

| Ex. no. | R | X | Y | Z |
|---|---|---|---|---|
| A1-1 | Me | Cl | CH₂OCH₂CF₃ | SO₂Me |
| A1-2 | c-Pr | Cl | SO₂Me | CF₃ |
| A1-3 | CH₂OMe | Me | SO₂Me | CF₃ |
| A1-4 | Me | Me | OEt | SO₂Me |
| A1-5 | Me | Cl | OEt | SO₂Me |
| A1-6 | Me | Cl | SEt | CF₃ |
| A1-7 | Me | Cl | SO₂Et | CF₃ |
| A1-8 | Et | Me | SO₂Me | CF₃ |
| A1-9 | Me | Cl | SOMe | c-Pr |
| A1-10 | Me | Cl | 5-cyano-4,5-dihydro-1,2-oxazol-3-yl | SO₂Et |
| A1-11 | CH₂OMe | Me | SMe | CF₃ |
| A1-12 | Et | Cl | SO₂Me | CF₃ |
| A1-13 | Me | Me | SO₂Me | CF₃ |
| A1-14 | Me | Cl | SOMe | CF₃ |
| A1-15 | CH₂OEt | Cl | SO₂Me | CF₃ |
| A1-16 | Me | Cl | 2H-1,2,3-triazol-2-yl | SO₂Me |
| A1-17 | Me | Cl | O—CH₂CH₂SMe | Cl |
| A1-18 | Me | Cl | OCH₂CH₂OCF₃ | SO₂Et |
| A1-19 | Me | Cl | OCH₂CF₃ | SO₂Me |
| A1-20 | Me | Cl | SO₂Me | Me |
| A1-21 | Me | CH₂OMe | SO₂Me | CF₃ |
| A1-22 | Me | Cl | OCH₂CH₂OEt | SO₂Et |
| A1-23 | Me | Cl | OCH₂CH₂Cl | SO₂Et |
| A1-24 | Et | Cl | 5-cyano-4,5-dihydro-1,2-oxazol-3-yl | SO₂Et |
| A1-25 | Me | Me | SMe | CF₃ |
| A1-26 | Me | Cl | OCH₂CH₂Cl | SO₂Me |
| A1-27 | Me | Cl | OCH₂CH₂SMe | Cl |
| A1-28 | Me | Cl | SCH₂-c-Pr | CF₃ |
| A1-29 | CH₂F | Me | SO₂Me | CF₃ |
| A1-30 | Me | Cl | O-propargyl | SO₂Me |
| A1-31 | Me | Cl | 1H-1,2,3-triazol-1-yl | CF₃ |
| A1-32 | H | Cl | CH₂OCH₂CF₃ | SO₂Me |
| A1-33 | Me | Cl | 3-Br-1H-pyrazol-1-yl | SO₂Me |
| A1-34 | c-Pr | Me | SOMe | CF₃ |
| A1-35 | Et | Cl | SO₂Me | SO₂Me |
| A1-36 | Me | Cl | SO₂Me | CF₃ |
| A1-37 | Me | Me | 4,5-dihydro-1,2-oxazol-3-yl | SO₂Me |
| A1-38 | Me | Me | 1H-pyrazol-1-yl | SO₂Me |
| A1-39 | Me | Cl | O—nPr | SO₂Me |
| A1-40 | Me | Cl | OCH₂CH₂CH₂OMe | SO₂Et |
| A1-41 | Me | Cl | O—nPr | SO₂Et |
| A1-42 | CH₂OMe | Cl | SOMe | CF₃ |
| A1-43 | CH₂OMe | Cl | SO₂Me | CF₃ |
| A1-44 | Me | Cl | 5-ethyl-4,5-dihydro-1,2-oxazol-3-yl | Cl |
| A1-45 | Me | Me | N(Me)CHO | CF₃ |
| A1-46 | Me | Cl | N(CO)-pyrrolidine | Cl |
| A1-47 | CF₃ | Me | SO₂Me | SO₂Me |
| A1-48 | Me | Me | 4-OMe-1H-pyrazol-1-yl | SO₂Me |
| A1-49 | Me | Me | 1H-1,2,3-triazol-1-yl | SO₂Me |
| A1-50 | Me | Cl | OCH₂CH₂CH₂OMe | SO₂Me |
| A1-51 | Me | Cl | OCHF₂ | SO₂Me |

TABLE 1-continued

Compounds of the general formula (I) in which A is CY

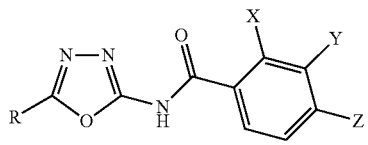

| Ex. no. | R | X | Y | Z |
|---|---|---|---|---|
| A1-52 | Me | Me | 1H-pyrazol-1-yl | CF₃ |
| A1-53 | Me | Cl | OCH₂CH₂CH₂SCF₃ | SO₂Me |
| A1-54 | CHF₂ | Me | SO₂Me | CF₃ |
| A1-55 | Me | Cl | 1H-pyrazol-1-yl | CF₃ |
| A1-56 | Me | Cl | OCH₂—cPr | SO₂Me |
| A1-57 | Me | Cl | OCH₂CH₂F | SO₂Me |
| A1-58 | Me | Me | SMe | C2F5 |
| A1-59 | Me | Cl | OMe | SO₂Me |
| A1-60 | Me | Me | SOMe | CF₃ |
| A1-61 | Me | Br | 1H-pyrazol-1-yl | C₂F₅ |

TABLE 2

Compounds of the general formula (I) in which A is nitrogen

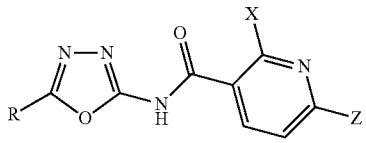

| Ex. no. | R | X | Z |
|---|---|---|---|
| A2-1 | Me | Me | CF₃ |
| A2-2 | pyrazin-2-yl | Cl | CF₃ |
| A2-3 | Me | Br | CF₃ |
| A2-4 | Me | Cl | CF₃ |

Preferred herbicides of group B1 are clethodim, sethoxydim, tepraloxydim, mesotrione, sulcotrione, tefuryltrione, tembotrione, bicyclopyrone, pinoxaden, tralkoxydim. Particularly preferred herbicides of group B1 are clethodim (B1-1), sulcotrione (B1-2), tefuryltrione (B1-3), tembotrione (B1-4), bicyclopyrone (B1-5), pinoxaden (B1-6).

Preferred herbicides of group B2 are dimethenamide, dimethenamide-P, napropamide, pethoxamid, propyzamide, diflufenican, flufenacet, mefenacet, picolinafen, propanil, acetochlor, alachlor, butachlor, metazachlor, metolachlor, S-metolachlor, pretilachlor, thenylchlor, asulam, carbetamide, desmedipham, phenmedipham, esprocarb, molinate, prosulfocarb, thiobencarb, amidosulfuron, chlorimuron-ethyl, cyclosulfamuron, ethoxysulfuron, flupyrsulfuron-methyl-sodium, foramsulfuron, iodosulfuron-methyl-sodium, mesosulfuron-methyl, nicosulfuron, orthosulfamuron, prosulfuron, pyrazosulfuron-ethyl, rimsulfuron, trifloxysulfuron (sodium), flucarbazone-sodium, propoxycarbazone-sodium, thiencarbazone-methyl, florasulam, metosulam, penoxsulam, metsulfuron-methyl, sulfosulfuron, thifensulfuron-methyl, tribenuron-methyl, tritosulfuron, pyroxsulam.

Particularly preferred herbicides of group B2 are dimethenamide-P (B2-1), napropamide (B2-2), diflufenican (B2-3), flufenacet (B2-4), mefenacet (B2-5), acetochlor (B2-6), metazachlor (B2-7), S-metolachlor (B2-8), asulam (B2-9), desmedipham (B2-10), phenmedipham (B2-11), molinate (B2-12), prosulfocarb (B2-13), amidosulfuron (B2-14), ethoxysulfuron (B2-15), foramsulfuron (B2-16), iodosulfuron-methyl-sodium (B2-17), mesosulfuron-methyl (B2-18), flucarbazone-sodium (B2-19), propoxycarbazone-sodium (B2-20), thiencarbazone-methyl (B2-21), florasulam (B2-22), metosulam (B2-23), metsulfuron-methyl (B2-24), sulfosulfuron (B2-25), thifensulfuron-methyl (B2-26), tribenuron-methyl (B2-27), tritosulfuron (B2-28), pyroxsulam (B2-29).

Preferred herbicides of group B3 are bromoxynil (B3-1) and ioxynil (B3-2).

Preferred herbicides of group B4 are benzofenap, topramezone, pyrasulfotole, isoxaflutole, imazamox, imazethapyr, oxadiargyl, oxadiazon, amicarbazone, carfentrazone-ethyl, sulfentrazone, uniconazole, cafenstrole, fentrazamide, 3-(3-chloro-5-{[1-methyl-3-(trifluoromethyl)-1H-pyrazol-5-yl]oxy}phenoxy)-1-methyl-5-(trifluoromethyl)-1H-pyrazole, 3-(3-iodo-5-{[1-methyl-3-(trifluoromethyl)-1H-pyrazol-5-yl]oxy}phenoxy)-1-methyl-5-(trifluoromethyl)-1H-pyrazole, 1-ethyl-3-(3-fluoro-5-{[1-methyl-3-(trifluoromethyl)-1H-pyrazol-5-yl]oxy}phenoxy)-5-(trifluoromethyl)-1H-pyrazole, pyraflufen-ethyl.

Particularly preferred herbicides of group B4 are pyrasulfotole (B4-1), isoxaflutole (B4-2), oxadiargyl (B4-3), oxadiazon (B4-4), amicarbazone (B4-5), fentrazamide (B4-6), 3-(3-chloro-5-{[1-methyl-3-(trifluoromethyl)-1H-pyrazol-5-yl]oxy}phenoxy)-1-methyl-5-(trifluoromethyl)-1H-pyrazole (B4-7), 3-(3-iodo-5-{[1-methyl-3-(trifluoromethyl)-1H-pyrazol-5-yl]oxy}phenoxy)-1-methyl-5-(trifluoromethyl)-1H-pyrazole (B4.8), 1-ethyl-3-(3-fluoro-5-{[1-methyl-3-(trifluoromethyl)-1H-pyrazol-5-yl]oxy}phenoxy)-5-(trifluoromethyl)-1H-pyrazole (B4-9), pyraflufen-ethyl (B4-10), imazamox (B4-11).

Preferred herbicides of group B5 are aminopyralid, benazolin, benfuresate, bentazone, cinidon-ethyl, clomazone, diquat dibromide, ethofumesate, flumiclorac-pentyl, flumioxazin, flurtamone, oxaziclomefone, pendimethalin, pyridate and trifluralin. Particularly preferred herbicides of group B5 are aminopyralid (B5-1), benfuresate (B5-2), ethofumesate (B5-3), flurtamone (B5-4) and oxaziclomefone (B5-5). Preferred herbicides of group B6 are dicamba (B6-1), clopyralid (B6-2), fluroxypyr (B6-3), picloram (B6-4), triclopyr (B6-5), quinclorac (B6-6).

Preferred herbicides of group B7 are anilofos (B7-1), glufosinate-ammonium (B7-2), L-glufosinate-ammonium (B7-3), glyphosate (B7-4), glyphosate-isopropyl-ammonium (B7-5), glyphosate-ammonium (B7-6), glyphosate-trimesium (=sulfosate (B7-7)), glyphosate-diammonium (B7-7), glyphosate-potassium (B7-8).

Preferred herbicides of group B8 are acifluorfen-sodium, aclonifen, fluoroglycofen-ethyl, oxyfluorfen, bifenox, dichlorprop-P, mecoprop-P, 2,4-D, MCPA, clodinafop-propargyl, cyhalofop-butyl, diclofop-methyl, diclofop-P-methyl, fenoxaprop-P-ethyl, fluazifop-P-butyl, quizalofop-P.

Particularly preferred herbicides of group B8 are aclonifen (B8-1), diclofop-methyl (B8-2), diclofop-P-methyl (B8-3), fenoxaprop-P-ethyl (B8-4), MCPA (B8-5), 2,4-D (B8-6), clodinafop-ethyl (B8-7).

Preferred herbicides of group B9 are bispyribac (sodium), pyriftalid, bromacil, lenacil, 2-chloro-4-fluoro-5-[3-methyl-2,6-dioxo-4-(trifluoromethyl)-3,6-dihydropyrimidin-1 (2H)-yl]-N-[methyl(1-methylethyl)sulfamoyl]benzamide. Particularly preferred herbicides of group B9 are bispyribac (sodium) (B9-1), bromacil (B9-2).

Preferred herbicides of group B10 are cumyluron (B10-1), daimuron (B10-2), diuron (B10-3), isoproturon (B10-4), diflufenzopyr (B10-5).

Preferred herbicides of group B11 are atrazine, simazine, terbuthylazine, ametryn, terbutryn, metamitron, metribuzin.

Particularly preferred herbicides of group B11 are metamitron (B11-1), metribuzin (B11-2), terbuthylazine (B11-2).

Examples of preferred compositions of herbicides (A) and herbicides (B) are given below.

(A1-1)+(B1-1), (A1-1)+(B1-2), (A1-1)+(B1-3), (A1-1)+(B1-4), (A1-1)+(B1-5), (A1-1)+(B1-6), (A1-1)+(B2-1), (A1-1)+(B2-2), (A1-1)+(B2-3), (A1-1)+(B2-4), (A1-1)+(B2-5), (A1-1)+(B2-6), (A1-1)+(B2-7), (A1-1)+(B2-8), (A1-1)+(B2-9), (A1-1)+(B2-10), (A1-1)+(B2-11), (A1-1)+(B2-12), (A1-1)+(B2-13), (A1-1)+(B2-14), (A1-1)+(B2-15), (A1-1)+(B2-16), (A1-1)+(B2-17), (A1-1)+(B2-18), (A1-1)+(B2-19), (A1-1)+(B2-20), (A1-1)+(B2-21), (A1-1)+(B2-22), (A1-1)+(B2-23), (A1-1)+(B2-24), (A1-1)+(B2-25), (A1-1)+(B2-26), (A1-1)+(B2-27), (A1-1)+(B2-28), (A1-1)+(B2-29), (A1-1)+(B3-1), (A1-1)+(B3-2), (A1-1)+(B4-1), (A1-1)+(B4-2), (A1-1)+(B4-3), (A1-1)+(B4-4), (A1-1)+(B4-5), (A1-1)+(B4-6), (A1-1)+(B4-7), (A1-1)+(B4-8), (A1-1)+(B4-9), (A1-1)+(B4-10), (A1-1)+(B4-11), (A1-1)+(B5-1), (A1-1)+(B5-2), (A1-1)+(B5-3), (A1-1)+(B5-4), (A1-1)+(B5-5), (A1-1)+(B6-1), (A1-1)+(B6-2), (A1-1)+(B6-3), (A1-1)+(B6-4), (A1-1)+(B6-5), (A1-1)+(B6-6), (A1-1)+(B7-1), (A1-1)+(B7-2), (A1-1)+(B7-3), (A1-1)+(B7-4), (A1-1)+(B7-5), (A1-1)+(B7-6), (A1-1)+(B7-7)), (A1-1)+(B7-7), (A1-1)+(B7-8), (A1-1)+(B8-1), (A1-1)+(B8-2), (A1-1)+(B8-3), (A1-1)+(B8-4), (A1-1)+(B8-5), (A1-1)+(B8-6), (A1-1)+(B8-7), (A1-1)+(B9-1), (A1-1)+(B9-2), (A1-1)+(B10-1), (A1-1)+(B10-2), (A1-1)+(B10-3), (A1-1)+(B10-4), (A1-1)+(B10-5), (A1-1)+(B11-1), (A1-1)+(B11-2), (A1-1)+(B11-2), (A1-2)+(B1-1), (A1-2)+(B1-2), (A1-2)+(B1-3), (A1-2)+(B1-4), (A1-2)+(B1-5), (A1-2)+(B1-6), (A1-2)+(B2-1), (A1-2)+(B2-2), (A1-2)+(B2-3), (A1-2)+(B2-4), (A1-2)+(B2-5), (A1-2)+(B2-6), (A1-2)+(B2-7), (A1-2)+(B2-8), (A1-2)+(B2-9), (A1-2)+(B2-10), (A1-2)+(B2-11), (A1-2)+(B2-12), (A1-2)+(B2-13), (A1-2)+(B2-14), (A1-2)+(B2-15), (A1-2)+(B2-16), (A1-2)+(B2-17), (A1-2)+(B2-18), (A1-2)+(B2-19), (A1-2)+(B2-20), (A1-2)+(B2-21), (A1-2)+(B2-22), (A1-2)+(B2-23), (A1-2)+(B2-24), (A1-2)+(B2-25), (A1-2)+(B2-26), (A1-2)+(B2-27), (A1-2)+(B2-28), (A1-2)+(B2-29), (A1-2)+(B3-1), (A1-2)+(B3-2), (A1-2)+(B4-1), (A1-2)+(B4-2), (A1-2)+(B4-3), (A1-2)+(B4-4), (A1-2)+(B4-5), (A1-2)+(B4-6), (A1-2)+(B4-7), (A1-2)+(B4-8), (A1-2)+(B4-9), (A1-2)+(B4-10), (A1-2)+(B4-11), (A1-2)+(B5-1), (A1-2)+(B5-2), (A1-2)+(B5-3), (A1-2)+(B5-4), (A1-2)+(B5-5), (A1-2)+(B6-1), (A1-2)+(B6-2), (A1-2)+(B6-3), (A1-2)+(B6-4), (A1-2)+(B6-5), (A1-2)+(B6-6), (A1-2)+(B7-1), (A1-2)+(B7-2), (A1-2)+(B7-3), (A1-2)+(B7-4), (A1-2)+(B7-5), (A1-2)+(B7-6), (A1-2)+(B7-7)), (A1-2)+(B7-7), (A1-2)+(B7-8), (A1-2)+(B8-1), (A1-2)+(B8-2), (A1-2)+(B8-3), (A1-2)+(B8-4), (A1-2)+(B8-5), (A1-2)+(B8-6), (A1-2)+(B8-7), (A1-2)+(B9-1), (A1-2)+(B9-2), (A1-2)+(B10-1), (A1-2)+(B10-2), (A1-2)+(B10-3), (A1-2)+(B10-4), (A1-2)+(B10-5), (A1-2)+(B11-1), (A1-2)+(B11-2), (A1-2)+(B11-2), (A1-3)+(B1-1), (A1-3)+(B1-2), (A1-3)+(B1-3), (A1-3)+(B1-4), (A1-3)+(B1-5), (A1-3)+(B1-6), (A1-3)+(B2-1), (A1-3)+(B2-2), (A1-3)+(B2-3), (A1-3)+(B2-4), (A1-3)+(B2-5), (A1-3)+(B2-6), (A1-3)+(B2-7), (A1-3)+(B2-8), (A1-3)+(B2-9), (A1-3)+(B2-10), (A1-3)+(B2-11), (A1-3)+(B2-12), (A1-3)+(B2-13), (A1-3)+(B2-14), (A1-3)+(B2-15), (A1-3)+(B2-16), (A1-3)+(B2-17), (A1-3)+(B2-18), (A1-3)+(B2-19), (A1-3)+(B2-20), (A1-3)+(B2-21), (A1-3)+(B2-22), (A1-3)+(B2-23), (A1-3)+(B2-24), (A1-3)+(B2-25), (A1-3)+(B2-26), (A1-3)+(B2-27), (A1-3)+(B2-28), (A1-3)+(B2-29), (A1-3)+(B3-1), (A1-3)+(B3-2), (A1-3)+(B4-1), (A1-3)+(B4-2), (A1-3)+(B4-3), (A1-3)+(B4-4), (A1-3)+(B4-5), (A1-3)+(B4-6), (A1-3)+(B4-7), (A1-3)+(B4-8), (A1-3)+(B4-9), (A1-3)+(B4-10), (A1-3)+(B4-11), (A1-3)+(B5-1), (A1-3)+(B5-2), (A1-3)+(B5-3), (A1-3)+(B5-4), (A1-3)+(B5-5), (A1-3)+(B6-1), (A1-3)+(B6-2), (A1-3)+(B6-3), (A1-3)+(B6-4), (A1-3)+(B6-5), (A1-3)+(B6-6), (A1-3)+(B7-1), (A1-3)+(B7-2), (A1-3)+(B7-3), (A1-3)+(B7-4), (A1-3)+(B7-5), (A1-3)+(B7-6), (A1-3)+(B7-7)), (A1-3)+(B7-7), (A1-3)+(B7-8), (A1-3)+(B8-1), (A1-3)+(B8-2), (A1-3)+(B8-3), (A1-3)+(B8-4), (A1-3)+(B8-5), (A1-3)+(B8-6), (A1-3)+(B8-7), (A1-3)+(B9-1), (A1-3)+(B9-2), (A1-3)+(B10-1), (A1-3)+(B10-2), (A1-3)+(B10-3), (A1-3)+(B10-4), (A1-3)+(B10-5), (A1-3)+(B11-1), (A1-3)+(B11-2), (A1-3)+(B11-2), (A1-4)+(B1-1), (A1-4)+(B1-2), (A1-4)+(B1-3), (A1-4)+(B1-4), (A1-4)+(B1-5), (A1-4)+(B1-6), (A1-4)+(B2-1), (A1-4)+(B2-2), (A1-4)+(B2-3), (A1-4)+(B2-4), (A1-4)+(B2-5), (A1-4)+(B2-6), (A1-4)+(B2-7), (A1-4)+(B2-8), (A1-4)+(B2-9), (A1-4)+(B2-10), (A1-4)+(B2-11), (A1-4)+(B2-12), (A1-4)+(B2-13), (A1-4)+(B2-14), (A1-4)+(B2-15), (A1-4)+(B2-16), (A1-4)+(B2-17), (A1-4)+(B2-18), (A1-4)+(B2-19), (A1-4)+(B2-20), (A1-4)+(B2-21), (A1-4)+(B2-22), (A1-4)+(B2-23), (A1-4)+(B2-24), (A1-4)+(B2-25), (A1-4)+(B2-26), (A1-4)+(B2-27), (A1-4)+(B2-28), (A1-4)+(B2-29), (A1-4)+(B3-1), (A1-4)+(B3-2), (A1-4)+(B4-1), (A1-4)+(B4-2), (A1-4)+(B4-3), (A1-4)+(B4-4), (A1-4)+(B4-5), (A1-4)+(B4-6), (A1-4)+(B4-7), (A1-4)+(B4-8), (A1-4)+(B4-9), (A1-4)+(B4-10), (A1-4)+(B4-11), (A1-4)+(B5-1), (A1-4)+(B5-2), (A1-4)+(B5-3), (A1-4)+(B5-4), (A1-4)+(B5-5), (A1-4)+(B6-1), (A1-4)+(B6-2), (A1-4)+(B6-3), (A1-4)+(B6-4), (A1-4)+(B6-5), (A1-4)+(B6-6), (A1-4)+(B7-1), (A1-4)+(B7-2), (A1-4)+(B7-3), (A1-4)+(B7-4), (A1-4)+(B7-5), (A1-4)+(B7-6), (A1-4)+(B7-7)), (A1-4)+(B7-7), (A1-4)+(B7-8), (A1-4)+(B8-1), (A1-4)+(B8-2), (A1-4)+(B8-3), (A1-4)+(B8-4), (A1-4)+(B8-5), (A1-4)+(B8-6), (A1-4)+(B8-7), (A1-4)+(B9-1), (A1-4)+(B9-2), (A1-4)+(B10-1), (A1-4)+(B10-2), (A1-4)+(B10-3), (A1-4)+(B10-4), (A1-4)+(B10-5), (A1-4)+(B11-1), (A1-4)+(B11-2), (A1-4)+(B11-2), (A1-5)+(B1-1), (A1-5)+(B1-2), (A1-5)+(B1-3), (A1-5)+(B1-4), (A1-5)+(B1-5), (A1-5)+(B1-6), (A1-5)+(B2-1), (A1-5)+(B2-2), (A1-5)+(B2-3), (A1-5)+(B2-4), (A1-5)+(B2-5), (A1-5)+(B2-6), (A1-5)+(B2-7), (A1-5)+(B2-8), (A1-5)+(B2-9), (A1-5)+(B2-10), (A1-5)+(B2-11), (A1-5)+(B2-12), (A1-5)+(B2-13), (A1-5)+(B2-14), (A1-5)+(B2-15), (A1-5)+(B2-16), (A1-5)+(B2-17), (A1-5)+(B2-18), (A1-5)+(B2-19), (A1-5)+(B2-20), (A1-5)+(B2-21), (A1-5)+(B2-22), (A1-5)+(B2-23), (A1-5)+(B2-24), (A1-5)+(B2-25), (A1-5)+(B2-26), (A1-5)+(B2-27), (A1-5)+(B2-28), (A1-5)+(B2-29), (A1-5)+(B3-1), (A1-5)+(B3-2), (A1-5)+(B4-1), (A1-5)+(B4-2), (A1-5)+(B4-3), (A1-5)+(B4-4), (A1-5)+(B4-5), (A1-5)+(B4-6), (A1-5)+(B4-7), (A1-5)+(B4-8), (A1-5)+(B4-9), (A1-5)+(B4-10), (A1-5)+(B4-11), (A1-5)+(B5-1), (A1-5)+(B5-2), (A1-5)+(B5-3), (A1-5)+(B5-4), (A1-5)+(B5-5), (A1-5)+(B6-1), (A1-5)+(B6-2), (A1-5)+(B6-3), (A1-5)+(B6-4), (A1-5)+(B6-5), (A1-5)+(B6-6), (A1-5)+(B7-1), (A1-5)+(B7-2), (A1-5)+(B7-3), (A1-5)+(B7-4), (A1-5)+(B7-5), (A1-5)+(B7-6), (A1-5)+(B7-7)), (A1-5)+(B7-7), (A1-5)+(B7-8), (A1-5)+(B8-1), (A1-5)+(B8-2), (A1-5)+(B8-3), (A1-5)+(B8-4), (A1-5)+(B8-5), (A1-5)+(B8-6), (A1-5)+(B8-7), (A1-5)+(B9-1), (A1-5)+(B9-2), (A1-5)+(B10-1), (A1-5)+(B10-2), (A1-5)+(B10-3), (A1-5)+(B10-4), (A1-5)+(B10-5), (A1-5)+(B11-1), (A1-5)+(B11-2), (A1-5)+(B11-2), (A1-6)+(B1-1), (A1-6)+(B1-2), (A1-6)+(B1-3), (A1-6)+(B1-4), (A1-6)+(B1-5), (A1-6)+(B1-6), (A1-6)+(B2-1), (A1-6)+(B2-2), (A1-6)+(B2-3), (A1-6)+(B2-4), (A1-6)+(B2-5), (A1-6)+(B2-6), (A1-6)+(B2-7), (A1-6)+(B2-8), (A1-6)+(B2-9), (A1-6)+(B2-10), (A1-6)+(B2-11), (A1-6)+(B2-12), (A1-6)+(B2-13), (A1-6)+(B2-14), (A1-6)+(B2-15), (A1-6)+(B2-16), (A1-6)+(B2-17), (A1-6)+(B2-18), (A1-6)+(B2-19), (A1-6)+(B2-20), (A1-6)+(B2-21), (A1-6)+(B2-22), (A1-6)+(B2-23), (A1-6)+(B2-24), (A1-6)+(B2-25), (A1-6)+(B2-26), (A1-6)+(B2-27), (A1-6)+(B2-28), (A1-6)+(B2-29), (A1-6)+(B3-1), (A1-6)+(B3-2), (A1-6)+(B4-1), (A1-6)+(B4-2), (A1-6)+(B4-3), (A1-6)+(B4-4), (A1-6)+(B4-5), (A1-6)+(B4-6), (A1-6)+(B4-7), (A1-6)+(B4-8), (A1-6)+(B4-9), (A1-6)+(B4-10), (A1-6)+(B4-11), (A1-6)+(B5-1), (A1-6)+(B5-2), (A1-6)+(B5-3), (A1-6)+(B5-4), (A1-6)+(B5-5), (A1-6)+(B6-1), (A1-6)+(B6-2), (A1-6)+(B6-3), (A1-6)+(B6-4), (A1-6)+(B6-5), (A1-6)+(B6-6), (A1-6)+(B7-1), (A1-6)+(B7-2), (A1-6)+(B7-3), (A1-6)+(B7-4), (A1-6)+(B7-5), (A1-6)+(B7-6), (A1-6)+(B7-7)), (A1-6)+(B7-7), (A1-6)+(B7-8), (A1-6)+(B8-1), (A1-6)+(B8-2), (A1-6)+(B8-3), (A1-6)+(B8-4), (A1-6)+(B8-5), (A1-6)+(B8-6), (A1-6)+(B8-7), (A1-6)+(B9-1), (A1-6)+(B9-2), (A1-6)+(B10-1), (A1-6)+(B10-2), (A1-6)+(B10-3), (A1-6)+(B10-4), (A1-6)+(B10-5), (A1-6)+(B11-1), (A1-6)+(B11-2), (A1-6)+(B11-2), (A1-7)+(B1-1), (A1-7)+(B1-2), (A1-7)+(B1-3), (A1-7)+(B1-4), (A1-7)+(B1-5), (A1-7)+(B1-6), (A1-7)+(B2-1), (A1-7)+(B2-2), (A1-7)+(B2-3), (A1-7)+(B2-4), (A1-7)+(B2-5), (A1-7)+(B2-6), (A1-7)+(B2-7), (A1-7)+(B2-8), (A1-7)+(B2-9), (A1-7)+(B2-10), (A1-7)+(B2-11), (A1-7)+(B2-12), (A1-7)+(B2-13), (A1-7)+(B2-14), (A1-7)+(B2-15), (A1-7)+(B2-16), (A1-7)+(B2-17), (A1-7)+(B2-18), (A1-7)+(B2-19), (A1-7)+(B2-20), (A1-7)+(B2-21), (A1-7)+(B2-22), (A1-7)+(B2-23), (A1-7)+(B2-24), (A1-7)+(B2-25), (A1-7)+(B2-26), (A1-7)+(B2-27), (A1-7)+(B2-28), (A1-7)+(B2-29), (A1-7)+(B3-1), (A1-7)+(B3-2), (A1-7)+(B4-1), (A1-7)+(B4-2), (A1-7)+(B4-3), (A1-7)+(B4-4), (A1-7)+(B4-5), (A1-7)+(B4-6), (A1-7)+(B4-7), (A1-7)+(B4-8), (A1-7)+(B4-9), (A1-7)+(B4-10), (A1-7)+(B4-11), (A1-7)+(B5-1), (A1-7)+(B5-2), (A1-7)+(B5-3), (A1-7)+(B5-4), (A1-7)+(B5-5), (A1-7)+(B6-1), (A1-7)+(B6-2), (A1-7)+(B6-3), (A1-7)+(B6-4), (A1-7)+(B6-5), (A1-7)+(B6-6), (A1-7)+(B7-1), (A1-7)+(B7-2), (A1-7)+(B7-3), (A1-7)+(B7-4), (A1-7)+(B7-5), (A1-7)+(B7-6), (A1-7)+(B7-7)), (A1-7)+(B7-7), (A1-7)+(B7-8), (A1-7)+(B8-1), (A1-7)+(B8-2), (A1-7)+(B8-3), (A1-7)+(B8-4), (A1-7)+(B8-5), (A1-7)+(B8-6), (A1-7)+(B8-7), (A1-7)+(B9-1), (A1-7)+(B9-2), (A1-7)+(B10-1), (A1-7)+(B10-2), (A1-7)+(B10-3), (A1-7)+(B10-4), (A1-7)+(B10-5), (A1-7)+(B11-1), (A1-7)+(B11-2), (A1-7)+(B11-2), (A1-8)+(B1-1), (A1-8)+(B1-2), (A1-8)+(B1-3), (A1-8)+(B1-4), (A1-8)+(B1-5), (A1-8)+(B1-6), (A1-8)+(B2-1), (A1-8)+(B2-2), (A1-8)+(B2-3), (A1-8)+(B2-4), (A1-8)+(B2-5), (A1-8)+(B2-6), (A1-8)+(B2-7), (A1-8)+(B2-8), (A1-8)+(B2-9), (A1-8)+(B2-10), (A1-8)+(B2-11), (A1-8)+(B2-12), (A1-8)+(B2-13), (A1-8)+(B2-14), (A1-8)+(B2-15), (A1-8)+(B2-16), (A1-8)+(B2-17), (A1-8)+(B2-18), (A1-8)+(B2-19), (A1-8)+(B2-20), (A1-8)+(B2-21), (A1-8)+(B2-22), (A1-8)+(B2-23), (A1-8)+(B2-24), (A1-8)+(B2-25), (A1-8)+(B2-26), (A1-8)+(B2-27), (A1-8)+(B2-28), (A1-8)+(B2-29), (A1-8)+(B3-1), (A1-8)+(B3-2), (A1-8)+(B4-1), (A1-8)+(B4-2), (A1-8)+(B4-3), (A1-8)+(B4-4), (A1-8)+(B4-5), (A1-8)+(B4-6), (A1-8)+(B4-7), (A1-8)+(B4-8), (A1-8)+(B4-9), (A1-8)+(B4-10), (A1-8)+(B4-11), (A1-8)+(B5-1), (A1-8)+(B5-2), (A1-8)+(B5-3), (A1-8)+(B5-4), (A1-8)+(B5-5), (A1-8)+(B6-1), (A1-8)+(B6-2), (A1-8)+(B6-3), (A1-8)+(B6-4), (A1-8)+(B6-5), (A1-8)+(B6-6), (A1-8)+(B7-1), (A1-8)+(B7-2), (A1-8)+(B7-3), (A1-8)+(B7-4), (A1-8)+(B7-5), (A1-8)+(B7-6), (A1-8)+(B7-7)), (A1-8)+(B7-7), (A1-8)+(B7-8), (A1-8)+(B8-1), (A1-8)+(B8-2), (A1-8)+(B8-3), (A1-8)+(B8-4), (A1-8)+

(B8-5), (A1-8)+(B8-6), (A1-8)+(B8-7), (A1-8)+(B9-1), (A1-8)+(B9-2), (A1-8)+(B10-1), (A1-8)+(B10-2), (A1-8)+(B10-3), (A1-8)+(B10-4), (A1-8)+(B10-5), (A1-8)+(B11-1), (A1-8)+(B11-2), (A1-8)+(B11-2), (A1-9)+(B1-1), (A1-9)+(B1-2), (A1-9)+(B1-3), (A1-9)+(B1-4), (A1-9)+(B1-5), (A1-9)+(B1-6), (A1-9)+(B2-1), (A1-9)+(B2-2), (A1-9)+(B2-3), (A1-9)+(B2-4), (A1-9)+(B2-5), (A1-9)+(B2-6), (A1-9)+(B2-7), (A1-9)+(B2-8), (A1-9)+(B2-9), (A1-9)+(B2-10), (A1-9)+(B2-11), (A1-9)+(B2-12), (A1-9)+(B2-13), (A1-9)+(B2-14), (A1-9)+(B2-15), (A1-9)+(B2-16), (A1-9)+(B2-17), (A1-9)+(B2-18), (A1-9)+(B2-19), (A1-9)+(B2-20), (A1-9)+(B2-21), (A1-9)+(B2-22), (A1-9)+(B2-23), (A1-9)+(B2-24), (A1-9)+(B2-25), (A1-9)+(B2-26), (A1-9)+(B2-27), (A1-9)+(B2-28), (A1-9)+(B2-29), (A1-9)+(B3-1), (A1-9)+(B3-2), (A1-9)+(B4-1), (A1-9)+(B4-2), (A1-9)+(B4-3), (A1-9)+(B4-4), (A1-9)+(B4-5), (A1-9)+(B4-6), (A1-9)+(B4-7), (A1-9)+(B4-8), (A1-9)+(B4-9), (A1-9)+(B4-10), (A1-9)+(B4-11), (A1-9)+(B5-1), (A1-9)+(B5-2), (A1-9)+(B5-3), (A1-9)+(B5-4), (A1-9)+(B5-5), (A1-9)+(B6-1), (A1-9)+(B6-2), (A1-9)+(B6-3), (A1-9)+(B6-4), (A1-9)+(B6-5), (A1-9)+(B6-6), (A1-9)+(B7-1), (A1-9)+(B7-2), (A1-9)+(B7-3), (A1-9)+(B7-4), (A1-9)+(B7-5), (A1-9)+(B7-6), (A1-9)+(B7-7)), (A1-9)+(B7-7), (A1-9)+(B7-8), (A1-9)+(B8-1), (A1-9)+(B8-2), (A1-9)+(B8-3), (A1-9)+(B8-4), (A1-9)+(B8-5), (A1-9)+(B8-6), (A1-9)+(B8-7), (A1-9)+(B9-1), (A1-9)+(B9-2), (A1-9)+(B10-1), (A1-9)+(B10-2), (A1-9)+(B10-3), (A1-9)+(B10-4), (A1-9)+(B10-5), (A1-9)+(B11-1), (A1-9)+(B11-2), (A1-9)+(B11-2), (A1-10)+(B1-1), (A1-10)+(B1-2), (A1-10)+(B1-3), (A1-10)+(B1-4), (A1-10)+(B1-5), (A1-10)+(B1-6), (A1-10)+(B2-1), (A1-10)+(B2-2), (A1-10)+(B2-3), (A1-10)+(B2-4), (A1-10)+(B2-5), (A1-10)+(B2-6), (A1-10)+(B2-7), (A1-10)+(B2-8), (A1-10)+(B2-9), (A1-10)+(B2-10), (A1-10)+(B2-11), (A1-10)+(B2-12), (A1-10)+(B2-13), (A1-10)+(B2-14), (A1-10)+(B2-15), (A1-10)+(B2-16), (A1-10)+(B2-17), (A1-10)+(B2-18), (A1-10)+(B2-19), (A1-10)+(B2-20), (A1-10)+(B2-21), (A1-10)+(B2-22), (A1-10)+(B2-23), (A1-10)+(B2-24), (A1-10)+(B2-25), (A1-10)+(B2-26), (A1-10)+(B2-27), (A1-10)+(B2-28), (A1-10)+(B2-29), (A1-10)+(B3-1), (A1-10)+(B3-2), (A1-10)+(B4-1), (A1-10)+(B4-2), (A1-10)+(B4-3), (A1-10)+(B4-4), (A1-10)+(B4-5), (A1-10)+(B4-6), (A1-10)+(B4-7), (A1-10)+(B4-8), (A1-10)+(B4-9), (A1-10)+(B4-10), (A1-10)+(B4-11), (A1-10)+(B5-1), (A1-10)+(B5-2), (A1-10)+(B5-3), (A1-10)+(B5-4), (A1-10)+(B5-5), (A1-10)+(B6-1), (A1-10)+(B6-2), (A1-10)+(B6-3), (A1-10)+(B6-4), (A1-10)+(B6-5), (A1-10)+(B6-6), (A1-10)+(B7-1), (A1-10)+(B7-2), (A1-10)+(B7-3), (A1-10)+(B7-4), (A1-10)+(B7-5), (A1-10)+(B7-6), (A1-10)+(B7-7)), (A1-10)+(B7-7), (A1-10)+(B7-8), (A1-10)+(B8-1), (A1-10)+(B8-2), (A1-10)+(B8-3), (A1-10)+(B8-4), (A1-10)+(B8-5), (A1-10)+(B8-6), (A1-10)+(B8-7), (A1-10)+(B9-1), (A1-10)+(B9-2), (A1-10)+(B10-1), (A1-10)+(B10-2), (A1-10)+(B10-3), (A1-10)+(B10-4), (A1-10)+(B10-5), (A1-10)+(B11-1), (A1-10)+(B11-2), (A1-10)+(B11-2), (A1-11)+(B1-1), (A1-11)+(B1-2), (A1-11)+(B1-3), (A1-11)+(B1-4), (A1-11)+(B1-5), (A1-11)+(B1-6), (A1-11)+(B2-1), (A1-11)+(B2-2), (A1-11)+(B2-3), (A1-11)+(B2-4), (A1-11)+(B2-5), (A1-11)+(B2-6), (A1-11)+(B2-7), (A1-11)+(B2-8), (A1-11)+(B2-9), (A1-11)+(B2-10), (A1-11)+(B2-11), (A1-11)+(B2-12), (A1-11)+(B2-13), (A1-11)+(B2-14), (A1-11)+(B2-15), (A1-11)+(B2-16), (A1-11)+(B2-17), (A1-11)+(B2-18), (A1-11)+(B2-19), (A1-11)+(B2-20), (A1-11)+(B2-21), (A1-11)+(B2-22), (A1-11)+(B2-23), (A1-11)+(B2-24), (A1-11)+(B2-25), (A1-11)+(B2-26), (A1-11)+(B2-27), (A1-11)+(B2-28), (A1-11)+(B2-29), (A1-11)+(B3-1), (A1-11)+(B3-2), (A1-11)+(B4-1), (A1-11)+(B4-2), (A1-11)+(B4-3), (A1-11)+(B4-4), (A1-11)+(B4-5), (A1-11)+(B4-6), (A1-11)+(B4-7), (A1-11)+(B4-8), (A1-11)+(B4-9), (A1-11)+(B4-10), (A1-11)+(B4-11), (A1-11)+(B5-1), (A1-11)+(B5-2), (A1-11)+(B5-3), (A1-11)+(B5-4), (A1-11)+(B5-5), (A1-11)+(B6-1), (A1-11)+(B6-2), (A1-11)+(B6-3), (A1-11)+(B6-4), (A1-11)+(B6-5), (A1-11)+(B6-6), (A1-11)+(B7-1), (A1-11)+(B7-2), (A1-11)+(B7-3), (A1-11)+(B7-4), (A1-11)+(B7-5), (A1-11)+(B7-6), (A1-11)+(B7-7)), (A1-11)+(B7-7), (A1-11)+(B7-8), (A1-11)+(B8-1), (A1-11)+(B8-2), (A1-11)+(B8-3), (A1-11)+(B8-4), (A1-11)+(B8-5), (A1-11)+(B8-6), (A1-11)+(B8-7), (A1-11)+(B9-1), (A1-11)+(B9-2), (A1-11)+(B10-1), (A1-11)+(B10-2), (A1-11)+(B10-3), (A1-11)+(B10-4), (A1-11)+(B10-5), (A1-11)+(B11-1), (A1-11)+(B11-2), (A1-11)+(B11-2), (A1-12)+(B1-1), (A1-12)+(B1-2), (A1-12)+(B1-3), (A1-12)+(B1-4), (A1-12)+(B1-5), (A1-12)+(B1-6), (A1-12)+(B2-1), (A1-12)+(B2-2), (A1-12)+(B2-3), (A1-12)+(B2-4), (A1-12)+(B2-5), (A1-12)+(B2-6), (A1-12)+(B2-7), (A1-12)+(B2-8), (A1-12)+(B2-9), (A1-12)+(B2-10), (A1-12)+(B2-11), (A1-12)+(B2-12), (A1-12)+(B2-13), (A1-12)+(B2-14), (A1-12)+(B2-15), (A1-12)+(B2-16), (A1-12)+(B2-17), (A1-12)+(B2-18), (A1-12)+(B2-19), (A1-12)+(B2-20), (A1-12)+(B2-21), (A1-12)+(B2-22), (A1-12)+(B2-23), (A1-12)+(B2-24), (A1-12)+(B2-25), (A1-12)+(B2-26), (A1-12)+(B2-27), (A1-12)+(B2-28), (A1-12)+(B2-29), (A1-12)+(B3-1), (A1-12)+(B3-2), (A1-12)+(B4-1), (A1-12)+(B4-2), (A1-12)+(B4-3), (A1-12)+(B4-4), (A1-12)+(B4-5), (A1-12)+(B4-6), (A1-12)+(B4-7), (A1-12)+(B4-8), (A1-12)+(B4-9), (A1-12)+(B4-10), (A1-12)+(B4-11), (A1-12)+(B5-1), (A1-12)+(B5-2), (A1-12)+(B5-3), (A1-12)+(B5-4), (A1-12)+(B5-5), (A1-12)+(B6-1), (A1-12)+(B6-2), (A1-12)+(B6-3), (A1-12)+(B6-4), (A1-12)+(B6-5), (A1-12)+(B6-6), (A1-12)+(B7-1), (A1-12)+(B7-2), (A1-12)+(B7-3), (A1-12)+(B7-4), (A1-12)+(B7-5), (A1-12)+(B7-6), (A1-12)+(B7-7)), (A1-12)+(B7-7), (A1-12)+(B7-8), (A1-12)+(B8-1), (A1-12)+(B8-2), (A1-12)+(B8-3), (A1-12)+(B8-4), (A1-12)+(B8-5), (A1-12)+(B8-6), (A1-12)+(B8-7), (A1-12)+(B9-1), (A1-12)+(B9-2), (A1-12)+(B10-1), (A1-12)+(B10-2), (A1-12)+(B10-3), (A1-12)+(B10-4), (A1-12)+(B10-5), (A1-12)+(B11-1), (A1-12)+(B11-2), (A1-12)+(B11-2), (A1-13)+(B1-1), (A1-13)+(B1-2), (A1-13)+(B1-3), (A1-13)+(B1-4), (A1-13)+(B1-5), (A1-13)+(B1-6), (A1-13)+(B2-1), (A1-13)+(B2-2), (A1-13)+(B2-3), (A1-13)+(B2-4), (A1-13)+(B2-5), (A1-13)+(B2-6), (A1-13)+(B2-7), (A1-13)+(B2-8), (A1-13)+(B2-9), (A1-13)+(B2-10), (A1-13)+(B2-11), (A1-13)+(B2-12), (A1-13)+(B2-13), (A1-13)+(B2-14), (A1-13)+(B2-15), (A1-13)+(B2-16), (A1-13)+(B2-17), (A1-13)+(B2-18), (A1-13)+(B2-19), (A1-13)+(B2-20), (A1-13)+(B2-21), (A1-13)+(B2-22), (A1-13)+(B2-23), (A1-13)+(B2-24), (A1-13)+(B2-25), (A1-13)+(B2-26), (A1-13)+(B2-27), (A1-13)+(B2-28), (A1-13)+(B2-29), (A1-13)+(B3-1), (A1-13)+(B3-2), (A1-13)+(B4-1), (A1-13)+(B4-2), (A1-13)+(B4-3), (A1-13)+(B4-4), (A1-13)+(B4-5), (A1-13)+(B4-6), (A1-13)+(B4-7), (A1-13)+(B4-8), (A1-13)+(B4-9), (A1-13)+(B4-10), (A1-13)+(B4-11), (A1-13)+(B5-1), (A1-13)+(B5-2), (A1-13)+(B5-3), (A1-13)+(B5-4), (A1-13)+(B5-5), (A1-13)+(B6-1), (A1-13)+(B6-2), (A1-13)+(B6-3), (A1-13)+(B6-4), (A1-13)+(B6-5), (A1-13)+(B6-6), (A1-13)+(B7-1), (A1-13)+(B7-2), (A1-13)+(B7-3), (A1-13)+(B7-4), (A1-13)+(B7-5), (A1-13)+(B7-6), (A1-13)+(B7-7)), (A1-13)+(B7-7), (A1-13)+(B7-8), (A1-13)+(B8-1), (A1-13)+(B8-2), (A1-13)+(B8-3), (A1-13)+(B8-4), (A1-13)+(B8-5), (A1-13)+(B8-6), (A1-13)+(B8-7), (A1-13)+(B9-1), (A1-13)+(B9-2), (A1-13)+(B10-1), (A1-

13)+(B10-2), (A1-13)+(B10-3), (A1-13)+(B10-4), (A1-13)+(B10-5), (A1-13)+(B11-1), (A1-13)+(B11-2), (A1-13)+(B11-2), (A1-14)+(B1-1), (A1-14)+(B1-2), (A1-14)+(B1-3), (A1-14)+(B1-4), (A1-14)+(B1-5), (A1-14)+(B1-6), (A1-14)+(B2-1), (A1-14)+(B2-2), (A1-14)+(B2-3), (A1-14)+(B2-4), (A1-14)+(B2-5), (A1-14)+(B2-6), (A1-14)+(B2-7), (A1-14)+(B2-8), (A1-14)+(B2-9), (A1-14)+(B2-10), (A1-14)+(B2-11), (A1-14)+(B2-12), (A1-14)+(B2-13), (A1-14)+(B2-14), (A1-14)+(B2-15), (A1-14)+(B2-16), (A1-14)+(B2-17), (A1-14)+(B2-18), (A1-14)+(B2-19), (A1-14)+(B2-20), (A1-14)+(B2-21), (A1-14)+(B2-22), (A1-14)+(B2-23), (A1-14)+(B2-24), (A1-14)+(B2-25), (A1-14)+(B2-26), (A1-14)+(B2-27), (A1-14)+(B2-28), (A1-14)+(B2-29), (A1-14)+(B3-1), (A1-14)+(B3-2), (A1-14)+(B4-1), (A1-14)+(B4-2), (A1-14)+(B4-3), (A1-14)+(B4-4), (A1-14)+(B4-5), (A1-14)+(B4-6), (A1-14)+(B4-7), (A1-14)+(B4-8), (A1-14)+(B4-9), (A1-14)+(B4-10), (A1-14)+(B4-11), (A1-14)+(B5-1), (A1-14)+(B5-2), (A1-14)+(B5-3), (A1-14)+(B5-4), (A1-14)+(B5-5), (A1-14)+(B6-1), (A1-14)+(B6-2), (A1-14)+(B6-3), (A1-14)+(B6-4), (A1-14)+(B6-5), (A1-14)+(B6-6), (A1-14)+(B7-1), (A1-14)+(B7-2), (A1-14)+(B7-3), (A1-14)+(B7-4), (A1-14)+(B7-5), (A1-14)+(B7-6), (A1-14)+(B7-7)), (A1-14)+(B7-7), (A1-14)+(B7-8), (A1-14)+(B8-1), (A1-14)+(B8-2), (A1-14)+(B8-3), (A1-14)+(B8-4), (A1-14)+(B8-5), (A1-14)+(B8-6), (A1-14)+(B8-7), (A1-14)+(B9-1), (A1-14)+(B9-2), (A1-14)+(B10-1), (A1-14)+(B10-2), (A1-14)+(B10-3), (A1-14)+(B10-4), (A1-14)+(B10-5), (A1-14)+(B11-1), (A1-14)+(B11-2), (A1-14)+(B11-2), (A1-15)+(B1-1), (A1-15)+(B1-2), (A1-15)+(B1-3), (A1-15)+(B1-4), (A1-15)+(B1-5), (A1-15)+(B1-6), (A1-15)+(B2-1), (A1-15)+(B2-2), (A1-15)+(B2-3), (A1-15)+(B2-4), (A1-15)+(B2-5), (A1-15)+(B2-6), (A1-15)+(B2-7), (A1-15)+(B2-8), (A1-15)+(B2-9), (A1-15)+(B2-10), (A1-15)+(B2-11), (A1-15)+(B2-12), (A1-15)+(B2-13), (A1-15)+(B2-14), (A1-15)+(B2-15), (A1-15)+(B2-16), (A1-15)+(B2-17), (A1-15)+(B2-18), (A1-15)+(B2-19), (A1-15)+(B2-20), (A1-15)+(B2-21), (A1-15)+(B2-22), (A1-15)+(B2-23), (A1-15)+(B2-24), (A1-15)+(B2-25), (A1-15)+(B2-26), (A1-15)+(B2-27), (A1-15)+(B2-28), (A1-15)+(B2-29), (A1-15)+(B3-1), (A1-15)+(B3-2), (A1-15)+(B4-1), (A1-15)+(B4-2), (A1-15)+(B4-3), (A1-15)+(B4-4), (A1-15)+(B4-5), (A1-15)+(B4-6), (A1-15)+(B4-7), (A1-15)+(B4-8), (A1-15)+(B4-9), (A1-15)+(B4-10), (A1-15)+(B4-11), (A1-15)+(B5-1), (A1-15)+(B5-2), (A1-15)+(B5-3), (A1-15)+(B5-4), (A1-15)+(B5-5), (A1-15)+(B6-1), (A1-15)+(B6-2), (A1-15)+(B6-3), (A1-15)+(B6-4), (A1-15)+(B6-5), (A1-15)+(B6-6), (A1-15)+(B7-1), (A1-15)+(B7-2), (A1-15)+(B7-3), (A1-15)+(B7-4), (A1-15)+(B7-5), (A1-15)+(B7-6), (A1-15)+(B7-7)), (A1-15)+(B7-7), (A1-15)+(B7-8), (A1-15)+(B8-1), (A1-15)+(B8-2), (A1-15)+(B8-3), (A1-15)+(B8-4), (A1-15)+(B8-5), (A1-15)+(B8-6), (A1-15)+(B8-7), (A1-15)+(B9-1), (A1-15)+(B9-2), (A1-15)+(B10-1), (A1-15)+(B10-2), (A1-15)+(B10-3), (A1-15)+(B10-4), (A1-15)+(B10-5), (A1-15)+(B11-1), (A1-15)+(B11-2), (A1-15)+(B11-2), (A1-16)+(B1-1), (A1-16)+(B1-2), (A1-16)+(B1-3), (A1-16)+(B1-4), (A1-16)+(B1-5), (A1-16)+(B1-6), (A1-16)+(B2-1), (A1-16)+(B2-2), (A1-16)+(B2-3), (A1-16)+(B2-4), (A1-16)+(B2-5), (A1-16)+(B2-6), (A1-16)+(B2-7), (A1-16)+(B2-8), (A1-16)+(B2-9), (A1-16)+(B2-10), (A1-16)+(B2-11), (A1-16)+(B2-12), (A1-16)+(B2-13), (A1-16)+(B2-14), (A1-16)+(B2-15), (A1-16)+(B2-16), (A1-16)+(B2-17), (A1-16)+(B2-18), (A1-16)+(B2-19), (A1-16)+(B2-20), (A1-16)+(B2-21), (A1-16)+(B2-22), (A1-16)+(B2-23), (A1-16)+(B2-24), (A1-16)+(B2-25), (A1-16)+(B2-26), (A1-16)+(B2-27), (A1-16)+(B2-28), (A1-16)+(B2-29), (A1-16)+(B3-1), (A1-16)+(B3-2), (A1-16)+(B4-1), (A1-16)+(B4-2), (A1-16)+(B4-3), (A1-16)+(B4-4), (A1-16)+(B4-5), (A1-16)+(B4-6), (A1-16)+(B4-7), (A1-16)+(B4-8), (A1-16)+(B4-9), (A1-16)+(B4-10), (A1-16)+(B4-11), (A1-16)+(B5-1), (A1-16)+(B5-2), (A1-16)+(B5-3), (A1-16)+(B5-4), (A1-16)+(B5-5), (A1-16)+(B6-1), (A1-16)+(B6-2), (A1-16)+(B6-3), (A1-16)+(B6-4), (A1-16)+(B6-5), (A1-16)+(B6-6), (A1-16)+(B7-1), (A1-16)+(B7-2), (A1-16)+(B7-3), (A1-16)+(B7-4), (A1-16)+(B7-5), (A1-16)+(B7-6), (A1-16)+(B7-7)), (A1-16)+(B7-7), (A1-16)+(B7-8), (A1-16)+(B8-1), (A1-16)+(B8-2), (A1-16)+(B8-3), (A1-16)+(B8-4), (A1-16)+(B8-5), (A1-16)+(B8-6), (A1-16)+(B8-7), (A1-16)+(B9-1), (A1-16)+(B9-2), (A1-16)+(B10-1), (A1-16)+(B10-2), (A1-16)+(B10-3), (A1-16)+(B10-4), (A1-16)+(B10-5), (A1-16)+(B11-1), (A1-16)+(B11-2), (A1-16)+(B11-2), (A1-17)+(B1-1), (A1-17)+(B1-2), (A1-17)+(B1-3), (A1-17)+(B1-4), (A1-17)+(B1-5), (A1-17)+(B1-6), (A1-17)+(B2-1), (A1-17)+(B2-2), (A1-17)+(B2-3), (A1-17)+(B2-4), (A1-17)+(B2-5), (A1-17)+(B2-6), (A1-17)+(B2-7), (A1-17)+(B2-8), (A1-17)+(B2-9), (A1-17)+(B2-10), (A1-17)+(B2-11), (A1-17)+(B2-12), (A1-17)+(B2-13), (A1-17)+(B2-14), (A1-17)+(B2-15), (A1-17)+(B2-16), (A1-17)+(B2-17), (A1-17)+(B2-18), (A1-17)+(B2-19), (A1-17)+(B2-20), (A1-17)+(B2-21), (A1-17)+(B2-22), (A1-17)+(B2-23), (A1-17)+(B2-24), (A1-17)+(B2-25), (A1-17)+(B2-26), (A1-17)+(B2-27), (A1-17)+(B2-28), (A1-17)+(B2-29), (A1-17)+(B3-1), (A1-17)+(B3-2), (A1-17)+(B4-1), (A1-17)+(B4-2), (A1-17)+(B4-3), (A1-17)+(B4-4), (A1-17)+(B4-5), (A1-17)+(B4-6), (A1-17)+(B4-7), (A1-17)+(B4-8), (A1-17)+(B4-9), (A1-17)+(B4-10), (A1-17)+(B4-11), (A1-17)+(B5-1), (A1-17)+(B5-2), (A1-17)+(B5-3), (A1-17)+(B5-4), (A1-17)+(B5-5), (A1-17)+(B6-1), (A1-17)+(B6-2), (A1-17)+(B6-3), (A1-17)+(B6-4), (A1-17)+(B6-5), (A1-17)+(B6-6), (A1-17)+(B7-1), (A1-17)+(B7-2), (A1-17)+(B7-3), (A1-17)+(B7-4), (A1-17)+(B7-5), (A1-17)+(B7-6), (A1-17)+(B7-7)), (A1-17)+(B7-7), (A1-17)+(B7-8), (A1-17)+(B8-1), (A1-17)+(B8-2), (A1-17)+(B8-3), (A1-17)+(B8-4), (A1-17)+(B8-5), (A1-17)+(B8-6), (A1-17)+(B8-7), (A1-17)+(B9-1), (A1-17)+(B9-2), (A1-17)+(B10-1), (A1-17)+(B10-2), (A1-17)+(B10-3), (A1-17)+(B10-4), (A1-17)+(B10-5), (A1-17)+(B11-1), (A1-17)+(B11-2), (A1-17)+(B11-2), (A1-18)+(B1-1), (A1-18)+(B1-2), (A1-18)+(B1-3), (A1-18)+(B1-4), (A1-18)+(B1-5), (A1-18)+(B1-6), (A1-18)+(B2-1), (A1-18)+(B2-2), (A1-18)+(B2-3), (A1-18)+(B2-4), (A1-18)+(B2-5), (A1-18)+(B2-6), (A1-18)+(B2-7), (A1-18)+(B2-8), (A1-18)+(B2-9), (A1-18)+(B2-10), (A1-18)+(B2-11), (A1-18)+(B2-12), (A1-18)+(B2-13), (A1-18)+(B2-14), (A1-18)+(B2-15), (A1-18)+(B2-16), (A1-18)+(B2-17), (A1-18)+(B2-18), (A1-18)+(B2-19), (A1-18)+(B2-20), (A1-18)+(B2-21), (A1-18)+(B2-22), (A1-18)+(B2-23), (A1-18)+(B2-24), (A1-18)+(B2-25), (A1-18)+(B2-26), (A1-18)+(B2-27), (A1-18)+(B2-28), (A1-18)+(B2-29), (A1-18)+(B3-1), (A1-18)+(B3-2), (A1-18)+(B4-1), (A1-18)+(B4-2), (A1-18)+(B4-3), (A1-18)+(B4-4), (A1-18)+(B4-5), (A1-18)+(B4-6), (A1-18)+(B4-7), (A1-18)+(B4-8), (A1-18)+(B4-9), (A1-18)+(B4-10), (A1-18)+(B4-11), (A1-18)+(B5-1), (A1-18)+(B5-2), (A1-18)+(B5-3), (A1-18)+(B5-4), (A1-18)+(B5-5), (A1-18)+(B6-1), (A1-18)+(B6-2), (A1-18)+(B6-3), (A1-18)+(B6-4), (A1-18)+(B6-5), (A1-18)+(B6-6), (A1-18)+(B7-1), (A1-18)+(B7-2), (A1-18)+(B7-3), (A1-18)+(B7-4), (A1-18)+(B7-5), (A1-18)+(B7-6), (A1-18)+(B7-7)), (A1-18)+(B7-7), (A1-18)+(B7-8), (A1-18)+(B8-1), (A1-18)+(B8-2), (A1-18)+(B8-3), (A1-18)+(B8-4), (A1-18)+(B8-5), (A1-18)+(B8-6), (A1-18)+(B8-7), (A1-18)+(B9-1), (A1-18)+(B9-2), (A1-18)+(B10-1), (A1-18)+(B10-2), (A1-18)+(B10-3), (A1-18)+(B10-4), (A1-18)+(B10-5), (A1-18)+(B11-1), (A1-18)+(B11-2), (A1-18)+(B11-2), (A1-19)+(B1-1), (A1-19)+(B1-2), (A1-19)+(B1-3), (A1-19)+(B1-4), (A1-19)+(B1-5), (A1-19)+(B1-6), (A1-19)+(B2-1), (A1-19)+(B2-2), (A1-19)+(B2-3), (A1-19)+(B2-4), (A1-19)+(B2-5), (A1-19)+(B2-6), (A1-19)+(B2-7), (A1-19)+(B2-8), (A1-19)+(B2-9), (A1-19)+(B2-10), (A1-19)+(B2-11), (A1-19)+(B2-12), (A1-19)+(B2-13), (A1-19)+(B2-14), (A1-19)+(B2-15), (A1-19)+(B2-16), (A1-19)+(B2-17), (A1-19)+(B2-18), (A1-19)+(B2-19), (A1-19)+(B2-20), (A1-19)+(B2-21), (A1-19)+(B2-22), (A1-19)+(B2-23), (A1-19)+(B2-24), (A1-19)+(B2-25), (A1-19)+(B2-26), (A1-19)+(B2-27), (A1-19)+(B2-28), (A1-19)+(B2-29), (A1-19)+(B3-1), (A1-19)+(B3-2), (A1-19)+(B4-1), (A1-19)+(B4-2), (A1-19)+(B4-3), (A1-19)+(B4-4), (A1-19)+(B4-5), (A1-19)+(B4-6), (A1-19)+(B4-7), (A1-19)+(B4-8), (A1-19)+(B4-9), (A1-19)+(B4-10), (A1-19)+(B4-11), (A1-19)+(B5-1), (A1-19)+(B5-2), (A1-19)+(B5-3), (A1-19)+(B5-4), (A1-19)+(B5-5), (A1-19)+(B6-1), (A1-19)+(B6-2), (A1-19)+(B6-3), (A1-19)+(B6-4), (A1-19)+(B6-5), (A1-19)+(B6-6), (A1-19)+(B7-1), (A1-19)+(B7-2), (A1-19)+(B7-3), (A1-19)+(B7-4), (A1-19)+(B7-5), (A1-19)+(B7-6), (A1-19)+(B7-7)), (A1-19)+(B7-7), (A1-19)+(B7-8), (A1-19)+(B8-1), (A1-19)+(B8-2), (A1-19)+(B8-3), (A1-19)+(B8-4), (A1-19)+(B8-5), (A1-19)+(B8-6), (A1-19)+(B8-7), (A1-19)+(B9-1), (A1-19)+(B9-2), (A1-19)+(B10-1), (A1-19)+(B10-2), (A1-19)+(B10-3), (A1-19)+(B10-4), (A1-19)+(B10-5), (A1-19)+(B11-1), (A1-19)+(B11-2), (A1-19)+(B11-2), (A1-20)+(B1-1), (A1-20)+(B1-2), (A1-20)+(B1-3), (A1-20)+(B1-4), (A1-20)+(B1-5), (A1-20)+(B1-6), (A1-20)+(B2-1), (A1-20)+(B2-2), (A1-20)+(B2-3), (A1-20)+(B2-4), (A1-20)+(B2-5), (A1-20)+(B2-6), (A1-20)+(B2-7), (A1-20)+(B2-8), (A1-20)+(B2-9), (A1-20)+(B2-10), (A1-20)+(B2-11), (A1-20)+(B2-12), (A1-20)+(B2-13), (A1-20)+(B2-14), (A1-20)+(B2-15), (A1-20)+(B2-16), (A1-20)+(B2-17), (A1-20)+(B2-18), (A1-20)+(B2-19), (A1-20)+(B2-20), (A1-20)+(B2-21), (A1-20)+(B2-22), (A1-20)+(B2-23), (A1-20)+(B2-24), (A1-20)+(B2-25), (A1-20)+(B2-26), (A1-20)+(B2-27), (A1-20)+(B2-28), (A1-20)+(B2-29), (A1-20)+(B3-1), (A1-20)+(B3-2), (A1-20)+(B4-1), (A1-20)+(B4-2), (A1-20)+(B4-3), (A1-20)+(B4-4), (A1-20)+(B4-5), (A1-20)+(B4-6), (A1-20)+(B4-7), (A1-20)+(B4-8), (A1-20)+(B4-9), (A1-20)+(B4-10), (A1-20)+(B4-11), (A1-20)+(B5-1), (A1-20)+(B5-2), (A1-20)+(B5-3), (A1-20)+(B5-4), (A1-20)+(B5-5), (A1-20)+(B6-1), (A1-20)+(B6-2), (A1-20)+(B6-3), (A1-20)+(B6-4), (A1-20)+(B6-5), (A1-20)+(B6-6), (A1-20)+(B7-1), (A1-20)+(B7-2), (A1-20)+(B7-3), (A1-20)+(B7-4), (A1-20)+(B7-5), (A1-20)+(B7-6), (A1-20)+(B7-7)), (A1-20)+(B7-7), (A1-20)+(B7-8), (A1-20)+(B8-1), (A1-20)+(B8-2), (A1-20)+(B8-3), (A1-20)+(B8-4), (A1-20)+(B8-5), (A1-20)+(B8-6), (A1-20)+(B8-7), (A1-20)+(B9-1), (A1-20)+(B9-2), (A1-20)+(B10-1), (A1-20)+(B10-2), (A1-20)+(B10-3), (A1-20)+(B10-4), (A1-20)+(B10-5), (A1-20)+(B11-1), (A1-20)+(B11-2), (A1-20)+(B11-2), (A1-21)+(B1-1), (A1-21)+(B1-2), (A1-21)+(B1-3), (A1-21)+(B1-4), (A1-21)+(B1-5), (A1-21)+(B1-6), (A1-21)+(B2-1), (A1-21)+(B2-2), (A1-21)+(B2-3), (A1-21)+(B2-4), (A1-21)+(B2-5), (A1-21)+(B2-6), (A1-21)+(B2-7), (A1-21)+(B2-8), (A1-21)+(B2-9), (A1-21)+(B2-10), (A1-21)+(B2-11), (A1-21)+(B2-12), (A1-21)+(B2-13), (A1-21)+(B2-14), (A1-21)+(B2-15), (A1-21)+(B2-16), (A1-21)+(B2-17), (A1-21)+(B2-18), (A1-21)+(B2-19), (A1-21)+(B2-20), (A1-21)+(B2-21), (A1-21)+(B2-22), (A1-21)+(B2-23), (A1-21)+(B2-24), (A1-21)+(B2-25), (A1-21)+(B2-26), (A1-21)+(B2-27), (A1-21)+(B2-28), (A1-21)+(B2-29), (A1-21)+(B3-1), (A1-21)+(B3-2), (A1-21)+(B4-1), (A1-21)+(B4-2), (A1-21)+(B4-3), (A1-21)+(B4-4), (A1-21)+(B4-5), (A1-21)+(B4-6), (A1-21)+(B4-7), (A1-21)+(B4-8), (A1-21)+(B4-9), (A1-21)+(B4-10), (A1-21)+(B4-11), (A1-21)+(B5-1), (A1-21)+(B5-2), (A1-21)+(B5-3), (A1-21)+(B5-4), (A1-21)+(B5-5), (A1-21)+(B6-1), (A1-21)+(B6-2), (A1-21)+(B6-3), (A1-21)+(B6-4), (A1-21)+(B6-5), (A1-21)+(B6-6), (A1-21)+(B7-1), (A1-21)+(B7-2), (A1-21)+(B7-3), (A1-21)+(B7-4), (A1-21)+(B7-5), (A1-21)+(B7-6), (A1-21)+(B7-7)), (A1-21)+(B7-7), (A1-21)+(B7-8), (A1-21)+(B8-1), (A1-21)+(B8-2), (A1-21)+(B8-3), (A1-21)+(B8-4), (A1-21)+(B8-5), (A1-21)+(B8-6), (A1-21)+(B8-7), (A1-21)+(B9-1), (A1-21)+(B9-2), (A1-21)+(B10-1), (A1-21)+(B10-2), (A1-21)+(B10-3), (A1-21)+(B10-4), (A1-21)+(B10-5), (A1-21)+(B11-1), (A1-21)+(B11-2), (A1-21)+(B11-2), (A1-22)+(B1-1), (A1-22)+(B1-2), (A1-22)+(B1-3), (A1-22)+(B1-4), (A1-22)+(B1-5), (A1-22)+(B1-6), (A1-22)+(B2-1), (A1-22)+(B2-2), (A1-22)+(B2-3), (A1-22)+(B2-4), (A1-22)+(B2-5), (A1-22)+(B2-6), (A1-22)+(B2-7), (A1-22)+(B2-8), (A1-22)+(B2-9), (A1-22)+(B2-10), (A1-22)+(B2-11), (A1-22)+(B2-12), (A1-22)+(B2-13), (A1-22)+(B2-14), (A1-22)+(B2-15), (A1-22)+(B2-16), (A1-22)+(B2-17), (A1-22)+(B2-18), (A1-22)+(B2-19), (A1-22)+(B2-20), (A1-22)+(B2-21), (A1-22)+(B2-22), (A1-22)+(B2-23), (A1-22)+(B2-24), (A1-22)+(B2-25), (A1-22)+(B2-26), (A1-22)+(B2-27), (A1-22)+(B2-28), (A1-22)+(B2-29), (A1-22)+(B3-1), (A1-22)+(B3-2), (A1-22)+(B4-1), (A1-22)+(B4-2), (A1-22)+(B4-3), (A1-22)+(B4-4), (A1-22)+(B4-5), (A1-22)+(B4-6), (A1-22)+(B4-7), (A1-22)+(B4-8), (A1-22)+(B4-9), (A1-22)+(B4-10), (A1-22)+(B4-11), (A1-22)+(B5-1), (A1-22)+(B5-2), (A1-22)+(B5-3), (A1-22)+(B5-4), (A1-22)+(B5-5), (A1-22)+(B6-1), (A1-22)+(B6-2), (A1-22)+(B6-3), (A1-22)+(B6-4), (A1-22)+(B6-5), (A1-22)+(B6-6), (A1-22)+(B7-1), (A1-22)+(B7-2), (A1-22)+(B7-3), (A1-22)+(B7-4), (A1-22)+(B7-5), (A1-22)+(B7-6), (A1-22)+(B7-7)), (A1-22)+(B7-7), (A1-22)+(B7-8), (A1-22)+(B8-1), (A1-22)+(B8-2), (A1-22)+(B8-3), (A1-22)+(B8-4), (A1-22)+(B8-5), (A1-22)+(B8-6), (A1-22)+(B8-7), (A1-22)+(B9-1), (A1-22)+(B9-2), (A1-22)+(B10-1), (A1-22)+(B10-2), (A1-22)+(B10-3), (A1-22)+(B10-4), (A1-22)+(B10-5), (A1-22)+(B11-1), (A1-22)+(B11-2), (A1-22)+(B11-2), (A1-23)+(B1-1), (A1-23)+(B1-2), (A1-23)+(B1-3), (A1-23)+(B1-4), (A1-23)+(B1-5), (A1-23)+(B1-6), (A1-23)+(B2-1), (A1-23)+(B2-2), (A1-23)+(B2-3), (A1-23)+(B2-4), (A1-23)+(B2-5), (A1-23)+(B2-6), (A1-23)+(B2-7), (A1-23)+(B2-8), (A1-23)+(B2-9), (A1-23)+(B2-10), (A1-23)+(B2-11), (A1-23)+(B2-12), (A1-23)+(B2-13), (A1-23)+(B2-14), (A1-23)+(B2-15), (A1-23)+(B2-16), (A1-23)+(B2-17), (A1-23)+(B2-18), (A1-23)+(B2-19), (A1-23)+(B2-20), (A1-23)+(B2-21), (A1-23)+(B2-22), (A1-23)+(B2-23), (A1-23)+(B2-24), (A1-23)+(B2-25), (A1-23)+(B2-26), (A1-23)+(B2-27), (A1-23)+(B2-28), (A1-23)+(B2-29), (A1-23)+(B3-1), (A1-23)+(B3-2), (A1-23)+(B4-1), (A1-23)+(B4-2), (A1-23)+(B4-3), (A1-23)+(B4-4), (A1-23)+(B4-5), (A1-23)+(B4-6), (A1-23)+(B4-7), (A1-23)+(B4-8), (A1-23)+(B4-9), (A1-23)+(B4-10), (A1-23)+(B4-11), (A1-23)+(B5-1), (A1-23)+(B5-2), (A1-23)+(B5-3), (A1-23)+(B5-4), (A1-23)+(B5-5), (A1-23)+(B6-1), (A1-23)+(B6-2), (A1-23)+(B6-3), (A1-23)+(B6-4), (A1-23)+(B6-5), (A1-23)+(B6-6), (A1-23)+(B7-1), (A1-23)+(B7-2), (A1-23)+(B7-3), (A1-23)+(B7-4), (A1-23)+(B7-5), (A1-23)+(B7-6), (A1-23)+(B7-7)), (A1-23)+(B7-7), (A1-23)+(B7-8), (A1-23)+(B8-1), (A1-23)+(B8-2), (A1-23)+(B8-3), (A1-23)+

(B8-4), (A1-23)+(B8-5), (A1-23)+(B8-6), (A1-23)+(B8-7), (A1-23)+(B9-1), (A1-23)+(B9-2), (A1-23)+(B10-1), (A1-23)+(B10-2), (A1-23)+(B10-3), (A1-23)+(B10-4), (A1-23)+(B10-5), (A1-23)+(B11-1), (A1-23)+(B11-2), (A1-23)+(B11-2), (A1-24)+(B1-1), (A1-24)+(B1-2), (A1-24)+(B1-3), (A1-24)+(B1-4), (A1-24)+(B1-5), (A1-24)+(B1-6), (A1-24)+(B2-1), (A1-24)+(B2-2), (A1-24)+(B2-3), (A1-24)+(B2-4), (A1-24)+(B2-5), (A1-24)+(B2-6), (A1-24)+(B2-7), (A1-24)+(B2-8), (A1-24)+(B2-9), (A1-24)+(B2-10), (A1-24)+(B2-11), (A1-24)+(B2-12), (A1-24)+(B2-13), (A1-24)+(B2-14), (A1-24)+(B2-15), (A1-24)+(B2-16), (A1-24)+(B2-17), (A1-24)+(B2-18), (A1-24)+(B2-19), (A1-24)+(B2-20), (A1-24)+(B2-21), (A1-24)+(B2-22), (A1-24)+(B2-23), (A1-24)+(B2-24), (A1-24)+(B2-25), (A1-24)+(B2-26), (A1-24)+(B2-27), (A1-24)+(B2-28), (A1-24)+(B2-29), (A1-24)+(B3-1), (A1-24)+(B3-2), (A1-24)+(B4-1), (A1-24)+(B4-2), (A1-24)+(B4-3), (A1-24)+(B4-4), (A1-24)+(B4-5), (A1-24)+(B4-6), (A1-24)+(B4-7), (A1-24)+(B4-8), (A1-24)+(B4-9), (A1-24)+(B4-10), (A1-24)+(B4-11), (A1-24)+(B5-1), (A1-24)+(B5-2), (A1-24)+(B5-3), (A1-24)+(B5-4), (A1-24)+(B5-5), (A1-24)+(B6-1), (A1-24)+(B6-2), (A1-24)+(B6-3), (A1-24)+(B6-4), (A1-24)+(B6-5), (A1-24)+(B6-6), (A1-24)+(B7-1), (A1-24)+(B7-2), (A1-24)+(B7-3), (A1-24)+(B7-4), (A1-24)+(B7-5), (A1-24)+(B7-6), (A1-24)+(B7-7)), (A1-24)+(B7-7), (A1-24)+(B7-8), (A1-24)+(B8-1), (A1-24)+(B8-2), (A1-24)+(B8-3), (A1-24)+(B8-4), (A1-24)+(B8-5), (A1-24)+(B8-6), (A1-24)+(B8-7), (A1-24)+(B9-1), (A1-24)+(B9-2), (A1-24)+(B10-1), (A1-24)+(B10-2), (A1-24)+(B10-3), (A1-24)+(B10-4), (A1-24)+(B10-5), (A1-24)+(B11-1), (A1-24)+(B11-2), (A1-24)+(B11-2), (A1-25)+(B1-1), (A1-25)+(B1-2), (A1-25)+(B1-3), (A1-25)+(B1-4), (A1-25)+(B1-5), (A1-25)+(B1-6), (A1-25)+(B2-1), (A1-25)+(B2-2), (A1-25)+(B2-3), (A1-25)+(B2-4), (A1-25)+(B2-5), (A1-25)+(B2-6), (A1-25)+(B2-7), (A1-25)+(B2-8), (A1-25)+(B2-9), (A1-25)+(B2-10), (A1-25)+(B2-11), (A1-25)+(B2-12), (A1-25)+(B2-13), (A1-25)+(B2-14), (A1-25)+(B2-15), (A1-25)+(B2-16), (A1-25)+(B2-17), (A1-25)+(B2-18), (A1-25)+(B2-19), (A1-25)+(B2-20), (A1-25)+(B2-21), (A1-25)+(B2-22), (A1-25)+(B2-23), (A1-25)+(B2-24), (A1-25)+(B2-25), (A1-25)+(B2-26), (A1-25)+(B2-27), (A1-25)+(B2-28), (A1-25)+(B2-29), (A1-25)+(B3-1), (A1-25)+(B3-2), (A1-25)+(B4-1), (A1-25)+(B4-2), (A1-25)+(B4-3), (A1-25)+(B4-4), (A1-25)+(B4-5), (A1-25)+(B4-6), (A1-25)+(B4-7), (A1-25)+(B4-8), (A1-25)+(B4-9), (A1-25)+(B4-10), (A1-25)+(B4-11), (A1-25)+(B5-1), (A1-25)+(B5-2), (A1-25)+(B5-3), (A1-25)+(B5-4), (A1-25)+(B5-5), (A1-25)+(B6-1), (A1-25)+(B6-2), (A1-25)+(B6-3), (A1-25)+(B6-4), (A1-25)+(B6-5), (A1-25)+(B6-6), (A1-25)+(B7-1), (A1-25)+(B7-2), (A1-25)+(B7-3), (A1-25)+(B7-4), (A1-25)+(B7-5), (A1-25)+(B7-6), (A1-25)+(B7-7)), (A1-25)+(B7-7), (A1-25)+(B7-8), (A1-25)+(B8-1), (A1-25)+(B8-2), (A1-25)+(B8-3), (A1-25)+(B8-4), (A1-25)+(B8-5), (A1-25)+(B8-6), (A1-25)+(B8-7), (A1-25)+(B9-1), (A1-25)+(B9-2), (A1-25)+(B10-1), (A1-25)+(B10-2), (A1-25)+(B10-3), (A1-25)+(B10-4), (A1-25)+(B10-5), (A1-25)+(B11-1), (A1-25)+(B11-2), (A1-25)+(B11-2), (A1-26)+(B1-1), (A1-26)+(B1-2), (A1-26)+(B1-3), (A1-26)+(B1-4), (A1-26)+(B1-5), (A1-26)+(B1-6), (A1-26)+(B2-1), (A1-26)+(B2-2), (A1-26)+(B2-3), (A1-26)+(B2-4), (A1-26)+(B2-5), (A1-26)+(B2-6), (A1-26)+(B2-7), (A1-26)+(B2-8), (A1-26)+(B2-9), (A1-26)+(B2-10), (A1-26)+(B2-11), (A1-26)+(B2-12), (A1-26)+(B2-13), (A1-26)+(B2-14), (A1-26)+(B2-15), (A1-26)+(B2-16), (A1-26)+(B2-17), (A1-26)+(B2-18), (A1-26)+(B2-19), (A1-26)+(B2-20), (A1-26)+(B2-21), (A1-26)+(B2-22), (A1-26)+(B2-23), (A1-26)+(B2-24), (A1-26)+(B2-25), (A1-26)+(B2-26), (A1-26)+(B2-27), (A1-26)+(B2-28), (A1-26)+(B2-29), (A1-26)+(B3-1), (A1-26)+(B3-2), (A1-26)+(B4-1), (A1-26)+(B4-2), (A1-26)+(B4-3), (A1-26)+(B4-4), (A1-26)+(B4-5), (A1-26)+(B4-6), (A1-26)+(B4-7), (A1-26)+(B4-8), (A1-26)+(B4-9), (A1-26)+(B4-10), (A1-26)+(B4-11), (A1-26)+(B5-1), (A1-26)+(B5-2), (A1-26)+(B5-3), (A1-26)+(B5-4), (A1-26)+(B5-5), (A1-26)+(B6-1), (A1-26)+(B6-2), (A1-26)+(B6-3), (A1-26)+(B6-4), (A1-26)+(B6-5), (A1-26)+(B6-6), (A1-26)+(B7-1), (A1-26)+(B7-2), (A1-26)+(B7-3), (A1-26)+(B7-4), (A1-26)+(B7-5), (A1-26)+(B7-6), (A1-26)+(B7-7)), (A1-26)+(B7-7), (A1-26)+(B7-8), (A1-26)+(B8-1), (A1-26)+(B8-2), (A1-26)+(B8-3), (A1-26)+(B8-4), (A1-26)+(B8-5), (A1-26)+(B8-6), (A1-26)+(B8-7), (A1-26)+(B9-1), (A1-26)+(B9-2), (A1-26)+(B10-1), (A1-26)+(B10-2), (A1-26)+(B10-3), (A1-26)+(B10-4), (A1-26)+(B10-5), (A1-26)+(B11-1), (A1-26)+(B11-2), (A1-26)+(B11-2), (A1-27)+(B1-1), (A1-27)+(B1-2), (A1-27)+(B1-3), (A1-27)+(B1-4), (A1-27)+(B1-5), (A1-27)+(B1-6), (A1-27)+(B2-1), (A1-27)+(B2-2), (A1-27)+(B2-3), (A1-27)+(B2-4), (A1-27)+(B2-5), (A1-27)+(B2-6), (A1-27)+(B2-7), (A1-27)+(B2-8), (A1-27)+(B2-9), (A1-27)+(B2-10), (A1-27)+(B2-11), (A1-27)+(B2-12), (A1-27)+(B2-13), (A1-27)+(B2-14), (A1-27)+(B2-15), (A1-27)+(B2-16), (A1-27)+(B2-17), (A1-27)+(B2-18), (A1-27)+(B2-19), (A1-27)+(B2-20), (A1-27)+(B2-21), (A1-27)+(B2-22), (A1-27)+(B2-23), (A1-27)+(B2-24), (A1-27)+(B2-25), (A1-27)+(B2-26), (A1-27)+(B2-27), (A1-27)+(B2-28), (A1-27)+(B2-29), (A1-27)+(B3-1), (A1-27)+(B3-2), (A1-27)+(B4-1), (A1-27)+(B4-2), (A1-27)+(B4-3), (A1-27)+(B4-4), (A1-27)+(B4-5), (A1-27)+(B4-6), (A1-27)+(B4-7), (A1-27)+(B4-8), (A1-27)+(B4-9), (A1-27)+(B4-10), (A1-27)+(B4-11), (A1-27)+(B5-1), (A1-27)+(B5-2), (A1-27)+(B5-3), (A1-27)+(B5-4), (A1-27)+(B5-5), (A1-27)+(B6-1), (A1-27)+(B6-2), (A1-27)+(B6-3), (A1-27)+(B6-4), (A1-27)+(B6-5), (A1-27)+(B6-6), (A1-27)+(B7-1), (A1-27)+(B7-2), (A1-27)+(B7-3), (A1-27)+(B7-4), (A1-27)+(B7-5), (A1-27)+(B7-6), (A1-27)+(B7-7)), (A1-27)+(B7-7), (A1-27)+(B7-8), (A1-27)+(B8-1), (A1-27)+(B8-2), (A1-27)+(B8-3), (A1-27)+(B8-4), (A1-27)+(B8-5), (A1-27)+(B8-6), (A1-27)+(B8-7), (A1-27)+(B9-1), (A1-27)+(B9-2), (A1-27)+(B10-1), (A1-27)+(B10-2), (A1-27)+(B10-3), (A1-27)+(B10-4), (A1-27)+(B10-5), (A1-27)+(B11-1), (A1-27)+(B11-2), (A1-27)+(B11-2), (A1-28)+(B1-1), (A1-28)+(B1-2), (A1-28)+(B1-3), (A1-28)+(B1-4), (A1-28)+(B1-5), (A1-28)+(B1-6), (A1-28)+(B2-1), (A1-28)+(B2-2), (A1-28)+(B2-3), (A1-28)+(B2-4), (A1-28)+(B2-5), (A1-28)+(B2-6), (A1-28)+(B2-7), (A1-28)+(B2-8), (A1-28)+(B2-9), (A1-28)+(B2-10), (A1-28)+(B2-11), (A1-28)+(B2-12), (A1-28)+(B2-13), (A1-28)+(B2-14), (A1-28)+(B2-15), (A1-28)+(B2-16), (A1-28)+(B2-17), (A1-28)+(B2-18), (A1-28)+(B2-19), (A1-28)+(B2-20), (A1-28)+(B2-21), (A1-28)+(B2-22), (A1-28)+(B2-23), (A1-28)+(B2-24), (A1-28)+(B2-25), (A1-28)+(B2-26), (A1-28)+(B2-27), (A1-28)+(B2-28), (A1-28)+(B2-29), (A1-28)+(B3-1), (A1-28)+(B3-2), (A1-28)+(B4-1), (A1-28)+(B4-2), (A1-28)+(B4-3), (A1-28)+(B4-4), (A1-28)+(B4-5), (A1-28)+(B4-6), (A1-28)+(B4-7), (A1-28)+(B4-8), (A1-28)+(B4-9), (A1-28)+(B4-10), (A1-28)+(B4-11), (A1-28)+(B5-1), (A1-28)+(B5-2), (A1-28)+(B5-3), (A1-28)+(B5-4), (A1-28)+(B5-5), (A1-28)+(B6-1), (A1-28)+(B6-2), (A1-28)+(B6-3), (A1-28)+(B6-4), (A1-28)+(B6-5), (A1-28)+(B6-6), (A1-28)+(B7-1), (A1-28)+(B7-2), (A1-28)+(B7-3), (A1-28)+(B7-4), (A1-28)+(B7-5), (A1-28)+(B7-6), (A1-28)+(B7-7)), (A1-28)+(B7-7), (A1-28)+(B7-8), (A1-

28)+(B8-1), (A1-28)+(B8-2), (A1-28)+(B8-3), (A1-28)+(B8-4), (A1-28)+(B8-5), (A1-28)+(B8-6), (A1-28)+(B8-7), (A1-28)+(B9-1), (A1-28)+(B9-2), (A1-28)+(B10-1), (A1-28)+(B10-2), (A1-28)+(B10-3), (A1-28)+(B10-4), (A1-28)+(B10-5), (A1-28)+(B11-1), (A1-28)+(B11-2), (A1-28)+(B11-2), (A1-29)+(B1-1), (A1-29)+(B1-2), (A1-29)+(B1-3), (A1-29)+(B1-4), (A1-29)+(B1-5), (A1-29)+(B1-6), (A1-29)+(B2-1), (A1-29)+(B2-2), (A1-29)+(B2-3), (A1-29)+(B2-4), (A1-29)+(B2-5), (A1-29)+(B2-6), (A1-29)+(B2-7), (A1-29)+(B2-8), (A1-29)+(B2-9), (A1-29)+(B2-10), (A1-29)+(B2-11), (A1-29)+(B2-12), (A1-29)+(B2-13), (A1-29)+(B2-14), (A1-29)+(B2-15), (A1-29)+(B2-16), (A1-29)+(B2-17), (A1-29)+(B2-18), (A1-29)+(B2-19), (A1-29)+(B2-20), (A1-29)+(B2-21), (A1-29)+(B2-22), (A1-29)+(B2-23), (A1-29)+(B2-24), (A1-29)+(B2-25), (A1-29)+(B2-26), (A1-29)+(B2-27), (A1-29)+(B2-28), (A1-29)+(B2-29), (A1-29)+(B3-1), (A1-29)+(B3-2), (A1-29)+(B4-1), (A1-29)+(B4-2), (A1-29)+(B4-3), (A1-29)+(B4-4), (A1-29)+(B4-5), (A1-29)+(B4-6), (A1-29)+(B4-7), (A1-29)+(B4-8), (A1-29)+(B4-9), (A1-29)+(B4-10), (A1-29)+(B4-11), (A1-29)+(B5-1), (A1-29)+(B5-2), (A1-29)+(B5-3), (A1-29)+(B5-4), (A1-29)+(B5-5), (A1-29)+(B6-1), (A1-29)+(B6-2), (A1-29)+(B6-3), (A1-29)+(B6-4), (A1-29)+(B6-5), (A1-29)+(B6-6), (A1-29)+(B7-1), (A1-29)+(B7-2), (A1-29)+(B7-3), (A1-29)+(B7-4), (A1-29)+(B7-5), (A1-29)+(B7-6), (A1-29)+(B7-7)), (A1-29)+(B7-7), (A1-29)+(B7-8), (A1-29)+(B8-1), (A1-29)+(B8-2), (A1-29)+(B8-3), (A1-29)+(B8-4), (A1-29)+(B8-5), (A1-29)+(B8-6), (A1-29)+(B8-7), (A1-29)+(B9-1), (A1-29)+(B9-2), (A1-29)+(B10-1), (A1-29)+(B10-2), (A1-29)+(B10-3), (A1-29)+(B10-4), (A1-29)+(B10-5), (A1-29)+(B11-1), (A1-29)+(B11-2), (A1-29)+(B11-2), (A1-30)+(B1-1), (A1-30)+(B1-2), (A1-30)+(B1-3), (A1-30)+(B1-4), (A1-30)+(B1-5), (A1-30)+(B1-6), (A1-30)+(B2-1), (A1-30)+(B2-2), (A1-30)+(B2-3), (A1-30)+(B2-4), (A1-30)+(B2-5), (A1-30)+(B2-6), (A1-30)+(B2-7), (A1-30)+(B2-8), (A1-30)+(B2-9), (A1-30)+(B2-10), (A1-30)+(B2-11), (A1-30)+(B2-12), (A1-30)+(B2-13), (A1-30)+(B2-14), (A1-30)+(B2-15), (A1-30)+(B2-16), (A1-30)+(B2-17), (A1-30)+(B2-18), (A1-30)+(B2-19), (A1-30)+(B2-20), (A1-30)+(B2-21), (A1-30)+(B2-22), (A1-30)+(B2-23), (A1-30)+(B2-24), (A1-30)+(B2-25), (A1-30)+(B2-26), (A1-30)+(B2-27), (A1-30)+(B2-28), (A1-30)+(B2-29), (A1-30)+(B3-1), (A1-30)+(B3-2), (A1-30)+(B4-1), (A1-30)+(B4-2), (A1-30)+(B4-3), (A1-30)+(B4-4), (A1-30)+(B4-5), (A1-30)+(B4-6), (A1-30)+(B4-7), (A1-30)+(B4-8), (A1-30)+(B4-9), (A1-30)+(B4-10), (A1-30)+(B4-11), (A1-30)+(B5-1), (A1-30)+(B5-2), (A1-30)+(B5-3), (A1-30)+(B5-4), (A1-30)+(B5-5), (A1-30)+(B6-1), (A1-30)+(B6-2), (A1-30)+(B6-3), (A1-30)+(B6-4), (A1-30)+(B6-5), (A1-30)+(B6-6), (A1-30)+(B7-1), (A1-30)+(B7-2), (A1-30)+(B7-3), (A1-30)+(B7-4), (A1-30)+(B7-5), (A1-30)+(B7-6), (A1-30)+(B7-7)), (A1-30)+(B7-7), (A1-30)+(B7-8), (A1-30)+(B8-1), (A1-30)+(B8-2), (A1-30)+(B8-3), (A1-30)+(B8-4), (A1-30)+(B8-5), (A1-30)+(B8-6), (A1-30)+(B8-7), (A1-30)+(B9-1), (A1-30)+(B9-2), (A1-30)+(B10-1), (A1-30)+(B10-2), (A1-30)+(B10-3), (A1-30)+(B10-4), (A1-30)+(B10-5), (A1-30)+(B11-1), (A1-30)+(B11-2), (A1-30)+(B11-2), (A1-31)+(B1-1), (A1-31)+(B1-2), (A1-31)+(B1-3), (A1-31)+(B1-4), (A1-31)+(B1-5), (A1-31)+(B1-6), (A1-31)+(B2-1), (A1-31)+(B2-2), (A1-31)+(B2-3), (A1-31)+(B2-4), (A1-31)+(B2-5), (A1-31)+(B2-6), (A1-31)+(B2-7), (A1-31)+(B2-8), (A1-31)+(B2-9), (A1-31)+(B2-10), (A1-31)+(B2-11), (A1-31)+(B2-12), (A1-31)+(B2-13), (A1-31)+(B2-14), (A1-31)+(B2-15), (A1-31)+(B2-16), (A1-31)+(B2-17), (A1-31)+(B2-18), (A1-31)+(B2-19), (A1-31)+(B2-20), (A1-31)+(B2-21), (A1-31)+(B2-22), (A1-31)+(B2-23), (A1-31)+(B2-24), (A1-31)+(B2-25), (A1-31)+(B2-26), (A1-31)+(B2-27), (A1-31)+(B2-28), (A1-31)+(B2-29), (A1-31)+(B3-1), (A1-31)+(B3-2), (A1-31)+(B4-1), (A1-31)+(B4-2), (A1-31)+(B4-3), (A1-31)+(B4-4), (A1-31)+(B4-5), (A1-31)+(B4-6), (A1-31)+(B4-7), (A1-31)+(B4-8), (A1-31)+(B4-9), (A1-31)+(B4-10), (A1-31)+(B4-11), (A1-31)+(B5-1), (A1-31)+(B5-2), (A1-31)+(B5-3), (A1-31)+(B5-4), (A1-31)+(B5-5), (A1-31)+(B6-1), (A1-31)+(B6-2), (A1-31)+(B6-3), (A1-31)+(B6-4), (A1-31)+(B6-5), (A1-31)+(B6-6), (A1-31)+(B7-1), (A1-31)+(B7-2), (A1-31)+(B7-3), (A1-31)+(B7-4), (A1-31)+(B7-5), (A1-31)+(B7-6), (A1-31)+(B7-7)), (A1-31)+(B7-7), (A1-31)+(B7-8), (A1-31)+(B8-1), (A1-31)+(B8-2), (A1-31)+(B8-3), (A1-31)+(B8-4), (A1-31)+(B8-5), (A1-31)+(B8-6), (A1-31)+(B8-7), (A1-31)+(B9-1), (A1-31)+(B9-2), (A1-31)+(B10-1), (A1-31)+(B10-2), (A1-31)+(B10-3), (A1-31)+(B10-4), (A1-31)+(B10-5), (A1-31)+(B11-1), (A1-31)+(B11-2), (A1-31)+(B11-2), (A1-32)+(B1-1), (A1-32)+(B1-2), (A1-32)+(B1-3), (A1-32)+(B1-4), (A1-32)+(B1-5), (A1-32)+(B1-6), (A1-32)+(B2-1), (A1-32)+(B2-2), (A1-32)+(B2-3), (A1-32)+(B2-4), (A1-32)+(B2-5), (A1-32)+(B2-6), (A1-32)+(B2-7), (A1-32)+(B2-8), (A1-32)+(B2-9), (A1-32)+(B2-10), (A1-32)+(B2-11), (A1-32)+(B2-12), (A1-32)+(B2-13), (A1-32)+(B2-14), (A1-32)+(B2-15), (A1-32)+(B2-16), (A1-32)+(B2-17), (A1-32)+(B2-18), (A1-32)+(B2-19), (A1-32)+(B2-20), (A1-32)+(B2-21), (A1-32)+(B2-22), (A1-32)+(B2-23), (A1-32)+(B2-24), (A1-32)+(B2-25), (A1-32)+(B2-26), (A1-32)+(B2-27), (A1-32)+(B2-28), (A1-32)+(B2-29), (A1-32)+(B3-1), (A1-32)+(B3-2), (A1-32)+(B4-1), (A1-32)+(B4-2), (A1-32)+(B4-3), (A1-32)+(B4-4), (A1-32)+(B4-5), (A1-32)+(B4-6), (A1-32)+(B4-7), (A1-32)+(B4-8), (A1-32)+(B4-9), (A1-32)+(B4-10), (A1-32)+(B4-11), (A1-32)+(B5-1), (A1-32)+(B5-2), (A1-32)+(B5-3), (A1-32)+(B5-4), (A1-32)+(B5-5), (A1-32)+(B6-1), (A1-32)+(B6-2), (A1-32)+(B6-3), (A1-32)+(B6-4), (A1-32)+(B6-5), (A1-32)+(B6-6), (A1-32)+(B7-1), (A1-32)+(B7-2), (A1-32)+(B7-3), (A1-32)+(B7-4), (A1-32)+(B7-5), (A1-32)+(B7-6), (A1-32)+(B7-7)), (A1-32)+(B7-7), (A1-32)+(B7-8), (A1-32)+(B8-1), (A1-32)+(B8-2), (A1-32)+(B8-3), (A1-32)+(B8-4), (A1-32)+(B8-5), (A1-32)+(B8-6), (A1-32)+(B8-7), (A1-32)+(B9-1), (A1-32)+(B9-2), (A1-32)+(B10-1), (A1-32)+(B10-2), (A1-32)+(B10-3), (A1-32)+(B10-4), (A1-32)+(B10-5), (A1-32)+(B11-1), (A1-32)+(B11-2), (A1-32)+(B11-2), (A1-33)+(B1-1), (A1-33)+(B1-2), (A1-33)+(B1-3), (A1-33)+(B1-4), (A1-33)+(B1-5), (A1-33)+(B1-6), (A1-33)+(B2-1), (A1-33)+(B2-2), (A1-33)+(B2-3), (A1-33)+(B2-4), (A1-33)+(B2-5), (A1-33)+(B2-6), (A1-33)+(B2-7), (A1-33)+(B2-8), (A1-33)+(B2-9), (A1-33)+(B2-10), (A1-33)+(B2-11), (A1-33)+(B2-12), (A1-33)+(B2-13), (A1-33)+(B2-14), (A1-33)+(B2-15), (A1-33)+(B2-16), (A1-33)+(B2-17), (A1-33)+(B2-18), (A1-33)+(B2-19), (A1-33)+(B2-20), (A1-33)+(B2-21), (A1-33)+(B2-22), (A1-33)+(B2-23), (A1-33)+(B2-24), (A1-33)+(B2-25), (A1-33)+(B2-26), (A1-33)+(B2-27), (A1-33)+(B2-28), (A1-33)+(B2-29), (A1-33)+(B3-1), (A1-33)+(B3-2), (A1-33)+(B4-1), (A1-33)+(B4-2), (A1-33)+(B4-3), (A1-33)+(B4-4), (A1-33)+(B4-5), (A1-33)+(B4-6), (A1-33)+(B4-7), (A1-33)+(B4-8), (A1-33)+(B4-9), (A1-33)+(B4-10), (A1-33)+(B4-11), (A1-33)+(B5-1), (A1-33)+(B5-2), (A1-33)+(B5-3), (A1-33)+(B5-4), (A1-33)+(B5-5), (A1-33)+(B6-1), (A1-33)+(B6-2), (A1-33)+(B6-3), (A1-33)+(B6-4), (A1-33)+(B6-5), (A1-33)+(B6-6), (A1-33)+(B7-1), (A1-33)+(B7-2), (A1-33)+(B7-3), (A1-33)+(B7-4), (A1-33)+(B7-5), (A1-33)+(B7-6), (A1-33)+(B7-7)), (A1-33)+(B7-7), (A1-33)+(B7-8), (A1-33)+(B8-1), (A1-33)+(B8-2), (A1-33)+(B8-3), (A1-33)+(B8-4), (A1-33)+(B8-5), (A1-33)+(B8-6), (A1-33)+(B8-7), (A1-33)+(B9-1), (A1-33)+(B9-2), (A1-33)+(B10-1), (A1-33)+(B10-2), (A1-33)+(B10-3), (A1-33)+(B10-4), (A1-33)+(B10-5), (A1-33)+(B11-1), (A1-33)+(B11-2), (A1-33)+(B11-2), (A1-34)+(B1-1), (A1-34)+(B1-2), (A1-34)+(B1-3), (A1-34)+(B1-4), (A1-34)+(B1-5), (A1-34)+(B1-6), (A1-34)+(B2-1), (A1-34)+(B2-2), (A1-34)+(B2-3), (A1-34)+(B2-4), (A1-34)+(B2-5), (A1-34)+(B2-6), (A1-34)+(B2-7), (A1-34)+(B2-8), (A1-34)+(B2-9), (A1-34)+(B2-10), (A1-34)+(B2-11), (A1-34)+(B2-12), (A1-34)+(B2-13), (A1-34)+(B2-14), (A1-34)+(B2-15), (A1-34)+(B2-16), (A1-34)+(B2-17), (A1-34)+(B2-18), (A1-34)+(B2-19), (A1-34)+(B2-20), (A1-34)+(B2-21), (A1-34)+(B2-22), (A1-34)+(B2-23), (A1-34)+(B2-24), (A1-34)+(B2-25), (A1-34)+(B2-26), (A1-34)+(B2-27), (A1-34)+(B2-28), (A1-34)+(B2-29), (A1-34)+(B3-1), (A1-34)+(B3-2), (A1-34)+(B4-1), (A1-34)+(B4-2), (A1-34)+(B4-3), (A1-34)+(B4-4), (A1-34)+(B4-5), (A1-34)+(B4-6), (A1-34)+(B4-7), (A1-34)+(B4-8), (A1-34)+(B4-9), (A1-34)+(B4-10), (A1-34)+(B4-11), (A1-34)+(B5-1), (A1-34)+(B5-2), (A1-34)+(B5-3), (A1-34)+(B5-4), (A1-34)+(B5-5), (A1-34)+(B6-1), (A1-34)+(B6-2), (A1-34)+(B6-3), (A1-34)+(B6-4), (A1-34)+(B6-5), (A1-34)+(B6-6), (A1-34)+(B7-1), (A1-34)+(B7-2), (A1-34)+(B7-3), (A1-34)+(B7-4), (A1-34)+(B7-5), (A1-34)+(B7-6), (A1-34)+(B7-7)), (A1-34)+(B7-7), (A1-34)+(B7-8), (A1-34)+(B8-1), (A1-34)+(B8-2), (A1-34)+(B8-3), (A1-34)+(B8-4), (A1-34)+(B8-5), (A1-34)+(B8-6), (A1-34)+(B8-7), (A1-34)+(B9-1), (A1-34)+(B9-2), (A1-34)+(B10-1), (A1-34)+(B10-2), (A1-34)+(B10-3), (A1-34)+(B10-4), (A1-34)+(B10-5), (A1-34)+(B11-1), (A1-34)+(B11-2), (A1-34)+(B11-2), (A1-35)+(B1-1), (A1-35)+(B1-2), (A1-35)+(B1-3), (A1-35)+(B1-4), (A1-35)+(B1-5), (A1-35)+(B1-6), (A1-35)+(B2-1), (A1-35)+(B2-2), (A1-35)+(B2-3), (A1-35)+(B2-4), (A1-35)+(B2-5), (A1-35)+(B2-6), (A1-35)+(B2-7), (A1-35)+(B2-8), (A1-35)+(B2-9), (A1-35)+(B2-10), (A1-35)+(B2-11), (A1-35)+(B2-12), (A1-35)+(B2-13), (A1-35)+(B2-14), (A1-35)+(B2-15), (A1-35)+(B2-16), (A1-35)+(B2-17), (A1-35)+(B2-18), (A1-35)+(B2-19), (A1-35)+(B2-20), (A1-35)+(B2-21), (A1-35)+(B2-22), (A1-35)+(B2-23), (A1-35)+(B2-24), (A1-35)+(B2-25), (A1-35)+(B2-26), (A1-35)+(B2-27), (A1-35)+(B2-28), (A1-35)+(B2-29), (A1-35)+(B3-1), (A1-35)+(B3-2), (A1-35)+(B4-1), (A1-35)+(B4-2), (A1-35)+(B4-3), (A1-35)+(B4-4), (A1-35)+(B4-5), (A1-35)+(B4-6), (A1-35)+(B4-7), (A1-35)+(B4-8), (A1-35)+(B4-9), (A1-35)+(B4-10), (A1-35)+(B4-11), (A1-35)+(B5-1), (A1-35)+(B5-2), (A1-35)+(B5-3), (A1-35)+(B5-4), (A1-35)+(B5-5), (A1-35)+(B6-1), (A1-35)+(B6-2), (A1-35)+(B6-3), (A1-35)+(B6-4), (A1-35)+(B6-5), (A1-35)+(B6-6), (A1-35)+(B7-1), (A1-35)+(B7-2), (A1-35)+(B7-3), (A1-35)+(B7-4), (A1-35)+(B7-5), (A1-35)+(B7-6), (A1-35)+(B7-7)), (A1-35)+(B7-7), (A1-35)+(B7-8), (A1-35)+(B8-1), (A1-35)+(B8-2), (A1-35)+(B8-3), (A1-35)+(B8-4), (A1-35)+(B8-5), (A1-35)+(B8-6), (A1-35)+(B8-7), (A1-35)+(B9-1), (A1-35)+(B9-2), (A1-35)+(B10-1), (A1-35)+(B10-2), (A1-35)+(B10-3), (A1-35)+(B10-4), (A1-35)+(B10-5), (A1-35)+(B11-1), (A1-35)+(B11-2), (A1-35)+(B11-2), (A1-36)+(B1-1), (A1-36)+(B1-2), (A1-36)+(B1-3), (A1-36)+(B1-4), (A1-36)+(B1-5), (A1-36)+(B1-6), (A1-36)+(B2-1), (A1-36)+(B2-2), (A1-36)+(B2-3), (A1-36)+(B2-4), (A1-36)+(B2-5), (A1-36)+(B2-6), (A1-36)+(B2-7), (A1-36)+(B2-8), (A1-36)+(B2-9), (A1-36)+(B2-10), (A1-36)+(B2-11), (A1-36)+(B2-12), (A1-36)+(B2-13), (A1-36)+(B2-14), (A1-36)+(B2-15), (A1-36)+(B2-16), (A1-36)+(B2-17), (A1-36)+(B2-18), (A1-36)+(B2-19), (A1-36)+(B2-20), (A1-36)+(B2-21), (A1-36)+(B2-22), (A1-36)+(B2-23), (A1-36)+(B2-24), (A1-36)+(B2-25), (A1-36)+(B2-26), (A1-36)+(B2-27), (A1-36)+(B2-28), (A1-36)+(B2-29), (A1-36)+(B3-1), (A1-36)+(B3-2), (A1-36)+(B4-1), (A1-36)+(B4-2), (A1-36)+(B4-3), (A1-36)+(B4-4), (A1-36)+(B4-5), (A1-36)+(B4-6), (A1-36)+(B4-7), (A1-36)+(B4-8), (A1-36)+(B4-9), (A1-36)+(B4-10), (A1-36)+(B4-11), (A1-36)+(B5-1), (A1-36)+(B5-2), (A1-36)+(B5-3), (A1-36)+(B5-4), (A1-36)+(B5-5), (A1-36)+(B6-1), (A1-36)+(B6-2), (A1-36)+(B6-3), (A1-36)+(B6-4), (A1-36)+(B6-5), (A1-36)+(B6-6), (A1-36)+(B7-1), (A1-36)+(B7-2), (A1-36)+(B7-3), (A1-36)+(B7-4), (A1-36)+(B7-5), (A1-36)+(B7-6), (A1-36)+(B7-7)), (A1-36)+(B7-7), (A1-36)+(B7-8), (A1-36)+(B8-1), (A1-36)+(B8-2), (A1-36)+(B8-3), (A1-36)+(B8-4), (A1-36)+(B8-5), (A1-36)+(B8-6), (A1-36)+(B8-7), (A1-36)+(B9-1), (A1-36)+(B9-2), (A1-36)+(B10-1), (A1-36)+(B10-2), (A1-36)+(B10-3), (A1-36)+(B10-4), (A1-36)+(B10-5), (A1-36)+(B11-1), (A1-36)+(B11-2), (A1-36)+(B11-2), (A1-37)+(B1-1), (A1-37)+(B1-2), (A1-37)+(B1-3), (A1-37)+(B1-4), (A1-37)+(B1-5), (A1-37)+(B1-6), (A1-37)+(B2-1), (A1-37)+(B2-2), (A1-37)+(B2-3), (A1-37)+(B2-4), (A1-37)+(B2-5), (A1-37)+(B2-6), (A1-37)+(B2-7), (A1-37)+(B2-8), (A1-37)+(B2-9), (A1-37)+(B2-10), (A1-37)+(B2-11), (A1-37)+(B2-12), (A1-37)+(B2-13), (A1-37)+(B2-14), (A1-37)+(B2-15), (A1-37)+(B2-16), (A1-37)+(B2-17), (A1-37)+(B2-18), (A1-37)+(B2-19), (A1-37)+(B2-20), (A1-37)+(B2-21), (A1-37)+(B2-22), (A1-37)+(B2-23), (A1-37)+(B2-24), (A1-37)+(B2-25), (A1-37)+(B2-26), (A1-37)+(B2-27), (A1-37)+(B2-28), (A1-37)+(B2-29), (A1-37)+(B3-1), (A1-37)+(B3-2), (A1-37)+(B4-1), (A1-37)+(B4-2), (A1-37)+(B4-3), (A1-37)+(B4-4), (A1-37)+(B4-5), (A1-37)+(B4-6), (A1-37)+(B4-7), (A1-37)+(B4-8), (A1-37)+(B4-9), (A1-37)+(B4-10), (A1-37)+(B4-11), (A1-37)+(B5-1), (A1-37)+(B5-2), (A1-37)+(B5-3), (A1-37)+(B5-4), (A1-37)+(B5-5), (A1-37)+(B6-1), (A1-37)+(B6-2), (A1-37)+(B6-3), (A1-37)+(B6-4), (A1-37)+(B6-5), (A1-37)+(B6-6), (A1-37)+(B7-1), (A1-37)+(B7-2), (A1-37)+(B7-3), (A1-37)+(B7-4), (A1-37)+(B7-5), (A1-37)+(B7-6), (A1-37)+(B7-7)), (A1-37)+(B7-7), (A1-37)+(B7-8), (A1-37)+(B8-1), (A1-37)+(B8-2), (A1-37)+(B8-3), (A1-37)+(B8-4), (A1-37)+(B8-5), (A1-37)+(B8-6), (A1-37)+(B8-7), (A1-37)+(B9-1), (A1-37)+(B9-2), (A1-37)+(B10-1), (A1-37)+(B10-2), (A1-37)+(B10-3), (A1-37)+(B10-4), (A1-37)+(B10-5), (A1-37)+(B11-1), (A1-37)+(B11-2), (A1-37)+(B11-2), (A1-38)+(B1-1), (A1-38)+(B1-2), (A1-38)+(B1-3), (A1-38)+(B1-4), (A1-38)+(B1-5), (A1-38)+(B1-6), (A1-38)+(B2-1), (A1-38)+(B2-2), (A1-38)+(B2-3), (A1-38)+(B2-4), (A1-38)+(B2-5), (A1-38)+(B2-6), (A1-38)+(B2-7), (A1-38)+(B2-8), (A1-38)+(B2-9), (A1-38)+(B2-10), (A1-38)+(B2-11), (A1-38)+(B2-12), (A1-38)+(B2-13), (A1-38)+(B2-14), (A1-38)+(B2-15), (A1-38)+(B2-16), (A1-38)+(B2-17), (A1-38)+(B2-18), (A1-38)+(B2-19), (A1-38)+(B2-20), (A1-38)+(B2-21), (A1-38)+(B2-22), (A1-38)+(B2-23), (A1-38)+(B2-24), (A1-38)+(B2-25), (A1-38)+(B2-26), (A1-38)+(B2-27), (A1-38)+(B2-28), (A1-38)+(B2-29), (A1-38)+(B3-1), (A1-38)+(B3-2), (A1-38)+(B4-1), (A1-38)+(B4-2), (A1-38)+(B4-3), (A1-38)+(B4-4), (A1-38)+(B4-5), (A1-38)+(B4-6), (A1-38)+(B4-7), (A1-38)+(B4-8), (A1-38)+(B4-9), (A1-38)+(B4-10), (A1-38)+(B4-11), (A1-38)+(B5-1), (A1-38)+(B5-2), (A1-38)+(B5-3), (A1-38)+(B5-4), (A1-38)+(B5-5), (A1-38)+(B6-1), (A1-38)+(B6-2), (A1-38)+(B6-3), (A1-38)+(B6-4), (A1-38)+(B6-5), (A1-38)+(B6-6), (A1-38)+(B7-1), (A1-38)+(B7-2), (A1-38)+

(B7-3), (A1-38)+(B7-4), (A1-38)+(B7-5), (A1-38)+(B7-6), (A1-38)+(B7-7)), (A1-38)+(B7-7), (A1-38)+(B7-8), (A1-38)+(B8-1), (A1-38)+(B8-2), (A1-38)+(B8-3), (A1-38)+(B8-4), (A1-38)+(B8-5), (A1-38)+(B8-6), (A1-38)+(B8-7), (A1-38)+(B9-1), (A1-38)+(B9-2), (A1-38)+(B10-1), (A1-38)+(B10-2), (A1-38)+(B10-3), (A1-38)+(B10-4), (A1-38)+(B10-5), (A1-38)+(B11-1), (A1-38)+(B11-2), (A1-38)+(B11-2), (A1-39)+(B1-1), (A1-39)+(B1-2), (A1-39)+(B1-3), (A1-39)+(B1-4), (A1-39)+(B1-5), (A1-39)+(B1-6), (A1-39)+(B2-1), (A1-39)+(B2-2), (A1-39)+(B2-3), (A1-39)+(B2-4), (A1-39)+(B2-5), (A1-39)+(B2-6), (A1-39)+(B2-7), (A1-39)+(B2-8), (A1-39)+(B2-9), (A1-39)+(B2-10), (A1-39)+(B2-11), (A1-39)+(B2-12), (A1-39)+(B2-13), (A1-39)+(B2-14), (A1-39)+(B2-15), (A1-39)+(B2-16), (A1-39)+(B2-17), (A1-39)+(B2-18), (A1-39)+(B2-19), (A1-39)+(B2-20), (A1-39)+(B2-21), (A1-39)+(B2-22), (A1-39)+(B2-23), (A1-39)+(B2-24), (A1-39)+(B2-25), (A1-39)+(B2-26), (A1-39)+(B2-27), (A1-39)+(B2-28), (A1-39)+(B2-29), (A1-39)+(B3-1), (A1-39)+(B3-2), (A1-39)+(B4-1), (A1-39)+(B4-2), (A1-39)+(B4-3), (A1-39)+(B4-4), (A1-39)+(B4-5), (A1-39)+(B4-6), (A1-39)+(B4-7), (A1-39)+(B4-8), (A1-39)+(B4-9), (A1-39)+(B4-10), (A1-39)+(B4-11), (A1-39)+(B5-1), (A1-39)+(B5-2), (A1-39)+(B5-3), (A1-39)+(B5-4), (A1-39)+(B5-5), (A1-39)+(B6-1), (A1-39)+(B6-2), (A1-39)+(B6-3), (A1-39)+(B6-4), (A1-39)+(B6-5), (A1-39)+(B6-6), (A1-39)+(B7-1), (A1-39)+(B7-2), (A1-39)+(B7-3), (A1-39)+(B7-4), (A1-39)+(B7-5), (A1-39)+(B7-6), (A1-39)+(B7-7)), (A1-39)+(B7-7), (A1-39)+(B7-8), (A1-39)+(B8-1), (A1-39)+(B8-2), (A1-39)+(B8-3), (A1-39)+(B8-4), (A1-39)+(B8-5), (A1-39)+(B8-6), (A1-39)+(B8-7), (A1-39)+(B9-1), (A1-39)+(B9-2), (A1-39)+(B10-1), (A1-39)+(B10-2), (A1-39)+(B10-3), (A1-39)+(B10-4), (A1-39)+(B10-5), (A1-39)+(B11-1), (A1-39)+(B11-2), (A1-39)+(B11-2), (A1-40)+(B1-1), (A1-40)+(B1-2), (A1-40)+(B1-3), (A1-40)+(B1-4), (A1-40)+(B1-5), (A1-40)+(B1-6), (A1-40)+(B2-1), (A1-40)+(B2-2), (A1-40)+(B2-3), (A1-40)+(B2-4), (A1-40)+(B2-5), (A1-40)+(B2-6), (A1-40)+(B2-7), (A1-40)+(B2-8), (A1-40)+(B2-9), (A1-40)+(B2-10), (A1-40)+(B2-11), (A1-40)+(B2-12), (A1-40)+(B2-13), (A1-40)+(B2-14), (A1-40)+(B2-15), (A1-40)+(B2-16), (A1-40)+(B2-17), (A1-40)+(B2-18), (A1-40)+(B2-19), (A1-40)+(B2-20), (A1-40)+(B2-21), (A1-40)+(B2-22), (A1-40)+(B2-23), (A1-40)+(B2-24), (A1-40)+(B2-25), (A1-40)+(B2-26), (A1-40)+(B2-27), (A1-40)+(B2-28), (A1-40)+(B2-29), (A1-40)+(B3-1), (A1-40)+(B3-2), (A1-40)+(B4-1), (A1-40)+(B4-2), (A1-40)+(B4-3), (A1-40)+(B4-4), (A1-40)+(B4-5), (A1-40)+(B4-6), (A1-40)+(B4-7), (A1-40)+(B4-8), (A1-40)+(B4-9), (A1-40)+(B4-10), (A1-40)+(B4-11), (A1-40)+(B5-1), (A1-40)+(B5-2), (A1-40)+(B5-3), (A1-40)+(B5-4), (A1-40)+(B5-5), (A1-40)+(B6-1), (A1-40)+(B6-2), (A1-40)+(B6-3), (A1-40)+(B6-4), (A1-40)+(B6-5), (A1-40)+(B6-6), (A1-40)+(B7-1), (A1-40)+(B7-2), (A1-40)+(B7-3), (A1-40)+(B7-4), (A1-40)+(B7-5), (A1-40)+(B7-6), (A1-40)+(B7-7)), (A1-40)+(B7-7), (A1-40)+(B7-8), (A1-40)+(B8-1), (A1-40)+(B8-2), (A1-40)+(B8-3), (A1-40)+(B8-4), (A1-40)+(B8-5), (A1-40)+(B8-6), (A1-40)+(B8-7), (A1-40)+(B9-1), (A1-40)+(B9-2), (A1-40)+(B10-1), (A1-40)+(B10-2), (A1-40)+(B10-3), (A1-40)+(B10-4), (A1-40)+(B10-5), (A1-40)+(B11-1), (A1-40)+(B11-2), (A1-40)+(B11-2), (A1-41)+(B1-1), (A1-41)+(B1-2), (A1-41)+(B1-3), (A1-41)+(B1-4), (A1-41)+(B1-5), (A1-41)+(B1-6), (A1-41)+(B2-1), (A1-41)+(B2-2), (A1-41)+(B2-3), (A1-41)+(B2-4), (A1-41)+(B2-5), (A1-41)+(B2-6), (A1-41)+(B2-7), (A1-41)+(B2-8), (A1-41)+(B2-9), (A1-41)+(B2-10), (A1-41)+(B2-11), (A1-41)+(B2-12), (A1-41)+(B2-13), (A1-41)+(B2-14), (A1-41)+(B2-15), (A1-41)+(B2-16), (A1-41)+(B2-17), (A1-41)+(B2-18), (A1-41)+(B2-19), (A1-41)+(B2-20), (A1-41)+(B2-21), (A1-41)+(B2-22), (A1-41)+(B2-23), (A1-41)+(B2-24), (A1-41)+(B2-25), (A1-41)+(B2-26), (A1-41)+(B2-27), (A1-41)+(B2-28), (A1-41)+(B2-29), (A1-41)+(B3-1), (A1-41)+(B3-2), (A1-41)+(B4-1), (A1-41)+(B4-2), (A1-41)+(B4-3), (A1-41)+(B4-4), (A1-41)+(B4-5), (A1-41)+(B4-6), (A1-41)+(B4-7), (A1-41)+(B4-8), (A1-41)+(B4-9), (A1-41)+(B4-10), (A1-41)+(B4-11), (A1-41)+(B5-1), (A1-41)+(B5-2), (A1-41)+(B5-3), (A1-41)+(B5-4), (A1-41)+(B5-5), (A1-41)+(B6-1), (A1-41)+(B6-2), (A1-41)+(B6-3), (A1-41)+(B6-4), (A1-41)+(B6-5), (A1-41)+(B6-6), (A1-41)+(B7-1), (A1-41)+(B7-2), (A1-41)+(B7-3), (A1-41)+(B7-4), (A1-41)+(B7-5), (A1-41)+(B7-6), (A1-41)+(B7-7)), (A1-41)+(B7-7), (A1-41)+(B7-8), (A1-41)+(B8-1), (A1-41)+(B8-2), (A1-41)+(B8-3), (A1-41)+(B8-4), (A1-41)+(B8-5), (A1-41)+(B8-6), (A1-41)+(B8-7), (A1-41)+(B9-1), (A1-41)+(B9-2), (A1-41)+(B10-1), (A1-41)+(B10-2), (A1-41)+(B10-3), (A1-41)+(B10-4), (A1-41)+(B10-5), (A1-41)+(B11-1), (A1-41)+(B11-2), (A1-41)+(B11-2), (A1-42)+(B1-1), (A1-42)+(B1-2), (A1-42)+(B1-3), (A1-42)+(B1-4), (A1-42)+(B1-5), (A1-42)+(B1-6), (A1-42)+(B2-1), (A1-42)+(B2-2), (A1-42)+(B2-3), (A1-42)+(B2-4), (A1-42)+(B2-5), (A1-42)+(B2-6), (A1-42)+(B2-7), (A1-42)+(B2-8), (A1-42)+(B2-9), (A1-42)+(B2-10), (A1-42)+(B2-11), (A1-42)+(B2-12), (A1-42)+(B2-13), (A1-42)+(B2-14), (A1-42)+(B2-15), (A1-42)+(B2-16), (A1-42)+(B2-17), (A1-42)+(B2-18), (A1-42)+(B2-19), (A1-42)+(B2-20), (A1-42)+(B2-21), (A1-42)+(B2-22), (A1-42)+(B2-23), (A1-42)+(B2-24), (A1-42)+(B2-25), (A1-42)+(B2-26), (A1-42)+(B2-27), (A1-42)+(B2-28), (A1-42)+(B2-29), (A1-42)+(B3-1), (A1-42)+(B3-2), (A1-42)+(B4-1), (A1-42)+(B4-2), (A1-42)+(B4-3), (A1-42)+(B4-4), (A1-42)+(B4-5), (A1-42)+(B4-6), (A1-42)+(B4-7), (A1-42)+(B4-8), (A1-42)+(B4-9), (A1-42)+(B4-10), (A1-42)+(B4-11), (A1-42)+(B5-1), (A1-42)+(B5-2), (A1-42)+(B5-3), (A1-42)+(B5-4), (A1-42)+(B5-5), (A1-42)+(B6-1), (A1-42)+(B6-2), (A1-42)+(B6-3), (A1-42)+(B6-4), (A1-42)+(B6-5), (A1-42)+(B6-6), (A1-42)+(B7-1), (A1-42)+(B7-2), (A1-42)+(B7-3), (A1-42)+(B7-4), (A1-42)+(B7-5), (A1-42)+(B7-6), (A1-42)+(B7-7)), (A1-42)+(B7-7), (A1-42)+(B7-8), (A1-42)+(B8-1), (A1-42)+(B8-2), (A1-42)+(B8-3), (A1-42)+(B8-4), (A1-42)+(B8-5), (A1-42)+(B8-6), (A1-42)+(B8-7), (A1-42)+(B9-1), (A1-42)+(B9-2), (A1-42)+(B10-1), (A1-42)+(B10-2), (A1-42)+(B10-3), (A1-42)+(B10-4), (A1-42)+(B10-5), (A1-42)+(B11-1), (A1-42)+(B11-2), (A1-42)+(B11-2), (A1-43)+(B1-1), (A1-43)+(B1-2), (A1-43)+(B1-3), (A1-43)+(B1-4), (A1-43)+(B1-5), (A1-43)+(B1-6), (A1-43)+(B2-1), (A1-43)+(B2-2), (A1-43)+(B2-3), (A1-43)+(B2-4), (A1-43)+(B2-5), (A1-43)+(B2-6), (A1-43)+(B2-7), (A1-43)+(B2-8), (A1-43)+(B2-9), (A1-43)+(B2-10), (A1-43)+(B2-11), (A1-43)+(B2-12), (A1-43)+(B2-13), (A1-43)+(B2-14), (A1-43)+(B2-15), (A1-43)+(B2-16), (A1-43)+(B2-17), (A1-43)+(B2-18), (A1-43)+(B2-19), (A1-43)+(B2-20), (A1-43)+(B2-21), (A1-43)+(B2-22), (A1-43)+(B2-23), (A1-43)+(B2-24), (A1-43)+(B2-25), (A1-43)+(B2-26), (A1-43)+(B2-27), (A1-43)+(B2-28), (A1-43)+(B2-29), (A1-43)+(B3-1), (A1-43)+(B3-2), (A1-43)+(B4-1), (A1-43)+(B4-2), (A1-43)+(B4-3), (A1-43)+(B4-4), (A1-43)+(B4-5), (A1-43)+(B4-6), (A1-43)+(B4-7), (A1-43)+(B4-8), (A1-43)+(B4-9), (A1-43)+(B4-10), (A1-43)+(B4-11), (A1-43)+(B5-1), (A1-43)+(B5-2), (A1-43)+(B5-3), (A1-43)+(B5-4), (A1-43)+(B5-5), (A1-43)+(B6-1), (A1-43)+(B6-2), (A1-43)+(B6-3), (A1-43)+(B6-4), (A1-43)+(B6-5), (A1-

43)+(B6-6), (A1-43)+(B7-1), (A1-43)+(B7-2), (A1-43)+(B7-3), (A1-43)+(B7-4), (A1-43)+(B7-5), (A1-43)+(B7-6), (A1-43)+(B7-7)), (A1-43)+(B7-7), (A1-43)+(B7-8), (A1-43)+(B8-1), (A1-43)+(B8-2), (A1-43)+(B8-3), (A1-43)+(B8-4), (A1-43)+(B8-5), (A1-43)+(B8-6), (A1-43)+(B8-7), (A1-43)+(B9-1), (A1-43)+(B9-2), (A1-43)+(B10-1), (A1-43)+(B10-2), (A1-43)+(B10-3), (A1-43)+(B10-4), (A1-43)+(B10-5), (A1-43)+(B11-1), (A1-43)+(B11-2), (A1-43)+(B11-2), (A1-44)+(B1-1), (A1-44)+(B1-2), (A1-44)+(B1-3), (A1-44)+(B1-4), (A1-44)+(B1-5), (A1-44)+(B1-6), (A1-44)+(B2-1), (A1-44)+(B2-2), (A1-44)+(B2-3), (A1-44)+(B2-4), (A1-44)+(B2-5), (A1-44)+(B2-6), (A1-44)+(B2-7), (A1-44)+(B2-8), (A1-44)+(B2-9), (A1-44)+(B2-10), (A1-44)+(B2-11), (A1-44)+(B2-12), (A1-44)+(B2-13), (A1-44)+(B2-14), (A1-44)+(B2-15), (A1-44)+(B2-16), (A1-44)+(B2-17), (A1-44)+(B2-18), (A1-44)+(B2-19), (A1-44)+(B2-20), (A1-44)+(B2-21), (A1-44)+(B2-22), (A1-44)+(B2-23), (A1-44)+(B2-24), (A1-44)+(B2-25), (A1-44)+(B2-26), (A1-44)+(B2-27), (A1-44)+(B2-28), (A1-44)+(B2-29), (A1-44)+(B3-1), (A1-44)+(B3-2), (A1-44)+(B4-1), (A1-44)+(B4-2), (A1-44)+(B4-3), (A1-44)+(B4-4), (A1-44)+(B4-5), (A1-44)+(B4-6), (A1-44)+(B4-7), (A1-44)+(B4-8), (A1-44)+(B4-9), (A1-44)+(B4-10), (A1-44)+(B4-11), (A1-44)+(B5-1), (A1-44)+(B5-2), (A1-44)+(B5-3), (A1-44)+(B5-4), (A1-44)+(B5-5), (A1-44)+(B6-1), (A1-44)+(B6-2), (A1-44)+(B6-3), (A1-44)+(B6-4), (A1-44)+(B6-5), (A1-44)+(B6-6), (A1-44)+(B7-1), (A1-44)+(B7-2), (A1-44)+(B7-3), (A1-44)+(B7-4), (A1-44)+(B7-5), (A1-44)+(B7-6), (A1-44)+(B7-7)), (A1-44)+(B7-7), (A1-44)+(B7-8), (A1-44)+(B8-1), (A1-44)+(B8-2), (A1-44)+(B8-3), (A1-44)+(B8-4), (A1-44)+(B8-5), (A1-44)+(B8-6), (A1-44)+(B8-7), (A1-44)+(B9-1), (A1-44)+(B9-2), (A1-44)+(B10-1), (A1-44)+(B10-2), (A1-44)+(B10-3), (A1-44)+(B10-4), (A1-44)+(B10-5), (A1-44)+(B11-1), (A1-44)+(B11-2), (A1-44)+(B11-2), (A1-45)+(B1-1), (A1-45)+(B1-2), (A1-45)+(B1-3), (A1-45)+(B1-4), (A1-45)+(B1-5), (A1-45)+(B1-6), (A1-45)+(B2-1), (A1-45)+(B2-2), (A1-45)+(B2-3), (A1-45)+(B2-4), (A1-45)+(B2-5), (A1-45)+(B2-6), (A1-45)+(B2-7), (A1-45)+(B2-8), (A1-45)+(B2-9), (A1-45)+(B2-10), (A1-45)+(B2-11), (A1-45)+(B2-12), (A1-45)+(B2-13), (A1-45)+(B2-14), (A1-45)+(B2-15), (A1-45)+(B2-16), (A1-45)+(B2-17), (A1-45)+(B2-18), (A1-45)+(B2-19), (A1-45)+(B2-20), (A1-45)+(B2-21), (A1-45)+(B2-22), (A1-45)+(B2-23), (A1-45)+(B2-24), (A1-45)+(B2-25), (A1-45)+(B2-26), (A1-45)+(B2-27), (A1-45)+(B2-28), (A1-45)+(B2-29), (A1-45)+(B3-1), (A1-45)+(B3-2), (A1-45)+(B4-1), (A1-45)+(B4-2), (A1-45)+(B4-3), (A1-45)+(B4-4), (A1-45)+(B4-5), (A1-45)+(B4-6), (A1-45)+(B4-7), (A1-45)+(B4-8), (A1-45)+(B4-9), (A1-45)+(B4-10), (A1-45)+(B4-11), (A1-45)+(B5-1), (A1-45)+(B5-2), (A1-45)+(B5-3), (A1-45)+(B5-4), (A1-45)+(B5-5), (A1-45)+(B6-1), (A1-45)+(B6-2), (A1-45)+(B6-3), (A1-45)+(B6-4), (A1-45)+(B6-5), (A1-45)+(B6-6), (A1-45)+(B7-1), (A1-45)+(B7-2), (A1-45)+(B7-3), (A1-45)+(B7-4), (A1-45)+(B7-5), (A1-45)+(B7-6), (A1-45)+(B7-7)), (A1-45)+(B7-7), (A1-45)+(B7-8), (A1-45)+(B8-1), (A1-45)+(B8-2), (A1-45)+(B8-3), (A1-45)+(B8-4), (A1-45)+(B8-5), (A1-45)+(B8-6), (A1-45)+(B8-7), (A1-45)+(B9-1), (A1-45)+(B9-2), (A1-45)+(B10-1), (A1-45)+(B10-2), (A1-45)+(B10-3), (A1-45)+(B10-4), (A1-45)+(B10-5), (A1-45)+(B11-1), (A1-45)+(B11-2), (A1-45)+(B11-2), (A1-46)+(B1-1), (A1-46)+(B1-2), (A1-46)+(B1-3), (A1-46)+(B1-4), (A1-46)+(B1-5), (A1-46)+(B1-6), (A1-46)+(B2-1), (A1-46)+(B2-2), (A1-46)+(B2-3), (A1-46)+(B2-4), (A1-46)+(B2-5), (A1-46)+(B2-6), (A1-46)+(B2-7), (A1-46)+(B2-8), (A1-46)+(B2-9), (A1-46)+(B2-10), (A1-46)+(B2-11), (A1-46)+(B2-12), (A1-46)+(B2-13), (A1-46)+(B2-14), (A1-46)+(B2-15), (A1-46)+(B2-16), (A1-46)+(B2-17), (A1-46)+(B2-18), (A1-46)+(B2-19), (A1-46)+(B2-20), (A1-46)+(B2-21), (A1-46)+(B2-22), (A1-46)+(B2-23), (A1-46)+(B2-24), (A1-46)+(B2-25), (A1-46)+(B2-26), (A1-46)+(B2-27), (A1-46)+(B2-28), (A1-46)+(B2-29), (A1-46)+(B3-1), (A1-46)+(B3-2), (A1-46)+(B4-1), (A1-46)+(B4-2), (A1-46)+(B4-3), (A1-46)+(B4-4), (A1-46)+(B4-5), (A1-46)+(B4-6), (A1-46)+(B4-7), (A1-46)+(B4-8), (A1-46)+(B4-9), (A1-46)+(B4-10), (A1-46)+(B4-11), (A1-46)+(B5-1), (A1-46)+(B5-2), (A1-46)+(B5-3), (A1-46)+(B5-4), (A1-46)+(B5-5), (A1-46)+(B6-1), (A1-46)+(B6-2), (A1-46)+(B6-3), (A1-46)+(B6-4), (A1-46)+(B6-5), (A1-46)+(B6-6), (A1-46)+(B7-1), (A1-46)+(B7-2), (A1-46)+(B7-3), (A1-46)+(B7-4), (A1-46)+(B7-5), (A1-46)+(B7-6), (A1-46)+(B7-7)), (A1-46)+(B7-7), (A1-46)+(B7-8), (A1-46)+(B8-1), (A1-46)+(B8-2), (A1-46)+(B8-3), (A1-46)+(B8-4), (A1-46)+(B8-5), (A1-46)+(B8-6), (A1-46)+(B8-7), (A1-46)+(B9-1), (A1-46)+(B9-2), (A1-46)+(B10-1), (A1-46)+(B10-2), (A1-46)+(B10-3), (A1-46)+(B10-4), (A1-46)+(B10-5), (A1-46)+(B11-1), (A1-46)+(B11-2), (A1-46)+(B11-2), (A1-47)+(B1-1), (A1-47)+(B1-2), (A1-47)+(B1-3), (A1-47)+(B1-4), (A1-47)+(B1-5), (A1-47)+(B1-6), (A1-47)+(B2-1), (A1-47)+(B2-2), (A1-47)+(B2-3), (A1-47)+(B2-4), (A1-47)+(B2-5), (A1-47)+(B2-6), (A1-47)+(B2-7), (A1-47)+(B2-8), (A1-47)+(B2-9), (A1-47)+(B2-10), (A1-47)+(B2-11), (A1-47)+(B2-12), (A1-47)+(B2-13), (A1-47)+(B2-14), (A1-47)+(B2-15), (A1-47)+(B2-16), (A1-47)+(B2-17), (A1-47)+(B2-18), (A1-47)+(B2-19), (A1-47)+(B2-20), (A1-47)+(B2-21), (A1-47)+(B2-22), (A1-47)+(B2-23), (A1-47)+(B2-24), (A1-47)+(B2-25), (A1-47)+(B2-26), (A1-47)+(B2-27), (A1-47)+(B2-28), (A1-47)+(B2-29), (A1-47)+(B3-1), (A1-47)+(B3-2), (A1-47)+(B4-1), (A1-47)+(B4-2), (A1-47)+(B4-3), (A1-47)+(B4-4), (A1-47)+(B4-5), (A1-47)+(B4-6), (A1-47)+(B4-7), (A1-47)+(B4-8), (A1-47)+(B4-9), (A1-47)+(B4-10), (A1-47)+(B4-11), (A1-47)+(B5-1), (A1-47)+(B5-2), (A1-47)+(B5-3), (A1-47)+(B5-4), (A1-47)+(B5-5), (A1-47)+(B6-1), (A1-47)+(B6-2), (A1-47)+(B6-3), (A1-47)+(B6-4), (A1-47)+(B6-5), (A1-47)+(B6-6), (A1-47)+(B7-1), (A1-47)+(B7-2), (A1-47)+(B7-3), (A1-47)+(B7-4), (A1-47)+(B7-5), (A1-47)+(B7-6), (A1-47)+(B7-7)), (A1-47)+(B7-7), (A1-47)+(B7-8), (A1-47)+(B8-1), (A1-47)+(B8-2), (A1-47)+(B8-3), (A1-47)+(B8-4), (A1-47)+(B8-5), (A1-47)+(B8-6), (A1-47)+(B8-7), (A1-47)+(B9-1), (A1-47)+(B9-2), (A1-47)+(B10-1), (A1-47)+(B10-2), (A1-47)+(B10-3), (A1-47)+(B10-4), (A1-47)+(B10-5), (A1-47)+(B11-1), (A1-47)+(B11-2), (A1-47)+(B11-2), (A1-48)+(B1-1), (A1-48)+(B1-2), (A1-48)+(B1-3), (A1-48)+(B1-4), (A1-48)+(B1-5), (A1-48)+(B1-6), (A1-48)+(B2-1), (A1-48)+(B2-2), (A1-48)+(B2-3), (A1-48)+(B2-4), (A1-48)+(B2-5), (A1-48)+(B2-6), (A1-48)+(B2-7), (A1-48)+(B2-8), (A1-48)+(B2-9), (A1-48)+(B2-10), (A1-48)+(B2-11), (A1-48)+(B2-12), (A1-48)+(B2-13), (A1-48)+(B2-14), (A1-48)+(B2-15), (A1-48)+(B2-16), (A1-48)+(B2-17), (A1-48)+(B2-18), (A1-48)+(B2-19), (A1-48)+(B2-20), (A1-48)+(B2-21), (A1-48)+(B2-22), (A1-48)+(B2-23), (A1-48)+(B2-24), (A1-48)+(B2-25), (A1-48)+(B2-26), (A1-48)+(B2-27), (A1-48)+(B2-28), (A1-48)+(B2-29), (A1-48)+(B3-1), (A1-48)+(B3-2), (A1-48)+(B4-1), (A1-48)+(B4-2), (A1-48)+(B4-3), (A1-48)+(B4-4), (A1-48)+(B4-5), (A1-48)+(B4-6), (A1-48)+(B4-7), (A1-48)+(B4-8), (A1-48)+(B4-9), (A1-48)+(B4-10), (A1-48)+(B4-11), (A1-48)+(B5-1), (A1-48)+(B5-2), (A1-48)+(B5-3), (A1-48)+(B5-4), (A1-48)+(B5-5), (A1-48)+(B6-1), (A1-48)+(B6-2), (A1-48)+(B6-3), (A1-48)+(B6-4), (A1-48)+(B6-5), (A1-48)+(B6-6), (A1-48)+(B7-1), (A1-48)+(B7-2), (A1-48)+(B7-3), (A1-48)+(B7-4), (A1-48)+(B7-5), (A1-48)+(B7-6), (A1-48)+(B7-7)), (A1-48)+(B7-7), (A1-48)+(B7-8), (A1-48)+(B8-1), (A1-48)+(B8-2), (A1-48)+(B8-3), (A1-48)+(B8-4), (A1-48)+(B8-5), (A1-48)+(B8-6), (A1-48)+(B8-7), (A1-48)+(B9-1), (A1-48)+(B9-2), (A1-48)+(B10-1), (A1-48)+(B10-2), (A1-48)+(B10-3), (A1-48)+(B10-4), (A1-48)+(B10-5), (A1-48)+(B11-1), (A1-48)+(B11-2), (A1-48)+(B11-2), (A1-49)+(B1-1), (A1-49)+(B1-2), (A1-49)+(B1-3), (A1-49)+(B1-4), (A1-49)+(B1-5), (A1-49)+(B1-6), (A1-49)+(B2-1), (A1-49)+(B2-2), (A1-49)+(B2-3), (A1-49)+(B2-4), (A1-49)+(B2-5), (A1-49)+(B2-6), (A1-49)+(B2-7), (A1-49)+(B2-8), (A1-49)+(B2-9), (A1-49)+(B2-10), (A1-49)+(B2-11), (A1-49)+(B2-12), (A1-49)+(B2-13), (A1-49)+(B2-14), (A1-49)+(B2-15), (A1-49)+(B2-16), (A1-49)+(B2-17), (A1-49)+(B2-18), (A1-49)+(B2-19), (A1-49)+(B2-20), (A1-49)+(B2-21), (A1-49)+(B2-22), (A1-49)+(B2-23), (A1-49)+(B2-24), (A1-49)+(B2-25), (A1-49)+(B2-26), (A1-49)+(B2-27), (A1-49)+(B2-28), (A1-49)+(B2-29), (A1-49)+(B3-1), (A1-49)+(B3-2), (A1-49)+(B4-1), (A1-49)+(B4-2), (A1-49)+(B4-3), (A1-49)+(B4-4), (A1-49)+(B4-5), (A1-49)+(B4-6), (A1-49)+(B4-7), (A1-49)+(B4-8), (A1-49)+(B4-9), (A1-49)+(B4-10), (A1-49)+(B4-11), (A1-49)+(B5-1), (A1-49)+(B5-2), (A1-49)+(B5-3), (A1-49)+(B5-4), (A1-49)+(B5-5), (A1-49)+(B6-1), (A1-49)+(B6-2), (A1-49)+(B6-3), (A1-49)+(B6-4), (A1-49)+(B6-5), (A1-49)+(B6-6), (A1-49)+(B7-1), (A1-49)+(B7-2), (A1-49)+(B7-3), (A1-49)+(B7-4), (A1-49)+(B7-5), (A1-49)+(B7-6), (A1-49)+(B7-7)), (A1-49)+(B7-7), (A1-49)+(B7-8), (A1-49)+(B8-1), (A1-49)+(B8-2), (A1-49)+(B8-3), (A1-49)+(B8-4), (A1-49)+(B8-5), (A1-49)+(B8-6), (A1-49)+(B8-7), (A1-49)+(B9-1), (A1-49)+(B9-2), (A1-49)+(B10-1), (A1-49)+(B10-2), (A1-49)+(B10-3), (A1-49)+(B10-4), (A1-49)+(B10-5), (A1-49)+(B11-1), (A1-49)+(B11-2), (A1-49)+(B11-2), (A1-50)+(B1-1), (A1-50)+(B1-2), (A1-50)+(B1-3), (A1-50)+(B1-4), (A1-50)+(B1-5), (A1-50)+(B1-6), (A1-50)+(B2-1), (A1-50)+(B2-2), (A1-50)+(B2-3), (A1-50)+(B2-4), (A1-50)+(B2-5), (A1-50)+(B2-6), (A1-50)+(B2-7), (A1-50)+(B2-8), (A1-50)+(B2-9), (A1-50)+(B2-10), (A1-50)+(B2-11), (A1-50)+(B2-12), (A1-50)+(B2-13), (A1-50)+(B2-14), (A1-50)+(B2-15), (A1-50)+(B2-16), (A1-50)+(B2-17), (A1-50)+(B2-18), (A1-50)+(B2-19), (A1-50)+(B2-20), (A1-50)+(B2-21), (A1-50)+(B2-22), (A1-50)+(B2-23), (A1-50)+(B2-24), (A1-50)+(B2-25), (A1-50)+(B2-26), (A1-50)+(B2-27), (A1-50)+(B2-28), (A1-50)+(B2-29), (A1-50)+(B3-1), (A1-50)+(B3-2), (A1-50)+(B4-1), (A1-50)+(B4-2), (A1-50)+(B4-3), (A1-50)+(B4-4), (A1-50)+(B4-5), (A1-50)+(B4-6), (A1-50)+(B4-7), (A1-50)+(B4-8), (A1-50)+(B4-9), (A1-50)+(B4-10), (A1-50)+(B4-11), (A1-50)+(B5-1), (A1-50)+(B5-2), (A1-50)+(B5-3), (A1-50)+(B5-4), (A1-50)+(B5-5), (A1-50)+(B6-1), (A1-50)+(B6-2), (A1-50)+(B6-3), (A1-50)+(B6-4), (A1-50)+(B6-5), (A1-50)+(B6-6), (A1-50)+(B7-1), (A1-50)+(B7-2), (A1-50)+(B7-3), (A1-50)+(B7-4), (A1-50)+(B7-5), (A1-50)+(B7-6), (A1-50)+(B7-7)), (A1-50)+(B7-7), (A1-50)+(B7-8), (A1-50)+(B8-1), (A1-50)+(B8-2), (A1-50)+(B8-3), (A1-50)+(B8-4), (A1-50)+(B8-5), (A1-50)+(B8-6), (A1-50)+(B8-7), (A1-50)+(B9-1), (A1-50)+(B9-2), (A1-50)+(B10-1), (A1-50)+(B10-2), (A1-50)+(B10-3), (A1-50)+(B10-4), (A1-50)+(B10-5), (A1-50)+(B11-1), (A1-50)+(B11-2), (A1-50)+(B11-2), (A1-51)+(B1-1), (A1-51)+(B1-2), (A1-51)+(B1-3), (A1-51)+(B1-4), (A1-51)+(B1-5), (A1-51)+(B1-6), (A1-51)+(B2-1), (A1-51)+(B2-2), (A1-51)+(B2-3), (A1-51)+(B2-4), (A1-51)+(B2-5), (A1-51)+(B2-6), (A1-51)+(B2-7), (A1-51)+(B2-8), (A1-51)+(B2-9), (A1-51)+(B2-10), (A1-51)+(B2-11), (A1-51)+(B2-12), (A1-51)+(B2-13), (A1-51)+(B2-14), (A1-51)+(B2-15), (A1-51)+(B2-16), (A1-51)+(B2-17), (A1-51)+(B2-18), (A1-51)+(B2-19), (A1-51)+(B2-20), (A1-51)+(B2-21), (A1-51)+(B2-22), (A1-51)+(B2-23), (A1-51)+(B2-24), (A1-51)+(B2-25), (A1-51)+(B2-26), (A1-51)+(B2-27), (A1-51)+(B2-28), (A1-51)+(B2-29), (A1-51)+(B3-1), (A1-51)+(B3-2), (A1-51)+(B4-1), (A1-51)+(B4-2), (A1-51)+(B4-3), (A1-51)+(B4-4), (A1-51)+(B4-5), (A1-51)+(B4-6), (A1-51)+(B4-7), (A1-51)+(B4-8), (A1-51)+(B4-9), (A1-51)+(B4-10), (A1-51)+(B4-11), (A1-51)+(B5-1), (A1-51)+(B5-2), (A1-51)+(B5-3), (A1-51)+(B5-4), (A1-51)+(B5-5), (A1-51)+(B6-1), (A1-51)+(B6-2), (A1-51)+(B6-3), (A1-51)+(B6-4), (A1-51)+(B6-5), (A1-51)+(B6-6), (A1-51)+(B7-1), (A1-51)+(B7-2), (A1-51)+(B7-3), (A1-51)+(B7-4), (A1-51)+(B7-5), (A1-51)+(B7-6), (A1-51)+(B7-7)), (A1-51)+(B7-7), (A1-51)+(B7-8), (A1-51)+(B8-1), (A1-51)+(B8-2), (A1-51)+(B8-3), (A1-51)+(B8-4), (A1-51)+(B8-5), (A1-51)+(B8-6), (A1-51)+(B8-7), (A1-51)+(B9-1), (A1-51)+(B9-2), (A1-51)+(B10-1), (A1-51)+(B10-2), (A1-51)+(B10-3), (A1-51)+(B10-4), (A1-51)+(B10-5), (A1-51)+(B11-1), (A1-51)+(B11-2), (A1-51)+(B11-2), (A1-52)+(B1-1), (A1-52)+(B1-2), (A1-52)+(B1-3), (A1-52)+(B1-4), (A1-52)+(B1-5), (A1-52)+(B1-6), (A1-52)+(B2-1), (A1-52)+(B2-2), (A1-52)+(B2-3), (A1-52)+(B2-4), (A1-52)+(B2-5), (A1-52)+(B2-6), (A1-52)+(B2-7), (A1-52)+(B2-8), (A1-52)+(B2-9), (A1-52)+(B2-10), (A1-52)+(B2-11), (A1-52)+(B2-12), (A1-52)+(B2-13), (A1-52)+(B2-14), (A1-52)+(B2-15), (A1-52)+(B2-16), (A1-52)+(B2-17), (A1-52)+(B2-18), (A1-52)+(B2-19), (A1-52)+(B2-20), (A1-52)+(B2-21), (A1-52)+(B2-22), (A1-52)+(B2-23), (A1-52)+(B2-24), (A1-52)+(B2-25), (A1-52)+(B2-26), (A1-52)+(B2-27), (A1-52)+(B2-28), (A1-52)+(B2-29), (A1-52)+(B3-1), (A1-52)+(B3-2), (A1-52)+(B4-1), (A1-52)+(B4-2), (A1-52)+(B4-3), (A1-52)+(B4-4), (A1-52)+(B4-5), (A1-52)+(B4-6), (A1-52)+(B4-7), (A1-52)+(B4-8), (A1-52)+(B4-9), (A1-52)+(B4-10), (A1-52)+(B4-11), (A1-52)+(B5-1), (A1-52)+(B5-2), (A1-52)+(B5-3), (A1-52)+(B5-4), (A1-52)+(B5-5), (A1-52)+(B6-1), (A1-52)+(B6-2), (A1-52)+(B6-3), (A1-52)+(B6-4), (A1-52)+(B6-5), (A1-52)+(B6-6), (A1-52)+(B7-1), (A1-52)+(B7-2), (A1-52)+(B7-3), (A1-52)+(B7-4), (A1-52)+(B7-5), (A1-52)+(B7-6), (A1-52)+(B7-7)), (A1-52)+(B7-7), (A1-52)+(B7-8), (A1-52)+(B8-1), (A1-52)+(B8-2), (A1-52)+(B8-3), (A1-52)+(B8-4), (A1-52)+(B8-5), (A1-52)+(B8-6), (A1-52)+(B8-7), (A1-52)+(B9-1), (A1-52)+(B9-2), (A1-52)+(B10-1), (A1-52)+(B10-2), (A1-52)+(B10-3), (A1-52)+(B10-4), (A1-52)+(B10-5), (A1-52)+(B11-1), (A1-52)+(B11-2), (A1-52)+(B11-2), (A1-53)+(B1-1), (A1-53)+(B1-2), (A1-53)+(B1-3), (A1-53)+(B1-4), (A1-53)+(B1-5), (A1-53)+(B1-6), (A1-53)+(B2-1), (A1-53)+(B2-2), (A1-53)+(B2-3), (A1-53)+(B2-4), (A1-53)+(B2-5), (A1-53)+(B2-6), (A1-53)+(B2-7), (A1-53)+(B2-8), (A1-53)+(B2-9), (A1-53)+(B2-10), (A1-53)+(B2-11), (A1-53)+(B2-12), (A1-53)+(B2-13), (A1-53)+(B2-14), (A1-53)+(B2-15), (A1-53)+(B2-16), (A1-53)+(B2-17), (A1-53)+(B2-18), (A1-53)+(B2-19), (A1-53)+(B2-20), (A1-53)+(B2-21), (A1-53)+(B2-22), (A1-53)+(B2-23), (A1-53)+(B2-24), (A1-53)+(B2-25), (A1-53)+(B2-26), (A1-53)+(B2-27), (A1-53)+(B2-28), (A1-53)+(B2-29), (A1-53)+(B3-1), (A1-53)+(B3-2), (A1-53)+(B4-1), (A1-53)+(B4-2), (A1-53)+(B4-3), (A1-53)+(B4-4), (A1-53)+(B4-5), (A1-53)+(B4-6), (A1-53)+(B4-7), (A1-53)+(B4-8), (A1-53)+(B4-9), (A1-53)+(B4-10), (A1-53)+(B4-11), (A1-53)+(B5-1), (A1-53)+(B5-2), (A1-53)+(B5-3), (A1-53)+

(B5-4), (A1-53)+(B5-5), (A1-53)+(B6-1), (A1-53)+(B6-2), (A1-53)+(B6-3), (A1-53)+(B6-4), (A1-53)+(B6-5), (A1-53)+(B6-6), (A1-53)+(B7-1), (A1-53)+(B7-2), (A1-53)+(B7-3), (A1-53)+(B7-4), (A1-53)+(B7-5), (A1-53)+(B7-6), (A1-53)+(B7-7)), (A1-53)+(B7-7), (A1-53)+(B7-8), (A1-53)+(B8-1), (A1-53)+(B8-2), (A1-53)+(B8-3), (A1-53)+(B8-4), (A1-53)+(B8-5), (A1-53)+(B8-6), (A1-53)+(B8-7), (A1-53)+(B9-1), (A1-53)+(B9-2), (A1-53)+(B10-1), (A1-53)+(B10-2), (A1-53)+(B10-3), (A1-53)+(B10-4), (A1-53)+(B10-5), (A1-53)+(B11-1), (A1-53)+(B11-2), (A1-53)+(B11-2), (A1-54)+(B1-1), (A1-54)+(B1-2), (A1-54)+(B1-3), (A1-54)+(B1-4), (A1-54)+(B1-5), (A1-54)+(B1-6), (A1-54)+(B2-1), (A1-54)+(B2-2), (A1-54)+(B2-3), (A1-54)+(B2-4), (A1-54)+(B2-5), (A1-54)+(B2-6), (A1-54)+(B2-7), (A1-54)+(B2-8), (A1-54)+(B2-9), (A1-54)+(B2-10), (A1-54)+(B2-11), (A1-54)+(B2-12), (A1-54)+(B2-13), (A1-54)+(B2-14), (A1-54)+(B2-15), (A1-54)+(B2-16), (A1-54)+(B2-17), (A1-54)+(B2-18), (A1-54)+(B2-19), (A1-54)+(B2-20), (A1-54)+(B2-21), (A1-54)+(B2-22), (A1-54)+(B2-23), (A1-54)+(B2-24), (A1-54)+(B2-25), (A1-54)+(B2-26), (A1-54)+(B2-27), (A1-54)+(B2-28), (A1-54)+(B2-29), (A1-54)+(B3-1), (A1-54)+(B3-2), (A1-54)+(B4-1), (A1-54)+(B4-2), (A1-54)+(B4-3), (A1-54)+(B4-4), (A1-54)+(B4-5), (A1-54)+(B4-6), (A1-54)+(B4-7), (A1-54)+(B4-8), (A1-54)+(B4-9), (A1-54)+(B4-10), (A1-54)+(B4-11), (A1-54)+(B5-1), (A1-54)+(B5-2), (A1-54)+(B5-3), (A1-54)+(B5-4), (A1-54)+(B5-5), (A1-54)+(B6-1), (A1-54)+(B6-2), (A1-54)+(B6-3), (A1-54)+(B6-4), (A1-54)+(B6-5), (A1-54)+(B6-6), (A1-54)+(B7-1), (A1-54)+(B7-2), (A1-54)+(B7-3), (A1-54)+(B7-4), (A1-54)+(B7-5), (A1-54)+(B7-6), (A1-54)+(B7-7)), (A1-54)+(B7-7), (A1-54)+(B7-8), (A1-54)+(B8-1), (A1-54)+(B8-2), (A1-54)+(B8-3), (A1-54)+(B8-4), (A1-54)+(B8-5), (A1-54)+(B8-6), (A1-54)+(B8-7), (A1-54)+(B9-1), (A1-54)+(B9-2), (A1-54)+(B10-1), (A1-54)+(B10-2), (A1-54)+(B10-3), (A1-54)+(B10-4), (A1-54)+(B10-5), (A1-54)+(B11-1), (A1-54)+(B11-2), (A1-54)+(B11-2), (A1-55)+(B1-1), (A1-55)+(B1-2), (A1-55)+(B1-3), (A1-55)+(B1-4), (A1-55)+(B1-5), (A1-55)+(B1-6), (A1-55)+(B2-1), (A1-55)+(B2-2), (A1-55)+(B2-3), (A1-55)+(B2-4), (A1-55)+(B2-5), (A1-55)+(B2-6), (A1-55)+(B2-7), (A1-55)+(B2-8), (A1-55)+(B2-9), (A1-55)+(B2-10), (A1-55)+(B2-11), (A1-55)+(B2-12), (A1-55)+(B2-13), (A1-55)+(B2-14), (A1-55)+(B2-15), (A1-55)+(B2-16), (A1-55)+(B2-17), (A1-55)+(B2-18), (A1-55)+(B2-19), (A1-55)+(B2-20), (A1-55)+(B2-21), (A1-55)+(B2-22), (A1-55)+(B2-23), (A1-55)+(B2-24), (A1-55)+(B2-25), (A1-55)+(B2-26), (A1-55)+(B2-27), (A1-55)+(B2-28), (A1-55)+(B2-29), (A1-55)+(B3-1), (A1-55)+(B3-2), (A1-55)+(B4-1), (A1-55)+(B4-2), (A1-55)+(B4-3), (A1-55)+(B4-4), (A1-55)+(B4-5), (A1-55)+(B4-6), (A1-55)+(B4-7), (A1-55)+(B4-8), (A1-55)+(B4-9), (A1-55)+(B4-10), (A1-55)+(B4-11), (A1-55)+(B5-1), (A1-55)+(B5-2), (A1-55)+(B5-3), (A1-55)+(B5-4), (A1-55)+(B5-5), (A1-55)+(B6-1), (A1-55)+(B6-2), (A1-55)+(B6-3), (A1-55)+(B6-4), (A1-55)+(B6-5), (A1-55)+(B6-6), (A1-55)+(B7-1), (A1-55)+(B7-2), (A1-55)+(B7-3), (A1-55)+(B7-4), (A1-55)+(B7-5), (A1-55)+(B7-6), (A1-55)+(B7-7)), (A1-55)+(B7-7), (A1-55)+(B7-8), (A1-55)+(B8-1), (A1-55)+(B8-2), (A1-55)+(B8-3), (A1-55)+(B8-4), (A1-55)+(B8-5), (A1-55)+(B8-6), (A1-55)+(B8-7), (A1-55)+(B9-1), (A1-55)+(B9-2), (A1-55)+(B10-1), (A1-55)+(B10-2), (A1-55)+(B10-3), (A1-55)+(B10-4), (A1-55)+(B10-5), (A1-55)+(B11-1), (A1-55)+(B11-2), (A1-55)+(B11-2), (A1-56)+(B1-1), (A1-56)+(B1-2), (A1-56)+(B1-3), (A1-56)+(B1-4), (A1-56)+(B1-5), (A1-56)+(B1-6), (A1-56)+(B2-1), (A1-56)+(B2-2), (A1-56)+(B2-3), (A1-56)+(B2-4), (A1-56)+(B2-5), (A1-56)+(B2-6), (A1-56)+(B2-7), (A1-56)+(B2-8), (A1-56)+(B2-9), (A1-56)+(B2-10), (A1-56)+(B2-11), (A1-56)+(B2-12), (A1-56)+(B2-13), (A1-56)+(B2-14), (A1-56)+(B2-15), (A1-56)+(B2-16), (A1-56)+(B2-17), (A1-56)+(B2-18), (A1-56)+(B2-19), (A1-56)+(B2-20), (A1-56)+(B2-21), (A1-56)+(B2-22), (A1-56)+(B2-23), (A1-56)+(B2-24), (A1-56)+(B2-25), (A1-56)+(B2-26), (A1-56)+(B2-27), (A1-56)+(B2-28), (A1-56)+(B2-29), (A1-56)+(B3-1), (A1-56)+(B3-2), (A1-56)+(B4-1), (A1-56)+(B4-2), (A1-56)+(B4-3), (A1-56)+(B4-4), (A1-56)+(B4-5), (A1-56)+(B4-6), (A1-56)+(B4-7), (A1-56)+(B4-8), (A1-56)+(B4-9), (A1-56)+(B4-10), (A1-56)+(B4-11), (A1-56)+(B5-1), (A1-56)+(B5-2), (A1-56)+(B5-3), (A1-56)+(B5-4), (A1-56)+(B5-5), (A1-56)+(B6-1), (A1-56)+(B6-2), (A1-56)+(B6-3), (A1-56)+(B6-4), (A1-56)+(B6-5), (A1-56)+(B6-6), (A1-56)+(B7-1), (A1-56)+(B7-2), (A1-56)+(B7-3), (A1-56)+(B7-4), (A1-56)+(B7-5), (A1-56)+(B7-6), (A1-56)+(B7-7)), (A1-56)+(B7-7), (A1-56)+(B7-8), (A1-56)+(B8-1), (A1-56)+(B8-2), (A1-56)+(B8-3), (A1-56)+(B8-4), (A1-56)+(B8-5), (A1-56)+(B8-6), (A1-56)+(B8-7), (A1-56)+(B9-1), (A1-56)+(B9-2), (A1-56)+(B10-1), (A1-56)+(B10-2), (A1-56)+(B10-3), (A1-56)+(B10-4), (A1-56)+(B10-5), (A1-56)+(B11-1), (A1-56)+(B11-2), (A1-56)+(B11-2), (A1-57)+(B1-1), (A1-57)+(B1-2), (A1-57)+(B1-3), (A1-57)+(B1-4), (A1-57)+(B1-5), (A1-57)+(B1-6), (A1-57)+(B2-1), (A1-57)+(B2-2), (A1-57)+(B2-3), (A1-57)+(B2-4), (A1-57)+(B2-5), (A1-57)+(B2-6), (A1-57)+(B2-7), (A1-57)+(B2-8), (A1-57)+(B2-9), (A1-57)+(B2-10), (A1-57)+(B2-11), (A1-57)+(B2-12), (A1-57)+(B2-13), (A1-57)+(B2-14), (A1-57)+(B2-15), (A1-57)+(B2-16), (A1-57)+(B2-17), (A1-57)+(B2-18), (A1-57)+(B2-19), (A1-57)+(B2-20), (A1-57)+(B2-21), (A1-57)+(B2-22), (A1-57)+(B2-23), (A1-57)+(B2-24), (A1-57)+(B2-25), (A1-57)+(B2-26), (A1-57)+(B2-27), (A1-57)+(B2-28), (A1-57)+(B2-29), (A1-57)+(B3-1), (A1-57)+(B3-2), (A1-57)+(B4-1), (A1-57)+(B4-2), (A1-57)+(B4-3), (A1-57)+(B4-4), (A1-57)+(B4-5), (A1-57)+(B4-6), (A1-57)+(B4-7), (A1-57)+(B4-8), (A1-57)+(B4-9), (A1-57)+(B4-10), (A1-57)+(B4-11), (A1-57)+(B5-1), (A1-57)+(B5-2), (A1-57)+(B5-3), (A1-57)+(B5-4), (A1-57)+(B5-5), (A1-57)+(B6-1), (A1-57)+(B6-2), (A1-57)+(B6-3), (A1-57)+(B6-4), (A1-57)+(B6-5), (A1-57)+(B6-6), (A1-57)+(B7-1), (A1-57)+(B7-2), (A1-57)+(B7-3), (A1-57)+(B7-4), (A1-57)+(B7-5), (A1-57)+(B7-6), (A1-57)+(B7-7)), (A1-57)+(B7-7), (A1-57)+(B7-8), (A1-57)+(B8-1), (A1-57)+(B8-2), (A1-57)+(B8-3), (A1-57)+(B8-4), (A1-57)+(B8-5), (A1-57)+(B8-6), (A1-57)+(B8-7), (A1-57)+(B9-1), (A1-57)+(B9-2), (A1-57)+(B10-1), (A1-57)+(B10-2), (A1-57)+(B10-3), (A1-57)+(B10-4), (A1-57)+(B10-5), (A1-57)+(B11-1), (A1-57)+(B11-2), (A1-57)+(B11-2), (A1-58)+(B1-1), (A1-58)+(B1-2), (A1-58)+(B1-3), (A1-58)+(B1-4), (A1-58)+(B1-5), (A1-58)+(B1-6), (A1-58)+(B2-1), (A1-58)+(B2-2), (A1-58)+(B2-3), (A1-58)+(B2-4), (A1-58)+(B2-5), (A1-58)+(B2-6), (A1-58)+(B2-7), (A1-58)+(B2-8), (A1-58)+(B2-9), (A1-58)+(B2-10), (A1-58)+(B2-11), (A1-58)+(B2-12), (A1-58)+(B2-13), (A1-58)+(B2-14), (A1-58)+(B2-15), (A1-58)+(B2-16), (A1-58)+(B2-17), (A1-58)+(B2-18), (A1-58)+(B2-19), (A1-58)+(B2-20), (A1-58)+(B2-21), (A1-58)+(B2-22), (A1-58)+(B2-23), (A1-58)+(B2-24), (A1-58)+(B2-25), (A1-58)+(B2-26), (A1-58)+(B2-27), (A1-58)+(B2-28), (A1-58)+(B2-29), (A1-58)+(B3-1), (A1-58)+(B3-2), (A1-58)+(B4-1), (A1-58)+(B4-2), (A1-58)+(B4-3), (A1-58)+(B4-4), (A1-58)+(B4-5), (A1-58)+(B4-6), (A1-58)+(B4-7), (A1-58)+(B4-8), (A1-58)+(B4-9), (A1-58)+(B4-10), (A1-58)+(B4-11), (A1-

58)+(B5-1), (A1-58)+(B5-2), (A1-58)+(B5-3), (A1-58)+(B5-4), (A1-58)+(B5-5), (A1-58)+(B6-1), (A1-58)+(B6-2), (A1-58)+(B6-3), (A1-58)+(B6-4), (A1-58)+(B6-5), (A1-58)+(B6-6), (A1-58)+(B7-1), (A1-58)+(B7-2), (A1-58)+(B7-3), (A1-58)+(B7-4), (A1-58)+(B7-5), (A1-58)+(B7-6), (A1-58)+(B7-7)), (A1-58)+(B7-7), (A1-58)+(B7-8), (A1-58)+(B8-1), (A1-58)+(B8-2), (A1-58)+(B8-3), (A1-58)+(B8-4), (A1-58)+(B8-5), (A1-58)+(B8-6), (A1-58)+(B8-7), (A1-58)+(B9-1), (A1-58)+(B9-2), (A1-58)+(B10-1), (A1-58)+(B10-2), (A1-58)+(B10-3), (A1-58)+(B10-4), (A1-58)+(B10-5), (A1-58)+(B11-1), (A1-58)+(B11-2), (A1-58)+(B11-2), (A1-59)+(B1-1), (A1-59)+(B1-2), (A1-59)+(B1-3), (A1-59)+(B1-4), (A1-59)+(B1-5), (A1-59)+(B1-6), (A1-59)+(B2-1), (A1-59)+(B2-2), (A1-59)+(B2-3), (A1-59)+(B2-4), (A1-59)+(B2-5), (A1-59)+(B2-6), (A1-59)+(B2-7), (A1-59)+(B2-8), (A1-59)+(B2-9), (A1-59)+(B2-10), (A1-59)+(B2-11), (A1-59)+(B2-12), (A1-59)+(B2-13), (A1-59)+(B2-14), (A1-59)+(B2-15), (A1-59)+(B2-16), (A1-59)+(B2-17), (A1-59)+(B2-18), (A1-59)+(B2-19), (A1-59)+(B2-20), (A1-59)+(B2-21), (A1-59)+(B2-22), (A1-59)+(B2-23), (A1-59)+(B2-24), (A1-59)+(B2-25), (A1-59)+(B2-26), (A1-59)+(B2-27), (A1-59)+(B2-28), (A1-59)+(B2-29), (A1-59)+(B3-1), (A1-59)+(B3-2), (A1-59)+(B4-1), (A1-59)+(B4-2), (A1-59)+(B4-3), (A1-59)+(B4-4), (A1-59)+(B4-5), (A1-59)+(B4-6), (A1-59)+(B4-7), (A1-59)+(B4-8), (A1-59)+(B4-9), (A1-59)+(B4-10), (A1-59)+(B4-11), (A1-59)+(B5-1), (A1-59)+(B5-2), (A1-59)+(B5-3), (A1-59)+(B5-4), (A1-59)+(B5-5), (A1-59)+(B6-1), (A1-59)+(B6-2), (A1-59)+(B6-3), (A1-59)+(B6-4), (A1-59)+(B6-5), (A1-59)+(B6-6), (A1-59)+(B7-1), (A1-59)+(B7-2), (A1-59)+(B7-3), (A1-59)+(B7-4), (A1-59)+(B7-5), (A1-59)+(B7-6), (A1-59)+(B7-7)), (A1-59)+(B7-7), (A1-59)+(B7-8), (A1-59)+(B8-1), (A1-59)+(B8-2), (A1-59)+(B8-3), (A1-59)+(B8-4), (A1-59)+(B8-5), (A1-59)+(B8-6), (A1-59)+(B8-7), (A1-59)+(B9-1), (A1-59)+(B9-2), (A1-59)+(B10-1), (A1-59)+(B10-2), (A1-59)+(B10-3), (A1-59)+(B10-4), (A1-59)+(B10-5), (A1-59)+(B11-1), (A1-59)+(B11-2), (A1-59)+(B11-2), (A1-60)+(B1-1), (A1-60)+(B1-2), (A1-60)+(B1-3), (A1-60)+(B1-4), (A1-60)+(B1-5), (A1-60)+(B1-6), (A1-60)+(B2-1), (A1-60)+(B2-2), (A1-60)+(B2-3), (A1-60)+(B2-4), (A1-60)+(B2-5), (A1-60)+(B2-6), (A1-60)+(B2-7), (A1-60)+(B2-8), (A1-60)+(B2-9), (A1-60)+(B2-10), (A1-60)+(B2-11), (A1-60)+(B2-12), (A1-60)+(B2-13), (A1-60)+(B2-14), (A1-60)+(B2-15), (A1-60)+(B2-16), (A1-60)+(B2-17), (A1-60)+(B2-18), (A1-60)+(B2-19), (A1-60)+(B2-20), (A1-60)+(B2-21), (A1-60)+(B2-22), (A1-60)+(B2-23), (A1-60)+(B2-24), (A1-60)+(B2-25), (A1-60)+(B2-26), (A1-60)+(B2-27), (A1-60)+(B2-28), (A1-60)+(B2-29), (A1-60)+(B3-1), (A1-60)+(B3-2), (A1-60)+(B4-1), (A1-60)+(B4-2), (A1-60)+(B4-3), (A1-60)+(B4-4), (A1-60)+(B4-5), (A1-60)+(B4-6), (A1-60)+(B4-7), (A1-60)+(B4-8), (A1-60)+(B4-9), (A1-60)+(B4-10), (A1-60)+(B4-11), (A1-60)+(B5-1), (A1-60)+(B5-2), (A1-60)+(B5-3), (A1-60)+(B5-4), (A1-60)+(B5-5), (A1-60)+(B6-1), (A1-60)+(B6-2), (A1-60)+(B6-3), (A1-60)+(B6-4), (A1-60)+(B6-5), (A1-60)+(B6-6), (A1-60)+(B7-1), (A1-60)+(B7-2), (A1-60)+(B7-3), (A1-60)+(B7-4), (A1-60)+(B7-5), (A1-60)+(B7-6), (A1-60)+(B7-7), (A1-60)+(B7-7), (A1-60)+(B7-8), (A1-60)+(B8-1), (A1-60)+(B8-2), (A1-60)+(B8-3), (A1-60)+(B8-4), (A1-60)+(B8-5), (A1-60)+(B8-6), (A1-60)+(B8-7), (A1-60)+(B9-1), (A1-60)+(B9-2), (A1-60)+(B10-1), (A1-60)+(B10-2), (A1-60)+(B10-3), (A1-60)+(B10-4), (A1-60)+(B10-5), (A1-60)+(B11-1), (A1-60)+(B11-2), (A1-60)+(B11-2), (A1-61)+(B1-1), (A1-61)+(B1-2), (A1-61)+(B1-3), (A1-61)+(B1-4), (A1-61)+(B1-5), (A1-61)+(B1-6), (A1-61)+(B2-1), (A1-61)+(B2-2), (A1-61)+(B2-3), (A1-61)+(B2-4), (A1-61)+(B2-5), (A1-61)+(B2-6), (A1-61)+(B2-7), (A1-61)+(B2-8), (A1-61)+(B2-9), (A1-61)+(B2-10), (A1-61)+(B2-11), (A1-61)+(B2-12), (A1-61)+(B2-13), (A1-61)+(B2-14), (A1-61)+(B2-15), (A1-61)+(B2-16), (A1-61)+(B2-17), (A1-61)+(B2-18), (A1-61)+(B2-19), (A1-61)+(B2-20), (A1-61)+(B2-21), (A1-61)+(B2-22), (A1-61)+(B2-23), (A1-61)+(B2-24), (A1-61)+(B2-25), (A1-61)+(B2-26), (A1-61)+(B2-27), (A1-61)+(B2-28), (A1-61)+(B2-29), (A1-61)+(B3-1), (A1-61)+(B3-2), (A1-61)+(B4-1), (A1-61)+(B4-2), (A1-61)+(B4-3), (A1-61)+(B4-4), (A1-61)+(B4-5), (A1-61)+(B4-6), (A1-61)+(B4-7), (A1-61)+(B4-8), (A1-61)+(B4-9), (A1-61)+(B4-10), (A1-61)+(B4-11), (A1-61)+(B5-1), (A1-61)+(B5-2), (A1-61)+(B5-3), (A1-61)+(B5-4), (A1-61)+(B5-5), (A1-61)+(B6-1), (A1-61)+(B6-2), (A1-61)+(B6-3), (A1-61)+(B6-4), (A1-61)+(B6-5), (A1-61)+(B6-6), (A1-61)+(B7-1), (A1-61)+(B7-2), (A1-61)+(B7-3), (A1-61)+(B7-4), (A1-61)+(B7-5), (A1-61)+(B7-6), (A1-61)+(B7-7)), (A1-61)+(B7-7), (A1-61)+(B7-8), (A1-61)+(B8-1), (A1-61)+(B8-2), (A1-61)+(B8-3), (A1-61)+(B8-4), (A1-61)+(B8-5), (A1-61)+(B8-6), (A1-61)+(B8-7), (A1-61)+(B9-1), (A1-61)+(B9-2), (A1-61)+(B10-1), (A1-61)+(B10-2), (A1-61)+(B10-3), (A1-61)+(B10-4), (A1-61)+(B10-5), (A1-61)+(B11-1), (A1-61)+(B11-2), (A1-61)+(B11-2), (A2-1)+(B1-1), (A2-1)+(B1-2), (A2-1)+(B1-3), (A2-1)+(B1-4), (A2-1)+(B1-5), (A2-1)+(B1-6), (A2-1)+(B2-1), (A2-1)+(B2-2), (A2-1)+(B2-3), (A2-1)+(B2-4), (A2-1)+(B2-5), (A2-1)+(B2-6), (A2-1)+(B2-7), (A2-1)+(B2-8), (A2-1)+(B2-9), (A2-1)+(B2-10), (A2-1)+(B2-11), (A2-1)+(B2-12), (A2-1)+(B2-13), (A2-1)+(B2-14), (A2-1)+(B2-15), (A2-1)+(B2-16), (A2-1)+(B2-17), (A2-1)+(B2-18), (A2-1)+(B2-19), (A2-1)+(B2-20), (A2-1)+(B2-21), (A2-1)+(B2-22), (A2-1)+(B2-23), (A2-1)+(B2-24), (A2-1)+(B2-25), (A2-1)+(B2-26), (A2-1)+(B2-27), (A2-1)+(B2-28), (A2-1)+(B2-29), (A2-1)+(B3-1), (A2-1)+(B3-2), (A2-1)+(B4-1), (A2-1)+(B4-2), (A2-1)+(B4-3), (A2-1)+(B4-4), (A2-1)+(B4-5), (A2-1)+(B4-6), (A2-1)+(B4-7), (A2-1)+(B4-8), (A2-1)+(B4-9), (A2-1)+(B4-10), (A2-1)+(B4-11), (A2-1)+(B5-1), (A2-1)+(B5-2), (A2-1)+(B5-3), (A2-1)+(B5-4), (A2-1)+(B5-5), (A2-1)+(B6-1), (A2-1)+(B6-2), (A2-1)+(B6-3), (A2-1)+(B6-4), (A2-1)+(B6-5), (A2-1)+(B6-6), (A2-1)+(B7-1), (A2-1)+(B7-2), (A2-1)+(B7-3), (A2-1)+(B7-4), (A2-1)+(B7-5), (A2-1)+(B7-6), (A2-1)+(B7-7)), (A2-1)+(B7-7), (A2-1)+(B7-8), (A2-1)+(B8-1), (A2-1)+(B8-2), (A2-1)+(B8-3), (A2-1)+(B8-4), (A2-1)+(B8-5), (A2-1)+(B8-6), (A2-1)+(B8-7), (A2-1)+(B9-1), (A2-1)+(B9-2), (A2-1)+(B10-1), (A2-1)+(B10-2), (A2-1)+(B10-3), (A2-1)+(B10-4), (A2-1)+(B10-5), (A2-1)+(B11-1), (A2-1)+(B11-2), (A2-1)+(B11-2), (A2-2)+(B1-1), (A2-2)+(B1-2), (A2-2)+(B1-3), (A2-2)+(B1-4), (A2-2)+(B1-5), (A2-2)+(B1-6), (A2-2)+(B2-1), (A2-2)+(B2-2), (A2-2)+(B2-3), (A2-2)+(B2-4), (A2-2)+(B2-5), (A2-2)+(B2-6), (A2-2)+(B2-7), (A2-2)+(B2-8), (A2-2)+(B2-9), (A2-2)+(B2-10), (A2-2)+(B2-11), (A2-2)+(B2-12), (A2-2)+(B2-13), (A2-2)+(B2-14), (A2-2)+(B2-15), (A2-2)+(B2-16), (A2-2)+(B2-17), (A2-2)+(B2-18), (A2-2)+(B2-19), (A2-2)+(B2-20), (A2-2)+(B2-21), (A2-2)+(B2-22), (A2-2)+(B2-23), (A2-2)+(B2-24), (A2-2)+(B2-25), (A2-2)+(B2-26), (A2-2)+(B2-27), (A2-2)+(B2-28), (A2-2)+(B2-29), (A2-2)+(B3-1), (A2-2)+(B3-2), (A2-2)+(B4-1), (A2-2)+(B4-2), (A2-2)+(B4-3), (A2-2)+(B4-4), (A2-2)+(B4-5), (A2-2)+(B4-6), (A2-2)+(B4-7), (A2-2)+(B4-8), (A2-2)+(B4-9), (A2-2)+(B4-10), (A2-2)+(B4-11), (A2-2)+(B5-1), (A2-2)+(B5-2), (A2-2)+(B5-3), (A2-2)+

(B5-4), (A2-2)+(B5-5), (A2-2)+(B6-1), (A2-2)+(B6-2), (A2-2)+(B6-3), (A2-2)+(B6-4), (A2-2)+(B6-5), (A2-2)+(B6-6), (A2-2)+(B7-1), (A2-2)+(B7-2), (A2-2)+(B7-3), (A2-2)+(B7-4), (A2-2)+(B7-5), (A2-2)+(B7-6), (A2-2)+(B7-7)), (A2-2)+(B7-7), (A2-2)+(B7-8), (A2-2)+(B8-1), (A2-2)+(B8-2), (A2-2)+(B8-3), (A2-2)+(B8-4), (A2-2)+(B8-5), (A2-2)+(B8-6), (A2-2)+(B8-7), (A2-2)+(B9-1), (A2-2)+(B9-2), (A2-2)+(B10-1), (A2-2)+(B10-2), (A2-2)+(B10-3), (A2-2)+(B10-4), (A2-2)+(B10-5), (A2-2)+(B11-1), (A2-2)+(B11-2), (A2-2)+(B11-2), (A2-3)+(B1-1), (A2-3)+(B1-2), (A2-3)+(B1-3), (A2-3)+(B1-4), (A2-3)+(B1-5), (A2-3)+(B1-6), (A2-3)+(B2-1), (A2-3)+(B2-2), (A2-3)+(B2-3), (A2-3)+(B2-4), (A2-3)+(B2-5), (A2-3)+(B2-6), (A2-3)+(B2-7), (A2-3)+(B2-8), (A2-3)+(B2-9), (A2-3)+(B2-10), (A2-3)+(B2-11), (A2-3)+(B2-12), (A2-3)+(B2-13), (A2-3)+(B2-14), (A2-3)+(B2-15), (A2-3)+(B2-16), (A2-3)+(B2-17), (A2-3)+(B2-18), (A2-3)+(B2-19), (A2-3)+(B2-20), (A2-3)+(B2-21), (A2-3)+(B2-22), (A2-3)+(B2-23), (A2-3)+(B2-24), (A2-3)+(B2-25), (A2-3)+(B2-26), (A2-3)+(B2-27), (A2-3)+(B2-28), (A2-3)+(B2-29), (A2-3)+(B3-1), (A2-3)+(B3-2), (A2-3)+(B4-1), (A2-3)+(B4-2), (A2-3)+(B4-3), (A2-3)+(B4-4), (A2-3)+(B4-5), (A2-3)+(B4-6), (A2-3)+(B4-7), (A2-3)+(B4-8), (A2-3)+(B4-9), (A2-3)+(B4-10), (A2-3)+(B4-11), (A2-3)+(B5-1), (A2-3)+(B5-2), (A2-3)+(B5-3), (A2-3)+(B5-4), (A2-3)+(B5-5), (A2-3)+(B6-1), (A2-3)+(B6-2), (A2-3)+(B6-3), (A2-3)+(B6-4), (A2-3)+(B6-5), (A2-3)+(B6-6), (A2-3)+(B7-1), (A2-3)+(B7-2), (A2-3)+(B7-3), (A2-3)+(B7-4), (A2-3)+(B7-5), (A2-3)+(B7-6), (A2-3)+(B7-7)), (A2-3)+(B7-7), (A2-3)+(B7-8), (A2-3)+(B8-1), (A2-3)+(B8-2), (A2-3)+(B8-3), (A2-3)+(B8-4), (A2-3)+(B8-5), (A2-3)+(B8-6), (A2-3)+(B8-7), (A2-3)+(B9-1), (A2-3)+(B9-2), (A2-3)+(B10-1), (A2-3)+(B10-2), (A2-3)+(B10-3), (A2-3)+(B10-4), (A2-3)+(B10-5), (A2-3)+(B11-1), (A2-3)+(B11-2), (A2-3)+(B11-2), (A2-4)+(B1-1), (A2-4)+(B1-2), (A2-4)+(B1-3), (A2-4)+(B1-4), (A2-4)+(B1-5), (A2-4)+(B1-6), (A2-4)+(B2-1), (A2-4)+(B2-2), (A2-4)+(B2-3), (A2-4)+(B2-4), (A2-4)+(B2-5), (A2-4)+(B2-6), (A2-4)+(B2-7), (A2-4)+(B2-8), (A2-4)+(B2-9), (A2-4)+(B2-10), (A2-4)+(B2-11), (A2-4)+(B2-12), (A2-4)+(B2-13), (A2-4)+(B2-14), (A2-4)+(B2-15), (A2-4)+(B2-16), (A2-4)+(B2-17), (A2-4)+(B2-18), (A2-4)+(B2-19), (A2-4)+(B2-20), (A2-4)+(B2-21), (A2-4)+(B2-22), (A2-4)+(B2-23), (A2-4)+(B2-24), (A2-4)+(B2-25), (A2-4)+(B2-26), (A2-4)+(B2-27), (A2-4)+(B2-28), (A2-4)+(B2-29), (A2-4)+(B3-1), (A2-4)+(B3-2), (A2-4)+(B4-1), (A2-4)+(B4-2), (A2-4)+(B4-3), (A2-4)+(B4-4), (A2-4)+(B4-5), (A2-4)+(B4-6), (A2-4)+(B4-7), (A2-4)+(B4-8), (A2-4)+(B4-9), (A2-4)+(B4-10), (A2-4)+(B4-11), (A2-4)+(B5-1), (A2-4)+(B5-2), (A2-4)+(B5-3), (A2-4)+(B5-4), (A2-4)+(B5-5), (A2-4)+(B6-1), (A2-4)+(B6-2), (A2-4)+(B6-3), (A2-4)+(B6-4), (A2-4)+(B6-5), (A2-4)+(B6-6), (A2-4)+(B7-1), (A2-4)+(B7-2), (A2-4)+(B7-3), (A2-4)+(B7-4), (A2-4)+(B7-5), (A2-4)+(B7-6), (A2-4)+(B7-7)), (A2-4)+(B7-7), (A2-4)+(B7-8), (A2-4)+(B8-1), (A2-4)+(B8-2), (A2-4)+(B8-3), (A2-4)+(B8-4), (A2-4)+(B8-5), (A2-4)+(B8-6), (A2-4)+(B8-7), (A2-4)+(B9-1), (A2-4)+(B9-2), (A2-4)+(B10-1), (A2-4)+(B10-2), (A2-4)+(B10-3), (A2-4)+(B10-4), (A2-4)+(B10-5), (A2-4)+(B11-1), (A2-4)+(B11-2), (A2-4)+(B11-2).

In the inventive herbicidal compositions, the application rate of the herbicides of the general formula (I) (component A) is typically 1 to 500 g of active ingredient (a.i.) per hectare, preferably 2 to 300 g of a.i./ha, more preferably 3 to 200 g of a.i./ha. The application rate of the herbicides of component B is typically 1 to 5000 g of active ingredient per hectare, preferably 2 to 3000 g of a.i./ha, more preferably 3 to 2000 g of a.i./ha. The application rate of the safeners of component C is typically 1 to 500 g of active ingredient per hectare, preferably 2 to 400 g of a.i./ha, more preferably 3 to 300 g of a.i./ha.

On application of the inventive herbicidal compositions, a very broad spectrum of harmful plants is controlled pre-emergence and post-emergence, for example annual and perennial mono- or dicotyledonous weeds and unwanted crop plants. The inventive herbicidal compositions are particularly suitable for use in crops such as cereals, corn, rice, soya, oilseed rape, sugar beet, cotton, sugar cane, and also for use in perennial crops, plantations and on non-crop land. They are likewise highly suitable for use in transgenic crops of corn, cereals, sugar beet, rice, cotton and *Glycine max.* (e.g. RR soya or LL soya) and crossbreeds thereof), *Phaseolus, Pisum, Vicia* and *Arachis*, or vegetable crops from various botanical groups such as potato, leek, cabbage, carrot, tomato, onion, and also perennial and plantation crops such as pome fruit and stone fruit, soft fruit, wine, Hevea, bananas, sugar cane, coffee, tea, citrus, nut plantations, lawn, palm crops and forest crops. For the use of the inventive herbicide-safener combinations (A)+(B), these crops are likewise preferred, particular preference being given to use in cereals (e.g. wheat, barley, rye, oats), rice, corn, millet/sorghum, sugar beet, sugar cane, sunflower, oilseed rape and cotton. The herbicide-safener combinations (A)+(B) can also be used in tolerant and non-tolerant mutant crops and tolerant and non-tolerant transgenic crops, preferably of corn, rice, cereals, oilseed rape, cotton, sugar beet and soya, for example those resistant to imidazolinone herbicides, atrazine, glufosinate, glyphosate, 2,4 D, dicamba and herbicides from the group of the inhibitors of hydroxyphenylpyruvate dioxygenase, such as sulcotrione, mesotrione, tembotrione, tefuryltrione, benzobicyclon, bicyclopyrone and ketospiradox.

A herbicidally effective amount in the context of the invention means an amount of one or more herbicides capable of adversely affecting plant growth. An antidotically effective amount in the context of the invention means an amount of one or more safeners capable of reducing the phytotoxic effect of crop protection active ingredients (for example of herbicides) on crop plants.

According to their properties, the safeners (C) present in the inventive herbicidal compositions can also be used for pretreatment of the seed of the crop plant (for example for dressing of the seed) or introduced into the seed furrows prior to sowing or employed together with the herbicide prior to or after emergence of the plants. Pre-emergence treatment includes both the treatment of the area under cultivation (including any water present in the area under cultivation, for example in the case of applications to rice) prior to sowing and the treatment of the areas under cultivation in which seeds have been sown but which are not yet covered by growing plants. Preference is given to application together with the herbicide. For this purpose, it is possible to use tank-mixes or ready-made formulations.

In a preferred embodiment, the seed (for example grains, seeds or vegetative propagation organs such as tubers or budded parts of shoots) or seedlings are pretreated with the safeners (C), optionally in combination with other active agrochemical ingredients. For pretreatment of the seed, the active ingredients can be applied to the seed, for example by dressing, or the active ingredients and the seed can be added to water or other solvents, and the active ingredients can be taken up, for example, by adsorption or diffusion in a dipping process or by swelling or pre-germination. For pretreatment of seedlings, the young plants can be contacted with the safeners, optionally in combination with other active agrochemical ingredients, for example by spraying, dipping or watering, and then transplanted and optionally aftertreated with the herbicides (A) and (B).

The seed or seedlings can be treated with the safeners (C) alone or together with other active agrochemical ingredients—such as fungicides, insecticides or plant fortifiers, fertilizers or swelling and germination accelerators. After the pretreatment application, the safeners may subsequently be applied once again before, after or together with one or more herbicides of the formula (I) (A) and herbicides (B), possibly also in combination with other known herbicides. The pretreatment of the seed or seedlings can achieve improved long-term efficacy of the safeners.

The present invention thus further provides a method of controlling unwanted plants in plant crops, which is characterized in that components (A), (B) and optionally (C) of the inventive herbicidal compositions are deployed, for example separately or together, on the plants (for example harmful plants such as mono- or dicotyledonous weeds or unwanted crop plants), the seed (for example grains, seeds or vegetative propagation organs such as tubers or budded parts of shoots) or the area on which the plants grow (for example the area under cultivation). One or more safeners (C) may be applied before, after or simultaneously with the herbicide(s) of the general formula (I) (A) and the herbicides (B) to the plants, the seed or the area on which the plants grow (for example the area under cultivation). In a preferred embodiment, the safeners (C) are used for seed treatment.

Unwanted plants are understood to mean all plants which grow at sites where they are unwanted. These may, for example, be harmful plants (for example monocotyledonous or dicotyledonous weeds or unwanted crop plants), including, for example, those which are resistant to certain active herbicidal compounds, such as glyphosate, atrazine, glufosinate or imidazolinone herbicides. Monocotyledonous weeds are classified, for example, in the genera *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera, Phalaris*. Dicotyledonous weeds are classified, for example, in the genera *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum, Euphorbia, Kochia, Biden, Stellaria*.

The invention also provides for the use of the inventive herbicidal compositions for controlling unwanted vegetation, preferably in plant crops.

The inventive herbicidal compositions can be prepared by known methods, for example as mixed formulations of the individual components, optionally with further active ingredients, additives and/or customary formulation auxiliaries, and these are then applied in a customary manner after dilution with water, or as tank mixes by joint dilution of the separately formulated or partly separately formulated individual components with water. Likewise possible is the application at different times (split application) of the separately formulated or partly separately formulated individual components. It is also possible to apply the individual components or the herbicidal compositions in a plurality of portions (sequential application), for example by pre-emergence applications followed by post-emergence applications or by early post-emergence applications followed by medium or late post-emergence applications. Preference is given to the joint or immediately successive application of the active ingredients in the respective combination.

The inventive herbicidal compositions can also be used for control of harmful plants in crops of genetically modified plants which are known or are yet to be developed.

In general, transgenic plants are characterized by particular advantageous properties, for example by resistances to certain pesticides, in particular certain herbicides, resistances to plant diseases or pathogens of plant diseases, such as certain insects or microorganisms such as fungi, bacteria or viruses. Other particular properties relate, for example, to the harvested material with regard to quantity, quality, storability, composition and specific constituents. For instance, there are known transgenic plants with an elevated starch content or altered starch quality, or those with a different fatty acid composition in the harvested material. Other particular properties may be tolerance or resistance to abiotic stressors, for example heat, low temperatures, drought, salinity and ultraviolet radiation.

Preference is given to the use of the inventive herbicidal compositions in economically important transgenic crops of useful plants and ornamentals, for example of cereals such as wheat, barley, rye, oats, millet/sorghum, rice, cassava and corn, or else crops of sugar beet, cotton, soybean, oilseed rape, potato, tomato, peas and other vegetables.

Conventional ways of producing novel plants which have modified properties in comparison to existing plants consist, for example, in traditional breeding methods and the generation of mutants. Alternatively, novel plants with modified properties can be generated with the aid of recombinant methods (see, for example, EP-A-0221044, EP-A-0131624). For example, there have been descriptions in several cases of:

genetic modifications of crop plants for the purpose of modifying the starch synthesized in the plants (for example WO 92/11376, WO 92/14827, WO 91/19806), transgenic crop plants which are resistant to particular herbicides of the glufosinate type (cf., for example, EP-A-0242236, EP-A-242246) or glyphosate type (WO 92/00377) or of the sulfonylurea type (EP-A-0257993, U.S. Pat. No. 5,013,659), transgenic crop plants, for example cotton, with the ability to produce *Bacillus thuringiensis* toxins (Bt toxins), which make the plants resistant to particular pests (EP-A-0142924, EP-A-0193259), transgenic crop plants with a modified fatty acid composition (WO 91/13972), genetically modified crop plants with novel constituents or secondary metabolites, for example novel phytoalexins, which bring about an increased disease resistance (EPA 309862, EPA0464461), genetically modified plants having reduced photorespiration, which have higher yields and higher stress tolerance (EPA 0305398), transgenic crop plants which produce pharmaceutically or diagnostically important proteins ("molecular pharming"), transgenic crop plants which feature higher yields or better quality, transgenic crop plants which feature a combination, for example, of the abovementioned novel properties ("gene stacking").

Numerous molecular biology techniques which can be used to produce novel transgenic plants with modified properties are known in principle; see, for example, I. Potrykus and G. Spangenberg (eds.) Gene Transfer to Plants, Springer Lab Manual (1995), Springer Verlag Berlin, Heidelberg, or Christou, "Trends in Plant Science" 1 (1996) 423-431).

For such recombinant manipulations, nucleic acid molecules which allow mutagenesis or sequence alteration by recombination of DNA sequences can be introduced into plasmids. With the aid of standard methods, it is possible, for example, to undertake base exchanges, remove parts of sequences or add natural or synthetic sequences. For the connection of the DNA fragments to one another, it is possible to add adapters or linkers to the fragments; see, for example, Sambrook et al., 1989, Molecular Cloning, A Laboratory Manual, 2nd ed., Cold Spring Harbor Laboratory Press, Cold Spring Harbor, N.Y.; or Winnacker "Gene und Klone", VCH Weinheim, 2nd edition, 1996.

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product.

To this end, it is firstly possible to use DNA molecules which encompass the entire coding sequence of a gene product inclusive of any flanking sequences which may be present, and also DNA molecules which only encompass portions of the coding sequence, in which case it is necessary for these portions to be long enough to have an antisense effect in the cells. It is also possible to use DNA sequences which have a high degree of homology to the coding sequences of a gene product, but are not completely identical to them.

When expressing nucleic acid molecules in plants, the protein synthesized may be localized in any desired compartment of the plant cell. However, to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants may be plants of any desired plant species, i.e. not only monocotyledonous but also dicotyledonous plants.

Thus, transgenic plants can be obtained whose properties are altered by overexpression, suppression or inhibition of homologous (=natural) genes or gene sequences or expression of heterologous (=foreign) genes or gene sequences.

Preferably the inventive compositions can be used in transgenic crops which are resistant to growth regulators such as, for example, dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active ingredients.

On employment of the inventive compositions in transgenic crops, not only do the effects toward harmful plants observed in other crops occur, but often also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also provides for the use of the inventive compositions for control of harmful plants in transgenic crop plants.

Preference is given to the use of the inventive compositions in economically important transgenic crops of useful plants and ornamentals, for example of cereals (e.g. wheat, barley, rye, oats), millet/sorghum, rice, cassava and corn, or else crops of sugar beet, cotton, soybean, oilseed rape, potato, tomato, peas and other vegetable crops.

The invention therefore also provides for the use of the inventive compositions for control of harmful plants in transgenic crop plants or crop plants having tolerance through selective breeding.

The herbicides (A), (B) and the safeners (C) can be converted together or separately to customary formulations, for example for application by spraying, watering, sprinkling and seed dressing, such as solutions, emulsions, suspensions, powders, foams, pastes, granules, aerosols, active ingredient-impregnated natural and synthetic substances, microencapsulations in polymeric substances. The formulations may comprise the customary auxiliaries and additives.

These formulations are produced in a known manner, for example by mixing the active ingredients with extenders, i.e. liquid solvents, pressurized liquefied gases and/or solid carriers, optionally with use of surfactants, i.e. emulsifiers and/or dispersants and/or foam formers.

If the extender used is water, it is also possible to use, for example, organic solvents as auxiliary solvents. Useful liquid solvents essentially include: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and the ethers and esters thereof, ketones such as acetone, methyl ethyl ketone, methyl isobutyl ketone or cyclohexanone, strongly polar solvents such as dimethylformamide or dimethyl sulfoxide, and water.

Useful solid carriers include: for example ammonium salts and ground natural minerals, such as kaolins, clays, talc, chalk, quartz, attapulgite, montmorillonite or diatomaceous earth, and ground synthetic minerals, such as finely divided silica, alumina and silicates; useful solid carriers for granules include: for example crushed and fractionated natural rocks, such as calcite, marble, pumice, sepiolite, dolomite and synthetic granules of inorganic and organic flours, and granules of organic material, such as sawdust, coconut shells, corn cobs and tobacco stalks; useful emulsifiers and/or foam formers include: for example nonionic and anionic emulsifiers, such as polyoxyethylene fatty acid esters, polyoxyethylene fatty alcohol ethers, e.g. alkylaryl polyglycol ethers, alkylsulfonates, alkylsulfates, arylsulfonates and protein hydrolyzates; useful dispersants include: for example lignosulfite waste liquors and methylcellulose.

In the formulations, it is possible to use tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids. Further additives may be mineral and vegetable oils.

It is possible to use colorants such as inorganic pigments, for example iron oxide, titanium oxide and Prussian blue, and organic colorants such as alizarin colorants, azo colorants and metal phthalocyanine colorants, and trace nutrients such as salts of iron, manganese, boron, copper, cobalt, molybdenum and zinc.

The formulations contain generally between 0.1 and 95 percent by weight of active ingredient, preferably between 0.5 and 90% by weight.

As such or in their formulations, the herbicides (A), (B) and the safeners (C) can also be used as a mixture with other active agrochemical ingredients for controlling unwanted vegetation, for example for controlling weeds or for controlling unwanted crop plants, finished formulations or tank mixes, for example, being possible.

Also possible are mixtures with other known active ingredients such as fungicides, insecticides, acaricides, nematicides, bird antifeedants, plant nutrients and soil structure improvers, and likewise with additives and formulation auxiliaries customary in crop protection.

The herbicides (A), (B) and the safeners (C) can be used as such, in the form of their formulations or the use forms prepared therefrom by further dilution, such as ready-to-use solutions, suspensions, emulsions, powders, pastes and granules. Application is typically accomplished, for example, by watering, sprinkling, spraying, broadcasting.

The active ingredients can be deployed on the plants, plant parts, seed or area under cultivation (farmland), preferably on the seed or the green plants and plant parts, and optionally additionally on the farmland. One means of application is the co-deployment of the active ingredients in the form of tank-mixes, by mixing the optimally formulated concentrated formulations of the individual active ingredients together in the tank with water and deploying the spray liquor obtained.

A co-formulation of the inventive combination of active ingredients (A), (B) and (C) has the advantage of easier applicability, because the amounts of the components can already be set in the optimal ratio with respect to one another. Moreover, the auxiliaries in the formulation can be optimized to one another.

For application, the formulations in commercial form are, if appropriate, diluted in a customary manner, for example in the case of wettable powders, emulsifiable concentrates, dispersions and water-dispersible granules with water. Dust-type formulations, granules for soil application or granules for scattering and sprayable solutions are not normally diluted further with other inert substances prior to application.

BIOLOGICAL EXAMPLES

All trials whose results are shown were conducted in a greenhouse by the methodology specified below. The effect of the inventive herbicidal compositions was examined on the following harmful plants 14 and 21 days after application:

*Echinochloa crus-galli* (ECHCG), *Eleusine indica* (ELEIN), *Setaria viridis* (SETVI), *Amaranthus retroflexus* (AMARE), *Chenopodium album* (CHEAL), *Kochia scoparia* (KCHSC), *Solanum nigrum* (SOLNI), *Avena fatua* (AVEFA), *Bromus sterilis* (BROST), *Lolium multiflorum* (LOLMU), *Phalaris minor* (PHAMI), *Poa annua* (POAAN), *Galium aparine* (GALAP), *Matricaria inodora* (MATIN) and *Polygonum convolvulus* (POLCO).

The harmful plant seeds were sown in pots (diameter 8 cm) with sandy loam soil and germinated under optimal conditions. The inventive herbicidal compositions or the active ingredients alone were applied post-emergence to the planted pots with a spray volume of 300 L/ha. The trial was conducted in a greenhouse under optimum growth conditions. The herbicidal effects were assessed visually by comparison of untreated and treated plants. The percentages mean: 0%=no effects, 100%=the plants die off completely). The percentages are used to calculate interactions between individual treatments and combination treatments according to S. R. Colby, Weeds 15, pages 20 to 22 (1967).

The abbreviations mean:

a.i.=active ingredient $E^C$=expected value according to Colby ($E^C$=A+B−A×B/100)

Diff: =difference (%) of measured value from expected value (%) (measured value minus expected value)

Assessment:

measured value E is greater than $E^C$:->synergism (+ diff.)

measured value E equals $E^C$:->additive effect measured value E is smaller than $E^C$:->antagonism(−diff.)

The results are shown in the tables below.

TABLE 1

Efficacy against ECHCG, 14 days after application

| Active ingredient | Dosage [g of a.i./ha] | Efficacy [%] |
|---|---|---|
| A1-3 | 4 | 40 |
| tembotrione | 0.5 | 10 |
| A1-3 + tembotrione | 4 + 0.5 | 75 (Ec = 46, Diff. = +29) |

TABLE 2

Efficacy against ECHCG, 14 days after application

| Active ingredient | Dosage [g of a.i./ha] | Efficacy [%] |
|---|---|---|
| A1-3 | 1 | 0 |
| tembotrione | 0.5 | 10 |
| A1-3 + tembotrione | 1 + 0.5 | 30 (Ec = 10, Diff. = +20) |

TABLE 3

Efficacy against ELEIN, 14 days after application

| Active ingredient | Dosage [g of a.i./ha] | Efficacy [%] |
|---|---|---|
| A1-3 | 4 | 50 |
| tembotrione | 2 | 40 |
| A1-3 + tembotrione | 4 + 2 | 75 (Ec = 70, Diff. = +5) |

TABLE 4

Efficacy against ELEIN, 14 days after application

| Active ingredient | Dosage [g of a.i./ha] | Efficacy [%] |
|---|---|---|
| A1-3 | 4 | 50 |
| tembotrione | 0.5 | 30 |
| A1-3 + tembotrione | 4 + 0.5 | 70 (Ec = 65, Diff. = +5) |

TABLE 5

Efficacy against KCHSC, 14 days after application

| Active ingredient | Dosage [g of a.i./ha] | Efficacy [%] |
|---|---|---|
| A1-3 | 4 | 40 |
| tembotrione | 2 | 20 |
| A1-3 + tembotrione | 4 + 2 | 70 (Ec = 52, Diff. = +18) |

TABLE 6

Efficacy against DIGSA, 14 days after application

| Active ingredient | Dosage [g of a.i./ha] | Efficacy [%] |
|---|---|---|
| A1-13 | 0.4 | 0 |
| foramsulfuron | 4 | 40 |
| A1-13 + foramsulfuron | 0.4 + 4 | 60 (Ec = 40, Diff. = +20) |

TABLE 7

Efficacy against ECHCG, 14 days after application

| Active ingredient | Dosage [g of a.i./ha] | Efficacy [%] |
|---|---|---|
| A1-13 | 0.4 | 0 |
| foramsulfuron | 1 | 60 |
| A1-13 + foramsulfuron | 0.4 + 1 | 75 (Ec = 60, Diff. = +15) |

TABLE 8

Efficacy against ECHCG, 14 days after application

| Active ingredient | Dosage [g of a.i./ha] | Efficacy [%] |
|---|---|---|
| A1-13 | 0.1 | 0 |
| foramsulfuron | 1 | 60 |
| A1-13 + foramsulfuron | 0.1 + 1 | 75 (Ec = 60, Diff. = +15) |

TABLE 9

Efficacy against SETVI, 14 days after application

| Active ingredient | Dosage [g of a.i./ha] | Efficacy [%] |
|---|---|---|
| A1-13 | 0.4 | 10 |
| foramsulfuron | 1 | 40 |
| A1-13 + foramsulfuron | 0.4 + 1 | 60 (Ec = 46, Diff. = +14) |

TABLE 10

Efficacy against SETVI, 14 days after application

| Active ingredient | Dosage [g of a.i./ha] | Efficacy [%] |
|---|---|---|
| A1-13 | 0.1 | 0 |
| foramsulfuron | 1 | 40 |
| A1-13 + foramsulfuron | 0.1 + 1 | 50 (Ec + 40, Diff. = +10) |

TABLE 11

Efficacy against CHEAL, 14 days after application

| Active ingredient | Dosage [g of a.i./ha] | Efficacy [%] |
|---|---|---|
| A1-13 | 0.4 | 10 |
| foramsulfuron | 1 | 50 |
| A1-13 + foramsulfuron | 0.4 + 1 | 65 (Ec = 55, Diff. = +10) |

TABLE 12

Efficacy against KCHSC, 14 days after application

| Active ingredient | Dosage [g of a.i./ha] | Efficacy [%] |
|---|---|---|
| A1-13 | 0.4 | 0 |
| foramsulfuron | 4 | 90 |
| A1-13 + foramsulfuron | 0.4 + 4 | 97 (Ec = 90, Diff. = +7) |

TABLE 13

Efficacy against KCHSC, 14 days after application

| Active ingredient | Dosage [g of a.i./ha] | Efficacy [%] |
|---|---|---|
| A1-13 | 0.1 | 0 |
| foramsulfuron | 1 | 80 |
| A1-13 + foramsulfuron | 0.1 + 1 | 85 (Ec = 80, Diff. = +5) |

TABLE 14

Efficacy against DIGSA, 14 days after application

| Active ingredient | Dosage [g of a.i./ha] | Efficacy [%] |
|---|---|---|
| A1-14 | 0.4 | 0 |
| bromoxynil | 400 | 0 |
| A1-14 + bromoxynil | 0.4 + 400 | 30 (Ec = 0, Diff. = +30) |

TABLE 15

Efficacy against DIGSA, 14 days after application

| Active ingredient | Dosage [g of a.i./ha] | Efficacy [%] |
|---|---|---|
| A1-14 | 0.4 | 0 |
| bromoxynil | 100 | 0 |
| A1-14 + bromoxynil | 0.4 + 100 | 30 (Ec = 0, Diff. = +30) |

TABLE 16

Efficacy against ECHCG, 14 days after application

| Active ingredient | Dosage [g of a.i./ha] | Efficacy [%] |
|---|---|---|
| A1-14 | 0.4 | 0 |
| bromoxynil | 400 | 0 |
| A1-14 + bromoxynil | 0.4 + 400 | 50 (Ec = 0, Diff. = +50) |

TABLE 17

Efficacy against ECHCG, 14 days after application

| Active ingredient | Dosage [g of a.i./ha] | Efficacy [%] |
|---|---|---|
| A1-14 | 0.4 | 0 |
| bromoxynil | 100 | 0 |
| A1-14 + bromoxynil | 0.4 + 100 | 30 (Ec = 0, Diff. = +30) |

TABLE 18

Efficacy against ELEIN, 14 days after application

| Active ingredient | Dosage [g of a.i./ha] | Efficacy [%] |
|---|---|---|
| A1-14 | 0.4 | 20 |
| bromoxynil | 400 | 0 |
| A1-14 + bromoxynil | 0.4 + 400 | 30 (Ec = 20, Diff. = +10) |

TABLE 19

Efficacy against ELEIN, 14 days after application

| Active ingredient | Dosage [g of a.i./ha] | Efficacy [%] |
|---|---|---|
| A1-14 | 0.4 | 20 |
| bromoxynil | 100 | 0 |
| A1-14 + bromoxynil | 0.4 + 100 | 30 (Ec = 20, Diff. = +10) |

TABLE 20

Efficacy against ELEIN, 14 days after application

| Active ingredient | Dosage [g of a.i./ha] | Efficacy [%] |
|---|---|---|
| A1-14 | 0.1 | 0 |
| bromoxynil | 400 | 0 |
| A1-14 + bromoxynil | 0.1 + 400 | 20 (Ec = 0, Diff. = +20) |

TABLE 21

Efficacy against ELEIN, 14 days after application

| Active ingredient | Dosage [g of a.i./ha] | Efficacy [%] |
|---|---|---|
| A1-14 | 0.1 | 0 |
| bromoxynil | 100 | 0 |
| A1-14 + bromoxynil | 0.1 + 100 | 20 (Ec = 0, Diff. = +20) |

TABLE 22

Efficacy against SETVI, 14 days after application

| Active ingredient | Dosage [g of a.i./ha] | Efficacy [%] |
|---|---|---|
| A1-14 | 0.1 | 0 |
| bromoxynil | 400 | 0 |
| A1-14 + bromoxynil | 0.1 + 400 | 20 (Ec = 0, Diff. = +20) |

TABLE 23

Efficacy against SETVI, 14 days after application

| Active ingredient | Dosage [g of a.i./ha] | Efficacy [%] |
|---|---|---|
| A1-14 | 0.1 | 0 |
| bromoxynil | 100 | 0 |
| A1-14 + bromoxynil | 0.1 + 100 | 20 (Ec = 0, Diff. = +20) |

TABLE 24

Efficacy against AMARE, 14 days after application

| Active ingredient | Dosage [g of a.i./ha] | Efficacy [%] |
|---|---|---|
| A1-14 | 0.1 | 0 |
| bromoxynil | 100 | 40 |
| A1-14 + bromoxynil | 0.1 + 100 | 50 (Ec = 40, Diff. = +10) |

TABLE 25

Efficacy against CHEAL, 14 days after application

| Active ingredient | Dosage [g of a.i./ha] | Efficacy [%] |
|---|---|---|
| A1-14 | 0.1 | 0 |
| bromoxynil | 400 | 85 |
| A1-14 + bromoxynil | 0.1 + 400 | 100 (Ec = 85, Diff. = +15) |

TABLE 26

Efficacy against DIGSA, 14 days after application

| Active ingredient | Dosage [g of a.i./ha] | Efficacy [%] |
|---|---|---|
| A1-36 | 0.5 | 10 |
| isoxaflutole | 10 | 10 |
| A1-36 + isoxaflutole | 0.5 + 10 | 30 (Ec = 19, Diff. = +11) |

TABLE 27

Efficacy against ECHCG, 14 days after application

| Active ingredient | Dosage [g of a.i./ha] | Efficacy [%] |
|---|---|---|
| A1-36 | 2 | 40 |
| isoxaflutole | 10 | 60 |
| A1-36 + isoxaflutole | 2 + 10 | 95 (Ec = 76, Diff. = +19) |

TABLE 28

Efficacy against ECHCG, 14 days after application

| Active ingredient | Dosage [g of a.i./ha] | Efficacy [%] |
|---|---|---|
| A1-36 | 2 | 40 |
| isoxaflutole | 2.5 | 10 |
| A1-36 + isoxaflutole | 2 + 2.5 | 70 (Ec = 46, Diff. = +24) |

TABLE 29

Efficacy against ECHCG, 14 days after application

| Active ingredient | Dosage [g of a.i./ha] | Efficacy [%] |
| --- | --- | --- |
| A1-36 | 0.5 | 10 |
| isoxaflutole | 10 | 60 |
| A1-36 + isoxaflutole | 0.5 + 10 | 70 (Ec = 64, Diff. = +6) |

TABLE 30

Efficacy against ELEIN, 14 days after application

| Active ingredient | Dosage [g of a.i./ha] | Efficacy [%] |
| --- | --- | --- |
| A1-36 | 2 | 50 |
| isoxaflutole | 10 | 60 |
| A1-36 + isoxaflutole | 2 + 10 | 93 (Ec = 80, Diff. = +13) |

TABLE 31

Efficacy against ELEIN, 14 days after application

| Active ingredient | Dosage [g of a.i./ha] | Efficacy [%] |
| --- | --- | --- |
| A1-36 | 2 | 50 |
| isoxaflutole | 2.5 | 20 |
| A1-36 + isoxaflutole | 2 + 2.5 | 85 (Ec = 60, Diff. = +25) |

TABLE 32

Efficacy against ECHCG, 14 days after application

| Active ingredient | Dosage [g of a.i./ha] | Efficacy [%] |
| --- | --- | --- |
| A2-1 | 4 | 50 |
| halauxifen | 2 | 10 |
| A2-1 + halauxifen | 4 + 2 | 70 (Ec = 55, Diff. = +15) |

TABLE 33

Efficacy against ECHCG, 14 days after application

| Active ingredient | Dosage [g of a.i./ha] | Efficacy [%] |
| --- | --- | --- |
| A2-1 | 4 | 50 |
| halauxifen | 0.5 | 0 |
| A2-1 + halauxifen | 4 + 0.5 | 60 (Ec = 50, Diff. = +10) |

TABLE 34

Efficacy against DIGSA, 14 days after application

| Active ingredient | Dosage [g of a.i./ha] | Efficacy [%] |
| --- | --- | --- |
| A1-55 | 0.5 | 20 |
| dicamba | 40 | 0 |
| A1-55 + dicamba | 0.5 + 40 | 30 (Ec = 20, Diff. = +10) |

TABLE 35

Efficacy against ELEIN, 14 days after application

| Active ingredient | Dosage [g of a.i./ha] | Efficacy [%] |
| --- | --- | --- |
| A1-55 | 2 | 40 |
| dicamba | 40 | 10 |
| A1-55 + dicamba | 2 + 40 | 65 (Ec = 46, Diff. = +19) |

TABLE 36

Efficacy against ELEIN, 14 days after application

| Active ingredient | Dosage [g of a.i./ha] | Efficacy [%] |
| --- | --- | --- |
| A1-55 | 2 | 40 |
| dicamba | 10 | 10 |
| A1-55 + dicamba | 2 + 10 | 65 (Ec = 46, Diff. = +19) |

TABLE 37

Efficacy against SETVI, 14 days after application

| Active ingredient | Dosage [g of a.i./ha] | Efficacy [%] |
| --- | --- | --- |
| A1-55 | 2 | 40 |
| dicamba | 40 | 0 |
| A1-55 + dicamba | 2 + 40 | 65 (Ec = 40, Diff. = +25) |

TABLE 38

Efficacy against SETVI, 14 days after application

| Active ingredient | Dosage [g of a.i./ha] | Efficacy [%] |
| --- | --- | --- |
| A1-55 | 2 | 40 |
| dicamba | 10 | 0 |
| A1-55 + dicamba | 2 + 10 | 65 (Ec = 40, Diff. = +25) |

TABLE 39

Efficacy against AMARE, 14 days after application

| Active ingredient | Dosage [g of a.i./ha] | Efficacy [%] |
| --- | --- | --- |
| A1-55 | 0.5 | 20 |
| dicamba | 40 | 65 |
| A1-55 + dicamba | 0.5 + 40 | 80 (Ec = 72, Diff. = +8) |

TABLE 40

Efficacy against CHEAL, 14 days after application

| Active ingredient | Dosage [g of a.i./ha] | Efficacy [%] |
| --- | --- | --- |
| A1-55 | 2 | 70 |
| dicamba | 10 | 50 |
| A1-55 + dicamba | 2 + 10 | 90 (Ec = 85, Diff. = +5) |

TABLE 41

Efficacy against KCHSC, 14 days after application

| Active ingredient | Dosage [g of a.i./ha] | Efficacy [%] |
|---|---|---|
| A1-57 | 1 | 40 |
| glyphosate | 50 | 30 |
| A1-57 + glyphosate | 1 + 50 | 65 (Ec = 58, Diff. = +7) |

TABLE 42

Efficacy against DIGSA, 14 days after application

| Active ingredient | Dosage [g of a.i./ha] | Efficacy [%] |
|---|---|---|
| A1-7 | 2 | 20 |
| fenoxaprop-P-ethyl | 5 | 30 |
| A1-7 + fenoxaprop-P-ethyl | 2 + 5 | 70 (Ec = 44, Diff. = +26) |

TABLE 43

Efficacy against AMARE, 14 days after application

| Active ingredient | Dosage [g of a.i./ha] | Efficacy [%] |
|---|---|---|
| A1-7 | 0.5 | 30 |
| fenoxaprop-P-ethyl | 20 | 0 |
| A1-7 + fenoxaprop-P-ethyl | 0.5 + 20 | 40 (Ec = 30, Diff. = +10) |

TABLE 44

Efficacy against AMARE, 14 days after application

| Active ingredient | Dosage [g of a.i./ha] | Efficacy [%] |
|---|---|---|
| A1-7 | 0.5 | 30 |
| fenoxaprop-P-ethyl | 5 | 0 |
| A1-7 + fenoxaprop-P-ethyl | 0.5 + 5 | 40 (Ec = 30, Diff. = +10) |

TABLE 45

Efficacy against CHEAL, 14 days after application

| Active ingredient | Dosage [g of a.i./ha] | Efficacy [%] |
|---|---|---|
| A1-7 | 2 | 50 |
| fenoxaprop-P-ethyl | 20 | 0 |
| A1-7 + fenoxaprop-P-ethyl | 2 + 20 | 70 (Ec = 50, Diff. = +20) |

TABLE 46

Efficacy against CHEAL, 14 days after application

| Active ingredient | Dosage [g of a.i./ha] | Efficacy [%] |
|---|---|---|
| A1-7 | 2 | 50 |
| fenoxaprop-P-ethyl | 5 | 0 |
| A1-7 + fenoxaprop-P-ethyl | 2 + 5 | 65 (Ec = 50, Diff. = +15) |

TABLE 47

Efficacy against CHEAL, 14 days after application

| Active ingredient | Dosage [g of a.i./ha] | Efficacy [%] |
|---|---|---|
| A1-7 | 0.5 | 0 |
| fenoxaprop-P-ethyl | 20 | 0 |
| A1-7 + fenoxaprop-P-ethyl | 0.5 + 20 | 20 (Ec = 0, Diff. = +20) |

TABLE 48

Efficacy against CHEAL, 14 days after application

| Active ingredient | Dosage [g of a.i./ha] | Efficacy [%] |
|---|---|---|
| A1-7 | 0.5 | 0 |
| fenoxaprop-P-ethyl | 5 | 0 |
| A1-7 + fenoxaprop-P-ethyl | 0.5 + 5 | 20 (Ec = 0, Diff. = +20) |

TABLE 49

Efficacy against KCHSC, 14 days after application

| Active ingredient | Dosage [g of a.i./ha] | [%] |
|---|---|---|
| A1-7 | 0.5 | 0 |
| fenoxaprop-P-ethyl | 20 | 0 |
| A1-7 + fenoxaprop-P-ethyl | 0.5 + 20 | 30 (Ec = 0, Diff. = +30) |

TABLE 50

Efficacy against KCHSC, 14 days after application

| Active ingredient | Dosage [g of a.i./ha] | Efficacy [%] |
|---|---|---|
| A1-7 | 0.5 | 0 |
| fenoxaprop-P-ethyl | 5 | 0 |
| A1-7 + fenoxaprop-P-ethyl | 0.5 + 5 | 20 (Ec = 0, Diff. = +20) |

TABLE 51

Efficacy against SOLNI, 14 days after application

| Active ingredient | Dosage [g of a.i./ha] | Efficacy [%] |
|---|---|---|
| A1-7 | 2 | 20 |
| fenoxaprop-P-ethyl | 20 | 0 |
| A1-7 + fenoxaprop-P-ethyl | 2 + 20 | 40 (Ec = 20, Diff. = +20) |

TABLE 52

Efficacy against SOLNI, 14 days after application

| Active ingredient | Dosage [g of a.i./ha] | Efficacy [%] |
|---|---|---|
| A1-7 | 2 | 20 |
| fenoxaprop-P-ethyl | 5 | 0 |
| A1-7 + fenoxaprop-P-ethyl | 2 + 5 | 40 (Ec = 20, Diff. = +20) |

TABLE 53

Efficacy against SOLNI, 14 days after application

| Active ingredient | Dosage [g of a.i./ha] | Efficacy [%] |
|---|---|---|
| A1-7 | 0.5 | 10 |
| fenoxaprop-P-ethyl | 20 | 0 |
| A1-7 + fenoxaprop-P-ethyl | 0.5 + 20 | 20 (Ec = 10, Diff. = +10) |

TABLE 54

Efficacy against SOLNI, 14 days after application

| Active ingredient | Dosage [g of a.i./ha] | Efficacy [%] |
|---|---|---|
| A1-7 | 0.5 | 10 |
| fenoxaprop-P-ethyl | 5 | 0 |
| A1-7 + fenoxaprop-P-ethyl | 0.5 +5 | 20 (Ec = 10, Diff. = +10) |

TABLE 55

Efficacy against DIGSA, 14 days after application

| Active ingredient | Dosage [g of a.i./ha] | Efficacy [%] |
|---|---|---|
| A1-60 | 4 | 93 |
| lenacil | 1200 | 0 |
| A1-60 + lenacil | 4 + 1200 | 99 (Ec = 93, Diff. = +6) |

TABLE 56

Efficacy against DIGSA, 14 days after application

| Active ingredient | Dosage [g of a.i./ha] | Efficacy [%] |
|---|---|---|
| A1-60 | 4 | 93 |
| lenacil | 300 | 0 |
| A1-60 + lenacil | 4 + 300 | 99 (Ec = 93, Diff. = +6) |

TABLE 57

Efficacy against ECHCG, 14 days after application

| Active ingredient | Dosage [g of a.i./ha] | Efficacy [%] |
|---|---|---|
| A1-60 | 4 | 90 |
| lenacil | 1200 | 0 |
| A1-60 + lenacil | 4 + 1200 | 99 (Ec = 90, Diff. = +9) |

TABLE 58

Efficacy against ECHCG, 14 days after application

| Active ingredient | Dosage [g of a.i./ha] | Efficacy [%] |
|---|---|---|
| A1-60 | 4 | 90 |
| lenacil | 300 | 0 |
| A1-60 + lenacil | 4 + 300 | 99 (Ec = 90, Diff. = +9) |

TABLE 59

Efficacy against ECHCG, 14 days after application

| Active ingredient | Dosage [g of a.i./ha] | Efficacy [%] |
|---|---|---|
| A1-60 | 1 | 65 |
| lenacil | 1200 | 0 |
| A1-60 + lenacil | 1 + 1200 | 75 (Ec = 65, Diff. = +10) |

TABLE 60

Efficacy against ECHCG, 14 days after application

| Active ingredient | Dosage [g of a.i./ha] | Efficacy [%] |
|---|---|---|
| A1-60 | 1 | 65 |
| lenacil | 300 | 0 |
| A1-60 + lenacil | 1 + 300 | 75 (Ec = 65, Diff. = +10) |

TABLE 61

Efficacy against ELEIN, 14 days after application

| Active ingredient | Dosage [g of a.i./ha] | Efficacy [%] |
|---|---|---|
| A1-60 | 4 | 90 |
| lenacil | 1200 | 0 |
| A1-60 + lenacil | 4 + 1200 | 99 (Ec = 90, Diff. = +9) |

TABLE 62

Efficacy against ELEIN, 14 days after application

| Active ingredient | Dosage [g of a.i./ha] | Efficacy [%] |
|---|---|---|
| A1-60 | 4 | 90 |
| lenacil | 300 | 0 |
| A1-60 + lenacil | 4 + 300 | 98 (Ec = 90, Diff. = +8) |

TABLE 63

Efficacy against ELEIN, 14 days after application

| Active ingredient | Dosage [g of a.i./ha] | Efficacy [%] |
|---|---|---|
| A1-60 | 1 | 70 |
| lenacil | 1200 | 0 |
| A1-60 + lenacil | 1 + 1200 | 75 (Ec = 70, Diff. = +5) |

TABLE 64

Efficacy against ELEIN, 14 days after application

| Active ingredient | Dosage [g of a.i./ha] | Efficacy [%] |
|---|---|---|
| A1-60 | 1 | 70 |
| lenacil | 300 | 0 |
| A1-60 + lenacil | 1 + 300 | 75 (Ec = 70, Diff. = +5) |

TABLE 65

Efficacy against SETVI, 14 days after application

| Active ingredient | Dosage [g of a.i./ha] | Efficacy [%] |
|---|---|---|
| A1-60 | 4 | 85 |
| lenacil | 1200 | 0 |
| A1-60 + lenacil | 4 + 1200 | 95 (Ec = 85, Diff. = +10) |

TABLE 66

Efficacy against SETVI, 14 days after application

| Active ingredient | Dosage [g of a.i./ha] | Efficacy [%] |
|---|---|---|
| A1-60 | 4 | 85 |
| lenacil | 300 | 0 |
| A1-60 + lenacil | 4 + 300 | 90 (Ec = 85, Diff. = +5) |

TABLE 67

Efficacy against SETVI, 14 days after application

| Active ingredient | Dosage [g of a.i./ha] | Efficacy [%] |
|---|---|---|
| A1-60 | 1 | 70 |
| lenacil | 1200 | 0 |
| A1-60 + lenacil | 1 + 1200 | 75 (Ec = 70, Diff. = +5) |

TABLE 68

Efficacy against AMARE, 14 days after application

| Active ingredient | Dosage [g of a.i./ha] | Efficacy [%] |
|---|---|---|
| A1-60 | 4 | 70 |
| lenacil | 1200 | 0 |
| A1-60 + lenacil | 4 + 1200 | 85 (Ec = 70, Diff. = +15) |

TABLE 69

Efficacy against SOLNI, 14 days after application

| Active ingredient | Dosage [g of a.i./ha] | Efficacy [%] |
|---|---|---|
| A1-60 | 4 | 65 |
| lenacil | 1200 | 0 |
| A1-60 + lenacil | 4 + 1200 | 100 (Ec = 65, Diff. = +35) |

TABLE 70

Efficacy against SOLNI, 14 days after application

| Active ingredient | Dosage [g of a.i./ha] | Efficacy [%] |
|---|---|---|
| A1-60 | 4 | 65 |
| lenacil | 300 | 0 |
| A1-60 + lenacil | 4 + 300 | 95 (Ec = 65, Diff. = +30) |

TABLE 71

Efficacy against SOLNI, 14 days after application

| Active ingredient | Dosage [g of a.i./ha] | Efficacy [%] |
|---|---|---|
| A1-60 | 1 | 65 |
| lenacil | 1200 | 0 |
| A1-60 + lenacil | 1 + 1200 | 80 (Ec = 65, Diff. = +15) |

TABLE 72

Efficacy against SOLNI, 14 days after application

| Active ingredient | Dosage [g of a.i./ha] | Efficacy [%] |
|---|---|---|
| A1-60 | 1 | 65 |
| lenacil | 300 | 0 |
| A1-60 + lenacil | 1 + 300 | 80 (Ec = 65, Diff. = +15) |

TABLE 73

Efficacy against DIGSA, 14 days after application

| Active ingredient | Dosage [g of a.i./ha] | Efficacy [%] |
|---|---|---|
| A1-13 | 0.4 | 0 |
| metribuzin | 20 | 20 |
| A1-13 + metribuzin | 0.4 + 20 | 60 (Ec = 20, Diff. = +40) |

TABLE 74

Efficacy against DIGSA, 14 days after application

| Active ingredient | Dosage [g of a.i./ha] | Efficacy [%] |
|---|---|---|
| A1-13 | 0.4 | 0 |
| metribuzin | 5 | 0 |
| A1-13 + metribuzin | 0.4 + 5 | 60 (Ec = 0, Diff. = +60) |

TABLE 75

Efficacy against ECHCG, 14 days after application

| Active ingredient | Dosage [g of a.i./ha] | Efficacy [%] |
|---|---|---|
| A1-13 | 0.4 | 0 |
| metribuzin | 20 | 30 |
| A1-13 + metribuzin | 0.4 + 20 | 75 (Ec = 30, Diff. = +45) |

TABLE 76

Efficacy against ECHCG, 14 days after application

| Active ingredient | Dosage [g of a.i./ha] | Efficacy [%] |
|---|---|---|
| A1-13 | 0.4 | 0 |
| metribuzin | 5 | 10 |
| A1-13 + metribuzin | 0.4 + 5 | 60 (Ec = 10, Diff. = +50) |

TABLE 77

Efficacy against ELEIN, 14 days after application

| Active ingredient | Dosage [g of a.i./ha] | Efficacy [%] |
| --- | --- | --- |
| A1-13 | 0.4 | 20 |
| metribuzin | 20 | 20 |
| A1-13 + metribuzin | 0.4 + 20 | 80 (Ec = 36, Diff. = +44) |

TABLE 78

Efficacy against ELEIN, 14 days after application

| Active ingredient | Dosage [g of a.i./ha] | Efficacy [%] |
| --- | --- | --- |
| A1-13 | 0.4 | 20 |
| metribuzin | 5 | 10 |
| A1-13 + metribuzin | 0.4 + 5 | 70 (Ec = 28, Diff. = +42) |

TABLE 79

Efficacy against SETVI, 14 days after application

| Active ingredient | Dosage [g of a.i./ha] | Efficacy [%] |
| --- | --- | --- |
| A1-13 | 0.4 | 10 |
| metribuzin | 20 | 30 |
| A1-13 + metribuzin | 0.4 + 20 | 60 (Ec = 37, Diff. = +23) |

TABLE 80

Efficacy against SETVI, 14 days after application

| Active ingredient | Dosage [g of a.i./ha] | Efficacy [%] |
| --- | --- | --- |
| A1-13 | 0.4 | 10 |
| metribuzin | 5 | 10 |
| A1-13 + metribuzin | 0.4 + 5 | 60 (Ec = 19, Diff. = +41) |

TABLE 81

Efficacy against AMARE, 14 days after application

| Active ingredient | Dosage [g of a.i./ha] | Efficacy [%] |
| --- | --- | --- |
| A1-13 | 0.4 | 0 |
| metribuzin | 20 | 30 |
| A1-13 + metribuzin | 0.4 + 20 | 60 (Ec = 30, Diff. = +30) |

TABLE 82

Efficacy against AMARE, 14 days after application

| Active ingredient | Dosage [g of a.i./ha] | Efficacy [%] |
| --- | --- | --- |
| A1-13 | 0.4 | 0 |
| metribuzin | 5 | 20 |
| A1-13 + metribuzin | 0.4 + 5 | 60 (Ec = 20, Diff. = +40) |

TABLE 83

Efficacy against CHEAL, 14 days after application

| Active ingredient | Dosage [g of a.i./ha] | Efficacy [%] |
| --- | --- | --- |
| A1-13 | 0.4 | 10 |
| metribuzin | 20 | 30 |
| A1-13 + metribuzin | 0.4 + 20 | 60 (Ec = 37, Diff. = +23) |

TABLE 84

Efficacy against CHEAL, 14 days after application

| Active ingredient | Dosage [g of a.i./ha] | Efficacy [%] |
| --- | --- | --- |
| A1-13 | 0.4 | 10 |
| metribuzin | 5 | 30 |
| A1-13 + metribuzin | 0.4 + 5 | 60 (Ec = 37, Diff. = +23) |

TABLE 85

Efficacy against CHEAL, 14 days after application

| Active ingredient | Dosage [g of a.i./ha] | Efficacy [%] |
| --- | --- | --- |
| A1-13 | 0.1 | 0 |
| metribuzin | 20 | 30 |
| A1-13 + metribuzin | 0.1 + 20 | 50 (Ec = 30, Diff. = +20) |

TABLE 86

Efficacy against KCHSC, 14 days after application

| Active ingredient | Dosage [g of a.i./ha] | Efficacy [%] |
| --- | --- | --- |
| A1-13 | 0.4 | 0 |
| metribuzin | 20 | 20 |
| A1-13 + metribuzin | 0.4 + 20 | 70 (Ec = 20, Diff. = +50) |

TABLE 87

Efficacy against KCHSC, 14 days after application

| Active ingredient | Dosage [g of a.i./ha] | Efficacy [%] |
| --- | --- | --- |
| A1-13 | 0.4 | 0 |
| metribuzin | 5 | 20 |
| A1-13 + metribuzin | 0.4 + 5 | 70 (Ec = 20, Diff. = +50) |

TABLE 88

Efficacy against KCHSC, 14 days after application

| Active ingredient | Dosage [g of a.i./ha] | Efficacy [%] |
| --- | --- | --- |
| A1-13 | 0.1 | 0 |
| metribuzin | 20 | 20 |

TABLE 88-continued

Efficacy against KCHSC, 14 days after application

| Active ingredient | Dosage [g of a.i./ha] | Efficacy [%] |
|---|---|---|
| A1-13 + metribuzin | 0.1 + 20 | 30 (Ec = 20, Diff. = +10) |

TABLE 89

Efficacy against SOLNI, 14 days after application

| Active ingredient | Dosage [g of a.i./ha] | Efficacy [%] |
|---|---|---|
| A1-13 | 0.4 | 20 |
| metribuzin | 20 | 0 |
| A1-13 + metribuzin | 0.4 + 20 | 80 (Ec = 20, Diff. = +60) |

TABLE 90

Efficacy against SOLNI, 14 days after application

| Active ingredient | Dosage [g of a.i./ha] | Efficacy [%] |
|---|---|---|
| A1-13 | 0.4 | 20 |
| metribuzin | 5 | 0 |
| A1-13 + metribuzin | 0.4 + 5 | 80 (Ec = 20, Diff. = +60) |

TABLE 91

Efficacy against SOLNI, 14 days after application

| Active ingredient | Dosage [g of a.i./ha] | Efficacy [%] |
|---|---|---|
| A1-13 | 0.1 | 10 |
| metribuzin | 20 | 0 |
| A1-13 + metribuzin | 0.1 + 20 | 30 (Ec = 10, Diff. = +20) |

TABLE 92

Efficacy against SOLNI, 14 days after application

| Active ingredient | Dosage [g of a.i./ha] | Efficacy [%] |
|---|---|---|
| A1-13 | 0.1 | 10 |
| metribuzin | 5 | 0 |
| A1-13 + metribuzin | 0.1 + 5 | 30 (Ec = 10, Diff. = +20) |

TABLE 93

Efficacy against ECHCG, 21 days after application

| Active ingredient | Dosage [g of a.i./ha] | Efficacy [%] |
|---|---|---|
| A1-3 | 4 | 10 |
| tembotrione | 2 | 60 |
| A1-3 + tembotrione | 4 + 2 | 70 (Ec = 64, Diff. = +6) |

TABLE 94

Efficacy against ECHCG, 21 days after application

| Active ingredient | Dosage [g of a.i./ha] | Efficacy [%] |
|---|---|---|
| A1-3 | 4 | 10 |
| tembotrione | 0.5 | 10 |
| A1-3 + tembotrione | 4 + 0.5 | 70 (Ec = 19, Diff. = +51) |

TABLE 95

Efficacy against ECHCG, 21 days after application

| Active ingredient | Dosage [g of a.i./ha] | Efficacy [%] |
|---|---|---|
| A1-3 | 1 | 0 |
| tembotrione | 0.5 | 10 |
| A1-3 + tembotrione | 1 + 0.5 | 30 (Ec = 10, Diff. = +20) |

TABLE 96

Efficacy against ELEIN, 21 days after application

| Active ingredient | Dosage [g of a.i./ha] | Efficacy [%] |
|---|---|---|
| A1-3 | 4 | 20 |
| tembotrione | 2 | 10 |
| A1-3 + tembotrione | 4 + 2 | 40 (Ec = 28, Diff. = +12) |

TABLE 97

Efficacy against ELEIN, 21 days after application

| Active ingredient | Dosage [g of a.i./ha] | Efficacy [%] |
|---|---|---|
| A1-3 | 4 | 20 |
| tembotrione | 0.5 | 0 |
| A1-3 + tembotrione | 4 + 0.5 | 40 (Ec = 20, Diff. = +20) |

TABLE 98

Efficacy against SETVI, 21 days after application

| Active ingredient | Dosage [g of a.i./ha] | Efficacy [%] |
|---|---|---|
| A1-3 | 4 | 20 |
| tembotrione | 0.5 | 0 |
| A1-3 + tembotrione | 4 + 0.5 | 30 (Ec = 20, Diff. = +10) |

TABLE 99

Efficacy against SETVI, 21 days after application

| Active ingredient | Dosage [g of a.i./ha] | Efficacy [%] |
|---|---|---|
| A1-3 | 1 | 10 |
| tembotrione | 2 | 10 |

TABLE 99-continued

Efficacy against SETVI, 21 days after application

| Active ingredient | Dosage [g of a.i./ha] | Efficacy [%] |
|---|---|---|
| A1-3 + tembotrione | 1 + 2 | 30 (Ec = 19, Diff. = +11) |

TABLE 100

Efficacy against CHEAL, 21 days after application

| Active ingredient | Dosage [g of a.i./ha] | Efficacy [%] |
|---|---|---|
| A1-3 | 1 | 20 |
| tembotrione | 2 | 30 |
| A1-3 + tembotrione | 1 + 2 | 93 (Ec = 44, Diff. = +49) |

TABLE 101

Efficacy against KCHSC, 21 days after application

| Active ingredient | Dosage [g of a.i./ha] | Efficacy [%] |
|---|---|---|
| A1-3 | 4 | 20 |
| tembotrione | 2 | 10 |
| A1-3 + tembotrione | 4 + 2 | 65 (Ec = 28, Diff. = +37) |

TABLE 102

Efficacy against KCHSC, 21 days after application

| Active ingredient | Dosage [g of a.i./ha] | Efficacy [%] |
|---|---|---|
| A1-3 | 4 | 20 |
| tembotrione | 0.5 | 0 |
| A1-3 + tembotrione | 4 + 0.5 | 30 (Ec = 20, Diff. = +10) |

TABLE 103

Efficacy against ECHCG, 21 days after application

| Active ingredient | Dosage [g of a.i./ha] | Efficacy [%] |
|---|---|---|
| A1-13 | 0.4 | 0 |
| foramsulfuron | 1 | 30 |
| A1-13 + foramsulfuron | 0.4 + 1 | 60 (Ec = 30, Diff. = +30) |

TABLE 104

Efficacy against ECHCG, 21 days after application

| Active ingredient | Dosage [g of a.i./ha] | Efficacy [%] |
|---|---|---|
| A1-13 | 0.1 | 0 |
| foramsulfuron | 1 | 30 |
| A1-13 + foramsulfuron | 0.1 + 1 | 60 (Ec = 30, Diff. = +30) |

TABLE 105

Efficacy against ELEIN, 21 days after application

| Active ingredient | Dosage [g of a.i./ha] | Efficacy [%] |
|---|---|---|
| A1-13 | 0.4 | 10 |
| foramsulfuron | 1 | 60 |
| A1-13 + foramsulfuron | 0.4 + 1 | 70 (Ec = 64, Diff. = +6) |

TABLE 106

Efficacy against ELEIN, 21 days after application

| Active ingredient | Dosage [g of a.i./ha] | Efficacy [%] |
|---|---|---|
| A1-13 | 0.1 | 0 |
| foramsulfuron | 1 | 60 |
| A1-13 + foramsulfuron | 0.1 + 1 | 65 (Ec = 60, Diff. = +5) |

TABLE 107

Efficacy against SETVI, 21 days after application

| Active ingredient | Dosage [g of a.i./ha] | Efficacy [%] |
|---|---|---|
| A1-13 | 0.4 | 10 |
| foramsulfuron | 4 | 50 |
| A1-13 + foramsulfuron | 0.4 + 4 | 60 (Ec = 55, Diff. = +5) |

TABLE 108

Efficacy against SETVI, 21 days after application

| Active ingredient | Dosage [g of a.i./ha] | Efficacy [%] |
|---|---|---|
| A1-13 | 0.1 | 0 |
| foramsulfuron | 1 | 20 |
| A1-13 + foramsulfuron | 0.1 + 1 | 30 (Ec = 20, Diff. = +10) |

TABLE 109

Efficacy against KCHSC, 21 days after application

| Active ingredient | Dosage [g of a.i./ha] | Efficacy [%] |
|---|---|---|
| A1-13 | 0.4 | 0 |
| foramsulfuron | 4 | 80 |
| A1-13 + foramsulfuron | 0.4 + 4 | 90 (Ec = 80, Diff. = +10) |

TABLE 110

Efficacy against AMARE, 21 days after application

| Active ingredient | Dosage [g of a.i./ha] | Efficacy [%] |
|---|---|---|
| A1-34 | 100 | 50 |
| thiencarbazone-methyl | 0.25 | 60 |

TABLE 110-continued

Efficacy against AMARE, 21 days after application

| Active ingredient | Dosage [g of a.i./ha] | Efficacy [%] |
|---|---|---|
| A1-34 + thiencarbazone-methyl | 100 + 0.25 | 95 (Ec = 80, Diff. = +15) |

TABLE 111

Efficacy against AMARE, 21 days after application

| Active ingredient | Dosage [g of a.i./ha] | Efficacy [%] |
|---|---|---|
| A1-34 | 25 | 30 |
| thiencarbazone-methyl | 0.25 | 60 |
| A1-34 + thiencarbazone-methyl | 25 + 0.25 | 90 (Ec = 72, Diff. = +18) |

TABLE 112

Efficacy against CHEAL, 21 days after application

| Active ingredient | Dosage [g of a.i./ha] | Efficacy [%] |
|---|---|---|
| A1-34 | 25 | 70 |
| thiencarbazone-methyl | 1 | 70 |
| A1-34 + thiencarbazone-methyl | 25 + 1 | 100 (Ec = 91, Diff. = +9) |

TABLE 113

Efficacy against CHEAL, 21 days after application

| Active ingredient | Dosage [g of a.i./ha] | Efficacy [%] |
|---|---|---|
| A1-34 | 25 | 70 |
| thiencarbazone-methyl | 0.25 | 50 |
| A1-34 + thiencarbazone-methyl | 25 + 0.25 | 90 (Ec = 85, Diff. = +5) |

TABLE 114

Efficacy against SOLNI, 21 days after application

| Active ingredient | Dosage [g of a.i./ha] | Efficacy [%] |
|---|---|---|
| A1-34 | 25 | 10 |
| thiencarbazone-methyl | 1 | 50 |
| A1-34 + thiencarbazone-methyl | 25 + 1 | 60 (Ec = 55, Diff. = +5) |

TABLE 115

Efficacy against DIGSA, 21 days after application

| Active ingredient | Dosage [g of a.i./ha] | Efficacy [%] |
|---|---|---|
| A1-14 | 0.4 | 0 |
| bromoxynil | 400 | 0 |
| A1-14 + bromoxynil | 0.4 + 400 | 10 (Ec = 0, Diff. = +10) |

TABLE 116

Efficacy against DIGSA, 21 days after application

| Active ingredient | Dosage [g of a.i./ha] | Efficacy [%] |
|---|---|---|
| A1-14 | 0.4 | 0 |
| bromoxynil | 100 | 0 |
| A1-14 + bromoxynil | 0.4 + 100 | 10 (Ec = 0, Diff. = +10) |

TABLE 117

Efficacy against ECHCG, 21 days after application

| Active ingredient | Dosage [g of a.i./ha] | Efficacy [%] |
|---|---|---|
| A1-14 | 0.4 | 0 |
| bromoxynil | 400 | 0 |
| A1-14 + bromoxynil | 0.4 + 400 | 30 (Ec = 0, Diff. = +30) |

TABLE 118

Efficacy against SETVI, 21 days after application

| Active ingredient | Dosage [g of a.i./ha] | Efficacy [%] |
|---|---|---|
| A1-14 | 0.4 | 0 |
| bromoxynil | 400 | 0 |
| A1-14 + bromoxynil | 0.4 + 400 | 30 (Ec = 0, Diff. = +30) |

TABLE 119

Efficacy against SETVI, 21 days after application

| Active ingredient | Dosage [g of a.i./ha] | Efficacy [%] |
|---|---|---|
| A1-14 | 0.4 | 0 |
| bromoxynil | 100 | 0 |
| A1-14 + bromoxynil | 0.4 + 100 | 10 (Ec = 0, Diff. = +10) |

TABLE 120

Efficacy against CHEAL, 21 days after application

| Active ingredient | Dosage [g of a.i./ha] | Efficacy [%] |
|---|---|---|
| A1-14 | 0.1 | 0 |
| bromoxynil | 400 | 75 |
| A1-14 + bromoxynil | 0.1 + 400 | 100 (Ec = 75, Diff. = +25) |

TABLE 121

Efficacy against DIGSA, 21 days after application

| Active ingredient | Dosage [g of a.i./ha] | Efficacy [%] |
|---|---|---|
| A1-36 | 0.5 | 10 |
| isoxaflutole | 10 | 0 |
| A1-36 + isoxaflutole | 0.5 + 10 | 20 (Ec = 10, Diff. = +10) |

TABLE 122

Efficacy against ECHCG, 21 days after application

| Active ingredient | Dosage [g of a.i./ha] | Efficacy [%] |
|---|---|---|
| A1-36 | 2 | 20 |
| isoxaflutole | 10 | 60 |
| A1-36 + isoxaflutole | 2 + 10 | 95 (Ec = 68, Diff. = +27) |

TABLE 123

Efficacy against ECHCG, 21 days after application

| Active ingredient | Dosage [g of a.i./ha] | Efficacy [%] |
|---|---|---|
| A1-36 | 2 | 20 |
| isoxaflutole | 2.5 | 10 |
| A1-36 + isoxaflutole | 2 + 2.5 | 70 (Ec = 28, Diff. = +42) |

TABLE 124

Efficacy against ECHCG, 21 days after application

| Active ingredient | Dosage [g of a.i./ha] | Efficacy [%] |
|---|---|---|
| A1-36 | 0.5 | 0 |
| isoxaflutole | 10 | 60 |
| A1-36 + isoxaflutole | 0.5 + 10 | 70 (Ec = 60, Diff. = +10) |

TABLE 125

Efficacy against ECHCG, 21 days after application

| Active ingredient | Dosage [g of a.i./ha] | Efficacy [%] |
|---|---|---|
| A1-36 | 0.5 | 0 |
| isoxaflutole | 2.5 | 10 |
| A1-36 + isoxaflutole | 0.5 + 2.5 | 20 (Ec = 10, Diff. = +10) |

TABLE 126

Efficacy against ELEIN, 21 days after application

| Active ingredient | Dosage [g of a.i./ha] | Efficacy [%] |
|---|---|---|
| A1-36 | 2 | 30 |
| isoxaflutole | 10 | 20 |
| A1-36 + isoxaflutole | 2 + 10 | 75 (Ec = 44, Diff. = +31) |

TABLE 127

Efficacy against ELEIN, 21 days after application

| Active ingredient | Dosage [g of a.i./ha] | Efficacy [%] |
|---|---|---|
| A1-36 | 2 | 30 |
| isoxaflutole | 2.5 | 0 |
| A1-36 + isoxaflutole | 2 + 2.5 | 65 (Ec = 30, Diff. = +35) |

TABLE 128

Efficacy against SETVI, 21 days after application

| Active ingredient | Dosage [g of a.i./ha] | Efficacy [%] |
|---|---|---|
| A1-36 | 2 | 65 |
| isoxaflutole | 10 | 0 |
| A1-36 + isoxaflutole | 2 + 10 | 70 (Ec = 65, Diff. = +5) |

TABLE 129

Efficacy against SETVI, 21 days after application

| Active ingredient | Dosage [g of a.i./ha] | Efficacy [%] |
|---|---|---|
| A1-36 | 2 | 65 |
| isoxaflutole | 2.5 | 0 |
| A1-36 + isoxaflutole | 2 + 2.5 | 70 (Ec = 65, Diff. = +5) |

TABLE 130

Efficacy against AMARE, 21 days after application

| Active ingredient | Dosage [g of a.i./ha] | Efficacy [%] |
|---|---|---|
| A1-36 | 2 | 70 |
| isoxaflutole | 2.5 | 40 |
| A1-36 + isoxaflutole | 2 + 2.5 | 93 (Ec = 82, Diff. = +11) |

TABLE 131

Efficacy against AMARE, 21 days after application

| Active ingredient | Dosage [g of a.i./ha] | Efficacy [%] |
|---|---|---|
| A1-36 | 0.5 | 20 |
| isoxaflutole | 2.5 | 40 |
| A1-36 + isoxaflutole | 0.5 + 2.5 | 70 (Ec = 52, Diff. = +18) |

TABLE 132

Efficacy against SOLNI, 21 days after application

| Active ingredient | Dosage [g of a.i./ha] | Efficacy [%] |
|---|---|---|
| A1-36 | 2 | 50 |
| isoxaflutole | 10 | 65 |
| A1-36 + isoxaflutole | 2 + 10 | 95 (Ec = 82.5, Diff. = +12.5) |

TABLE 133

Efficacy against ECHCG, 21 days after application

| Active ingredient | Dosage [g of a.i./ha] | Efficacy [%] |
|---|---|---|
| A2-1 | 4 | 40 |
| halauxifen | 2 | 20 |
| A2-1 + halauxifen | 4 + 2 | 65 (Ec = 52, Diff. = +13) |

TABLE 134

Efficacy against ELEIN, 21 days after application

| Active ingredient | Dosage [g of a.i./ha] | Efficacy [%] |
|---|---|---|
| A2-1 | 4 | 60 |
| halauxifen | 2 | 0 |
| A2-1 + halauxifen | 4 + 2 | 70 (Ec = 60, Diff. = +10) |

TABLE 135

Efficacy against ELEIN, 21 days after application

| Active ingredient | Dosage [g of a.i./ha] | Efficacy [%] |
|---|---|---|
| A2-1 | 4 | 60 |
| halauxifen | 0.5 | 0 |
| A2-1 + halauxifen | 4 + 0.5 | 65 (Ec = 60, Diff. = +5) |

TABLE 136

Efficacy against SETVI, 21 days after application

| Active ingredient | Dosage [g of a.i./ha] | Efficacy [%] |
|---|---|---|
| A2-1 | 4 | 20 |
| halauxifen | 2 | 0 |
| A2-1 + halauxifen | 4 + 2 | 30 (Ec = 20, Diff. = +10) |

TABLE 137

Efficacy against KCHSC, 21 days after application

| Active ingredient | Dosage [g of a.i./ha] | Efficacy [%] |
|---|---|---|
| A2-1 | 4 | 40 |
| halauxifen | 2 | 30 |
| A2-1 + halauxifen | 4 + 2 | 65 (Ec = 58, Diff. = +7) |

TABLE 138

Efficacy against KCHSC, 21 days after application

| Active ingredient | Dosage [g of a.i./ha] | Efficacy [%] |
|---|---|---|
| A2-1 | 4 | 40 |
| halauxifen | 0.5 | 20 |
| A2-1 + halauxifen | 4 + 0.5 | 65 (Ec = 52, Diff. = +13) |

TABLE 139

Efficacy against SOLNI, 21 days after application

| Active ingredient | Dosage [g of a.i./ha] | Efficacy [%] |
|---|---|---|
| A2-1 | 1 | 10 |
| halauxifen | 0.5 | 50 |
| A2-1 + halauxifen | 1 + 0.5 | 60 (Ec = 55, Diff. = +5) |

TABLE 140

Efficacy against DIGSA, 21 days after application

| Active ingredient | Dosage [g of a.i./ha] | Efficacy [%] |
|---|---|---|
| A1-55 | 2 | 30 |
| dicamba | 40 | 0 |
| A1-55 + dicamba | 2 + 40 | 40 (Ec = 30, Diff. = +10) |

TABLE 141

Efficacy against ELEIN, 21 days after application

| Active ingredient | Dosage [g of a.i./ha] | Efficacy [%] |
|---|---|---|
| A1-55 | 2 | 30 |
| dicamba | 40 | 0 |
| A1-55 + dicamba | 2 + 40 | 50 (Ec = 30, Diff. = +20) |

TABLE 142

Efficacy against ELEIN, 21 days after application

| Active ingredient | Dosage [g of a.i./ha] | Efficacy [%] |
|---|---|---|
| A1-55 | 2 | 30 |
| dicamba | 10 | 0 |
| A1-55 + dicamba | 2 + 10 | 50 (Ec = 30, Diff. = +20) |

TABLE 143

Efficacy against SETVI, 21 days after application

| Active ingredient | Dosage [g of a.i./ha] | Efficacy [%] |
|---|---|---|
| A1-55 | 2 | 30 |
| dicamba | 40 | 0 |
| A1-55 + dicamba | 2 + 40 | 50 (Ec = 30, Diff. = +20) |

TABLE 144

Efficacy against SETVI, 21 days after application

| Active ingredient | Dosage [g of a.i./ha] | Efficacy [%] |
|---|---|---|
| A1-55 | 2 | 30 |
| dicamba | 10 | 0 |
| A1-55 + dicamba | 2 + 10 | 40 (Ec = 30, Diff. = +10) |

TABLE 145

Efficacy against AMARE, 21 days after application

| Active ingredient | Dosage [g of a.i./ha] | Efficacy [%] |
|---|---|---|
| A1-55 | 0.5 | 10 |
| dicamba | 40 | 65 |
| A1-55 + dicamba | 0.5 + 40 | 75 (Ec = 68.5, Diff. = +6.5) |

TABLE 146

Efficacy against ELEIN, 21 days after application

| Active ingredient | Dosage [g of a.i./ha] | Efficacy [%] |
|---|---|---|
| A1-57 | 1 | 10 |
| glyphosate | 50 | 0 |
| A1-57 + glyphosate | 1 + 50 | 20 (Ec = 10, Diff. = +10) |

TABLE 147

Efficacy against CHEAL, 21 days after application

| Active ingredient | Dosage [g of a.i./ha] | Efficacy [%] |
|---|---|---|
| A1-57 | 1 | 30 |
| glyphosate | 50 | 30 |
| A1-57 + glyphosate | 1 + 50 | 65 (Ec = 51, Diff. = +14) |

TABLE 148

Efficacy against KCHSC, 21 days after application

| Active ingredient | Dosage [g of a.i./ha] | Efficacy [%] |
|---|---|---|
| A1-57 | 1 | 20 |
| glyphosate | 200 | 30 |
| A1-57 + glyphosate | 1 + 200 | 50 (Ec = 44, Diff. = +6) |

TABLE 149

Efficacy against KCHSC, 21 days after application

| Active ingredient | Dosage [g of a.i./ha] | Efficacy [%] |
|---|---|---|
| A1-57 | 1 | 20 |
| glyphosate | 50 | 10 |
| A1-57 + glyphosate | 1 + 50 | 40 (Ec = 28, Diff. = +12) |

TABLE 150

Efficacy against DIGSA, 21 days after application

| Active ingredient | Dosage [g of a.i./ha] | Efficacy [%] |
|---|---|---|
| A1-7 | 2 | 10 |
| fenoxaprop-P-ethyl | 5 | 10 |
| A1-7 + fenoxaprop-P-ethyl | 2 + 5 | 30 (Ec = 19, Diff. = +11) |

TABLE 151

Efficacy against SETVI, 21 days after application

| Active ingredient | Dosage [g of a.i./ha] | Efficacy [%] |
|---|---|---|
| A1-7 | 2 | 75 |
| fenoxaprop-P-ethyl | 20 | 80 |
| A1-7 + fenoxaprop-P-ethyl | 2 + 20 | 100 (Ec = 95, Diff.= +5) |

TABLE 152

Efficacy against SETVI, 21 days after application

| Active ingredient | Dosage [g of a.i./ha] | Efficacy [%] |
|---|---|---|
| A1-7 | 0.5 | 30 |
| fenoxaprop-P-ethyl | 20 | 80 |
| A1-7 + fenoxaprop-P-ethyl | 0.5 + 20 | 100 (Ec = 86, Diff. = +14) |

TABLE 153

Efficacy against CHEAL, 21 days after application

| Active ingredient | Dosage [g of a.i./ha] | Efficacy [%] |
|---|---|---|
| A1-7 | 2 | 20 |
| fenoxaprop-P-ethyl | 20 | 0 |
| A1-7 + fenoxaprop-P-ethyl | 2 + 20 | 60 (Ec = 20, Diff. = +40) |

TABLE 154

Efficacy against CHEAL, 21 days after application

| Active ingredient | Dosage [g of a.i./ha] | Efficacy [%] |
|---|---|---|
| A1-7 | 2 | 20 |
| fenoxaprop-P-ethyl | 5 | 0 |
| A1-7 + fenoxaprop-P-ethyl | 2 + 5 | 50 (Ec = 20, Diff. = +30) |

TABLE 155

Efficacy against CHEAL, 21 days after application

| Active ingredient | Dosage [g of a.i./ha] | Efficacy [%] |
|---|---|---|
| A1-7 | 0.5 | 10 |
| fenoxaprop-P-ethyl | 20 | 0 |
| A1-7 + fenoxaprop-P-ethyl | 0.5 + 20 | 30 (Ec = 10, Diff. = +20) |

TABLE 156

Efficacy against CHEAL, 21 days after application

| Active ingredient | Dosage [g of a.i./ha] | Efficacy [%] |
|---|---|---|
| A1-7 | 0.5 | 10 |
| fenoxaprop-P-ethyl | 5 | 0 |
| A1-7 + fenoxaprop-P-ethyl | 0.5 + 5 | 20 (Ec = 10, Diff. = +10) |

TABLE 157

Efficacy against KCHSC, 21 days after application

| Active ingredient | Dosage [g of a.i./ha] | Efficacy [%] |
|---|---|---|
| A1-7 | 0.5 | 10 |
| fenoxaprop-P-ethyl | 20 | 0 |
| A1-7 + fenoxaprop-P-ethyl | 0.5 + 20 | 20 (Ec = 10, Diff. = +10) |

TABLE 158

Efficacy against SOLNI, 21 days after application

| Active ingredient | Dosage [g of a.i./ha] | Efficacy [%] |
|---|---|---|
| A1-7 | 2 | 10 |
| fenoxaprop-P-ethyl | 20 | 0 |
| A1-7 + fenoxaprop-P-ethyl | 2 + 20 | 20 (Ec = 10, Diff. = +10) |

TABLE 159

Efficacy against SOLNI, 21 days after application

| Active ingredient | Dosage [g of a.i./ha] | Efficacy [%] |
|---|---|---|
| A1-7 | 2 | 10 |
| fenoxaprop-P-ethyl | 5 | 0 |
| A1-7 + fenoxaprop-P-ethyl | 2 + 5 | 20 (Ec = 10, Diff. = +10) |

TABLE 160

Efficacy against SOLNI, 21 days after application

| Active ingredient | Dosage [g of a.i./ha] | Efficacy [%] |
|---|---|---|
| A1-7 | 0.5 | 0 |
| fenoxaprop-P-ethyl | 20 | 0 |
| A1-7 + fenoxaprop-P-ethyl | 0.5 + 20 | 10 (Ec = 0, Diff. = +10) |

TABLE 161

Efficacy against SOLNI, 21 days after application

| Active ingredient | Dosage [g of a.i./ha] | Efficacy [%] |
|---|---|---|
| A1-7 | 0.5 | 0 |
| fenoxaprop-P-ethyl | 5 | 0 |
| A1-7 + fenoxaprop-P-ethyl | 0.5 + 5 | 10 (Ec = 0, Diff. = +10) |

TABLE 162

Efficacy against DIGSA, 21 days after application

| Active ingredient | Dosage [g of a.i./ha] | Efficacy [%] |
|---|---|---|
| A1-60 | 4 | 70 |
| lenacil | 1200 | 0 |
| A1-60 + lenacil | 4 + 1200 | 97 (Ec = 70, Diff. = +27) |

TABLE 163

Efficacy against DIGSA, 21 days after application

| Active ingredient | Dosage [g of a.i./ha] | Efficacy [%] |
|---|---|---|
| A1-60 | 4 | 70 |
| lenacil | 300 | 0 |
| A1-60 + lenacil | 4 + 300 | 95 (Ec = 70, Diff. = +25) |

TABLE 164

Efficacy against ECHCG, 21 days after application

| Active ingredient | Dosage [g of a.i./ha] | Efficacy [%] |
|---|---|---|
| A1-60 | 4 | 75 |
| lenacil | 1200 | 0 |
| A1-60 + lenacil | 4 + 1200 | 100 (Ec = 75, Diff. = +25) |

TABLE 165

Efficacy against ECHCG, 21 days after application

| Active ingredient | Dosage [g of a.i./ha] | Efficacy [%] |
|---|---|---|
| A1-60 | 4 | 75 |
| lenacil | 300 | 0 |
| A1-60 + lenacil | 4 + 300 | 100 (Ec = 75, Diff. = +25) |

TABLE 166

Efficacy against ECHCG, 21 days after application

| Active ingredient | Dosage [g of a.i./ha] | Efficacy [%] |
|---|---|---|
| A1-60 | 1 | 40 |
| lenacil | 1200 | 0 |
| A1-60 + lenacil | 1 + 1200 | 70 (Ec = 40, Diff. = +30) |

TABLE 167

Efficacy against ECHCG, 21 days after application

| Active ingredient | Dosage [g of a.i./ha] | Efficacy [%] |
|---|---|---|
| A1-60 | 1 | 40 |
| lenacil | 300 | 0 |
| A1-60 + lenacil | 1 + 300 | 70 (Ec = 40, Diff. = +30) |

TABLE 168

Efficacy against ELEIN, 21 days after application

| Active ingredient | Dosage [g of a.i./ha] | Efficacy [%] |
|---|---|---|
| A1-60 | 4 | 75 |
| lenacil | 1200 | 0 |
| A1-60 + lenacil | 4 + 1200 | 98 (Ec = 75, Diff. = +23) |

TABLE 169

| Efficacy against ELEIN, 21 days after application | | |
|---|---|---|
| Active ingredient | Dosage [g of a.i./ha] | Efficacy [%] |
| A1-60 | 4 | 75 |
| lenacil | 300 | 0 |
| A1-60 + lenacil | 4 + 300 | 95 (Ec = 75, Diff. = +20) |

TABLE 170

| Efficacy against ELEIN, 21 days after application | | |
|---|---|---|
| Active ingredient | Dosage [g of a.i./ha] | Efficacy [%] |
| A1-60 | 1 | 40 |
| lenacil | 1200 | 0 |
| A1-60 + lenacil | 1 + 1200 | 70 (Ec = 40, Diff. = +30) |

TABLE 171

| Efficacy against ELEIN, 21 days after application | | |
|---|---|---|
| Active ingredient | Dosage [g of a.i./ha] | Efficacy [%] |
| A1-60 | 1 | 40 |
| lenacil | 300 | 0 |
| A1-60 + lenacil | 1 + 300 | 95 (Ec = 40, Diff. = +55) |

TABLE 172

| Efficacy against SETVI, 21 days after application | | |
|---|---|---|
| Active ingredient | Dosage [g of a.i./ha] | Efficacy [%] |
| A1-60 | 4 | 70 |
| lenacil | 1200 | 0 |
| A1-60 + lenacil | 4 + 1200 | 85 (Ec = 70, Diff. = +15) |

TABLE 173

| Efficacy against SETVI, 21 days after application | | |
|---|---|---|
| Active ingredient | Dosage [g of a.i./ha] | Efficacy [%] |
| A1-60 | 4 | 70 |
| lenacil | 300 | 0 |
| A1-60 + lenacil | 4 + 300 | 75 (Ec = 70, Diff. = +5) |

TABLE 174

| Efficacy against SETVI, 21 days after application | | |
|---|---|---|
| Active ingredient | Dosage [g of a.i./ha] | Efficacy [%] |
| A1-60 | 1 | 50 |
| lenacil | 1200 | 0 |
| A1-60 + lenacil | 1 + 1200 | 80 (Ec = 50, Diff. = +30) |

TABLE 175

| Efficacy against AMARE, 21 days after application | | |
|---|---|---|
| Active ingredient | Dosage [g of a.i./ha] | Efficacy [%] |
| A1-60 | 4 | 60 |
| lenacil | 1200 | 0 |
| A1-60 + lenacil | 4 + 1200 | 65 (Ec = 60, Diff. = +5) |

TABLE 176

| Efficacy against AMARE, 21 days after application | | |
|---|---|---|
| Active ingredient | Dosage [g of a.i./ha] | Efficacy [%] |
| A1-60 | 1 | 20 |
| lenacil | 1200 | 0 |
| A1-60 + lenacil | 1 + 1200 | 30 (Ec = 20, Diff. = +10) |

TABLE 177

| Efficacy against AMARE, 21 days after application | | |
|---|---|---|
| Active ingredient | Dosage [g of a.i./ha] | Efficacy [%] |
| A1-60 | 1 | 20 |
| lenacil | 300 | 0 |
| A1-60 + lenacil | 1 + 300 | 30 (Ec = 20, Diff. = +10) |

TABLE 178

| Efficacy against SOLNI, 21 days after application | | |
|---|---|---|
| Active ingredient | Dosage [g of a.i./ha] | Efficacy [%] |
| A1-60 | 4 | 30 |
| lenacil | 1200 | 0 |
| A1-60 + lenacil | 4 + 1200 | 100 (Ec = 30, Diff. = +70) |

TABLE 179

| Efficacy against SOLNI, 21 days after application | | |
|---|---|---|
| Active ingredient | Dosage [g of a.i./ha] | Efficacy [%] |
| A1-60 | 4 | 30 |
| lenacil | 300 | 0 |
| A1-60 + lenacil | 4 + 300 | 80 (Ec = 30, Diff. = +50) |

TABLE 180

| Efficacy against SOLNI, 21 days after application | | |
|---|---|---|
| Active ingredient | Dosage [g of a.i./ha] | Efficacy [%] |
| A1-60 | 1 | 20 |
| lenacil | 1200 | 0 |
| A1-60 + lenacil | 1 + 1200 | 60 (Ec = 20, Diff. = +40) |

TABLE 181

Efficacy against SOLNI, 21 days after application

| Active ingredient | Dosage [g of a.i./ha] | Efficacy [%] |
|---|---|---|
| A1-60 | 1 | 20 |
| lenacil | 300 | 0 |
| A1-60 + lenacil | 1 + 300 | 60 (Ec = 20, Diff. = +40) |

TABLE 182

Efficacy against ECHCG, 21 days after application

| Active ingredient | Dosage [g of a.i./ha] | Efficacy [%] |
|---|---|---|
| A1-13 | 0.4 | 0 |
| metribuzin | 20 | 0 |
| A1-13 + metribuzin | 0.4 + 20 | 75 (Ec = 0, Diff. = +75) |

TABLE 183

Efficacy against ECHCG, 21 days after application

| Active ingredient | Dosage [g of a.i./ha] | Efficacy [%] |
|---|---|---|
| A1-13 | 0.4 | 0 |
| metribuzin | 5 | 0 |
| A1-13 + metribuzin | 0.4 + 5 | 60 (Ec = 0, Diff. = +60) |

TABLE 184

Efficacy against ECHCG, 21 days after application

| Active ingredient | Dosage [g of a.i./ha] | Efficacy [%] |
|---|---|---|
| A1-13 | 0.1 | 0 |
| metribuzin | 20 | 0 |
| A1-13 + metribuzin | 0.1 + 20 | 20 (Ec = 0, Diff. = +20) |

TABLE 185

Efficacy against ELEIN, 21 days after application

| Active ingredient | Dosage [g of a.i./ha] | Efficacy [%] |
|---|---|---|
| A1-13 | 0.4 | 10 |
| metribuzin | 20 | 0 |
| A1-13 + metribuzin | 0.4 + 20 | 70 (Ec = 10, Diff. = +60) |

TABLE 186

Efficacy against ELEIN, 21 days after application

| Active ingredient | Dosage [g of a.i./ha] | Efficacy [%] |
|---|---|---|
| A1-13 | 0.4 | 10 |
| metribuzin | 5 | 0 |
| A1-13 + metribuzin | 0.4 + 5 | 60 (Ec = 10, Diff. = +50) |

TABLE 187

Efficacy against ELEIN, 21 days after application

| Active ingredient | Dosage [g of a.i./ha] | Efficacy [%] |
|---|---|---|
| A1-13 | 0.1 | 0 |
| metribuzin | 20 | 0 |
| A1-13 + metribuzin | 0.1 + 20 | 10 (Ec = 0, Diff. = +10) |

TABLE 188

Efficacy against SETVI, 21 days after application

| Active ingredient | Dosage [g of a.i./ha] | Efficacy [%] |
|---|---|---|
| A1-13 | 0.4 | 10 |
| metribuzin | 20 | 0 |
| A1-13 + metribuzin | 0.4 + 20 | 50 (Ec = 10, Diff. = +40) |

TABLE 189

Efficacy against SETVI, 21 days after application

| Active ingredient | Dosage [g of a.i./ha] | Efficacy [%] |
|---|---|---|
| A1-13 | 0.4 | 10 |
| metribuzin | 5 | 0 |
| A1-13 + metribuzin | 0.4 + 5 | 40 (Ec = 10, Diff. = +30) |

TABLE 190

Efficacy against SETVI, 21 days after application

| Active ingredient | Dosage [g of a.i./ha] | Efficacy [%] |
|---|---|---|
| A1-13 | 0.1 | 0 |
| metribuzin | 20 | 0 |
| A1-13 + metribuzin | 0.1 + 20 | 10 (Ec = 0, Diff. = +10) |

TABLE 191

Efficacy against AMARE, 21 days after application

| Active ingredient | Dosage [g of a.i./ha] | Efficacy [%] |
|---|---|---|
| A1-13 | 0.4 | 10 |
| metribuzin | 20 | 10 |
| A1-13 + metribuzin | 0.4 + 20 | 30 (Ec = 19, Diff. = +11) |

TABLE 192

Efficacy against AMARE, 21 days after application

| Active ingredient | Dosage [g of a.i./ha] | Efficacy [%] |
|---|---|---|
| A1-13 | 0.4 | 10 |
| metribuzin | 5 | 0 |
| A1-13 + metribuzin | 0.4 + 5 | 30 (Ec = 10, Diff. = +20) |

TABLE 193

Efficacy against CHEAL, 21 days after application

| Active ingredient | Dosage [g of a.i./ha] | Efficacy [%] |
|---|---|---|
| A1-13 | 0.1 | 0 |
| metribuzin | 20 | 20 |
| A1-13 + metribuzin | 0.1 + 20 | 30 (Ec = 20, Diff. = +10) |

TABLE 194

Efficacy against CHEAL, 21 days after application

| Active ingredient | Dosage [g of a.i./ha] | Efficacy [%] |
|---|---|---|
| A1-13 | 0.1 | 0 |
| metribuzin | 5 | 20 |
| A1-13 + metribuzin | 0.1 + 5 | 30 (Ec = 20, Diff. = +10) |

TABLE 195

Efficacy against KCHSC, 21 days after application

| Active ingredient | Dosage [g of a.i./ha] | Efficacy [%] |
|---|---|---|
| A1-13 | 0.4 | 0 |
| metribuzin | 20 | 10 |
| A1-13 + metribuzin | 0.4 + 20 | 65 (Ec = 10, Diff. = +55) |

TABLE 196

Efficacy against KCHSC, 21 days after application

| Active ingredient | Dosage [g of a.i./ha] | Efficacy [%] |
|---|---|---|
| A1-13 | 0.4 | 0 |
| metribuzin | 5 | 0 |
| A1-13 + metribuzin | 0.4 + 5 | 60 (Ec = 0, Diff. = +60) |

TABLE 197

Efficacy against KCHSC, 21 days after application

| Active ingredient | Dosage [g of a.i./ha] | Efficacy [%] |
|---|---|---|
| A1-13 | 0.1 | 0 |
| metribuzin | 20 | 10 |
| A1-13 + metribuzin | 0.1 + 20 | 20 (Ec = 10, Diff. = +10) |

TABLE 198

Efficacy against KCHSC, 21 days after application

| Active ingredient | Dosage [g of a.i./ha] | Efficacy [%] |
|---|---|---|
| A1-13 | 0.1 | 0 |
| metribuzin | 5 | 0 |
| A1-13 + metribuzin | 0.1 + 5 | 10 (Ec = 0, Diff. = +10) |

TABLE 199

Efficacy against SOLNI, 21 days after application

| Active ingredient | Dosage [g of a.i./ha] | Efficacy [%] |
|---|---|---|
| A1-13 | 0.4 | 10 |
| metribuzin | 20 | 0 |
| A1-13 + metribuzin | 0.4 + 20 | 50 (Ec = 10, Diff. = +40) |

TABLE 200

Efficacy against SOLNI, 21 days after application

| Active ingredient | Dosage [g of a.i./ha] | Efficacy [%] |
|---|---|---|
| A1-13 | 0.4 | 10 |
| metribuzin | 5 | 0 |
| A1-13 + metribuzin | 0.4 + 5 | 65 (Ec = 10, Diff. = +55) |

TABLE 201

Efficacy against AVEFA, 14 days after application

| Active ingredient | Dosage [g of a.i./ha] | Efficacy [%] |
|---|---|---|
| A1-3 | 20 | 0 |
| pinoxaden | 20 | 20 |
| A1-3 + pinoxaden | 20 + 20 | 30 (Ec = 20, Diff. = +10) |

TABLE 202

Efficacy against AVEFA, 14 days after application

| Active ingredient | Dosage [g of a.i./ha] | Efficacy [%] |
|---|---|---|
| A1-3 | 5 | 0 |
| pinoxaden | 5 | 0 |
| A1-3 + pinoxaden | 5 + 5 | 15 (Ec = 0, Diff. = +15) |

TABLE 203

Efficacy against BROST, 14 days after application

| Active ingredient | Dosage [g of a.i./ha] | Efficacy [%] |
|---|---|---|
| A1-3 | 20 | 5 |
| pinoxaden | 20 | 10 |
| A1-3 + pinoxaden | 20 + 20 | 30 (Ec = 14.5, Diff. = +15.5) |

TABLE 204

Efficacy against BROST, 14 days after application

| Active ingredient | Dosage [g of a.i./ha] | Efficacy [%] |
|---|---|---|
| A1-3 | 20 | 5 |
| pinoxaden | 5 | 0 |
| A1-3 + pinoxaden | 20 + 5 | 25 (Ec = 5, Diff. = +20) |

TABLE 205

Efficacy against BROST, 14 days after application

| Active ingredient | Dosage [g of a.i./ha] | Efficacy [%] |
|---|---|---|
| A1-3 | 5 | 0 |
| pinoxaden | 20 | 10 |
| A1-3 + pinoxaden | 5 + 20 | 30 (Ec = 10, Diff. = +20) |

TABLE 206

Efficacy against BROST, 14 days after application

| Active ingredient | Dosage [g of a.i./ha] | Efficacy [%] |
|---|---|---|
| A1-3 | 5 | 0 |
| pinoxaden | 5 | 0 |
| A1-3 + pinoxaden | 5 + 5 | 15 (Ec = 0, Diff. = +15) |

TABLE 207

Efficacy against LOLMU, 14 days after application

| Active ingredient | Dosage [g of a.i./ha] | Efficacy [%] |
| --- | --- | --- |
| A1-3 | 5 | 0 |
| pinoxaden | 20 | 85 |
| A1-3 + pinoxaden | 5 + 20 | 90 (Ec = 85, Diff. = +5) |

TABLE 208

Efficacy against PHAMI, 14 days after application

| Active ingredient | Dosage [g of a.i./ha] | Efficacy [%] |
| --- | --- | --- |
| A1-3 | 20 | 20 |
| pinoxaden | 20 | 50 |
| A1-3 + pinoxaden | 20 + 20 | 85 (Ec = 60, Diff. = +25) |

TABLE 209

Efficacy against PHAMI, 14 days after application

| Active ingredient | Dosage [g of a.i./ha] | Efficacy [%] |
| --- | --- | --- |
| A1-3 | 20 | 20 |
| pinoxaden | 5 | 10 |
| A1-3 + pinoxaden | 20 + 5 | 50 (Ec = 28, Diff. = +22) |

TABLE 210

Efficacy against PHAMI, 14 days after application

| Active ingredient | Dosage [g of a.i./ha] | Efficacy [%] |
| --- | --- | --- |
| A1-3 | 5 | 0 |
| pinoxaden | 20 | 50 |
| A1-3 + pinoxaden | 5 + 20 | 60 (Ec = 50, Diff. = +10) |

TABLE 211

Efficacy against PHAMI, 14 days after application

| Active ingredient | Dosage [g of a.i./ha] | Efficacy [%] |
| --- | --- | --- |
| A1-3 | 5 | 0 |
| pinoxaden | 5 | 10 |
| A1-3 + pinoxaden | 5 + 5 | 15 (Ec = 10, Diff. = +5) |

TABLE 212

Efficacy against POAAN, 14 days after application

| Active ingredient | Dosage [g of a.i./ha] | Efficacy [%] |
| --- | --- | --- |
| A1-3 | 20 | 5 |
| pinoxaden | 20 | 0 |
| A1-3 + pinoxaden | 20 + 20 | 35 (Ec = 5, Diff. = +30) |

TABLE 213

Efficacy against POAAN, 14 days after application

| Active ingredient | Dosage [g of a.i./ha] | Efficacy [%] |
| --- | --- | --- |
| A1-3 | 20 | 5 |
| pinoxaden | 5 | 0 |
| A1-3 + pinoxaden | 20 + 5 | 15 (Ec = 5, Diff. = +10) |

TABLE 214

Efficacy against POAAN, 14 days after application

| Active ingredient | Dosage [g of a.i./ha] | Efficacy [%] |
| --- | --- | --- |
| A1-3 | 5 | 0 |
| pinoxaden | 20 | 0 |
| A1-3 + pinoxaden | 5 + 20 | 20 (Ec = 0, Diff. = +20) |

TABLE 215

Efficacy against GALAP, 14 days after application

| Active ingredient | Dosage [g of a.i./ha] | Efficacy [%] |
| --- | --- | --- |
| A1-3 | 5 | 40 |
| pinoxaden | 20 | 0 |
| A1-3 + pinoxaden | 5 + 20 | 50 (Ec = 40, Diff. = +10) |

TABLE 216

Efficacy against MATIN, 14 days after application

| Active ingredient | Dosage [g of a.i./ha] | Efficacy [%] |
| --- | --- | --- |
| A1-3 | 5 | 30 |
| pinoxaden | 20 | 0 |
| A1-3 + pinoxaden | 5 + 20 | 35 (Ec = 30, Diff. = +5) |

TABLE 217

Efficacy against POLCO, 14 days after application

| Active ingredient | Dosage [g of a.i./ha] | Efficacy [%] |
| --- | --- | --- |
| A1-3 | 20 | 10 |
| pinoxaden | 20 | 0 |
| A1-3 + pinoxaden | 20 + 20 | 40 (Ec = 10, Diff. = +30) |

TABLE 218

Efficacy against POLCO, 14 days after application

| Active ingredient | Dosage [g of a.i./ha] | Efficacy [%] |
| --- | --- | --- |
| A1-3 | 20 | 10 |
| pinoxaden | 5 | 0 |
| A1-3 + pinoxaden | 20 + 5 | 40 (Ec = 10, Diff. = +30) |

TABLE 219

Efficacy against POLCO, 14 days after application

| Active ingredient | Dosage [g of a.i./ha] | Efficacy [%] |
|---|---|---|
| A1-3 | 5 | 0 |
| pinoxaden | 20 | 0 |
| A1-3 + pinoxaden | 5 + 20 | 40 (Ec = 0, Diff. = +40) |

TABLE 220

Efficacy against POLCO, 14 days after application

| Active ingredient | Dosage [g of a.i./ha] | Efficacy [%] |
|---|---|---|
| A1-3 | 5 | 0 |
| pinoxaden | 5 | 0 |
| A1-3 + pinoxaden | 5 + 5 | 20 (Ec = 0, Diff. = +20) |

TABLE 221

Efficacy against AVEFA, 14 days after application

| Active ingredient | Dosage [g of a.i./ha] | Efficacy [%] |
|---|---|---|
| A1-13 | 10 | 35 |
| mesosulfuron-methyl | 10 | 5 |
| A1-13 + mesosulfuron-methyl | 10 + 10 | 60 (Ec = 38.25, Diff. = +21.75) |

TABLE 222

Efficacy against PHAMI, 14 days after application

| Active ingredient | Dosage [g of a.i./ha] | Efficacy [%] |
|---|---|---|
| A1-13 | 10 | 30 |
| mesosulfuron-methyl | 10 | 5 |
| A1-13 + mesosulfuron-methyl | 10 + 10 | 40 (Ec = 33.5, Diff. = +6.5) |

TABLE 223

Efficacy against PHAMI, 14 days after application

| Active ingredient | Dosage [g of a.i./ha] | Efficacy [%] |
|---|---|---|
| A1-13 | 10 | 30 |
| mesosulfuron-methyl | 2.5 | 0 |
| A1-13 + mesosulfuron-methyl | 10 + 2.5 | 40 (Ec = 30, Diff. = +10) |

TABLE 224

Efficacy against PHAMI, 14 days after application

| Active ingredient | Dosage [g of a.i./ha] | Efficacy [%] |
|---|---|---|
| A1-13 | 2.5 | 30 |
| mesosulfuron-methyl | 10 | 5 |
| A1-13 + mesosulfuron-methyl | 2.5 + 10 | 40 (Ec = 33.5, Diff. = +6.5) |

TABLE 225

Efficacy against POAAN, 14 days after application

| Active ingredient | Dosage [g of a.i./ha] | Efficacy [%] |
|---|---|---|
| A1-13 | 10 | 40 |
| mesosulfuron-methyl | 10 | 40 |
| A1-13 + mesosulfuron-methyl | 10 + 10 | 70 (Ec = 64, Diff. = +6) |

TABLE 226

Efficacy against POAAN, 14 days after application

| Active ingredient | Dosage [g of a.i./ha] | Efficacy [%] |
|---|---|---|
| A1-13 | 2.5 | 20 |
| mesosulfuron-methyl | 10 | 40 |
| A1-13 + mesosulfuron-methyl | 2.5 + 10 | 70 (Ec = 52, Diff. = +18) |

TABLE 227

Efficacy against POAAN, 14 days after application

| Active ingredient | Dosage [g of a.i./ha] | Efficacy [%] |
|---|---|---|
| A1-13 | 2.5 | 20 |
| mesosulfuron-methyl | 2.5 | 15 |
| A1-13 + mesosulfuron-methyl | 2.5 + 2.5 | 40 (Ec = 32, Diff. = +8) |

TABLE 228

Efficacy against GALAP, 14 days after application

| Active ingredient | Dosage [g of a.i./ha] | Efficacy [%] |
|---|---|---|
| A1-13 | 10 | 50 |
| mesosulfuron-methyl | 10 | 30 |
| A1-13 + mesosulfuron-methyl | 10 + 10 | 75 (Ec = 65, Diff. = +10) |

TABLE 229

Efficacy against GALAP, 14 days after application

| Active ingredient | Dosage [g of a.i./ha] | Efficacy [%] |
|---|---|---|
| A1-13 | 10 | 50 |
| mesosulfuron-methyl | 2.5 | 30 |
| A1-13 + mesosulfuron-methyl | 10 + 2.5 | 70 (Ec = 65, Diff. = +5) |

TABLE 230

Efficacy against MATIN, 14 days after application

| Active ingredient | Dosage [g of a.i./ha] | Efficacy [%] |
|---|---|---|
| A1-13 | 10 | 40 |
| mesosulfuron-methyl | 10 | 0 |
| A1-13 + mesosulfuron-methyl | 10 + 10 | 70 (Ec = 40, Diff. = +30) |

TABLE 231

Efficacy against MATIN, 14 days after application

| Active ingredient | Dosage [g of a.i./ha] | Efficacy [%] |
|---|---|---|
| A1-13 | 10 | 40 |
| mesosulfuron-methyl | 2.5 | 0 |
| A1-13 + mesosulfuron-methyl | 10 + 2.5 | 65 (Ec = 40, Diff. = +25) |

TABLE 232

Efficacy against MATIN, 14 days after application

| Active ingredient | Dosage [g of a.i./ha] | Efficacy [%] |
|---|---|---|
| A1-13 | 2.5 | 30 |
| mesosulfuron-methyl | 10 | 0 |
| A1-13 + mesosulfuron-methyl | 2.5 + 10 | 40 (Ec = 30, Diff. = +10) |

TABLE 233

Efficacy against BROST, 14 days after application

| Active ingredient | Dosage [g of a.i./ha] | Efficacy [%] |
|---|---|---|
| A1-34 | 50 | 10 |
| iodosulfuron-methyl-sodium | 2 | 15 |
| A1-34 + iodosulfuron-methyl-sodium | 50 + 2 | 30 (Ec = 23.5, Diff. = +6.5) |

TABLE 234

Efficacy against LOLMU, 14 days after application

| Active ingredient | Dosage [g of a.i./ha] | Efficacy [%] |
|---|---|---|
| A1-34 | 200 | 30 |
| iodosulfuron-methyl-sodium | 2 | 30 |
| A1-34 + iodosulfuron-methyl-sodium | 200 + 2 | 60 (Ec = 51, Diff. = +9) |

TABLE 235

Efficacy against LOLMU, 14 days after application

| Active ingredient | Dosage [g of a.i./ha] | Efficacy [%] |
|---|---|---|
| A1-34 | 200 | 30 |
| iodosulfuron-methyl-sodium | 0.5 | 0 |
| A1-34 + iodosulfuron-methyl-sodium | 200 + 0.5 | 40 (Ec = 30, Diff. = +10) |

TABLE 236

Efficacy against LOLMU, 14 days after application

| Active ingredient | Dosage [g of a.i./ha] | Efficacy [%] |
|---|---|---|
| A1-34 | 50 | 5 |
| iodosulfuron-methyl-sodium | 0.5 | 0 |
| A1-34 + iodosulfuron-methyl-sodium | 50 + 0.5 | 15 (Ec = 5, Diff. = +10) |

TABLE 237

Efficacy against PHAMI, 14 days after application

| Active ingredient | Dosage [g of a.i./ha] | Efficacy [%] |
|---|---|---|
| A1-34 | 200 | 60 |
| iodosulfuron-methyl-sodium | 0.5 | 10 |
| A1-34 + iodosulfuron-methyl-sodium | 200 + 0.5 | 70 (Ec = 64, Diff. = +6) |

TABLE 238

Efficacy against POAAN, 14 days after application

| Active ingredient | Dosage [g of a.i./ha] | Efficacy [%] |
|---|---|---|
| A1-34 | 200 | 85 |
| iodosulfuron-methyl-sodium | 2 | 20 |
| A1-34 + iodosulfuron-methyl-sodium | 200 + 2 | 93 (Ec = 88, Diff. = +5) |

TABLE 239

Efficacy against POAAN, 14 days after application

| Active ingredient | Dosage [g of a.i./ha] | Efficacy [%] |
|---|---|---|
| A1-34 | 200 | 85 |
| iodosulfuron-methyl-sodium | 0.5 | 0 |
| A1-34 + iodosulfuron-methyl-sodium | 200 + 0.5 | 95 (Ec = 85, Diff. = +10) |

TABLE 240

Efficacy against GALAP, 14 days after application

| Active ingredient | Dosage [g of a.i./ha] | Efficacy [%] |
|---|---|---|
| A1-34 | 50 | 50 |
| iodosulfuron-methyl-sodium | 0.5 | 30 |
| A1-34 + iodosulfuron-methyl-sodium | 50 + 0.5 | 70 (Ec = 65, Diff. = +5) |

TABLE 241

Efficacy against POLCO, 14 days after application

| Active ingredient | Dosage [g of a.i./ha] | Efficacy [%] |
|---|---|---|
| A1-34 | 200 | 30 |
| iodosulfuron-methyl-sodium | 2 | 30 |
| A1-34 + iodosulfuron-methyl-sodium | 200 + 2 | 60 (Ec = 51, Diff. = +9) |

TABLE 242

Efficacy against POLCO, 14 days after application

| Active ingredient | Dosage [g of a.i./ha] | Efficacy [%] |
|---|---|---|
| A1-34 | 200 | 30 |
| iodosulfuron-methyl-sodium | 0.5 | 15 |
| A1-34 + iodosulfuron-methyl-sodium | 200 + 0.5 | 60 (Ec = 40.5, Diff. = +19.5) |

TABLE 243

Efficacy against BROST, 14 days after application

| Active ingredient | Dosage [g of a.i./ha] | Efficacy [%] |
|---|---|---|
| A1-14 | 10 | 3 |
| pyrasulfotole | 25 | 0 |
| A1-14 + pyrasulfotole | 10 + 25 | 10 (Ec = 3, Diff. = +7) |

TABLE 244

Efficacy against BROST, 14 days after application

| Active ingredient | Dosage [g of a.i./ha] | Efficacy [%] |
|---|---|---|
| A1-14 | 2.5 | 0 |
| pyrasulfotole | 25 | 0 |
| A1-14 + pyrasulfotole | 2.5 + 25 | 10 (Ec = 0, Diff. = +10) |

TABLE 245

Efficacy against LOLMU, 14 days after application

| Active ingredient | Dosage [g of a.i./ha] | Efficacy [%] |
|---|---|---|
| A1-14 | 10 | 0 |
| pyrasulfotole | 100 | 0 |
| A1-14 + pyrasulfotole | 10 + 100 | 20 (Ec = 0, Diff. = +20) |

TABLE 246

Efficacy against LOLMU, 14 days after application

| Active ingredient | Dosage [g of a.i./ha] | Efficacy [%] |
|---|---|---|
| A1-14 | 2.5 | 0 |
| pyrasulfotole | 100 | 0 |
| A1-14 + pyrasulfotole | 2.5 + 100 | 15 (Ec = 0, Diff. = +15) |

TABLE 247

Efficacy against LOLMU, 14 days after application

| Active ingredient | Dosage [g of a.i./ha] | Efficacy [%] |
|---|---|---|
| A1-14 | 2.5 | 0 |
| pyrasulfotole | 25 | 0 |
| A1-14 + pyrasulfotole | 2.5 + 25 | 15 (Ec = 0, Diff. = +15) |

TABLE 248

Efficacy against PHAMI, 14 days after application

| Active ingredient | Dosage [g of a.i./ha] | Efficacy [%] |
|---|---|---|
| A1-14 | 10 | 25 |
| pyrasulfotole | 100 | 5 |
| A1-14 + pyrasulfotole | 10 + 100 | 40 (Ec = 28.75, Diff. = +11.25) |

TABLE 249

Efficacy against PHAMI, 14 days after application

| Active ingredient | Dosage [g of a.i./ha] | Efficacy [%] |
|---|---|---|
| A1-14 | 2.5 | 0 |
| pyrasulfotole | 100 | 5 |
| A1-14 + pyrasulfotole | 2.5 + 100 | 30 (Ec = 5, Diff. = +25) |

TABLE 250

Efficacy against PHAMI, 14 days after application

| Active ingredient | Dosage [g of a.i./ha] | Efficacy [%] |
|---|---|---|
| A1-14 | 2.5 | 0 |
| pyrasulfotole | 25 | 0 |
| A1-14 + pyrasulfotole | 2.5 + 25 | 10 (Ec = 0, Diff. = +10) |

TABLE 251

Efficacy against POAAN, 14 days after application

| Active ingredient | Dosage [g of a.i./ha] | Efficacy [%] |
|---|---|---|
| A1-14 | 2.5 | 10 |
| pyrasulfotole | 100 | 0 |
| A1-14 + pyrasulfotole | 2.5 + 100 | 25 (Ec = 10, Diff. = +15) |

TABLE 252

Efficacy against POAAN, 14 days after application

| Active ingredient | Dosage [g of a.i./ha] | Efficacy [%] |
|---|---|---|
| A1-14 | 2.5 | 10 |
| pyrasulfotole | 25 | 0 |
| A1-14 + pyrasulfotole | 2.5 + 25 | 20 (Ec = 10, Diff. = +10) |

TABLE 253

Efficacy against MATIN, 14 days after application

| Active ingredient | Dosage [g of a.i./ha] | Efficacy [%] |
|---|---|---|
| A1-14 | 10 | 60 |
| pyrasulfotole | 100 | 15 |
| A1-14 + pyrasulfotole | 10 + 100 | 80 (Ec = 66, Diff. = +14) |

TABLE 254

Efficacy against MATIN, 14 days after application

| Active ingredient | Dosage [g of a.i./ha] | Efficacy [%] |
|---|---|---|
| A1-14 | 10 | 60 |
| pyrasulfotole | 25 | 0 |
| A1-14 + pyrasulfotole | 10 + 25 | 70 (Ec = 60, Diff. = +10) |

TABLE 255

Efficacy against MATIN, 14 days after application

| Active ingredient | Dosage [g of a.i./ha] | Efficacy [%] |
|---|---|---|
| A1-14 | 2.5 | 50 |
| pyrasulfotole | 100 | 15 |
| A1-14 + pyrasulfotole | 2.5 + 100 | 70 (Ec = 57.5, Diff. = +12.5) |

TABLE 256

Efficacy against POLCO, 14 days after application

| Active ingredient | Dosage [g of a.i./ha] | Efficacy [%] |
|---|---|---|
| A1-14 | 10 | 20 |
| pyrasulfotole | 100 | 60 |
| A1-14 + pyrasulfotole | 10 + 100 | 85 (Ec = 68, Diff. = +17) |

TABLE 257

Efficacy against POLCO, 14 days after application

| Active ingredient | Dosage [g of a.i./ha] | Efficacy [%] |
|---|---|---|
| A1-14 | 10 | 20 |
| pyrasulfotole | 25 | 50 |
| A1-14 + pyrasulfotole | 10 + 25 | 95 (Ec = 60, Diff. = +35) |

TABLE 258

Efficacy against POLCO, 14 days after application

| Active ingredient | Dosage [g of a.i./ha] | Efficacy [%] |
|---|---|---|
| A1-14 | 2.5 | 20 |
| pyrasulfotole | 100 | 60 |
| A1-14 + pyrasulfotole | 2.5 + 100 | 75 (Ec = 68, Diff. = +7) |

TABLE 259

Efficacy against POLCO, 14 days after application

| Active ingredient | Dosage [g of a.i./ha] | Efficacy [%] |
|---|---|---|
| A1-14 | 2.5 | 20 |
| pyrasulfotole | 25 | 50 |
| A1-14 + pyrasulfotole | 2.5 + 25 | 65 (Ec = 60, Diff. = +5) |

TABLE 260

Efficacy against AVEFA, 14 days after application

| Active ingredient | Dosage [g of a.i./ha] | Efficacy [%] |
|---|---|---|
| A1-36 | 10 | 15 |
| flurtamone | 320 | 15 |
| A1-36 + flurtamone | 10 + 320 | 40 (Ec = 27.75, Diff. = +12.25) |

TABLE 261

Efficacy against AVEFA, 14 days after application

| Active ingredient | Dosage [g of a.i./ha] | Efficacy [%] |
|---|---|---|
| A1-36 | 10 | 15 |
| flurtamone | 80 | 0 |
| A1-36 + flurtamone | 10 + 80 | 30 (Ec = 15, Diff. = +15) |

TABLE 262

Efficacy against AVEFA, 14 days after application

| Active ingredient | Dosage [g of a.i./ha] | Efficacy [%] |
|---|---|---|
| A1-36 | 2.5 | 0 |
| flurtamone | 320 | 15 |
| A1-36 + flurtamone | 2.5 + 320 | 30 (Ec = 15, Diff. = +15) |

TABLE 263

Efficacy against AVEFA, 14 days after application

| Active ingredient | Dosage [g of a.i./ha] | Efficacy [%] |
|---|---|---|
| A1-36 | 2.5 | 0 |
| flurtamone | 80 | 0 |
| A1-36 + flurtamone | 2.5 + 80 | 15 (Ec = 0, Diff. = +15) |

TABLE 264

Efficacy against BROST, 14 days after application

| Active ingredient | Dosage [g of a.i./ha] | Efficacy [%] |
|---|---|---|
| A1-36 | 2.5 | 0 |
| flurtamone | 320 | 10 |
| A1-36 + flurtamone | 2.5 + 320 | 15 (Ec = 0, Diff. = +5) |

TABLE 265

Efficacy against BROST, 14 days after application

| Active ingredient | Dosage [g of a.i./ha] | Efficacy [%] |
|---|---|---|
| A1-36 | 2.5 | 0 |
| flurtamone | 80 | 0 |
| A1-36 + flurtamone | 2.5 + 80 | 15 (Ec = 0, Diff. = +15) |

TABLE 266

Efficacy against LOLMU, 14 days after application

| Active ingredient | Dosage [g of a.i./ha] | Efficacy [%] |
|---|---|---|
| A1-36 | 10 | 3 |
| flurtamone | 80 | 30 |
| A1-36 + flurtamone | 10 + 80 | 60 (Ec = 32.1, Diff. = +27.9) |

TABLE 267

Efficacy against PHAMI, 14 days after application

| Active ingredient | Dosage [g of a.i./ha] | Efficacy [%] |
|---|---|---|
| A1-36 | 10 | 30 |
| flurtamone | 320 | 50 |
| A1-36 + flurtamone | 10 + 320 | 75 (Ec = 65, Diff. = +10) |

TABLE 268

Efficacy against PHAMI, 14 days after application

| Active ingredient | Dosage [g of a.i./ha] | Efficacy [%] |
|---|---|---|
| A1-36 | 10 | 30 |
| flurtamone | 80 | 40 |
| A1-36 + flurtamone | 10 + 80 | 65 (Ec = 58, Diff. = +7) |

TABLE 269

Efficacy against PHAMI, 14 days after application

| Active ingredient | Dosage [g of a.i./ha] | Efficacy [%] |
|---|---|---|
| A1-36 | 2.5 | 0 |
| flurtamone | 320 | 50 |
| A1-36 + flurtamone | 2.5 + 320 | 85 (Ec = 50, Diff. = +35) |

TABLE 270

Efficacy against GALAP, 14 days after application

| Active ingredient | Dosage [g of a.i./ha] | Efficacy [%] |
|---|---|---|
| A1-36 | 10 | 25 |
| flurtamone | 320 | 80 |
| A1-36 + flurtamone | 10 + 320 | 100 (Ec = 85, Diff. = +15) |

TABLE 271

Efficacy against GALAP, 14 days after application

| Active ingredient | Dosage [g of a.i./ha] | Efficacy [%] |
|---|---|---|
| A1-36 | 10 | 25 |
| flurtamone | 80 | 40 |
| A1-36 + flurtamone | 10 + 80 | 60 (Ec = 55, Diff. = +5) |

TABLE 272

Efficacy against GALAP, 14 days after application

| Active ingredient | Dosage [g of a.i./ha] | Efficacy [%] |
|---|---|---|
| A1-36 | 2.5 | 5 |
| flurtamone | 80 | 40 |
| A1-36 + flurtamone | 2.5 + 80 | 70 (Ec = 43, Diff. = +27) |

TABLE 273

Efficacy against MATIN, 14 days after application

| Active ingredient | Dosage [g of a.i./ha] | Efficacy [%] |
|---|---|---|
| A1-36 | 10 | 40 |
| flurtamone | 320 | 50 |
| A1-36 + flurtamone | 10 + 320 | 97 (Ec = 70, Diff. = +27) |

TABLE 274

Efficacy against MATIN, 14 days after application

| Active ingredient | Dosage [g of a.i./ha] | Efficacy [%] |
|---|---|---|
| A1-36 | 10 | 40 |
| flurtamone | 80 | 50 |
| A1-36 + flurtamone | 10 + 80 | 97 (Ec = 70, Diff. = +27) |

TABLE 275

Efficacy against MATIN, 14 days after application

| Active ingredient | Dosage [g of a.i./ha] | Efficacy [%] |
|---|---|---|
| A1-36 | 2.5 | 15 |
| flurtamone | 320 | 50 |
| A1-36 + flurtamone | 2.5 + 320 | 90 (Ec = 57.5, Diff. = +32.5) |

TABLE 276

Efficacy against MATIN, 14 days after application

| Active ingredient | Dosage [g of a.i./ha] | Efficacy [%] |
|---|---|---|
| A1-36 | 2.5 | 15 |
| flurtamone | 80 | 50 |
| A1-36 + flurtamone | 2.5 + 80 | 80 (Ec = 57.5, Diff. = +22.5) |

TABLE 277

Efficacy against POLCO, 14 days after application

| Active ingredient | Dosage [g of a.i./ha] | Efficacy [%] |
|---|---|---|
| A1-36 | 2.5 | 0 |
| flurtamone | 320 | 30 |
| A1-36 + flurtamone | 2.5 + 320 | 40 (Ec = 30, Diff. = +10) |

TABLE 278

Efficacy against POLCO, 14 days after application

| Active ingredient | Dosage [g of a.i./ha] | Efficacy [%] |
|---|---|---|
| A1-36 | 2.5 | 0 |
| flurtamone | 80 | 50 |
| A1-36 + flurtamone | 2.5 + 80 | 70 (Ec = 50, Diff. = +20) |

TABLE 279

Efficacy against AVEFA, 14 days after application

| Active ingredient | Dosage [g of a.i./ha] | Efficacy [%] |
|---|---|---|
| A2-1 | 50 | 0 |
| fluroxypyr | 80 | 0 |
| A2-1 + fluroxypyr | 50 + 80 | 20 (Ec = 0, Diff. = +20) |

TABLE 280

Efficacy against AVEFA, 14 days after application

| Active ingredient | Dosage [g of a.i./ha] | Efficacy [%] |
|---|---|---|
| A2-1 | 12.5 | 0 |
| fluroxypyr | 80 | 0 |
| A2-1 + fluroxypyr | 12.5 + 80 | 15 (Ec = 0, Diff. = +15) |

TABLE 281

Efficacy against BROST, 14 days after application

| Active ingredient | Dosage [g of a.i./ha] | Efficacy [%] |
|---|---|---|
| A2-1 | 12.5 | 0 |
| fluroxypyr | 80 | 0 |
| A2-1 + fluroxypyr | 12.5 + 80 | 15 (Ec = 0, Diff. = +15) |

TABLE 282

Efficacy against LOLMU, 14 days after application

| Active ingredient | Dosage [g of a.i./ha] | Efficacy [%] |
|---|---|---|
| A2-1 | 50 | 0 |
| fluroxypyr | 80 | 0 |
| A2-1 + fluroxypyr | 50 + 80 | 20 (Ec = 0, Diff. = +20) |

TABLE 283

Efficacy against LOLMU, 14 days after application

| Active ingredient | Dosage [g of a.i./ha] | Efficacy [%] |
|---|---|---|
| A2-1 | 12.5 | 0 |
| fluroxypyr | 80 | 0 |
| A2-1 + fluroxypyr | 12.5 + 80 | 20 (Ec = 0, Diff. = +20) |

TABLE 284

Efficacy against PHAMI, 14 days after application

| Active ingredient | Dosage [g of a.i./ha] | Efficacy [%] |
|---|---|---|
| A2-1 | 12.5 | 15 |
| fluroxypyr | 80 | 15 |
| A2-1 + fluroxypyr | 12.5 + 80 | 35 (Ec = 27.75, Diff. = +7.25) |

TABLE 285

Efficacy against POAAN, 14 days after application

| Active ingredient | Dosage [g of a.i./ha] | Efficacy [%] |
|---|---|---|
| A2-1 | 12.5 | 15 |
| fluroxypyr | 20 | 0 |
| A2-1 + fluroxypyr | 12.5 + 20 | 20 (Ec = 15, Diff. = +5) |

TABLE 286

Efficacy against POLCO, 14 days after application

| Active ingredient | Dosage [g of a.i./ha] | Efficacy [%] |
|---|---|---|
| A2-1 | 50 | 70 |
| fluroxypyr | 20 | 70 |
| A2-1 + fluroxypyr | 50 + 20 | 100 (Ec = 91, Diff. = +9) |

TABLE 287

Efficacy against AVEFA, 14 days after application

| Active ingredient | Dosage [g of a.i./ha] | Efficacy [%] |
|---|---|---|
| A1-55 | 2.5 | 0 |
| glufosinate-ammonium | 100 | 25 |
| A1-55 + glufosinate-ammonium | 2.5 + 100 | 40 (Ec = 25, Diff. = +15) |

TABLE 288

Efficacy against AVEFA, 14 days after application

| Active ingredient | Dosage [g of a.i./ha] | Efficacy [%] |
|---|---|---|
| A1-55 | 2.5 | 0 |
| glufosinate-ammonium | 25 | 0 |
| A1-55 + glufosinate-ammonium | 2.5 + 25 | 10 (Ec = 0, Diff. = +10) |

TABLE 289

Efficacy against BROST, 14 days after application

| Active ingredient | Dosage [g of a.i./ha] | Efficacy [%] |
|---|---|---|
| A1-55 | 2.5 | 5 |
| glufosinate-ammonium | 100 | 15 |
| A1-55 + glufosinate-ammonium | 2.5 + 100 | 40 (Ec = 19.25, Diff. = +20.75) |

TABLE 290

Efficacy against LOLMU, 14 days after application

| Active ingredient | Dosage [g of a.i./ha] | Efficacy [%] |
|---|---|---|
| A1-55 | 10 | 15 |
| glufosinate-ammonium | 25 | 0 |
| A1-55 + glufosinate-ammonium | 10 + 25 | 20 (Ec = 15, Diff. = +5) |

TABLE 291

Efficacy against LOLMU, 14 days after application

| Active ingredient | Dosage [g of a.i./ha] | Efficacy [%] |
|---|---|---|
| A1-55 | 2.5 | 0 |
| glufosinate-ammonium | 100 | 25 |
| A1-55 + glufosinate-ammonium | 2.5 + 100 | 40 (Ec = 25, Diff. = +15) |

TABLE 292

Efficacy against LOLMU, 14 days after application

| Active ingredient | Dosage [g of a.i./ha] | Efficacy [%] |
|---|---|---|
| A1-55 | 2.5 | 0 |
| glufosinate-ammonium | 25 | 0 |
| A1-55 + glufosinate-ammonium | 2.5 + 25 | 15 (Ec = 0, Diff. = +15) |

TABLE 293

Efficacy against PHAMI, 14 days after application

| Active ingredient | Dosage [g of a.i./ha] | Efficacy [%] |
|---|---|---|
| A1-55 | 10 | 25 |
| glufosinate-ammonium | 100 | 15 |
| A1-55 + glufosinate-ammonium | 10 + 100 | 65 (Ec = 36.25, Diff. = +28.75) |

TABLE 294

Efficacy against PHAMI, 14 days after application

| Active ingredient | Dosage [g of a.i./ha] | Efficacy [%] |
|---|---|---|
| A1-55 | 10 | 25 |
| glufosinate-ammonium | 25 | 0 |
| A1-55 + glufosinate-ammonium | 10 + 25 | 50 (Ec = 25, Diff. = +25) |

TABLE 295

Efficacy against PHAMI, 14 days after application

| Active ingredient | Dosage [g of a.i./ha] | Efficacy [%] |
|---|---|---|
| A1-55 | 2.5 | 0 |
| glufosinate-ammonium | 100 | 15 |
| A1-55 + glufosinate-ammonium | 2.5 + 100 | 65 (Ec = 15, Diff. = +50) |

TABLE 296

Efficacy against PHAMI, 14 days after application

| Active ingredient | Dosage [g of a.i./ha] | Efficacy [%] |
|---|---|---|
| A1-55 | 2.5 | 0 |
| glufosinate-ammonium | 25 | 0 |
| A1-55 + glufosinate-ammonium | 2.5 + 25 | 40 (Ec = 0, Diff. = +40) |

TABLE 297

Efficacy against POAAN, 14 days after application

| Active ingredient | Dosage [g of a.i./ha] | Efficacy [%] |
|---|---|---|
| A1-55 | 10 | 20 |
| glufosinate-ammonium | 100 | 0 |
| A1-55 + glufosinate-ammonium | 10 + 100 | 40 (Ec = 20, Diff. = +20) |

TABLE 298

Efficacy against POAAN, 14 days after application

| Active ingredient | Dosage [g of a.i./ha] | Efficacy [%] |
|---|---|---|
| A1-55 | 2.5 | 5 |
| glufosinate-ammonium | 100 | 0 |
| A1-55 + glufosinate-ammonium | 2.5 + 100 | 30 (Ec = 5, Diff. = +25) |

TABLE 299

Efficacy against GALAP, 14 days after application

| Active ingredient | Dosage [g of a.i./ha] | Efficacy [%] |
|---|---|---|
| A1-55 | 10 | 30 |
| glufosinate-ammonium | 25 | 0 |
| A1-55 + glufosinate-ammonium | 10 + 25 | 60 (Ec = 30, Diff. = +30) |

TABLE 300

Efficacy against GALAP, 14 days after application

| Active ingredient | Dosage [g of a.i./ha] | Efficacy [%] |
|---|---|---|
| A1-55 | 2.5 | 0 |
| glufosinate-ammonium | 25 | 0 |
| A1-55 + glufosinate-ammonium | 2.5 + 25 | 30 (Ec = 0, Diff. = +30) |

TABLE 301

Efficacy against MATIN, 14 days after application

| Active ingredient | Dosage [g of a.i./ha] | Efficacy [%] |
|---|---|---|
| A1-55 | 10 | 30 |
| glufosinate-ammonium | 100 | 30 |
| A1-55 + glufosinate-ammonium | 10 + 100 | 95 (Ec = 51, Diff. = +44) |

TABLE 302

Efficacy against MATIN, 14 days after application

| Active ingredient | Dosage [g of a.i./ha] | Efficacy [%] |
|---|---|---|
| A1-55 | 10 | 30 |
| glufosinate-ammonium | 25 | 0 |
| A1-55 + glufosinate-ammonium | 10 + 25 | 95 (Ec = 30, Diff. = +65) |

TABLE 303

Efficacy against MATIN, 14 days after application

| Active ingredient | Dosage [g of a.i./ha] | Efficacy [%] |
|---|---|---|
| A1-55 | 2.5 | 0 |
| glufosinate-ammonium | 100 | 30 |
| A1-55 + glufosinate-ammonium | 2.5 + 100 | 80 (Ec = 30, Diff. = +50) |

TABLE 304

Efficacy against MATIN, 14 days after application

| Active ingredient | Dosage [g of a.i./ha] | Efficacy [%] |
|---|---|---|
| A1-55 | 2.5 | 0 |
| glufosinate-ammonium | 25 | 0 |
| A1-55 + glufosinate-ammonium | 2.5 + 25 | 70 (Ec = 0, Diff. = +70) |

TABLE 305

Efficacy against POLCO, 14 days after application

| Active ingredient | Dosage [g of a.i./ha] | Efficacy [%] |
|---|---|---|
| A1-55 | 10 | 0 |
| glufosinate-ammonium | 100 | 25 |
| A1-55 + glufosinate-ammonium | 10 + 100 | 50 (Ec = 25, Diff. = +25) |

TABLE 306

Efficacy against POLCO, 14 days after application

| Active ingredient | Dosage [g of a.i./ha] | Efficacy [%] |
|---|---|---|
| A1-55 | 10 | 0 |
| glufosinate-ammonium | 25 | 0 |
| A1-55 + glufosinate-ammonium | 10 + 25 | 70 (Ec = 0, Diff. = +70) |

TABLE 307

Efficacy against POLCO, 14 days after application

| Active ingredient | Dosage [g of a.i./ha] | Efficacy [%] |
|---|---|---|
| A1-55 | 2.5 | 0 |
| glufosinate-ammonium | 100 | 25 |
| A1-55 + glufosinate-ammonium | 2.5 + 100 | 50 (Ec = 25, Diff. = +25) |

TABLE 308

Efficacy against POLCO, 14 days after application

| Active ingredient | Dosage [g of a.i./ha] | Efficacy [%] |
|---|---|---|
| A1-55 | 2.5 | 0 |
| glufosinate-ammonium | 25 | 0 |
| A1-55 + glufosinate-ammonium | 2.5 + 25 | 15 (Ec = 0, Diff. = +15) |

TABLE 309

Efficacy against AVEFA, 14 days after application

| Active ingredient | Dosage [g of a.i./ha] | Efficacy [%] |
|---|---|---|
| A1-57 | 50 | 0 |
| aclonifen | 800 | 0 |
| A1-57 + aclonifen | 50 + 800 | 50 (Ec = 0, Diff. = +50) |

TABLE 310

Efficacy against AVEFA, 14 days after application

| Active ingredient | Dosage [g of a.i./ha] | Efficacy [%] |
|---|---|---|
| A1-57 | 50 | 0 |
| aclonifen | 200 | 0 |
| A1-57 + aclonifen | 50 + 200 | 20 (Ec = 0, Diff. = +20) |

TABLE 311

Efficacy against AVEFA, 14 days after application

| Active ingredient | Dosage [g of a.i./ha] | Efficacy [%] |
|---|---|---|
| A1-57 | 12.5 | 0 |
| aclonifen | 800 | 0 |
| A1-57 + aclonifen | 12.5 + 800 | 35 (Ec = 0, Diff. = +35) |

TABLE 312

Efficacy against AVEFA, 14 days after application

| Active ingredient | Dosage [g of a.i./ha] | Efficacy [%] |
|---|---|---|
| A1-57 | 12.5 | 0 |
| aclonifen | 200 | 0 |
| A1-57 + aclonifen | 12.5 + 200 | 5 (Ec = 0, Diff. = +5) |

TABLE 313

Efficacy against BROST, 14 days after application

| Active ingredient | Dosage [g of a.i./ha] | Efficacy [%] |
|---|---|---|
| A1-57 | 50 | 40 |
| aclonifen | 800 | 0 |
| A1-57 + aclonifen | 50 + 800 | 50 (Ec = 40, Diff. = +10) |

TABLE 314

Efficacy against BROST, 14 days after application

| Active ingredient | Dosage [g of a.i./ha] | Efficacy [%] |
|---|---|---|
| A1-57 | 12.5 | 0 |
| aclonifen | 800 | 0 |
| A1-57 + aclonifen | 12.5 + 800 | 40 (Ec = 0, Diff. = +40) |

TABLE 315

Efficacy against BROST, 14 days after application

| Active ingredient | Dosage [g of a.i./ha] | Efficacy [%] |
|---|---|---|
| A1-57 | 12.5 | 0 |
| aclonifen | 200 | 0 |
| A1-57 + aclonifen | 12.5 + 200 | 10 (Ec = 0, Diff. = +10) |

TABLE 316

Efficacy against LOLMU, 14 days after application

| Active ingredient | Dosage [g of a.i./ha] | Efficacy [%] |
|---|---|---|
| A1-57 | 50 | 35 |
| aclonifen | 800 | 0 |
| A1-57 + aclonifen | 50 + 800 | 40 (Ec = 35, Diff. = +5) |

TABLE 317

Efficacy against LOLMU, 14 days after application

| Active ingredient | Dosage [g of a.i./ha] | Efficacy [%] |
|---|---|---|
| A1-57 | 12.5 | 0 |
| aclonifen | 800 | 0 |
| A1-57 + aclonifen | 12.5 + 800 | 10 (Ec = 0, Diff. = +10) |

TABLE 318

Efficacy against PHAMI, 14 days after application

| Active ingredient | Dosage [g of a.i./ha] | Efficacy [%] |
|---|---|---|
| A1-57 | 50 | 70 |
| aclonifen | 200 | 0 |
| A1-57 + aclonifen | 50 + 200 | 85 (Ec = 70, Diff. = +15) |

TABLE 319

Efficacy against PHAMI, 14 days after application

| Active ingredient | Dosage [g of a.i./ha] | Efficacy [%] |
|---|---|---|
| A1-57 | 12.5 | 50 |
| aclonifen | 800 | 40 |
| A1-57 + aclonifen | 12.5 + 800 | 85 (Ec = 70, Diff. = +15) |

TABLE 320

Efficacy against PHAMI, 14 days after application

| Active ingredient | Dosage [g of a.i./ha] | Efficacy [%] |
|---|---|---|
| A1-57 | 12.5 | 50 |
| aclonifen | 200 | 0 |
| A1-57 + aclonifen | 12.5 + 200 | 60 (Ec = 50, Diff. = +10) |

TABLE 321

Efficacy against POAAN, 14 days after application

| Active ingredient | Dosage [g of a.i./ha] | Efficacy [%] |
|---|---|---|
| A1-57 | 50 | 50 |
| aclonifen | 800 | 30 |
| A1-57 + aclonifen | 50 + 800 | 85 (Ec = 65, Diff. = +20) |

TABLE 322

Efficacy against POAAN, 14 days after application

| Active ingredient | Dosage [g of a.i./ha] | Efficacy [%] |
|---|---|---|
| A1-57 | 50 | 50 |
| aclonifen | 200 | 0 |
| A1-57 + aclonifen | 50 + 200 | 80 (Ec = 50, Diff. = +30) |

TABLE 323

Efficacy against POAAN, 14 days after application

| Active ingredient | Dosage [g of a.i./ha] | Efficacy [%] |
|---|---|---|
| A1-57 | 12.5 | 15 |
| aclonifen | 800 | 30 |
| A1-57 + aclonifen | 12.5 + 800 | 70 (Ec = 40.5, Diff. = +29.5) |

TABLE 324

Efficacy against POAAN, 14 days after application

| Active ingredient | Dosage [g of a.i./ha] | Efficacy [%] |
|---|---|---|
| A1-57 | 12.5 | 15 |
| aclonifen | 200 | 0 |
| A1-57 + aclonifen | 12.5 + 200 | 45 (Ec = 15, Diff. = +30) |

TABLE 325

Efficacy against GALAP, 14 days after application

| Active ingredient | Dosage [g of a.i./ha] | Efficacy [%] |
|---|---|---|
| A1-57 | 50 | 60 |
| aclonifen | 200 | 20 |
| A1-57 + aclonifen | 50 + 200 | 80 (Ec = 68, Diff. = +12) |

TABLE 326

Efficacy against GALAP, 14 days after application

| Active ingredient | Dosage [g of a.i./ha] | Efficacy [%] |
|---|---|---|
| A1-57 | 12.5 | 30 |
| aclonifen | 200 | 20 |
| A1-57 + aclonifen | 12.5 + 200 | 65 (Ec = 44, Diff. = +21) |

TABLE 327

Efficacy against MATIN, 14 days after application

| Active ingredient | Dosage [g of a.i./ha] | Efficacy [%] |
|---|---|---|
| A1-57 | 50 | 85 |
| aclonifen | 800 | 0 |
| A1-57 + aclonifen | 50 + 800 | 95 (Ec = 85, Diff. = +10) |

TABLE 328

Efficacy against MATIN, 14 days after application

| Active ingredient | Dosage [g of a.i./ha] | Efficacy [%] |
|---|---|---|
| A1-57 | 12.5 | 60 |
| aclonifen | 800 | 0 |
| A1-57 + aclonifen | 12.5 + 800 | 93 (Ec = 60, Diff. = +33) |

TABLE 329

Efficacy against MATIN, 14 days after application

| Active ingredient | Dosage [g of a.i./ha] | Efficacy [%] |
|---|---|---|
| A1-57 | 12.5 | 60 |
| aclonifen | 200 | 0 |
| A1-57 + aclonifen | 12.5 + 200 | 75 (Ec = 60, Diff. = +15) |

TABLE 330

Efficacy against POLCO, 14 days after application

| Active ingredient | Dosage [g of a.i./ha] | Efficacy [%] |
|---|---|---|
| A1-57 | 12.5 | 65 |
| aclonifen | 800 | 10 |
| A1-57 + aclonifen | 12.5 + 800 | 85 (Ec = 68.5, Diff. = +16.5) |

TABLE 331

Efficacy against POLCO, 14 days after application

| Active ingredient | Dosage [g of a.i./ha] | Efficacy [%] |
|---|---|---|
| A1-57 | 12.5 | 65 |
| aclonifen | 200 | 0 |
| A1-57 + aclonifen | 12.5 + 200 | 85 (Ec = 65, Diff. = +20) |

TABLE 332

Efficacy against AVEFA, 14 days after application

| Active ingredient | Dosage [g of a.i./ha] | Efficacy [%] |
|---|---|---|
| A1-7 | 2.5 | 15 |
| saflufenacil | 2 | 0 |
| A1-7 + saflufenacil | 2.5 + 2 | 20 (Ec = 15, Diff. = +5) |

TABLE 333

Efficacy against LOLMU, 14 days after application

| Active ingredient | Dosage [g of a.i./ha] | Efficacy [%] |
|---|---|---|
| A1-7 | 2.5 | 0 |
| saflufenacil | 8 | 10 |
| A1-7 + saflufenacil | 2.5 + 8 | 15 (Ec = 10, Diff. = +5) |

TABLE 334

Efficacy against LOLMU, 14 days after application

| Active ingredient | Dosage [g of a.i./ha] | Efficacy [%] |
|---|---|---|
| A1-7 | 2.5 | 0 |
| saflufenacil | 2 | 0 |
| A1-7 + saflufenacil | 2.5 + 2 | 10 (Ec = 0, Diff. = +10) |

TABLE 335

Efficacy against POLCO, 14 days after application

| Active ingredient | Dosage [g of a.i./ha] | Efficacy [%] |
|---|---|---|
| A1-7 | 10 | 25 |
| saflufenacil | 8 | 10 |
| A1-7 + saflufenacil | 10 + 8 | 80 (Ec = 32.5, Diff. = +47.5) |

TABLE 336

Efficacy against POLCO, 14 days after application

| Active ingredient | Dosage [g of a.i./ha] | Efficacy [%] |
|---|---|---|
| A1-7 | 10 | 25 |
| saflufenacil | 2 | 0 |
| A1-7 + saflufenacil | 10 + 2 | 75 (Ec = 25, Diff. = +50) |

TABLE 337

Efficacy against POLCO, 14 days after application

| Active ingredient | Dosage [g of a.i./ha] | Efficacy [%] |
|---|---|---|
| A1-7 | 2.5 | 10 |
| saflufenacil | 8 | 10 |
| A1-7 + saflufenacil | 2.5 + 8 | 93 (Ec = 19, Diff. = +74) |

TABLE 338

Efficacy against POLCO, 14 days after application

| Active ingredient | Dosage [g of a.i./ha] | Efficacy [%] |
|---|---|---|
| A1-7 | 2.5 | 10 |
| saflufenacil | 2 | 0 |
| A1-7 + saflufenacil | 2.5 + 2 | 75 (Ec = 10, Diff. = +65) |

TABLE 339

Efficacy against AVEFA, 14 days after application

| Active ingredient | Dosage [g of a.i./ha] | Efficacy [%] |
|---|---|---|
| A1-60 | 10 | 0 |
| isoproturon | 1600 | 35 |
| A1-60 + isoproturon | 10 + 1600 | 50 (Ec = 35, Diff. = +15) |

TABLE 340

Efficacy against AVEFA, 14 days after application

| Active ingredient | Dosage [g of a.i./ha] | Efficacy [%] |
|---|---|---|
| A1-60 | 10 | 0 |
| isoproturon | 400 | 0 |
| A1-60 + isoproturon | 10 + 400 | 50 (Ec = 0, Diff. = +50) |

TABLE 341

Efficacy against AVEFA, 14 days after application

| Active ingredient | Dosage [g of a.i./ha] | Efficacy [%] |
|---|---|---|
| A1-60 | 2.5 | 0 |
| isoproturon | 400 | 0 |
| A1-60 + isoproturon | 2.5 + 400 | 15 (Ec = 0, Diff. = +15) |

TABLE 342

Efficacy against BROST, 14 days after application

| Active ingredient | Dosage [g of a.i./ha] | Efficacy [%] |
|---|---|---|
| A1-60 | 10 | 15 |
| isoproturon | 1600 | 5 |
| A1-60 + isoproturon | 10 + 1600 | 60 (Ec = 19.25, Diff. = +40.75) |

TABLE 343

Efficacy against BROST, 14 days after application

| Active ingredient | Dosage [g of a.i./ha] | Efficacy [%] |
|---|---|---|
| A1-60 | 10 | 15 |
| isoproturon | 400 | 0 |
| A1-60 + isoproturon | 10 + 400 | 40 (Ec = 15, Diff. = +25) |

TABLE 344

Efficacy against BROST, 14 days after application

| Active ingredient | Dosage [g of a.i./ha] | Efficacy [%] |
|---|---|---|
| A1-60 | 2.5 | 0 |
| isoproturon | 1600 | 5 |
| A1-60 + isoproturon | 2.5 + 1600 | 20 (Ec = 5, Diff. = +15) |

TABLE 345

Efficacy against BROST, 14 days after application

| Active ingredient | Dosage [g of a.i./ha] | Efficacy [%] |
|---|---|---|
| A1-60 | 2.5 | 0 |
| isoproturon | 400 | 0 |
| A1-60 + isoproturon | 2.5 + 400 | 15 (Ec = 0, Diff. = +15) |

TABLE 346

Efficacy against LOLMU, 14 days after application

| Active ingredient | Dosage [g of a.i./ha] | Efficacy [%] |
|---|---|---|
| A1-60 | 10 | 0 |
| isoproturon | 1600 | 15 |
| A1-60 + isoproturon | 10 + 1600 | 50 (Ec = 15, Diff. = +35) |

TABLE 347

Efficacy against LOLMU, 14 days after application

| Active ingredient | Dosage [g of a.i./ha] | Efficacy [%] |
|---|---|---|
| A1-60 | 10 | 0 |
| isoproturon | 400 | 0 |
| A1-60 + isoproturon | 10 + 400 | 30 (Ec = 0, Diff. = +30) |

TABLE 348

Efficacy against LOLMU, 14 days after application

| Active ingredient | Dosage [g of a.i./ha] | Efficacy [%] |
|---|---|---|
| A1-60 | 2.5 | 0 |
| isoproturon | 1600 | 15 |
| A1-60 + isoproturon | 2.5 + 1600 | 25 (Ec = 15, Diff. = +10) |

TABLE 349

Efficacy against LOLMU, 14 days after application

| Active ingredient | Dosage [g of a.i./ha] | Efficacy [%] |
|---|---|---|
| A1-60 | 2.5 | 0 |
| isoproturon | 400 | 0 |
| A1-60 + isoproturon | 2.5 + 400 | 15 (Ec = 0, Diff. = +15) |

TABLE 350

Efficacy against PHAMI, 14 days after application

| Active ingredient | Dosage [g of a.i./ha] | Efficacy [%] |
|---|---|---|
| A1-60 | 10 | 25 |
| isoproturon | 1600 | 80 |
| A1-60 + isoproturon | 10 + 1600 | 95 (Ec = 85, Diff. = +10) |

TABLE 351

Efficacy against PHAMI, 14 days after application

| Active ingredient | Dosage [g of a.i./ha] | Efficacy [%] |
|---|---|---|
| A1-60 | 10 | 25 |
| isoproturon | 400 | 35 |
| A1-60 + isoproturon | 10 + 400 | 85 (Ec = 51.25, Diff. = +33.75) |

TABLE 352

Efficacy against PHAMI, 14 days after application

| Active ingredient | Dosage [g of a.i./ha] | Efficacy [%] |
|---|---|---|
| A1-60 | 2.5 | 10 |
| isoproturon | 400 | 35 |
| A1-60 + isoproturon | 2.5 + 400 | 50 (Ec = 41.5, Diff. = +8.5) |

TABLE 353

Efficacy against POAAN, 14 days after application

| Active ingredient | Dosage [g of a.i./ha] | Efficacy [%] |
|---|---|---|
| A1-60 | 10 | 10 |
| isoproturon | 1600 | 80 |
| A1-60 + isoproturon | 10 + 1600 | 90 (Ec = 82, Diff. = +8) |

TABLE 354

Efficacy against POAAN, 14 days after application

| Active ingredient | Dosage [g of a.i./ha] | Efficacy [%] |
|---|---|---|
| A1-60 | 10 | 10 |
| isoproturon | 400 | 60 |
| A1-60 + isoproturon | 10 + 400 | 95 (Ec = 64, Diff. = +31) |

TABLE 355

Efficacy against POAAN, 14 days after application

| Active ingredient | Dosage [g of a.i./ha] | Efficacy [%] |
|---|---|---|
| A1-60 | 2.5 | 0 |
| isoproturon | 1600 | 80 |
| A1-60 + isoproturon | 2.5 + 1600 | 85 (Ec = 80, Diff. = +5) |

TABLE 356

Efficacy against GALAP, 14 days after application

| Active ingredient | Dosage [g of a.i./ha] | Efficacy [%] |
|---|---|---|
| A1-60 | 10 | 30 |
| isoproturon | 1600 | 20 |
| A1-60 + isoproturon | 10 + 1600 | 65 (Ec = 44, Diff. = +21) |

TABLE 357

Efficacy against GALAP, 14 days after application

| Active ingredient | Dosage [g of a.i./ha] | Efficacy [%] |
|---|---|---|
| A1-60 | 10 | 30 |
| isoproturon | 400 | 10 |
| A1-60 + isoproturon | 10 + 400 | 65 (Ec = 37, Diff. = +28) |

TABLE 358

Efficacy against GALAP, 14 days after application

| Active ingredient | Dosage [g of a.i./ha] | Efficacy [%] |
|---|---|---|
| A1-60 | 2.5 | 25 |
| isoproturon | 1600 | 20 |
| A1-60 + isoproturon | 2.5 + 1600 | 65 (Ec = 40, Diff. = +25) |

TABLE 359

Efficacy against GALAP, 14 days after application

| Active ingredient | Dosage [g of a.i./ha] | Efficacy [%] |
|---|---|---|
| A1-60 | 2.5 | 25 |
| isoproturon | 400 | 10 |
| A1-60 + isoproturon | 2.5 + 400 | 60 (Ec = 32.5, Diff. = +27.5) |

TABLE 360

Efficacy against PHAMI, 14 days after application

| Active ingredient | Dosage [g of a.i./ha] | Efficacy [%] |
|---|---|---|
| A1-13 | 10 | 30 |
| indaziflam | 40 | 10 |
| A1-13 + indaziflam | 10 + 40 | 60 (Ec = 37, Diff. = +23) |

TABLE 361

Efficacy against PHAMI, 14 days after application

| Active ingredient | Dosage [g of a.i./ha] | Efficacy [%] |
|---|---|---|
| A1-13 | 2.5 | 30 |
| indaziflam | 40 | 10 |
| A1-13 + indaziflam | 2.5 + 40 | 70 (Ec = 37, Diff. = +33) |

TABLE 362

Efficacy against GALAP, 14 days after application

| Active ingredient | Dosage [g of a.i./ha] | Efficacy [%] |
|---|---|---|
| A1-13 | 10 | 50 |
| indaziflam | 40 | 60 |
| A1-13 + indaziflam | 10 + 40 | 95 (Ec = 80, Diff. = +15) |

TABLE 363

Efficacy against GALAP, 14 days after application

| Active ingredient | Dosage [g of a.i./ha] | Efficacy [%] |
|---|---|---|
| A1-13 | 2.5 | 40 |
| indaziflam | 10 | 50 |
| A1-13 + indaziflam | 2.5 + 10 | 75 (Ec = 70, Diff. = +5) |

TABLE 364

Efficacy against MATIN, 14 days after application

| Active ingredient | Dosage [g of a.i./ha] | Efficacy [%] |
|---|---|---|
| A1-13 | 10 | 40 |
| indaziflam | 10 | 30 |
| A1-13 + indaziflam | 10 + 10 | 70 (Ec = 58, Diff. = +12) |

TABLE 365

Efficacy against MATIN, 14 days after application

| Active ingredient | Dosage [g of a.i./ha] | Efficacy [%] |
|---|---|---|
| A1-13 | 2.5 | 30 |
| indaziflam | 10 | 30 |
| A1-13 + indaziflam | 2.5 + 10 | 70 (Ec = 51, Diff. = +19) |

TABLE 366

Efficacy against LOLMU, 21 days after application

| Active ingredient | Dosage [g of a.i./ha] | Efficacy [%] |
|---|---|---|
| A1-3 | 20 | 5 |
| pinoxaden | 5 | 30 |
| A1-3 + pinoxaden | 20 + 5 | 40 (Ec = 33.5, Diff. = +6.5) |

TABLE 367

Efficacy against LOLMU, 21 days after application

| Active ingredient | Dosage [g of a.i./ha] | Efficacy [%] |
|---|---|---|
| A1-3 | 5 | 0 |
| pinoxaden | 20 | 80 |
| A1-3 + pinoxaden | 5 + 20 | 90 (Ec = 80, Diff. = +10) |

TABLE 368

Efficacy against PHAMI, 21 days after application

| Active ingredient | Dosage [g of a.i./ha] | Efficacy [%] |
|---|---|---|
| A1-3 | 20 | 5 |
| pinoxaden | 20 | 20 |
| A1-3 + pinoxaden | 20 + 20 | 80 (Ec = 24, Diff. = +56) |

TABLE 369

Efficacy against PHAMI, 21 days after application

| Active ingredient | Dosage [g of a.i./ha] | Efficacy [%] |
|---|---|---|
| A1-3 | 20 | 5 |
| pinoxaden | 5 | 10 |
| A1-3 + pinoxaden | 20 + 5 | 20 (Ec = 14.5, Diff. = +5.5) |

TABLE 370

Efficacy against POAAN, 21 days after application

| Active ingredient | Dosage [g of a.i./ha] | Efficacy [%] |
|---|---|---|
| A1-3 | 20 | 3 |
| pinoxaden | 20 | 0 |
| A1-3 + pinoxaden | 20 + 20 | 20 (Ec = 3, Diff. = +17) |

TABLE 371

Efficacy against POAAN, 21 days after application

| Active ingredient | Dosage [g of a.i./ha] | Efficacy [%] |
|---|---|---|
| A1-3 | 5 | 0 |
| pinoxaden | 20 | 0 |
| A1-3 + pinoxaden | 5 + 20 | 15 (Ec = 0, Diff. = +15) |

TABLE 372

Efficacy against GALAP, 21 days after application

| Active ingredient | Dosage [g of a.i./ha] | Efficacy [%] |
|---|---|---|
| A1-3 | 20 | 5 |
| pinoxaden | 20 | 0 |
| A1-3 + pinoxaden | 20 + 20 | 30 (Ec = 5, Diff. = +25) |

TABLE 373

Efficacy against GALAP, 21 days after application

| Active ingredient | Dosage [g of a.i./ha] | Efficacy [%] |
|---|---|---|
| A1-3 | 20 | 5 |
| pinoxaden | 5 | 0 |
| A1-3 + pinoxaden | 20 + 5 | 30 (Ec = 5, Diff. = +25) |

TABLE 374

Efficacy against GALAP, 21 days after application

| Active ingredient | Dosage [g of a.i./ha] | Efficacy [%] |
|---|---|---|
| A1-3 | 5 | 5 |
| pinoxaden | 20 | 0 |
| A1-3 + pinoxaden | 5 + 20 | 20 (Ec = 5, Diff. = +15) |

TABLE 375

Efficacy against POLCO, 21 days after application

| Active ingredient | Dosage [g of a.i./ha] | Efficacy [%] |
|---|---|---|
| A1-3 | 20 | 5 |
| pinoxaden | 20 | 0 |
| A1-3 + pinoxaden | 20 + 20 | 15 (Ec = 5, Diff. = +10) |

TABLE 376

Efficacy against POLCO, 21 days after application

| Active ingredient | Dosage [g of a.i./ha] | Efficacy [%] |
|---|---|---|
| A1-3 | 20 | 5 |
| pinoxaden | 5 | 0 |
| A1-3 + pinoxaden | 20 + 5 | 15 (Ec = 5, Diff. = +10) |

TABLE 377

Efficacy against AVEFA, 21 days after application

| Active ingredient | Dosage [g of a.i./ha] | Efficacy [%] |
|---|---|---|
| A1-13 | 10 | 3 |
| mesosulfuron-methyl | 10 | 0 |
| A1-13 + mesosulfuron-methyl | 10 + 10 | 15 (Ec = 3, Diff. = +12) |

TABLE 378

Efficacy against AVEFA, 21 days after application

| Active ingredient | Dosage [g of a.i./ha] | Efficacy [%] |
|---|---|---|
| A1-13 | 2.5 | 0 |
| mesosulfuron-methyl | 10 | 0 |
| A1-13 + mesosulfuron-methyl | 2.5 + 10 | 15 (Ec = 0, Diff. = +15) |

TABLE 379

Efficacy against BROST, 21 days after application

| Active ingredient | Dosage [g of a.i./ha] | Efficacy [%] |
|---|---|---|
| A1-13 | 10 | 5 |
| mesosulfuron-methyl | 10 | 0 |
| A1-13 + mesosulfuron-methyl | 10 + 10 | 20 (Ec = 5, Diff. = +15) |

TABLE 380

Efficacy against BROST, 21 days after application

| Active ingredient | Dosage [g of a.i./ha] | Efficacy [%] |
|---|---|---|
| A1-13 | 2.5 | 0 |
| mesosulfuron-methyl | 10 | 0 |
| A1-13 + mesosulfuron-methyl | 2.5 + 10 | 35 (Ec = 0, Diff. = +35) |

TABLE 381

Efficacy against BROST, 21 days after application

| Active ingredient | Dosage [g of a.i./ha] | Efficacy [%] |
|---|---|---|
| A1-13 | 2.5 | 0 |
| mesosulfuron-methyl | 2.5 | 0 |
| A1-13 + mesosulfuron-methyl | 2.5 + 2.5 | 20 (Ec = 0, Diff. = +20) |

TABLE 382

Efficacy against LOLMU, 21 days after application

| Active ingredient | Dosage [g of a.i./ha] | Efficacy [%] |
|---|---|---|
| A1-13 | 10 | 5 |
| mesosulfuron-methyl | 10 | 15 |
| A1-13 + mesosulfuron-methyl | 10 + 10 | 35 (Ec = 19.25, Diff. = +15.75) |

TABLE 383

Efficacy against PHAMI, 21 days after application

| Active ingredient | Dosage [g of a.i./ha] | Efficacy [%] |
|---|---|---|
| A1-13 | 10 | 20 |
| mesosulfuron-methyl | 10 | 5 |
| A1-13 + mesosulfuron-methyl | 10 + 10 | 40 (Ec = 24, Diff. = +16) |

TABLE 384

Efficacy against PHAMI, 21 days after application

| Active ingredient | Dosage [g of a.i./ha] | Efficacy [%] |
|---|---|---|
| A1-13 | 2.5 | 15 |
| mesosulfuron-methyl | 10 | 5 |
| A1-13 + mesosulfuron-methyl | 2.5 + 10 | 30 (Ec = 19.25, Diff. = +10.75) |

TABLE 385

Efficacy against PHAMI, 21 days after application

| Active ingredient | Dosage [g of a.i./ha] | Efficacy [%] |
|---|---|---|
| A1-13 | 2.5 | 15 |
| mesosulfuron-methyl | 2.5 | 0 |
| A1-13 + mesosulfuron-methyl | 2.5 + 2.5 | 20 (Ec = 15, Diff. = +5) |

TABLE 386

Efficacy against POAAN, 21 days after application

| Active ingredient | Dosage [g of a.i./ha] | Efficacy [%] |
|---|---|---|
| A1-13 | 2.5 | 10 |
| mesosulfuron-methyl | 10 | 40 |
| A1-13 + mesosulfuron-methyl | 2.5 + 10 | 60 (Ec = 46, Diff. = +14) |

TABLE 387

Efficacy against POLCO, 21 days after application

| Active ingredient | Dosage [g of a.i./ha] | Efficacy [%] |
|---|---|---|
| A1-13 | 10 | 0 |
| mesosulfuron-methyl | 10 | 0 |
| A1-13 + mesosulfuron-methyl | 10 + 10 | 15 (Ec = 0, Diff. = +15) |

TABLE 388

Efficacy against POLCO, 21 days after application

| Active ingredient | Dosage [g of a.i./ha] | Efficacy [%] |
|---|---|---|
| A1-13 | 2.5 | 0 |
| mesosulfuron-methyl | 10 | 0 |
| A1-13 + mesosulfuron-methyl | 2.5 + 10 | 10 (Ec = 0, Diff. = +10) |

TABLE 389

Efficacy against AVEFA, 21 days after application

| Active ingredient | Dosage [g of a.i./ha] | Efficacy [%] |
|---|---|---|
| A1-34 | 200 | 5 |
| iodosulfuron-methyl-sodium | 2 | 5 |
| A1-34 + iodosulfuron-methyl-sodium | 200 + 2 | 15 (Ec = 9.75, Diff. = +5.25) |

TABLE 390

Efficacy against BROST, 21 days after application

| Active ingredient | Dosage [g of a.i./ha] | Efficacy [%] |
|---|---|---|
| A1-34 | 200 | 35 |
| iodosulfuron-methyl-sodium | 2 | 0 |
| A1-34 + iodosulfuron-methyl-sodium | 200 + 2 | 40 (Ec = 35, Diff. = +5) |

TABLE 391

Efficacy against BROST, 21 days after application

| Active ingredient | Dosage [g of a.i./ha] | Efficacy [%] |
|---|---|---|
| A1-34 | 50 | 15 |
| iodosulfuron-methyl-sodium | 2 | 0 |
| A1-34 + iodosulfuron-methyl-sodium | 50 + 2 | 20 (Ec = 15, Diff. = +5) |

TABLE 392

Efficacy against GALAP, 21 days after application

| Active ingredient | Dosage [g of a.i./ha] | Efficacy [%] |
|---|---|---|
| A1-34 | 200 | 40 |
| iodosulfuron-methyl-sodium | 2 | 25 |
| A1-34 + iodosulfuron-methyl-sodium | 200 + 2 | 70 (Ec = 55, Diff. = +15) |

TABLE 393

Efficacy against GALAP, 21 days after application

| Active ingredient | Dosage [g of a.i./ha] | Efficacy [%] |
|---|---|---|
| A1-34 | 50 | 20 |
| iodosulfuron-methyl-sodium | 0.5 | 0 |
| A1-34 + iodosulfuron-methyl-sodium | 50 + 0.5 | 40 (Ec = 20, Diff. = +20) |

TABLE 394

Efficacy against MATIN, 21 days after application

| Active ingredient | Dosage [g of a.i./ha] | Efficacy [%] |
|---|---|---|
| A1-34 | 50 | 50 |
| iodosulfuron-methyl-sodium | 0.5 | 70 |
| A1-34 + iodosulfuron-methyl-sodium | 50 + 0.5 | 90 (Ec = 85, Diff. = +5) |

TABLE 395

Efficacy against POLCO, 21 days after application

| Active ingredient | Dosage [g of a.i./ha] | Efficacy [%] |
|---|---|---|
| A1-34 | 50 | 0 |
| iodosulfuron-methyl-sodium | 2 | 0 |
| A1-34 + iodosulfuron-methyl-sodium | 50 + 2 | 15 (Ec = 0, Diff. = +15) |

TABLE 396

Efficacy against POLCO, 21 days after application

| Active ingredient | Dosage [g of a.i./ha] | Efficacy [%] |
|---|---|---|
| A1-34 | 50 | 0 |
| iodosulfuron-methyl-sodium | 0.5 | 0 |
| A1-34 + iodosulfuron-methyl-sodium | 50 + 0.5 | 15 (Ec = 0, Diff. = +15) |

TABLE 397

Efficacy against BROST, 21 days after application

| Active ingredient | Dosage [g of a.i./ha] | Efficacy [%] |
|---|---|---|
| A1-14 | 10 | 0 |
| pyrasulfotole | 100 | 0 |
| A1-14 + pyrasulfotole | 10 + 100 | 5 (Ec = 0, Diff. = +5) |

TABLE 398

Efficacy against PHAMI, 21 days after application

| Active ingredient | Dosage [g of a.i./ha] | Efficacy [%] |
|---|---|---|
| A1-14 | 2.5 | 0 |
| pyrasulfotole | 100 | 0 |
| A1-14 + pyrasulfotole | 2.5 + 100 | 30 (Ec = 0, Diff. = +30) |

TABLE 399

Efficacy against PHAMI, 21 days after application

| Active ingredient | Dosage [g of a.i./ha] | Efficacy [%] |
|---|---|---|
| A1-14 | 2.5 | 0 |
| pyrasulfotole | 25 | 0 |
| A1-14 + pyrasulfotole | 2.5 + 25 | 20 (Ec = 0, Diff. = +20) |

TABLE 400

Efficacy against POAAN, 21 days after application

| Active ingredient | Dosage [g of a.i./ha] | Efficacy [%] |
|---|---|---|
| A1-14 | 2.5 | 0 |
| pyrasulfotole | 100 | 0 |
| A1-14 + pyrasulfotole | 2.5 + 100 | 15 (Ec = 0, Diff. = +15) |

TABLE 401

Efficacy against POAAN, 21 days after application

| Active ingredient | Dosage [g of a.i./ha] | Efficacy [%] |
|---|---|---|
| A1-14 | 2.5 | 0 |
| pyrasulfotole | 25 | 0 |
| A1-14 + pyrasulfotole | 2.5 + 25 | 15 (Ec = 0, Diff. = +15) |

TABLE 402

Efficacy against GALAP, 21 days after application

| Active ingredient | Dosage [g of a.i./ha] | Efficacy [%] |
|---|---|---|
| A1-14 | 10 | 15 |
| pyrasulfotole | 25 | 40 |
| A1-14 + pyrasulfotole | 10 + 25 | 60 (Ec = 49, Diff. = +11) |

TABLE 403

Efficacy against GALAP, 21 days after application

| Active ingredient | Dosage [g of a.i./ha] | Efficacy [%] |
|---|---|---|
| A1-14 | 2.5 | 0 |
| pyrasulfotole | 25 | 40 |
| A1-14 + pyrasulfotole | 2.5 + 25 | 50 (Ec = 40, Diff. = +10) |

TABLE 404

Efficacy against MATIN, 21 days after application

| Active ingredient | Dosage [g of a.i./ha] | Efficacy [%] |
|---|---|---|
| A1-14 | 2.5 | 30 |
| pyrasulfotole | 100 | 3 |
| A1-14 + pyrasulfotole | 2.5 + 100 | 40 (Ec = 32.1, Diff. = +7.9) |

TABLE 405

Efficacy against POLCO, 21 days after application

| Active ingredient | Dosage [g of a.i./ha] | Efficacy [%] |
|---|---|---|
| A1-14 | 10 | 3 |
| pyrasulfotole | 100 | 30 |
| A1-14 + pyrasulfotole | 10 + 100 | 70 (Ec = 32.1, Diff. = +37.9) |

TABLE 406

Efficacy against POLCO, 21 days after application

| Active ingredient | Dosage [g of a.i./ha] | Efficacy [%] |
|---|---|---|
| A1-14 | 10 | 3 |
| pyrasulfotole | 25 | 0 |
| A1-14 + pyrasulfotole | 10 + 25 | 80 (Ec = 3, Diff. = +77) |

TABLE 407

Efficacy against POLCO, 21 days after application

| Active ingredient | Dosage [g of a.i./ha] | Efficacy [%] |
|---|---|---|
| A1-14 | 2.5 | 0 |
| pyrasulfotole | 100 | 30 |
| A1-14 + pyrasulfotole | 2.5 + 100 | 60 (Ec = 30, Diff. = +30) |

TABLE 408

Efficacy against POLCO, 21 days after application

| Active ingredient | Dosage [g of a.i./ha] | Efficacy [%] |
|---|---|---|
| A1-14 | 2.5 | 0 |
| pyrasulfotole | 25 | 0 |
| A1-14 + pyrasulfotole | 2.5 + 25 | 50 (Ec = 0, Diff. = +50) |

TABLE 409

Efficacy against AVEFA, 21 days after application

| Active ingredient | Dosage [g of a.i./ha] | Efficacy [%] |
|---|---|---|
| A1-36 | 10 | 15 |
| flurtamone | 320 | 0 |
| A1-36 + flurtamone | 10 + 320 | 40 (Ec = 15, Diff. = +25) |

TABLE 410

Efficacy against AVEFA, 21 days after application

| Active ingredient | Dosage [g of a.i./ha] | Efficacy [%] |
|---|---|---|
| A1-36 | 10 | 15 |
| flurtamone | 80 | 0 |
| A1-36 + flurtamone | 10 + 80 | 30 (Ec = 15, Diff. = +15) |

TABLE 411

Efficacy against AVEFA, 21 days after application

| Active ingredient | Dosage [g of a.i./ha] | Efficacy [%] |
|---|---|---|
| A1-36 | 2.5 | 10 |
| flurtamone | 320 | 0 |
| A1-36 + flurtamone | 2.5 + 320 | 30 (Ec = 10, Diff. = +20) |

TABLE 412

Efficacy against AVEFA, 21 days after application

| Active ingredient | Dosage [g of a.i./ha] | Efficacy [%] |
|---|---|---|
| A1-36 | 2.5 | 10 |
| flurtamone | 80 | 0 |
| A1-36 + flurtamone | 2.5 + 80 | 20 (Ec = 10, Diff. = +10) |

TABLE 413

Efficacy against BROST, 21 days after application

| Active ingredient | Dosage [g of a.i./ha] | Efficacy [%] |
|---|---|---|
| A1-36 | 2.5 | 5 |
| flurtamone | 320 | 10 |
| A1-36 + flurtamone | 2.5 + 320 | 20 (Ec = 14.5, Diff. = +5.5) |

TABLE 414

Efficacy against BROST, 21 days after application

| Active ingredient | Dosage [g of a.i./ha] | Efficacy [%] |
|---|---|---|
| A1-36 | 2.5 | 5 |
| flurtamone | 80 | 0 |
| A1-36 + flurtamone | 2.5 + 80 | 15 (Ec = 5, Diff. = +10) |

TABLE 415

Efficacy against LOLMU, 21 days after application

| Active ingredient | Dosage [g of a.i./ha] | Efficacy [%] |
|---|---|---|
| A1-36 | 10 | 0 |
| flurtamone | 80 | 20 |
| A1-36 + flurtamone | 10 + 80 | 60 (Ec = 20, Diff. = +40) |

TABLE 416

Efficacy against PHAMI, 21 days after application

| Active ingredient | Dosage [g of a.i./ha] | Efficacy [%] |
|---|---|---|
| A1-36 | 10 | 20 |
| flurtamone | 80 | 40 |
| A1-36 + flurtamone | 10 + 80 | 80 (Ec = 52, Diff. = +28) |

TABLE 417

Efficacy against GALAP, 21 days after application

| Active ingredient | Dosage [g of a.i./ha] | Efficacy [%] |
|---|---|---|
| A1-36 | 10 | 25 |
| flurtamone | 320 | 70 |
| A1-36 + flurtamone | 10 + 320 | 95 (Ec = 77.5, Diff. = +17.5) |

TABLE 418

Efficacy against GALAP, 21 days after application

| Active ingredient | Dosage [g of a.i./ha] | Efficacy [%] |
|---|---|---|
| A1-36 | 10 | 25 |
| flurtamone | 80 | 0 |
| A1-36 + flurtamone | 10 + 80 | 60 (Ec = 25, Diff. = +35) |

TABLE 419

Efficacy against GALAP, 21 days after application

| Active ingredient | Dosage [g of a.i./ha] | Efficacy [%] |
|---|---|---|
| A1-36 | 2.5 | 0 |
| flurtamone | 80 | 0 |
| A1-36 + flurtamone | 2.5 + 80 | 70 (Ec = 0, Diff. = +70) |

TABLE 420

Efficacy against MATIN, 21 days after application

| Active ingredient | Dosage [g of a.i./ha] | Efficacy [%] |
|---|---|---|
| A1-36 | 10 | 15 |
| flurtamone | 320 | 30 |
| A1-36 + flurtamone | 10 + 320 | 97 (Ec = 40.5, Diff. = +56.5) |

TABLE 421

Efficacy against MATIN, 21 days after application

| Active ingredient | Dosage [g of a.i./ha] | Efficacy [%] |
|---|---|---|
| A1-36 | 10 | 15 |
| flurtamone | 80 | 25 |
| A1-36 + flurtamone | 10 + 80 | 98 (Ec = 36.25, Diff. = +61.75) |

TABLE 422

Efficacy against MATIN, 21 days after application

| Active ingredient | Dosage [g of a.i./ha] | Efficacy [%] |
|---|---|---|
| A1-36 | 2.5 | 0 |
| flurtamone | 320 | 30 |
| A1-36 + flurtamone | 2.5 + 320 | 80 (Ec = 30, Diff. = +50) |

TABLE 423

Efficacy against MATIN, 21 days after application

| Active ingredient | Dosage [g of a.i./ha] | Efficacy [%] |
|---|---|---|
| A1-36 | 2.5 | 0 |
| flurtamone | 80 | 25 |
| A1-36 + flurtamone | 2.5 + 80 | 60 (Ec = 25, Diff. = +35) |

TABLE 424

Efficacy against POLCO, 21 days after application

| Active ingredient | Dosage [g of a.i./ha] | Efficacy [%] |
|---|---|---|
| A1-36 | 10 | 3 |
| flurtamone | 320 | 30 |
| A1-36 + flurtamone | 10 + 320 | 40 (Ec = 32.1, Diff. = +7.9) |

TABLE 425

Efficacy against POLCO, 21 days after application

| Active ingredient | Dosage [g of a.i./ha] | Efficacy [%] |
|---|---|---|
| A1-36 | 10 | 3 |
| flurtamone | 80 | 0 |
| A1-36 + flurtamone | 10 + 80 | 30 (Ec = 3, Diff. = +27) |

TABLE 426

Efficacy against AVEFA, 21 days after application

| Active ingredient | Dosage [g of a.i./ha] | Efficacy [%] |
|---|---|---|
| A2-1 | 50 | 0 |
| fluroxypyr | 80 | 0 |
| A2-1 + fluroxypyr | 50 + 80 | 15 (Ec = 0, Diff. = +15) |

TABLE 427

Efficacy against AVEFA, 21 days after application

| Active ingredient | Dosage [g of a.i./ha] | Efficacy [%] |
|---|---|---|
| A2-1 | 12.5 | 0 |
| fluroxypyr | 80 | 0 |
| A2-1 + fluroxypyr | 12.5 + 80 | 15 (Ec = 0, Diff. = +15) |

TABLE 428

Efficacy against BROST, 21 days after application

| Active ingredient | Dosage [g of a.i./ha] | Efficacy [%] |
|---|---|---|
| A2-1 | 50 | 0 |
| fluroxypyr | 80 | 0 |
| A2-1 + fluroxypyr | 50 + 80 | 15 (Ec = 0, Diff. = +15) |

TABLE 429

Efficacy against LOLMU, 21 days after application

| Active ingredient | Dosage [g of a.i./ha] | Efficacy [%] |
|---|---|---|
| A2-1 | 50 | 0 |
| fluroxypyr | 80 | 0 |
| A2-1 + fluroxypyr | 50 + 80 | 10 (Ec = 0, Diff. = +10) |

TABLE 430

Efficacy against PHAMI, 21 days after application

| Active ingredient | Dosage [g of a.i./ha] | Efficacy [%] |
|---|---|---|
| A2-1 | 50 | 15 |
| fluroxypyr | 80 | 0 |
| A2-1 + fluroxypyr | 50 + 80 | 30 (Ec = 15, Diff. = +15) |

TABLE 431

Efficacy against PHAMI, 21 days after application

| Active ingredient | Dosage [g of a.i./ha] | Efficacy [%] |
|---|---|---|
| A2-1 | 12.5 | 0 |
| fluroxypyr | 80 | 0 |
| A2-1 + fluroxypyr | 12.5 + 80 | 20 (Ec = 0, Diff. = +20) |

TABLE 432

Efficacy against POAAN, 21 days after application

| Active ingredient | Dosage [g of a.i./ha] | Efficacy [%] |
|---|---|---|
| A2-1 | 12.5 | 0 |
| fluroxypyr | 80 | 10 |
| A2-1 + fluroxypyr | 12.5 + 80 | 15 (Ec = 10, Diff. = +5) |

TABLE 433

Efficacy against POAAN, 21 days after application

| Active ingredient | Dosage [g of a.i./ha] | Efficacy [%] |
|---|---|---|
| A2-1 | 12.5 | 0 |
| fluroxypyr | 20 | 0 |
| A2-1 + fluroxypyr | 12.5 + 20 | 10 (Ec = 0, Diff. = +10) |

TABLE 434

Efficacy against MATIN, 21 days after application

| Active ingredient | Dosage [g of a.i./ha] | Efficacy [%] |
|---|---|---|
| A2-1 | 50 | 85 |
| fluroxypyr | 80 | 50 |
| A2-1 + fluroxypyr | 50 + 80 | 98 (Ec = 92.5, Diff. = +5.5) |

TABLE 435

Efficacy against MATIN, 21 days after application

| Active ingredient | Dosage [g of a.i./ha] | Efficacy [%] |
|---|---|---|
| A2-1 | 50 | 85 |
| fluroxypyr | 20 | 20 |
| A2-1 + fluroxypyr | 50 + 20 | 95 (Ec = 88, Diff. = +7) |

TABLE 436

Efficacy against MATIN, 21 days after application

| Active ingredient | Dosage [g of a.i./ha] | Efficacy [%] |
|---|---|---|
| A2-1 | 12.5 | 80 |
| fluroxypyr | 80 | 50 |
| A2-1 + fluroxypyr | 12.5 + 80 | 95 (Ec = 90, Diff. = +5) |

TABLE 437

Efficacy against MATIN, 21 days after application

| Active ingredient | Dosage [g of a.i./ha] | Efficacy [%] |
|---|---|---|
| A2-1 | 12.5 | 80 |
| fluroxypyr | 20 | 20 |
| A2-1 + fluroxypyr | 12.5 + 20 | 93 (Ec = 84, Diff. = +9) |

TABLE 438

Efficacy against POLCO, 21 days after application

| Active ingredient | Dosage [g of a.i./ha] | Efficacy [%] |
|---|---|---|
| A2-1 | 50 | 60 |
| fluroxypyr | 20 | 80 |
| A2-1 + fluroxypyr | 50 + 20 | 100 (Ec = 92, Diff. = +8) |

TABLE 439

Efficacy against POLCO, 21 days after application

| Active ingredient | Dosage [g of a.i./ha] | Efficacy [%] |
|---|---|---|
| A2-1 | 12.5 | 20 |
| fluroxypyr | 20 | 80 |
| A2-1 + fluroxypyr | 12.5 + 20 | 90 (Ec = 84, Diff. = +6) |

TABLE 440

Efficacy against AVEFA, 21 days after application

| Active ingredient | Dosage [g of a.i./ha] | Efficacy [%] |
|---|---|---|
| A1-55 | 10 | 10 |
| glufosinate-ammonium | 100 | 20 |
| A1-55 + glufosinate-ammonium | 10 + 100 | 40 (Ec = 28, Diff. = +12) |

TABLE 441

Efficacy against AVEFA, 21 days after application

| Active ingredient | Dosage [g of a.i./ha] | Efficacy [%] |
|---|---|---|
| A1-55 | 2.5 | 0 |
| glufosinate-ammonium | 100 | 20 |
| A1-55 + glufosinate-ammonium | 2.5 + 100 | 35 (Ec = 20, Diff. = +15) |

TABLE 442

Efficacy against BROST, 21 days after application

| Active ingredient | Dosage [g of a.i./ha] | Efficacy [%] |
|---|---|---|
| A1-55 | 10 | 10 |
| glufosinate-ammonium | 25 | 0 |
| A1-55 + glufosinate-ammonium | 10 + 25 | 20 (Ec = 10, Diff. = +10) |

TABLE 443

Efficacy against BROST, 21 days after application

| Active ingredient | Dosage [g of a.i./ha] | Efficacy [%] |
|---|---|---|
| A1-55 | 2.5 | 0 |
| glufosinate-ammonium | 100 | 15 |
| A1-55 + glufosinate-ammonium | 2.5 + 100 | 20 (Ec = 15, Diff. = +5) |

TABLE 444

Efficacy against LOLMU, 21 days after application

| Active ingredient | Dosage [g of a.i./ha] | Efficacy [%] |
|---|---|---|
| A1-55 | 10 | 10 |
| glufosinate-ammonium | 100 | 15 |
| A1-55 + glufosinate-ammonium | 10 + 100 | 30 (Ec = 23.5, Diff. = +6.5) |

TABLE 445

Efficacy against LOLMU, 21 days after application

| Active ingredient | Dosage [g of a.i./ha] | Efficacy [%] |
|---|---|---|
| A1-55 | 2.5 | 0 |
| glufosinate-ammonium | 100 | 15 |
| A1-55 + glufosinate-ammonium | 2.5 + 100 | 20 (Ec = 15, Diff. = +5) |

TABLE 446

Efficacy against PHAMI, 21 days after application

| Active ingredient | Dosage [g of a.i./ha] | Efficacy [%] |
|---|---|---|
| A1-55 | 10 | 5 |
| glufosinate-ammonium | 100 | 10 |
| A1-55 + glufosinate-ammonium | 10 + 100 | 40 (Ec = 14.5, Diff. = +25.5) |

TABLE 447

Efficacy against PHAMI, 21 days after application

| Active ingredient | Dosage [g of a.i./ha] | Efficacy [%] |
|---|---|---|
| A1-55 | 10 | 5 |
| glufosinate-ammonium | 25 | 0 |
| A1-55 + glufosinate-ammonium | 10 + 25 | 20 (Ec = 5, Diff. = +15) |

TABLE 448

Efficacy against PHAMI, 21 days after application

| Active ingredient | Dosage [g of a.i./ha] | Efficacy [%] |
|---|---|---|
| A1-55 | 2.5 | 0 |
| glufosinate-ammonium | 100 | 10 |
| A1-55 + glufosinate-ammonium | 2.5 + 100 | 40 (Ec = 10, Diff. = +30) |

TABLE 449

Efficacy against PHAMI, 21 days after application

| Active ingredient | Dosage [g of a.i./ha] | Efficacy [%] |
|---|---|---|
| A1-55 | 2.5 | 0 |
| glufosinate-ammonium | 25 | 0 |
| A1-55 + glufosinate-ammonium | 2.5 + 25 | 20 (Ec = 0, Diff. = +20) |

TABLE 450

Efficacy against POAAN, 21 days after application

| Active ingredient | Dosage [g of a.i./ha] | Efficacy [%] |
|---|---|---|
| A1-55 | 10 | 0 |
| glufosinate-ammonium | 100 | 5 |
| A1-55 + glufosinate-ammonium | 10 + 100 | 15 (Ec = 5, Diff. = +10) |

TABLE 451

Efficacy against POAAN, 21 days after application

| Active ingredient | Dosage [g of a.i./ha] | Efficacy [%] |
|---|---|---|
| A1-55 | 2.5 | 0 |
| glufosinate-ammonium | 100 | 5 |
| A1-55 + glufosinate-ammonium | 2.5 + 100 | 15 (Ec = 5, Diff. = +10) |

TABLE 452

Efficacy against GALAP, 21 days after application

| Active ingredient | Dosage [g of a.i./ha] | Efficacy [%] |
|---|---|---|
| A1-55 | 10 | 15 |
| glufosinate-ammonium | 25 | 0 |
| A1-55 + glufosinate-ammonium | 10 + 25 | 30 (Ec = 15, Diff. = +15) |

TABLE 453

Efficacy against MATIN, 21 days after application

| Active ingredient | Dosage [g of a.i./ha] | Efficacy [%] |
|---|---|---|
| A1-55 | 10 | 20 |
| glufosinate-ammonium | 100 | 15 |
| A1-55 + glufosinate-ammonium | 10 + 100 | 90 (Ec = 32, Diff. = +58) |

TABLE 454

Efficacy against MATIN, 21 days after application

| Active ingredient | Dosage [g of a.i./ha] | Efficacy [%] |
|---|---|---|
| A1-55 | 10 | 20 |
| glufosinate-ammonium | 25 | 0 |
| A1-55 + glufosinate-ammonium | 10 + 25 | 80 (Ec = 20, Diff. = +60) |

TABLE 455

Efficacy against MATIN, 21 days after application

| Active ingredient | Dosage [g of a.i./ha] | Efficacy [%] |
|---|---|---|
| A1-55 | 2.5 | 0 |
| glufosinate-ammonium | 100 | 15 |
| A1-55 + glufosinate-ammonium | 2.5 + 100 | 70 (Ec = 15, Diff. = +55) |

TABLE 456

Efficacy against MATIN, 21 days after application

| Active ingredient | Dosage [g of a.i./ha] | Efficacy [%] |
|---|---|---|
| A1-55 | 2.5 | 0 |
| glufosinate-ammonium | 25 | 0 |
| A1-55 + glufosinate-ammonium | 2.5 + 25 | 40 (Ec = 0, Diff. = +40) |

TABLE 457

Efficacy against POLCO, 21 days after application

| Active ingredient | Dosage [g of a.i./ha] | Efficacy [%] |
|---|---|---|
| A1-55 | 10 | 0 |
| glufosinate-ammonium | 100 | 5 |
| A1-55 + glufosinate-ammonium | 10 + 100 | 15 (Ec = 5, Diff. = +10) |

TABLE 458

Efficacy against POLCO, 21 days after application

| Active ingredient | Dosage [g of a.i./ha] | Efficacy [%] |
|---|---|---|
| A1-55 | 10 | 0 |
| glufosinate-ammonium | 25 | 0 |
| A1-55 + glufosinate-ammonium | 10 + 25 | 20 (Ec = 0, Diff. = +20) |

TABLE 459

Efficacy against AVEFA, 21 days after application

| Active ingredient | Dosage [g of a.i./ha] | Efficacy [%] |
|---|---|---|
| A1-57 | 12.5 | 0 |
| aclonifen | 800 | 0 |
| A1-57 + aclonifen | 12.5 + 800 | 15 (Ec = 0, Diff. = +15) |

TABLE 460

Efficacy against BROST, 21 days after application

| Active ingredient | Dosage [g of a.i./ha] | Efficacy [%] |
|---|---|---|
| A1-57 | 50 | 15 |
| aclonifen | 800 | 0 |
| A1-57 + aclonifen | 50 + 800 | 20 (Ec = 15, Diff. = +5) |

TABLE 461

Efficacy against BROST, 21 days after application

| Active ingredient | Dosage [g of a.i./ha] | Efficacy [%] |
|---|---|---|
| A1-57 | 12.5 | 0 |
| aclonifen | 800 | 0 |
| A1-57 + aclonifen | 12.5 + 800 | 10 (Ec = 0, Diff. = +10) |

TABLE 462

Efficacy against PHAMI, 21 days after application

| Active ingredient | Dosage [g of a.i./ha] | Efficacy [%] |
|---|---|---|
| A1-57 | 12.5 | 20 |
| aclonifen | 800 | 15 |
| A1-57 + aclonifen | 12.5 + 800 | 40 (Ec = 32, Diff. = +8) |

TABLE 463

Efficacy against PHAMI, 21 days after application

| Active ingredient | Dosage [g of a.i./ha] | Efficacy [%] |
|---|---|---|
| A1-57 | 12.5 | 20 |
| aclonifen | 200 | 0 |
| A1-57 + aclonifen | 12.5 + 200 | 30 (Ec = 20, Diff. = +10) |

TABLE 464

Efficacy against POAAN, 21 days after application

| Active ingredient | Dosage [g of a.i./ha] | Efficacy [%] |
|---|---|---|
| A1-57 | 50 | 35 |
| aclonifen | 800 | 10 |
| A1-57 + aclonifen | 50 + 800 | 85 (Ec = 41.5, Diff. = +43.5) |

TABLE 465

Efficacy against POAAN, 21 days after application

| Active ingredient | Dosage [g of a.i./ha] | Efficacy [%] |
|---|---|---|
| A1-57 | 50 | 35 |
| aclonifen | 200 | 0 |
| A1-57 + aclonifen | 50 + 200 | 60 (Ec = 35, Diff. = +25) |

TABLE 466

Efficacy against POAAN, 21 days after application

| Active ingredient | Dosage [g of a.i./ha] | Efficacy [%] |
|---|---|---|
| A1-57 | 12.5 | 10 |
| aclonifen | 800 | 10 |
| A1-57 + aclonifen | 12.5 + 800 | 40 (Ec = 19, Diff. = +21) |

TABLE 467

Efficacy against GALAP, 21 days after application

| Active ingredient | Dosage [g of a.i./ha] | Efficacy [%] |
|---|---|---|
| A1-57 | 50 | 40 |
| aclonifen | 800 | 20 |
| A1-57 + aclonifen | 50 + 800 | 70 (Ec = 52, Diff. = +18) |

TABLE 468

Efficacy against MATIN, 21 days after application

| Active ingredient | Dosage [g of a.i./ha] | Efficacy [%] |
|---|---|---|
| A1-57 | 50 | 80 |
| aclonifen | 800 | 0 |
| A1-57 + aclonifen | 50 + 800 | 85 (Ec = 80, Diff. = +5) |

TABLE 469

Efficacy against POLCO, 21 days after application

| Active ingredient | Dosage [g of a.i./ha] | Efficacy [%] |
|---|---|---|
| A1-57 | 12.5 | 50 |
| aclonifen | 200 | 0 |
| A1-57 + aclonifen | 12.5 + 200 | 60 (Ec = 50, Diff. = +10) |

TABLE 470

Efficacy against BROST, 21 days after application

| Active ingredient | Dosage [g of a.i./ha] | Efficacy [%] |
|---|---|---|
| A1-7 | 10 | 5 |
| saflufenacil | 8 | 5 |
| A1-7 + saflufenacil | 10 + 8 | 15 (Ec = 9.75, Diff. = +5.25) |

TABLE 471

Efficacy against POLCO, 21 days after application

| Active ingredient | Dosage [g of a.i./ha] | Efficacy [%] |
|---|---|---|
| A1-7 | 10 | 10 |
| saflufenacil | 8 | 0 |
| A1-7 + saflufenacil | 10 + 8 | 60 (Ec = 10, Diff. = +50) |

TABLE 472

Efficacy against POLCO, 21 days after application

| Active ingredient | Dosage [g of a.i./ha] | Efficacy [%] |
|---|---|---|
| A1-7 | 10 | 10 |
| saflufenacil | 2 | 0 |
| A1-7 + saflufenacil | 10 + 2 | 40 (Ec = 10, Diff. = +30) |

TABLE 473

Efficacy against POLCO, 21 days after application

| Active ingredient | Dosage [g of a.i./ha] | Efficacy [%] |
|---|---|---|
| A1-7 | 2.5 | 0 |
| saflufenacil | 8 | 0 |
| A1-7 + saflufenacil | 2.5 + 8 | 80 (Ec = 0, Diff. = +80) |

TABLE 474

Efficacy against POLCO, 21 days after application

| Active ingredient | Dosage [g of a.i./ha] | Efficacy [%] |
|---|---|---|
| A1-7 | 2.5 | 0 |
| saflufenacil | 2 | 0 |
| A1-7 + saflufenacil | 2.5 + 2 | 50 (Ec = 0, Diff. = +50) |

TABLE 475

Efficacy against AVEFA, 21 days after application

| Active ingredient | Dosage [g of a.i./ha] | Efficacy [%] |
|---|---|---|
| A1-60 | 10 | 5 |
| isoproturon | 1600 | 15 |
| A1-60 + isoproturon | 10 + 1600 | 40 (Ec = 19.25, Diff. = +20.75) |

TABLE 476

Efficacy against AVEFA, 21 days after application

| Active ingredient | Dosage [g of a.i./ha] | Efficacy [%] |
|---|---|---|
| A1-60 | 10 | 5 |
| isoproturon | 400 | 0 |
| A1-60 + isoproturon | 10 + 400 | 40 (Ec = 5, Diff. = +35) |

TABLE 477

Efficacy against AVEFA, 21 days after application

| Active ingredient | Dosage [g of a.i./ha] | Efficacy [%] |
|---|---|---|
| A1-60 | 2.5 | 0 |
| isoproturon | 400 | 0 |
| A1-60 + isoproturon | 2.5 + 400 | 10 (Ec = 0, Diff. = +10) |

TABLE 478

Efficacy against BROST, 21 days after application

| Active ingredient | Dosage [g of a.i./ha] | Efficacy [%] |
|---|---|---|
| A1-60 | 10 | 5 |
| isoproturon | 1600 | 0 |
| A1-60 + isoproturon | 10 + 1600 | 30 (Ec = 5, Diff. = +25) |

TABLE 479

Efficacy against BROST, 21 days after application

| Active ingredient | Dosage [g of a.i./ha] | Efficacy [%] |
|---|---|---|
| A1-60 | 10 | 5 |
| isoproturon | 400 | 0 |
| A1-60 + isoproturon | 10 + 400 | 15 (Ec = 5, Diff. = +10) |

TABLE 480

Efficacy against LOLMU, 21 days after application

| Active ingredient | Dosage [g of a.i./ha] | Efficacy [%] |
|---|---|---|
| A1-60 | 10 | 3 |
| isoproturon | 1600 | 0 |
| A1-60 + isoproturon | 10 + 1600 | 30 (Ec = 3, Diff. = +27) |

TABLE 481

Efficacy against LOLMU, 21 days after application

| Active ingredient | Dosage [g of a.i./ha] | Efficacy [%] |
|---|---|---|
| A1-60 | 10 | 3 |
| isoproturon | 400 | 0 |
| A1-60 + isoproturon | 10 + 400 | 15 (Ec = 3, Diff. = +12) |

TABLE 482

Efficacy against PHAMI, 21 days after application

| Active ingredient | Dosage [g of a.i./ha] | Efficacy [%] |
| --- | --- | --- |
| A1-60 | 10 | 20 |
| isoproturon | 400 | 15 |
| A1-60 + isoproturon | 10 + 400 | 80 (Ec = 32, Diff. = +48) |

TABLE 483

Efficacy against PHAMI, 21 days after application

| Active ingredient | Dosage [g of a.i./ha] | Efficacy [%] |
| --- | --- | --- |
| A1-60 | 2.5 | 0 |
| isoproturon | 400 | 15 |
| A1-60 + isoproturon | 2.5 + 400 | 20 (Ec = 15, Diff. = +5) |

TABLE 484

Efficacy against POAAN, 21 days after application

| Active ingredient | Dosage [g of a.i./ha] | Efficacy [%] |
| --- | --- | --- |
| A1-60 | 10 | 20 |
| isoproturon | 400 | 30 |
| A1-60 + isoproturon | 10 + 400 | 80 (Ec = 44, Diff. = +36) |

TABLE 485

Efficacy against GALAP, 21 days after application

| Active ingredient | Dosage [g of a.i./ha] | Efficacy [%] |
| --- | --- | --- |
| A1-60 | 10 | 0 |
| isoproturon | 1600 | 0 |
| A1-60 + isoproturon | 10 + 1600 | 40 (Ec = 0, Diff. = +40) |

TABLE 486

Efficacy against GALAP, 21 days after application

| Active ingredient | Dosage [g of a.i./ha] | Efficacy [%] |
| --- | --- | --- |
| A1-60 | 10 | 0 |
| isoproturon | 400 | 0 |
| A1-60 + isoproturon | 10 + 400 | 50 (Ec = 0, Diff. = +50) |

TABLE 487

Efficacy against GALAP, 21 days after application

| Active ingredient | Dosage [g of a.i./ha] | Efficacy [%] |
| --- | --- | --- |
| A1-60 | 2.5 | 0 |
| isoproturon | 1600 | 0 |
| A1-60 + isoproturon | 2.5 + 1600 | 40 (Ec = 0, Diff. = +40) |

TABLE 488

Efficacy against GALAP, 21 days after application

| Active ingredient | Dosage [g of a.i./ha] | Efficacy [%] |
| --- | --- | --- |
| A1-60 | 2.5 | 0 |
| isoproturon | 400 | 0 |
| A1-60 + isoproturon | 2.5 + 400 | 40 (Ec = 0, Diff. = +40) |

TABLE 489

Efficacy against MATIN, 21 days after application

| Active ingredient | Dosage [g of a.i./ha] | Efficacy [%] |
| --- | --- | --- |
| A1-60 | 10 | 40 |
| isoproturon | 400 | 90 |
| A1-60 + isoproturon | 10 + 400 | 100 (Ec = 94, Diff. = +6) |

TABLE 490

Efficacy against MATIN, 21 days after application

| Active ingredient | Dosage [g of a.i./ha] | Efficacy [%] |
| --- | --- | --- |
| A1-60 | 2.5 | 0 |
| isoproturon | 400 | 90 |
| A1-60 + isoproturon | 2.5 + 400 | 100 (Ec = 90, Diff. = +10) |

TABLE 491

Efficacy against AVEFA, 21 days after application

| Active ingredient | Dosage [g of a.i./ha] | Efficacy [%] |
| --- | --- | --- |
| A1-13 | 10 | 3 |
| indaziflam | 40 | 10 |
| A1-13 + indaziflam | 10 + 40 | 20 (Ec = 12.7, Diff. = +7.3) |

TABLE 492

Efficacy against AVEFA, 21 days after application

| Active ingredient | Dosage [g of a.i./ha] | Efficacy [%] |
| --- | --- | --- |
| A1-13 | 2.5 | 0 |
| indaziflam | 40 | 10 |
| A1-13 + indaziflam | 2.5 + 40 | 30 (Ec = 10, Diff. = +20) |

TABLE 493

Efficacy against BROST, 21 days after application

| Active ingredient | Dosage [g of a.i./ha] | Efficacy [%] |
| --- | --- | --- |
| A1-13 | 10 | 5 |
| indaziflam | 10 | 0 |
| A1-13 + indaziflam | 10 + 10 | 10 (Ec = 5, Diff. = +5) |

TABLE 494

Efficacy against LOLMU, 21 days after application

| Active ingredient | Dosage [g of a.i./ha] | Efficacy [%] |
|---|---|---|
| A1-13 | 10 | 5 |
| indaziflam | 10 | 0 |
| A1-13 + indaziflam | 10 + 10 | 10 (Ec = 5, Diff. = +5) |

TABLE 495

Efficacy against PHAMI, 21 days after application

| Active ingredient | Dosage [g of a.i./ha] | Efficacy [%] |
|---|---|---|
| A1-13 | 10 | 20 |
| indaziflam | 40 | 10 |
| A1-13 + indaziflam | 10 + 40 | 40 (Ec = 28, Diff. = +12) |

TABLE 496

Efficacy against PHAMI, 21 days after application

| Active ingredient | Dosage [g of a.i./ha] | Efficacy [%] |
|---|---|---|
| A1-13 | 2.5 | 15 |
| indaziflam | 40 | 10 |
| A1-13 + indaziflam | 2.5 + 40 | 40 (Ec = 23.5, Diff. = +16.5) |

TABLE 497

Efficacy against POAAN, 21 days after application

| Active ingredient | Dosage [g of a.i./ha] | Efficacy [%] |
|---|---|---|
| A1-13 | 10 | 20 |
| indaziflam | 10 | 0 |
| A1-13 + indaziflam | 10 + 10 | 40 (Ec = 20, Diff. = +20) |

TABLE 498

Efficacy against GALAP, 21 days after application

| Active ingredient | Dosage [g of a.i./ha] | Efficacy [%] |
|---|---|---|
| A1-13 | 10 | 60 |
| indaziflam | 40 | 35 |
| A1-13 + indaziflam | 10 + 40 | 85 (Ec = 74, Diff. = +11) |

The invention claimed is:

1. A herbicidal composition comprising
   (A) one or more compounds of formula (I) or salts thereof as component A

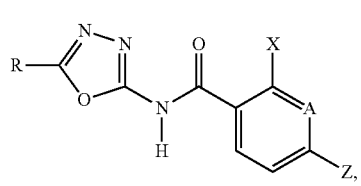

(I)

in which
   A is CY,
   R is $(C_1-C_4)$-alkyl, cyclopropyl, methoxymethyl, or methoxyethyl,
   X is halogen or $(C_1-C_6)$-alkyl,
   Y is $OR^1$ or $S(O)_n R^2$,
   Z is halo-$(C_1-C_6)$-alkyl or $S(O)_n R^2$,
   $R^1$ is $(C_1-C_6)$-alkyl or $(C_1-C_6)$-haloalkyl,
   $R^2$ is $(C_1-C_6)$-alkyl, and
   n is 1 or 2,
   and
   (B) synergistically effective amounts of one or more herbicides selected from the group consisting of B1, B2, B4, B5, B8, and B11 as component B:
      B1 1,3-diketo compounds selected from the group consisting of tembotrione and pinoxaden at a weight ratio of component A to the 1,3-diketo compound of from 1:4 to 8:1,
      B2 (sulfon)amides selected from the group consisting of foramsulfuron, iodo-sulfuron-methyl-sodium, mesosulfuron-methyl, and thiencarbazone-methyl at a weight ratio of component A to the (sulfon)amide of from 1:10 to 400:1,
      B4 azoles selected from the group consisting of pyrasulfotole, and isoxaflutole at a weight ratio of component A to the azole of from 1:40 to 1:1.25,
      B5 an herbicide that is flurtamone at a weight ratio of component A to flurtamone of from 1:128 to 1:8,
      B8 phenyl ethers selected from the group consisting of aclonifen and fenoxaprop-P-ethyl at a weight ratio of component A to the phenyl ether of from 1:64 to 1:2.5, and
      B11 a triazine selected from the group consisting of indaziflam and metribuzin at a weight ratio of component A to the triazine of from 1:200 to 1:4.

2. The herbicidal composition as claimed in claim 1 comprising
   (A) one or more compounds of formula (I) or salts thereof as component A in which
      (1) A is CY, R is methoxymethyl, X is methyl, Y is $SO_2CH_3$, and Z is trifluoro-methyl,
      (2) A is CY, R is methyl, X is chlorine, Y is $SO_2CH_2CH_3$, and Z is trifluoromethyl,
      (3) A is CY, R is methyl, X is methyl, Y is $SO_2CH_3$, Z is trifluoromethyl,
      (4) A is CY, R is methyl, X is chlorine, Y is $SOCH_3$, and Z is trifluoromethyl,
      (5) A is CY, R is cyclopropyl, X is methyl, Y is $SOCH_3$, Z is trifluoromethyl,
      (6) A is CY, R is methyl, X is chlorine, Y is $SO_2CH_3$, and Z is trifluoromethyl, or
      (7) A is CY, R is methyl, X is chlorine, Y is $OCH_2CH_2F$, and Z is $SO_2CH_3$,
   and
   (B) synergistically effective amounts of one or more herbicides selected from the group consisting of B1, B2, B4, B5, B8, and B11 as component B:
      B1 1,3-diketo compounds selected from the group consisting of tembotrione and pinoxaden at a weight ratio of component A to the 1,3-diketo compound of from 1:4 to 8:1,
      B2 (sulfon)amides selected from the group consisting of foramsulfuron, iodo-sulfuron-methyl-sodium, mesosulfuron-methyl, and thiencarbazone-methyl at a weight ratio of component A to the (sulfon)amide of from 1:10 to 400:1,
      B4 azoles selected from the group consisting of pyrasulfotole, and isoxaflutole at a weight ratio of component A to the azole of from 1:40 to 1:1.25,
      B5 an herbicide that is flurtamone at a weight ratio of component A to flurtamone of from 1:128 to 1:8, B8 phenyl ethers selected from the group consisting of aclonifen and fenoxaprop-P-ethyl at a weight ratio of component A to the phenyl ether of from 1:64 to 1:2.5, and B11 a triazine selected from the group consisting of indaziflam and metribuzin at a weight ratio of component A to the triazine of from 1:200 to 1:4.

3. The herbicidal composition as claimed in claim 1 additionally comprising, as component C, one or more safeners selected from the group consisting of benoxacor, cloquintocet-mexyl, cyprosulfamide, dichlormid, fenclorim, fenchlorazole, furilazole, isoxadifen-ethyl, mefenpyr-diethyl, 4-(dichloroacetyl)-1-oxa-4-azaspiro [4.5] decane, and 2,2,5-trimethyl-3-(dichloroacetyl)-1,3-oxazolidine.

4. A method of controlling harmful plants in crops, comprising applying a herbicidally active amount of a herbicidal composition as claimed in claim 1 to the harmful plants, plants, plant seeds or an area on which plants grow.

5. The method as claimed in claim 4, wherein the plants are selected from the group consisting of sugar cane, corn, wheat, rye, barley, oats, rice, sorghum, cotton and soya.

6. The method as claimed in claim 4, wherein the plants have been genetically modified.

\* \* \* \* \*